US010613090B2

(12) United States Patent
Daily et al.

(10) Patent No.: US 10,613,090 B2
(45) Date of Patent: Apr. 7, 2020

(54) METHODS OF DETECTING CANCER

(71) Applicant: Ascendant Diagnostics, LLC, Springdale, AR (US)

(72) Inventors: Anna Daily, Fayetteville, AR (US); Lindsay Rutherford, Fayetteville, AR (US)

(73) Assignee: Ascendant Diagnostics, LLC, Springdale, AR (US)

( * ) Notice: Subject to any disclaimer, the term of this patent is extended or adjusted under 35 U.S.C. 154(b) by 0 days.

(21) Appl. No.: 14/707,089

(22) Filed: May 8, 2015

(65) Prior Publication Data
US 2016/0003786 A1 Jan. 7, 2016

Related U.S. Application Data

(60) Provisional application No. 61/991,061, filed on May 9, 2014.

(51) Int. Cl.
| | |
|---|---|
| C12Q 1/6886 | (2018.01) |
| G01N 33/574 | (2006.01) |
| G01N 30/72 | (2006.01) |
| H01J 49/40 | (2006.01) |
| H01J 49/00 | (2006.01) |

(52) U.S. Cl.
CPC ..... *G01N 33/57415* (2013.01); *C12Q 1/6886* (2013.01); *G01N 30/7233* (2013.01); *G01N 33/57488* (2013.01); *G01N 33/57496* (2013.01); *C12Q 2600/158* (2013.01); *H01J 49/00* (2013.01); *H01J 49/40* (2013.01)

(58) Field of Classification Search
CPC .......................... G01N 33/57415; C12Q 1/6886
USPC ......................................................... 435/7.23
See application file for complete search history.

(56) References Cited

U.S. PATENT DOCUMENTS

| | | | |
|---|---|---|---|
| 7,662,580 B2 * | 2/2010 | Georges ........... | G01N 33/57415 435/7.23 |
| 7,951,529 B2 | 5/2011 | Li | |
| 10,451,625 B2 | 10/2019 | Daily et al. | |
| 2004/0029114 A1 | 2/2004 | Mack et al. | |
| 2006/0019256 A1 | 1/2006 | Clarke et al. | |
| 2009/0035801 A1 | 2/2009 | Goldknopf et al. | |
| 2009/0215102 A1 | 8/2009 | Moses et al. | |
| 2010/0184049 A1 * | 7/2010 | Goodison ............ | C12Q 1/6886 435/6.11 |
| 2010/0190656 A1 | 7/2010 | Li | |
| 2011/0212851 A1 | 9/2011 | Wong et al. | |
| 2012/0183555 A1 | 7/2012 | Chang et al. | |
| 2014/0186332 A1 * | 7/2014 | Ezrin ................... | G01N 33/689 424/130.1 |
| 2015/0141273 A1 | 5/2015 | Bosch | |
| 2016/0161492 A1 | 6/2016 | Daily et al. | |
| 2019/0277851 A1 | 9/2019 | Daily et al. | |

FOREIGN PATENT DOCUMENTS

| | | |
|---|---|---|
| WO | WO1998035229 A1 | 8/1998 |
| WO | WO2001013117 A2 | 2/2001 |
| WO | WO2001071357 A2 | 9/2001 |
| WO | WO2008014458 A2 | 1/2008 |
| WO | WO 2008/054764 A2 | 5/2008 |
| WO | WO 2009/097692 A1 | 8/2009 |
| WO | WO2010053816 A2 | 5/2010 |
| WO | WO 2011/100472 A1 | 8/2011 |
| WO | WO2012116979 A1 | 9/2012 |
| WO | WO2013106913 A1 | 7/2013 |
| WO | WO2013154422 A1 | 10/2013 |
| WO | WO2013186639 A2 | 12/2013 |
| WO | WO 2014/133855 A1 | 9/2014 |

OTHER PUBLICATIONS

Caffery (Sjogren's Syndrome: A Clinical and Biochemical Analysis, 2009, Waterloo, Ontario, Canada).*
Esmaeli et al (Arch Ophthalmol, 2002, 120(9): 1180-1182).*
Reifenstein (Gynecologic Oncology, 1974, 2: 377-414).*
Armstrong, K., Handorf, E. A., Chen, J., & Bristol Demeter, M. N. (2013). Breast cancer risk prediction and mammography biopsy decisions: a model-based study. American Journal of Preventive Medicine, 44(1), 15-22. doi:10.1016/j.amepre.2012.10.002
Böhm, D., Keller, K., Pieter, J., Boehm, N., Wolters, D., Siggelkow, W., et al. (2012). Comparison of tear protein levels in breast cancer patients and healthy controls using a de novo proteomic approach. Oncology Reports, 28(2), 429-438. doi:10.3892/or.2012.1849.
Böhm, D., Keller, K., Wehrwein, N., Lebrecht, A., Schmidt, M., Kölbl, H., & Grus, F.-H. (2011). Serum proteome profiling of primary breast cancer indicates a specific biomarker profile. Oncology Reports, 26(5), 1051-1056. doi:10.3892/or.2011.1420.
Brown, M. L., Houn, F., Sickles, E. A., & Kessler, L. G. (1995). Screening Mammography in Community Practice: Positive Predictive. American Journal of Radiology, 165, 1373-1377.
Grady, D. (2012). Study of Breast Biopsies Finds Surgery Used Too Extensively. New York Times, 1-4.
Kolb, T., Lichy, J., & Newhouse, J. (2002). Comparison of the performance of screening mammography, physical examination, and breast US and evaluation of factors that influence them: an analysis of 27,825 patient evaluations. Radiology, 225(1), 165-175.

(Continued)

*Primary Examiner* — Sean E Aeder
(74) *Attorney, Agent, or Firm* — Cooley LLP; Michael Rutherford

(57) ABSTRACT

The present disclosure is directed toward methods and kits for detecting cancer, and in particular breast cancer, in a subject by measuring the levels of at least one of the identified markers, as compared to a control. The expression of the markers in Table 2A is increased in samples from subjects with cancer as compared to the expression level in subjects without cancer and the expression of the markers in Table 2B are decreased in samples from subjects with cancer as compared to the expression level in subjects without cancer. The sample may be lacrimal secretions or eye wash fluid, saliva, or other biological fluids. The kits may include an eye wash kit, collection tubes and protease inhibitors, or protein stabilizers.

5 Claims, 3 Drawing Sheets

Specification includes a Sequence Listing.

(56) References Cited

OTHER PUBLICATIONS

Lebrecht, A., Boehm, D., Schmidt, M., Koelbl, H., & Grus, F. H. (2009a). Surface-enhanced Laser Desorption/Ionisation Time-of-flight Mass Spectrometry to Detect Breast Cancer 30 Markers in Tears and Serum. Cancer Genomics & Proteomics, 6(2), 75-83.
Lebrecht, A., Boehm, D., Schmidt, M., Koelbl, H., Schwirz, R. L., & Grus, F. H. (2009b). Diagnosis of breast cancer by tear proteomic pattern. Cancer Genomics & Proteomics, 6(3), 177-182.
Li, J., Zhang, Z., Rosenzweig, J., Wang, Y., & Chan, D. (2002). Proteomics and bioinformatics approaches for identification of serum biomarkers to detect breast cancer. Clin Chem, 48(8), 1296-1304.
Luftner, D., & Possinger, K. (2002). Nuclear matrix proteins as biomarkers for breast cancer. Expert Rev Mol Diagn, 2(1), 23-31. doi:ERM020106 [pii] 10.1586/14737159.2.1.23.
Schiess, R., Wollscheid, B., & Aebersold, R. (2009). Targeted proteomic strategy for clinical 10 biomarker discovery. Molecular Oncology, 3(1), 33-44. doi:10.1016/j.molonc.2008.12.001.
Wu, K., & Zhang, Y. (2007). Clinical application of tear proteomics: Present and future prospects. Proteomics. Clinical Applications, 1(9), 972-982. doi:10.1002/prca.200700125.
Bigenwald et al., "Is Mammography Adequate for Screening Women with Inherited BRCA Mutations and Low Breast Density?," Cancer Epidemiol Biomarkers Prev 17(3): 706-711 (2008).
Braun, Michael, et al. "Down-regulation of microfilamental network-associated proteins in leukocytes of breast cancer patients: potential application to predictive diagnosis." Cancer Genomics-Proteomics 6.1: 31-40 (2009).
Cancemi, Patrizia, et al. "Large-scale proteomic identification of S100 proteins in breast cancer tissues." BMC Cancer 10.1: 476 (2010).
Celis, Julio E., et al. "Molecular pathology of breast apocrine carcinomas: a protein expression signature specific for benign apocrine metaplasia." FEBS Letters 580.12: 2935-2944 (2006).
Chen, Xiang, et al. "Comparative profiling of triple-negative breast carcinomas tissue glycoproteome by sequential purification of glycoproteins and stable isotope labeling." Cellular Physiology and Biochemistry 38.1: 110-121 (2016).
Colak, Dilek, et al. "Age-specific gene expression signatures for breast tumors and cross-species conserved potential cancer progression markers in young women." PLOS ONE 8.5: e63204 (2013).
Cross, S. S., et al. "Expression of S100 proteins in normal human tissues and common cancers using tissue microarrays: S100A6, S100A8, S100A9 and S100A11 are all overexpressed in common cancers." Histopathology 46.3: 256-269 (2005).
European Patent Application No. 16168524.3, Extended European Search Report dated Feb. 6, 2017, 22 pages.
European Patent Application No. 16168524.3, Partial European Search Report dated Oct. 24, 2016, 9 pages.
Fusco, Ornella, et al. "90K (MAC-2 BP) gene expression in breast cancer and evidence for the production of 90K by peripheral-blood mononuclear cells." International Journal of Cancer 79.1: 23-26 (1998).
Gunaldi, Meral, et al. "Diagnostic importance of S100A9 and S100A12 in breast cancer." Biomedicine & Pharmacotherapy 76: 52-56 (2015).
Iacobelli, S., et al. "Prognostic value of a novel circulating serum 90K antigen in breast cancer." British Journal of Cancer 69.1: 172-176 (1994).
Klifa et al., "Magnetic resonance imaging for secondary assessment of breast density in a high-risk cohort," Magnetic Resonance Imaging 28(1):8-15 (2010).

Kormelink, Tom Groot, et al. "Immunoglobulin free light chains are biomarkers of poor prognosis in basal-like breast cancer and are potential targets in tumor-associated inflammation." Oncotarget 5.10: 3159-3167 (2014).
Koths, K., et al. "Cloning and characterization of a human Mac-2-binding protein, a new member of the superfamily defined by the macrophage scavenger receptor cysteine-rich domain." Journal of Biological Chemistry 268.19: 14245-14249 (1993).
Lee, Han-Byoel, et al. "Development and Validation of a Novel Plasma Protein Signature for Breast Cancer Diagnosis by Using Multiple Reaction Monitoring-based Mass Spectrometry." Anticancer Research 35.11: 6271-6280 (2015).
Pisano et al., "Diagnostic Performance of Digital versus Film Mammography for Breast Cancer Screening," The New England Journal of Medicine (2005); 353(17): 1773-1783.
Seth, Arun, et al. "Gene expression profiling of ductal carcinomas in situ and invasive breast tumors." Anticancer Research 23.3A: 2043-2051 (2002).
Tabár et al., "Swedish Two-County Trial: Impact of Mammographic Screening on Breast Cancer Mortality during 3 Decades," Radiology (2011); 260(3): 658-663.
Vachon et al., "Mammographic density, breast cancer risk and risk prediction," Breast Cancer Research (2007); 9.6: 217 (2007). (doi:10.1186/bcr1829).
Zhang, Lei, et al. "Discovery and preclinical validation of salivary transcriptomic and proteomic biomarkers for the non-invasive detection of breast cancer." PLOS ONE 5.12 : e15573 (2010).
Whelan, S.A., et al., "Mass Spectrometry (LC-MS/MS) Identified Proteomic Biosignatures of Breast Cancer in Proximal Fluid." J. Proteome Res. (2012); 11(10): 5034-5045.
U.S. Appl. No. 14/879,982, Office Action dated May 22, 2017, 15 pages.
Braidotti, et al., "DMBT1 expression is down-regulated in breast cancer." BMC Cancer (2004); 4: 46, 9 pages.
Bundred, et al., "Is apocrine differentiation in breast carcinoma of prognostic significance?" British Journal of Cancer (1990); 62: 113-117.
Catanzaro, et al., "Oncogenic Ras induces inflammatory cytokine production by upregulating the squamous cell carcinoma antigens SerpinB3/B4." Nature Communications (2014); Article No. 3729 (2014), 12 pages.
Do, et al., "Associations between the Expression of Mucins (MUC1, MUC2, MUC5AC, and MUC6) and Clinicopathologic Parameters of Human Breast Ductal Carcinomas." J Breast Cancer (2013); 16(2) 152-158.
Freije, et al., "Human Zn-$\alpha_2$-glycoprotein cDNA cloning and expression analysis in benign and malignant breast tissues." FEBS Letters (1991); 290(1-2): 247-249.
Opstal-Van Winden, et al., "Searching for early breast cancer biomarkers by serum protein profiling of pre-diagnostic serum; a nested case-control study." BMC Cancer (2011); 11: 381, 8 pages.
Storr et al., "Calpain system protein expression in basal-like and triple-negative invasive breast cancer." Annals of Oncology (2012); 23(9): 2289-2296.
Xue, et al., "Zinc-$\alpha$-2-Glycoprotein: A Candidate Biomarker for Colon Cancer Diagnosis in Chinese Population." Int. J. Mol. Sci. (2015), 16(1): 691-703.
U.S. Appl. No. 14/879,982, Office Action dated Nov. 8, 2017, 13 pages.
Plavina et al., "Increased Plasma Concentrations of Cytoskeletal and Ca2+Binding Proteins and Their Peptides in Psoriasis Patients," Clinical Chemistry, vol. 54, No. 11, Nov. 1, 2008 (Nov. 1, 2008), pp. 1805-1814.
U.S. Appl. No. 14/879,982, Office Action dated Oct. 4, 2018, 17 pages.

* cited by examiner

SEQUENCE LISTING

```
<160> NUMBER OF SEQ ID NOS: 335

<210> SEQ ID NO 1
<211> LENGTH: 9
<212> TYPE: PRT
<213> ORGANISM: Homo sapiens

<400> SEQUENCE: 1

Ala Glu Phe Gln Asp Ala Leu Glu Lys
1               5

<210> SEQ ID NO 2
<211> LENGTH: 9
<212> TYPE: PRT
<213> ORGANISM: Homo sapiens

<400> SEQUENCE: 2

Asp His Ala Val Asp Leu Ile Gln Lys
1               5
```

```
<210> SEQ ID NO 3
<211> LENGTH: 9
<212> TYPE: PRT
<213> ORGANISM: Homo sapiens

<400> SEQUENCE: 3

Asp Lys Gly Gln Ala Gly Leu Gln Arg
1               5

<210> SEQ ID NO 4
<211> LENGTH: 13
<212> TYPE: PRT
<213> ORGANISM: Homo sapiens

<400> SEQUENCE: 4

Glu Met Ser Gly Ser Pro Ala Ser Gly Ile Pro Val Lys
1               5                   10

<210> SEQ ID NO 5
<211> LENGTH: 7
<212> TYPE: PRT
<213> ORGANISM: Homo sapiens

<400> SEQUENCE: 5

Phe Ala Cys Tyr Tyr Pro Arg
1               5

<210> SEQ ID NO 6
<211> LENGTH: 10
<212> TYPE: PRT
<213> ORGANISM: Homo sapiens

<400> SEQUENCE: 6

Phe Gly Leu Leu Asp Glu Asp Gly Lys Lys
1               5                   10

<210> SEQ ID NO 7
<211> LENGTH: 17
<212> TYPE: PRT
<213> ORGANISM: Homo sapiens

<400> SEQUENCE: 7

Gly His Leu Phe Leu Gln Thr Asp Gln Pro Ile Tyr Asn Pro Gly Gln
1               5                   10                  15

Arg

<210> SEQ ID NO 8
<211> LENGTH: 11
<212> TYPE: PRT
<213> ORGANISM: Homo sapiens

<400> SEQUENCE: 8

Gly Leu Cys Val Ala Thr Pro Val Gln Leu Arg
1               5                   10

<210> SEQ ID NO 9
<211> LENGTH: 9
<212> TYPE: PRT
<213> ORGANISM: Homo sapiens

<400> SEQUENCE: 9

Gly Ile Gln Asp Glu Asp Gly Tyr Arg
1               5
```

```
<210> SEQ ID NO 10
<211> LENGTH: 14
<212> TYPE: PRT
<213> ORGANISM: Homo sapiens

<400> SEQUENCE: 10

Gly Pro Glu Val Gln Leu Val Ala His Ser Pro Trp Leu Lys
1               5                   10

<210> SEQ ID NO 11
<211> LENGTH: 13
<212> TYPE: PRT
<213> ORGANISM: Homo sapiens

<400> SEQUENCE: 11

Gly Ser Phe Glu Phe Pro Val Gly Asp Ala Val Ser Lys
1               5                   10

<210> SEQ ID NO 12
<211> LENGTH: 15
<212> TYPE: PRT
<213> ORGANISM: Homo sapiens

<400> SEQUENCE: 12

His Leu Val Pro Gly Ala Pro Phe Leu Leu Gln Ala Leu Val Arg
1               5                   10                  15

<210> SEQ ID NO 13
<211> LENGTH: 17
<212> TYPE: PRT
<213> ORGANISM: Homo sapiens

<400> SEQUENCE: 13

Leu Leu Ala Thr Leu Cys Ser Ala Glu Val Cys Gln Cys Ala Glu Gly
1               5                   10                  15

Lys

<210> SEQ ID NO 14
<211> LENGTH: 12
<212> TYPE: PRT
<213> ORGANISM: Homo sapiens

<400> SEQUENCE: 14

Leu Asn Met Gly Ile Thr Asp Leu Gln Gly Leu Arg
1               5                   10

<210> SEQ ID NO 15
<211> LENGTH: 9
<212> TYPE: PRT
<213> ORGANISM: Homo sapiens

<400> SEQUENCE: 15

Ile Thr Gln Val Leu His Phe Thr Lys
1               5

<210> SEQ ID NO 16
<211> LENGTH: 6
<212> TYPE: PRT
<213> ORGANISM: Homo sapiens

<400> SEQUENCE: 16

Asn Val Asn Phe Gln Lys
1               5
```

```
<210> SEQ ID NO 17
<211> LENGTH: 9
<212> TYPE: PRT
<213> ORGANISM: Homo sapiens

<400> SEQUENCE: 17

Gln Gly Ser Phe Gln Gly Gly Phe Arg
1               5

<210> SEQ ID NO 18
<211> LENGTH: 9
<212> TYPE: PRT
<213> ORGANISM: Homo sapiens

<400> SEQUENCE: 18

Ser Cys Gly Leu His Gln Leu Leu Arg
1               5

<210> SEQ ID NO 19
<211> LENGTH: 9
<212> TYPE: PRT
<213> ORGANISM: Homo sapiens

<400> SEQUENCE: 19

Val Asp Phe Thr Leu Ser Ser Glu Arg
1               5

<210> SEQ ID NO 20
<211> LENGTH: 11
<212> TYPE: PRT
<213> ORGANISM: Homo sapiens

<400> SEQUENCE: 20

Val Asp Val Gln Ala Gly Ala Cys Glu Gly Lys
1               5                   10

<210> SEQ ID NO 21
<211> LENGTH: 7
<212> TYPE: PRT
<213> ORGANISM: Homo sapiens

<400> SEQUENCE: 21

Val Phe Ala Leu Asp Gln Lys
1               5

<210> SEQ ID NO 22
<211> LENGTH: 10
<212> TYPE: PRT
<213> ORGANISM: Homo sapiens

<400> SEQUENCE: 22

Val Gly Asp Thr Ile Asn Ile Asn Ile Arg
1               5                   10

<210> SEQ ID NO 23
<211> LENGTH: 15
<212> TYPE: PRT
<213> ORGANISM: Homo sapiens

<400> SEQUENCE: 23

Val Leu Ser Leu Ala Gln Glu Gln Val Gly Gly Ser Pro Glu Lys
1               5                   10                  15
```

<210> SEQ ID NO 24
<211> LENGTH: 26
<212> TYPE: PRT
<213> ORGANISM: Homo sapiens

<400> SEQUENCE: 24

```
Val Thr Ala Ser Asp Pro Leu Asp Thr Leu Gly Ser Glu Gly Ala Leu
 1               5                  10                  15
Ser Pro Gly Gly Val Ala Ser Leu Leu Arg
            20                  25
```

<210> SEQ ID NO 25
<211> LENGTH: 16
<212> TYPE: PRT
<213> ORGANISM: Homo sapiens

<400> SEQUENCE: 25

```
Tyr Leu Asp Lys Thr Glu Gln Trp Ser Thr Leu Pro Pro Glu Thr Lys
 1               5                  10                  15
```

<210> SEQ ID NO 26
<211> LENGTH: 1744
<212> TYPE: PRT
<213> ORGANISM: Homo sapiens

<400> SEQUENCE: 26

```
Met Arg Leu Leu Trp Gly Leu Ile Trp Ala Ser Ser Phe Phe Thr Leu
 1               5                  10                  15
Ser Leu Gln Lys Pro Arg Leu Leu Leu Phe Ser Pro Ser Val Val His
            20                  25                  30
Leu Gly Val Pro Leu Ser Val Gly Val Gln Leu Gln Asp Val Pro Arg
        35                  40                  45
Gly Gln Val Val Lys Gly Ser Val Phe Leu Arg Asn Pro Ser Arg Asn
    50                  55                  60
Asn Val Pro Cys Ser Pro Lys Val Asp Phe Thr Leu Ser Ser Glu Arg
65                  70                  75                  80
Asp Phe Ala Leu Leu Ser Leu Gln Val Pro Leu Lys Asp Ala Lys Ser
                85                  90                  95
Cys Gly Leu His Gln Leu Leu Arg Gly Pro Glu Val Gln Leu Val Ala
            100                 105                 110
His Ser Pro Trp Leu Lys Asp Ser Leu Ser Arg Thr Thr Asn Ile Gln
        115                 120                 125
Gly Ile Asn Leu Leu Phe Ser Ser Arg Arg Gly His Leu Phe Leu Gln
    130                 135                 140
Thr Asp Gln Pro Ile Tyr Asn Pro Gly Gln Arg Val Arg Tyr Arg Val
145                 150                 155                 160
Phe Ala Leu Asp Gln Lys Met Arg Pro Ser Thr Asp Thr Ile Thr Val
                165                 170                 175
Met Val Glu Asn Ser His Gly Leu Arg Val Arg Lys Lys Glu Val Tyr
            180                 185                 190
Met Pro Ser Ser Ile Phe Gln Asp Asp Phe Val Ile Pro Asp Ile Ser
        195                 200                 205
Glu Pro Gly Thr Trp Lys Ile Ser Ala Arg Phe Ser Asp Gly Leu Glu
    210                 215                 220
Ser Asn Ser Ser Thr Gln Phe Glu Val Lys Lys Tyr Val Leu Pro Asn
225                 230                 235                 240
Phe Glu Val Lys Ile Thr Pro Gly Lys Pro Tyr Ile Leu Thr Val Pro
                245                 250                 255
```

-continued

Gly His Leu Asp Glu Met Gln Leu Asp Ile Gln Ala Arg Tyr Ile Tyr
                260                 265                 270

Gly Lys Pro Val Gln Gly Val Ala Tyr Val Arg Phe Gly Leu Leu Asp
            275                 280                 285

Glu Asp Gly Lys Lys Thr Phe Phe Arg Gly Leu Glu Ser Gln Thr Lys
        290                 295                 300

Leu Val Asn Gly Gln Ser His Ile Ser Leu Ser Lys Ala Glu Phe Gln
305                 310                 315                 320

Asp Ala Leu Glu Lys Leu Asn Met Gly Ile Thr Asp Leu Gln Gly Leu
                325                 330                 335

Arg Leu Tyr Val Ala Ala Ile Ile Glu Ser Pro Gly Gly Glu Met
                340                 345                 350

Glu Glu Ala Glu Leu Thr Ser Trp Tyr Phe Val Ser Ser Pro Phe Ser
            355                 360                 365

Leu Asp Leu Ser Lys Thr Lys Arg His Leu Val Pro Gly Ala Pro Phe
        370                 375                 380

Leu Leu Gln Ala Leu Val Arg Glu Met Ser Gly Ser Pro Ala Ser Gly
385                 390                 395                 400

Ile Pro Val Lys Val Ser Ala Thr Val Ser Pro Gly Ser Val Pro
                405                 410                 415

Glu Val Gln Asp Ile Gln Gln Asn Thr Asp Gly Ser Gly Gln Val Ser
            420                 425                 430

Ile Pro Ile Ile Ile Pro Gln Thr Ile Ser Glu Leu Gln Leu Ser Val
        435                 440                 445

Ser Ala Gly Ser Pro His Pro Ala Ile Ala Arg Leu Thr Val Ala Ala
450                 455                 460

Pro Pro Ser Gly Gly Pro Gly Phe Leu Ser Ile Glu Arg Pro Asp Ser
465                 470                 475                 480

Arg Pro Pro Arg Val Gly Asp Thr Leu Asn Leu Asn Leu Arg Ala Val
                485                 490                 495

Gly Ser Gly Ala Thr Phe Ser His Tyr Tyr Tyr Met Ile Leu Ser Arg
            500                 505                 510

Gly Gln Ile Val Phe Met Asn Arg Glu Pro Lys Arg Thr Leu Thr Ser
        515                 520                 525

Val Ser Val Phe Val Asp His His Leu Ala Pro Ser Phe Tyr Phe Val
530                 535                 540

Ala Phe Tyr Tyr His Gly Asp His Pro Val Ala Asn Ser Leu Arg Val
545                 550                 555                 560

Asp Val Gln Ala Gly Ala Cys Glu Gly Lys Leu Glu Leu Ser Val Asp
                565                 570                 575

Gly Ala Lys Gln Tyr Arg Asn Gly Glu Ser Val Lys Leu His Leu Glu
            580                 585                 590

Thr Asp Ser Leu Ala Leu Val Ala Leu Gly Ala Leu Asp Thr Ala Leu
        595                 600                 605

Tyr Ala Ala Gly Ser Lys Ser His Lys Pro Leu Asn Met Gly Lys Val
        610                 615                 620

Phe Glu Ala Met Asn Ser Tyr Asp Leu Gly Cys Gly Pro Gly Gly Gly
625                 630                 635                 640

Asp Ser Ala Leu Gln Val Phe Gln Ala Ala Gly Leu Ala Phe Ser Asp
                645                 650                 655

Gly Asp Gln Trp Thr Leu Ser Arg Lys Arg Leu Ser Cys Pro Lys Glu
            660                 665                 670

-continued

```
Lys Thr Thr Arg Lys Lys Arg Asn Val Asn Phe Gln Lys Ala Ile Asn
            675                 680                 685

Glu Lys Leu Gly Gln Tyr Ala Ser Pro Thr Ala Lys Arg Cys Cys Gln
    690                 695                 700

Asp Gly Val Thr Arg Leu Pro Met Met Arg Ser Cys Glu Gln Arg Ala
705                 710                 715                 720

Ala Arg Val Gln Gln Pro Asp Cys Arg Glu Pro Phe Leu Ser Cys Cys
                725                 730                 735

Gln Phe Ala Glu Ser Leu Arg Lys Lys Ser Arg Asp Lys Gly Gln Ala
            740                 745                 750

Gly Leu Gln Arg Ala Leu Glu Ile Leu Gln Glu Glu Asp Leu Ile Asp
        755                 760                 765

Glu Asp Asp Ile Pro Val Arg Ser Phe Phe Pro Glu Asn Trp Leu Trp
770                 775                 780

Arg Val Glu Thr Val Asp Arg Phe Gln Ile Leu Thr Leu Trp Leu Pro
785                 790                 795                 800

Asp Ser Leu Thr Thr Trp Glu Ile His Gly Leu Ser Leu Ser Lys Thr
                805                 810                 815

Lys Gly Leu Cys Val Ala Thr Pro Val Gln Leu Arg Val Phe Arg Glu
            820                 825                 830

Phe His Leu His Leu Arg Leu Pro Met Ser Val Arg Arg Phe Glu Gln
        835                 840                 845

Leu Glu Leu Arg Pro Val Leu Tyr Asn Tyr Leu Asp Lys Asn Leu Thr
    850                 855                 860

Val Ser Val His Val Ser Pro Val Glu Gly Leu Cys Leu Ala Gly Gly
865                 870                 875                 880

Gly Gly Leu Ala Gln Gln Val Leu Val Pro Ala Gly Ser Ala Arg Pro
                885                 890                 895

Val Ala Phe Ser Val Val Pro Thr Ala Ala Ala Val Ser Leu Lys
            900                 905                 910

Val Val Ala Arg Gly Ser Phe Glu Phe Pro Val Gly Asp Ala Val Ser
        915                 920                 925

Lys Val Leu Gln Ile Glu Lys Glu Gly Ala Ile His Arg Glu Glu Leu
    930                 935                 940

Val Tyr Glu Leu Asn Pro Leu Asp His Arg Gly Arg Thr Leu Glu Ile
945                 950                 955                 960

Pro Gly Asn Ser Asp Pro Asn Met Ile Pro Asp Gly Asp Phe Asn Ser
                965                 970                 975

Tyr Val Arg Val Thr Ala Ser Asp Pro Leu Asp Thr Leu Gly Ser Glu
            980                 985                 990

Gly Ala Leu Ser Pro Gly Gly Val Ala Ser Leu Leu Arg Leu Pro Arg
        995                 1000                1005

Gly Cys Gly Glu Gln Thr Met Ile Tyr Leu Ala Pro Thr Leu Ala
    1010                1015                1020

Ala Ser Arg Tyr Leu Asp Lys Thr Glu Gln Trp Ser Thr Leu Pro
    1025                1030                1035

Pro Glu Thr Lys Asp His Ala Val Asp Leu Ile Gln Lys Gly Tyr
    1040                1045                1050

Met Arg Ile Gln Gln Phe Arg Lys Ala Asp Gly Ser Tyr Ala Ala
    1055                1060                1065

Trp Leu Ser Arg Asp Ser Ser Thr Trp Leu Thr Ala Phe Val Leu
    1070                1075                1080

Lys Val Leu Ser Leu Ala Gln Glu Gln Val Gly Gly Ser Pro Glu
```

-continued

```
                1085                1090                1095

Lys Leu Gln Glu Thr Ser Asn Trp Leu Leu Ser Gln Gln Gln Ala
            1100                1105                1110

Asp Gly Ser Phe Gln Asp Pro Cys Pro Val Leu Asp Arg Ser Met
            1115                1120                1125

Gln Gly Gly Leu Val Gly Asn Asp Glu Thr Val Ala Leu Thr Ala
            1130                1135                1140

Phe Val Thr Ile Ala Leu His His Gly Leu Ala Val Phe Gln Asp
            1145                1150                1155

Glu Gly Ala Glu Pro Leu Lys Gln Arg Val Glu Ala Ser Ile Ser
            1160                1165                1170

Lys Ala Asn Ser Phe Leu Gly Glu Lys Ala Ser Ala Gly Leu Leu
            1175                1180                1185

Gly Ala His Ala Ala Ala Ile Thr Ala Tyr Ala Leu Thr Leu Thr
            1190                1195                1200

Lys Ala Pro Val Asp Leu Leu Gly Val Ala His Asn Asn Leu Met
            1205                1210                1215

Ala Met Ala Gln Glu Thr Gly Asp Asn Leu Tyr Trp Gly Ser Val
            1220                1225                1230

Thr Gly Ser Gln Ser Asn Ala Val Ser Pro Thr Pro Ala Pro Arg
            1235                1240                1245

Asn Pro Ser Asp Pro Met Pro Gln Ala Pro Ala Leu Trp Ile Glu
            1250                1255                1260

Thr Thr Ala Tyr Ala Leu Leu His Leu Leu Leu His Glu Gly Lys
            1265                1270                1275

Ala Glu Met Ala Asp Gln Ala Ser Ala Trp Leu Thr Arg Gln Gly
            1280                1285                1290

Ser Phe Gln Gly Gly Phe Arg Ser Thr Gln Asp Thr Val Ile Ala
            1295                1300                1305

Leu Asp Ala Leu Ser Ala Tyr Trp Ile Ala Ser His Thr Thr Glu
            1310                1315                1320

Glu Arg Gly Leu Asn Val Thr Leu Ser Ser Thr Gly Arg Asn Gly
            1325                1330                1335

Phe Lys Ser His Ala Leu Gln Leu Asn Asn Arg Gln Ile Arg Gly
            1340                1345                1350

Leu Glu Glu Glu Leu Gln Phe Ser Leu Gly Ser Lys Ile Asn Val
            1355                1360                1365

Lys Val Gly Gly Asn Ser Lys Gly Thr Leu Lys Val Leu Arg Thr
            1370                1375                1380

Tyr Asn Val Leu Asp Met Lys Asn Thr Thr Cys Gln Asp Leu Gln
            1385                1390                1395

Ile Glu Val Thr Val Lys Gly His Val Glu Tyr Thr Met Glu Ala
            1400                1405                1410

Asn Glu Asp Tyr Glu Asp Tyr Glu Tyr Asp Glu Leu Pro Ala Lys
            1415                1420                1425

Asp Asp Pro Asp Ala Pro Leu Gln Pro Val Thr Pro Leu Gln Leu
            1430                1435                1440

Phe Glu Gly Arg Arg Asn Arg Arg Arg Glu Ala Pro Lys Val
            1445                1450                1455

Val Glu Glu Gln Glu Ser Arg Val His Tyr Thr Val Cys Ile Trp
            1460                1465                1470

Arg Asn Gly Lys Val Gly Leu Ser Gly Met Ala Ile Ala Asp Val
            1475                1480                1485
```

```
Thr Leu Leu Ser Gly Phe His Ala Leu Arg Ala Asp Leu Glu Lys
    1490                1495                1500

Leu Thr Ser Leu Ser Asp Arg Tyr Val Ser His Phe Glu Thr Glu
    1505                1510                1515

Gly Pro His Val Leu Leu Tyr Phe Asp Ser Val Pro Thr Ser Arg
    1520                1525                1530

Glu Cys Val Gly Phe Glu Ala Val Gln Glu Val Pro Val Gly Leu
    1535                1540                1545

Val Gln Pro Ala Ser Ala Thr Leu Tyr Asp Tyr Tyr Asn Pro Glu
    1550                1555                1560

Arg Arg Cys Ser Val Phe Tyr Gly Ala Pro Ser Lys Ser Arg Leu
    1565                1570                1575

Leu Ala Thr Leu Cys Ser Ala Glu Val Cys Gln Cys Ala Glu Gly
    1580                1585                1590

Lys Cys Pro Arg Gln Arg Arg Ala Leu Glu Arg Gly Leu Gln Asp
    1595                1600                1605

Glu Asp Gly Tyr Arg Met Lys Phe Ala Cys Tyr Tyr Pro Arg Val
    1610                1615                1620

Glu Tyr Gly Phe Gln Val Lys Val Leu Arg Glu Asp Ser Arg Ala
    1625                1630                1635

Ala Phe Arg Leu Phe Glu Thr Lys Ile Thr Gln Val Leu His Phe
    1640                1645                1650

Thr Lys Asp Val Lys Ala Ala Asn Gln Met Arg Asn Phe Leu
    1655                1660                1665

Val Arg Ala Ser Cys Arg Leu Arg Leu Glu Pro Gly Lys Glu Tyr
    1670                1675                1680

Leu Ile Met Gly Leu Asp Gly Ala Thr Tyr Asp Leu Glu Gly His
    1685                1690                1695

Pro Gln Tyr Leu Leu Asp Ser Asn Ser Trp Ile Glu Glu Met Pro
    1700                1705                1710

Ser Glu Arg Leu Cys Arg Ser Thr Arg Gln Arg Ala Ala Cys Ala
    1715                1720                1725

Gln Leu Asn Asp Phe Leu Gln Glu Tyr Gly Thr Gln Gly Cys Gln
    1730                1735                1740

Val

<210> SEQ ID NO 27
<211> LENGTH: 12
<212> TYPE: PRT
<213> ORGANISM: Homo sapiens

<400> SEQUENCE: 27

Tyr Lys Glu Glu Asn Asp Asp Phe Ala Ser Phe Arg
1               5                   10

<210> SEQ ID NO 28
<211> LENGTH: 16
<212> TYPE: PRT
<213> ORGANISM: Homo sapiens

<400> SEQUENCE: 28

Ala Asp Leu Phe Tyr Asp Val Glu Ala Leu Asp Leu Glu Ser Pro Lys
1               5                   10                  15

<210> SEQ ID NO 29
<211> LENGTH: 525
```

<212> TYPE: PRT
<213> ORGANISM: Homo sapiens

<400> SEQUENCE: 29

```
Met Lys Ala Leu Ile Ala Ala Leu Leu Ile Thr Leu Gln Tyr Ser
1               5                   10                  15

Cys Ala Val Ser Pro Thr Asp Cys Ser Ala Val Glu Pro Glu Ala Glu
            20                  25                  30

Lys Ala Leu Asp Leu Ile Asn Lys Arg Arg Asp Gly Tyr Leu Phe
        35                  40                  45

Gln Leu Leu Arg Ile Ala Asp Ala His Leu Asp Arg Val Glu Asn Thr
    50                  55                  60

Thr Val Tyr Tyr Leu Val Leu Asp Val Gln Glu Ser Asp Cys Ser Val
65                  70                  75                  80

Leu Ser Arg Lys Tyr Trp Asn Asp Cys Glu Pro Pro Asp Ser Arg Arg
                85                  90                  95

Pro Ser Glu Ile Val Ile Gly Gln Cys Lys Val Ile Ala Thr Arg His
            100                 105                 110

Ser His Glu Ser Gln Asp Leu Arg Val Ile Asp Phe Asn Cys Thr Thr
        115                 120                 125

Ser Ser Val Ser Ser Ala Leu Ala Asn Thr Lys Asp Ser Pro Val Leu
    130                 135                 140

Ile Asp Phe Phe Glu Asp Thr Glu Arg Tyr Arg Lys Gln Ala Asn Lys
145                 150                 155                 160

Ala Leu Glu Lys Tyr Lys Glu Glu Asn Asp Asp Phe Ala Ser Phe Arg
                165                 170                 175

Val Asp Arg Ile Glu Arg Val Ala Arg Val Arg Gly Gly Glu Gly Thr
            180                 185                 190

Gly Tyr Phe Val Asp Phe Ser Val Arg Asn Cys Pro Arg His His Phe
        195                 200                 205

Pro Arg His Pro Asn Val Phe Gly Phe Cys Arg Ala Asp Leu Phe Tyr
    210                 215                 220

Asp Val Glu Ala Leu Asp Leu Glu Ser Pro Lys Asn Leu Val Ile Asn
225                 230                 235                 240

Cys Glu Val Phe Asp Pro Gln Glu His Glu Asn Ile Asn Gly Val Pro
                245                 250                 255

Pro His Leu Gly His Pro Phe His Trp Gly Gly His Glu Arg Ser Ser
            260                 265                 270

Thr Thr Lys Pro Pro Phe Lys Pro His Gly Ser Arg Asp His His His
        275                 280                 285

Pro His Lys Pro His Glu His Gly Pro Pro Pro Pro Asp Glu Arg
    290                 295                 300

Asp His Ser His Gly Pro Pro Leu Pro Gln Gly Pro Pro Leu Leu
305                 310                 315                 320

Pro Met Ser Cys Ser Ser Cys Gln His Ala Thr Phe Gly Thr Asn Gly
                325                 330                 335

Ala Gln Arg His Ser His Asn Asn Asn Ser Ser Asp Leu His Pro His
            340                 345                 350

Lys His His Ser His Glu Gln His Pro His Gly His Pro His Ala
        355                 360                 365

His His Pro His Glu His Asp Thr His Arg Gln His Pro His Gly His
    370                 375                 380

His Pro His Gly His His Pro His Gly His His Pro His Gly His His
385                 390                 395                 400
```

```
Pro His Gly His His Pro His Cys His Asp Phe Gln Asp Tyr Gly Pro
            405                 410                 415

Cys Asp Pro Pro His Asn Gln Gly His Cys Cys His Gly His Gly
            420                 425                 430

Pro Pro Pro Gly His Leu Arg Arg Gly Pro Gly Lys Gly Pro Arg
            435                 440                 445

Pro Phe His Cys Arg Gln Ile Gly Ser Val Tyr Arg Leu Pro Leu
            450                 455                 460

Arg Lys Gly Glu Val Leu Pro Leu Pro Glu Ala Asn Phe Pro Ser Phe
465                 470                 475                 480

Pro Leu Pro His His Lys His Pro Leu Lys Pro Asp Asn Gln Pro Phe
            485                 490                 495

Pro Gln Ser Val Ser Glu Ser Cys Pro Gly Lys Phe Lys Ser Gly Phe
            500                 505                 510

Pro Gln Val Ser Met Phe Phe Thr His Thr Phe Pro Lys
            515                 520                 525

<210> SEQ ID NO 30
<211> LENGTH: 11
<212> TYPE: PRT
<213> ORGANISM: Homo sapiens

<400> SEQUENCE: 30

Glu Gln Gln Ala Leu Gln Thr Val Cys Leu Lys
1               5                   10

<210> SEQ ID NO 31
<211> LENGTH: 12
<212> TYPE: PRT
<213> ORGANISM: Homo sapiens

<400> SEQUENCE: 31

Thr Phe His Glu Ala Ser Glu Asp Cys Ile Ser Arg
1               5                   10

<210> SEQ ID NO 32
<211> LENGTH: 202
<212> TYPE: PRT
<213> ORGANISM: Homo sapiens

<400> SEQUENCE: 32

Met Glu Leu Trp Gly Ala Tyr Leu Leu Leu Cys Leu Phe Ser Leu Leu
1               5                   10                  15

Thr Gln Val Thr Thr Glu Pro Pro Thr Gln Lys Pro Lys Lys Ile Val
                20                  25                  30

Asn Ala Lys Lys Asp Val Val Asn Thr Lys Met Phe Glu Glu Leu Lys
            35                  40                  45

Ser Arg Leu Asp Thr Leu Ala Gln Glu Val Ala Leu Leu Lys Glu Gln
        50                  55                  60

Gln Ala Leu Gln Thr Val Cys Leu Lys Gly Thr Lys Val His Met Lys
65                  70                  75                  80

Cys Phe Leu Ala Phe Thr Gln Thr Lys Thr Phe His Glu Ala Ser Glu
                85                  90                  95

Asp Cys Ile Ser Arg Gly Gly Thr Leu Gly Thr Pro Gln Thr Gly Ser
            100                 105                 110

Glu Asn Asp Ala Leu Tyr Glu Tyr Leu Arg Gln Ser Val Gly Asn Glu
        115                 120                 125
```

```
Ala Glu Ile Trp Leu Gly Leu Asn Asp Met Ala Ala Glu Gly Thr Trp
    130                 135                 140

Val Asp Met Thr Gly Ala Arg Ile Ala Tyr Lys Asn Trp Glu Thr Glu
145                 150                 155                 160

Ile Thr Ala Gln Pro Asp Gly Gly Lys Thr Glu Asn Cys Ala Val Leu
                165                 170                 175

Ser Gly Ala Ala Asn Gly Lys Trp Phe Asp Lys Arg Cys Arg Asp Gln
            180                 185                 190

Leu Pro Tyr Ile Cys Gln Phe Gly Ile Val
            195                 200
```

<210> SEQ ID NO 33
<211> LENGTH: 13
<212> TYPE: PRT
<213> ORGANISM: Homo sapiens

<400> SEQUENCE: 33

```
Glu Asn Phe Pro Asp Thr Leu Asn Cys Ala Glu Val Lys
1               5                   10
```

<210> SEQ ID NO 34
<211> LENGTH: 260
<212> TYPE: PRT
<213> ORGANISM: Homo sapiens

<400> SEQUENCE: 34

```
Met Gly Arg Pro Arg Pro Arg Ala Ala Lys Thr Trp Met Phe Leu Leu
1               5                   10                  15

Leu Leu Gly Gly Ala Trp Ala Gly His Ser Arg Ala Gln Glu Asp Lys
            20                  25                  30

Val Leu Gly Gly His Glu Cys Gln Pro His Ser Gln Pro Trp Gln Ala
        35                  40                  45

Ala Leu Phe Gln Gly Gln Gln Leu Leu Cys Gly Gly Val Leu Val Gly
    50                  55                  60

Gly Asn Trp Val Leu Thr Ala Ala His Cys Lys Lys Pro Lys Tyr Thr
65                  70                  75                  80

Val Arg Leu Gly Asp His Ser Leu Gln Asn Lys Asp Gly Pro Glu Gln
                85                  90                  95

Glu Ile Pro Val Val Gln Ser Ile Pro His Pro Cys Tyr Asn Ser Ser
            100                 105                 110

Asp Val Glu Asp His Asn His Asp Leu Met Leu Leu Gln Leu Arg Asp
        115                 120                 125

Gln Ala Ser Leu Gly Ser Lys Val Lys Pro Ile Ser Leu Ala Asp His
    130                 135                 140

Cys Thr Gln Pro Gly Gln Lys Cys Thr Val Ser Gly Trp Gly Thr Val
145                 150                 155                 160

Thr Ser Pro Arg Glu Asn Phe Pro Asp Thr Leu Asn Cys Ala Glu Val
                165                 170                 175

Lys Ile Phe Pro Gln Lys Lys Cys Glu Asp Ala Tyr Pro Gly Gln Ile
            180                 185                 190

Thr Asp Gly Met Val Cys Ala Gly Ser Ser Lys Gly Ala Asp Thr Cys
        195                 200                 205

Gln Gly Asp Ser Gly Gly Pro Leu Val Cys Asp Gly Ala Leu Gln Gly
    210                 215                 220

Ile Thr Ser Trp Gly Ser Asp Pro Cys Gly Arg Ser Lys Pro Gly
225                 230                 235                 240
```

```
Val Tyr Thr Asn Ile Cys Arg Tyr Leu Asp Trp Ile Lys Lys Ile Ile
                245                 250                 255
Gly Ser Lys Gly
            260

<210> SEQ ID NO 35
<211> LENGTH: 17
<212> TYPE: PRT
<213> ORGANISM: Homo sapiens

<400> SEQUENCE: 35

Ala Ile Asp Glu Asp Cys Ser Gln Tyr Glu Pro Ile Pro Gly Ser Gln
1               5                   10                  15
Lys

<210> SEQ ID NO 36
<211> LENGTH: 17
<212> TYPE: PRT
<213> ORGANISM: Homo sapiens

<400> SEQUENCE: 36

Leu Gly Ser Leu Gly Ala Ala Cys Glu Gln Thr Gln Thr Glu Gly Ala
1               5                   10                  15
Lys

<210> SEQ ID NO 37
<211> LENGTH: 11
<212> TYPE: PRT
<213> ORGANISM: Homo sapiens

<400> SEQUENCE: 37

Gln Ala Gln Cys Gly Gln Asp Phe Gln Cys Lys
1               5                   10

<210> SEQ ID NO 38
<211> LENGTH: 584
<212> TYPE: PRT
<213> ORGANISM: Homo sapiens

<400> SEQUENCE: 38

Met Phe Ala Val Val Phe Phe Ile Leu Ser Leu Met Thr Cys Gln Pro
1               5                   10                  15

Gly Val Thr Ala Gln Glu Lys Val Asn Gln Arg Val Arg Arg Ala Ala
                20                  25                  30

Thr Pro Ala Ala Val Thr Cys Gln Leu Ser Asn Trp Ser Glu Trp Thr
            35                  40                  45

Asp Cys Phe Pro Cys Gln Asp Lys Lys Tyr Arg His Arg Ser Leu Leu
        50                  55                  60

Gln Pro Asn Lys Phe Gly Gly Thr Ile Cys Ser Gly Asp Ile Trp Asp
65                  70                  75                  80

Gln Ala Ser Cys Ser Ser Ser Thr Thr Cys Val Arg Gln Ala Gln Cys
                85                  90                  95

Gly Gln Asp Phe Gln Cys Lys Glu Thr Gly Arg Cys Leu Lys Arg His
                100                 105                 110

Leu Val Cys Asn Gly Asp Gln Asp Cys Leu Asp Gly Ser Asp Glu Asp
            115                 120                 125

Asp Cys Glu Asp Val Arg Ala Ile Asp Glu Asp Cys Ser Gln Tyr Glu
        130                 135                 140

Pro Ile Pro Gly Ser Gln Lys Ala Ala Leu Gly Tyr Asn Ile Leu Thr
```

-continued

```
        145                 150                 155                 160
        Gln Glu Asp Ala Gln Ser Val Tyr Asp Ala Ser Tyr Tyr Gly Gly Gln
                        165                 170                 175
        Cys Glu Thr Val Tyr Asn Gly Glu Trp Arg Glu Leu Arg Tyr Asp Ser
                        180                 185                 190
        Thr Cys Glu Arg Leu Tyr Tyr Gly Asp Glu Lys Tyr Phe Arg Lys
                    195                 200                 205
        Pro Tyr Asn Phe Leu Lys Tyr His Phe Glu Ala Leu Ala Asp Thr Gly
                    210                 215                 220
        Ile Ser Ser Glu Phe Tyr Asp Asn Ala Asn Asp Leu Leu Ser Lys Val
        225                 230                 235                 240
        Lys Lys Asp Lys Ser Asp Ser Phe Gly Val Thr Ile Gly Ile Gly Pro
                        245                 250                 255
        Ala Gly Ser Pro Leu Leu Val Gly Val Gly Val Ser His Ser Gln Asp
                    260                 265                 270
        Thr Ser Phe Leu Asn Glu Leu Asn Lys Tyr Asn Glu Lys Lys Phe Ile
                    275                 280                 285
        Phe Thr Arg Ile Phe Thr Lys Val Gln Thr Ala His Phe Lys Met Arg
                    290                 295                 300
        Lys Asp Asp Ile Met Leu Asp Glu Gly Met Leu Gln Ser Leu Met Glu
        305                 310                 315                 320
        Leu Pro Asp Gln Tyr Asn Tyr Gly Met Tyr Ala Lys Phe Ile Asn Asp
                        325                 330                 335
        Tyr Gly Thr His Tyr Ile Thr Ser Gly Ser Met Gly Gly Ile Tyr Glu
                        340                 345                 350
        Tyr Ile Leu Val Ile Asp Lys Ala Lys Met Glu Ser Leu Gly Ile Thr
                    355                 360                 365
        Ser Arg Asp Ile Thr Thr Cys Phe Gly Gly Ser Leu Gly Ile Gln Tyr
                370                 375                 380
        Glu Asp Lys Ile Asn Val Gly Gly Gly Leu Ser Gly Asp His Cys Lys
        385                 390                 395                 400
        Lys Phe Gly Gly Gly Lys Thr Glu Arg Ala Arg Lys Ala Met Ala Val
                        405                 410                 415
        Glu Asp Ile Ile Ser Arg Val Arg Gly Gly Ser Ser Gly Trp Ser Gly
                    420                 425                 430
        Gly Leu Ala Gln Asn Arg Ser Thr Ile Thr Tyr Arg Ser Trp Gly Arg
                    435                 440                 445
        Ser Leu Lys Tyr Asn Pro Val Val Ile Asp Phe Glu Met Gln Pro Ile
                    450                 455                 460
        His Glu Val Leu Arg His Thr Ser Leu Gly Pro Leu Glu Ala Lys Arg
        465                 470                 475                 480
        Gln Asn Leu Arg Arg Ala Leu Asp Gln Tyr Leu Met Glu Phe Asn Ala
                        485                 490                 495
        Cys Arg Cys Gly Pro Cys Phe Asn Asn Gly Val Pro Ile Leu Glu Gly
                    500                 505                 510
        Thr Ser Cys Arg Cys Gln Cys Arg Leu Gly Ser Leu Gly Ala Ala Cys
                    515                 520                 525
        Glu Gln Thr Gln Thr Glu Gly Ala Lys Ala Asp Gly Ser Trp Ser Cys
                530                 535                 540
        Trp Ser Ser Trp Ser Val Cys Arg Ala Gly Ile Gln Glu Arg Arg Arg
        545                 550                 555                 560
        Glu Cys Asp Asn Pro Ala Pro Gln Asn Gly Gly Ala Ser Cys Pro Gly
                        565                 570                 575
```

```
Arg Lys Val Gln Thr Gln Ala Cys
            580

<210> SEQ ID NO 39
<211> LENGTH: 10
<212> TYPE: PRT
<213> ORGANISM: Homo sapiens

<400> SEQUENCE: 39

Thr Leu Gln Cys Ala Asn Ile Gln Leu Arg
1               5                   10

<210> SEQ ID NO 40
<211> LENGTH: 11
<212> TYPE: PRT
<213> ORGANISM: Homo sapiens

<400> SEQUENCE: 40

Ile Thr Asp Asn Met Leu Cys Ala Gly Thr Lys
1               5                   10

<210> SEQ ID NO 41
<211> LENGTH: 277
<212> TYPE: PRT
<213> ORGANISM: Homo sapiens

<400> SEQUENCE: 41

Met Trp Pro Leu Ala Leu Val Ile Ala Ser Leu Thr Leu Ala Leu Ser
1               5                   10                  15

Gly Gly Val Ser Gln Glu Ser Ser Lys Val Leu Asn Thr Asn Gly Thr
            20                  25                  30

Ser Gly Phe Leu Pro Gly Gly Tyr Thr Cys Phe Pro His Ser Gln Pro
        35                  40                  45

Trp Gln Ala Ala Leu Leu Val Gln Gly Arg Leu Leu Cys Gly Gly Val
    50                  55                  60

Leu Val His Pro Lys Trp Val Leu Thr Ala Ala His Cys Leu Lys Glu
65                  70                  75                  80

Gly Leu Lys Val Tyr Leu Gly Lys His Ala Leu Gly Arg Val Glu Ala
                85                  90                  95

Gly Glu Gln Val Arg Glu Val Val His Ser Ile Pro His Pro Glu Tyr
            100                 105                 110

Arg Arg Ser Pro Thr His Leu Asn His Asp His Asp Ile Met Leu Leu
        115                 120                 125

Glu Leu Gln Ser Pro Val Gln Leu Thr Gly Tyr Ile Gln Thr Leu Pro
    130                 135                 140

Leu Ser His Asn Asn Arg Leu Thr Pro Gly Thr Thr Cys Arg Val Ser
145                 150                 155                 160

Gly Trp Gly Thr Thr Thr Ser Pro Gln Val Asn Tyr Pro Lys Thr Leu
                165                 170                 175

Gln Cys Ala Asn Ile Gln Leu Arg Ser Asp Glu Glu Cys Arg Gln Val
            180                 185                 190

Tyr Pro Gly Lys Ile Thr Asp Asn Met Leu Cys Ala Gly Thr Lys Glu
        195                 200                 205

Gly Gly Lys Asp Ser Cys Glu Gly Asp Ser Gly Gly Pro Leu Val Cys
    210                 215                 220

Asn Arg Thr Leu Tyr Gly Ile Val Ser Trp Gly Asp Phe Pro Cys Gly
225                 230                 235                 240
```

```
Gln Pro Asp Arg Pro Gly Val Tyr Thr Arg Val Ser Arg Tyr Val Leu
            245                 250                 255

Trp Ile Arg Glu Thr Ile Arg Lys Tyr Glu Thr Gln Gln Gln Lys Trp
        260                 265                 270

Leu Lys Gly Pro Gln
        275

<210> SEQ ID NO 42
<211> LENGTH: 11
<212> TYPE: PRT
<213> ORGANISM: Homo sapiens

<400> SEQUENCE: 42

Ala Ala Ser Gly Thr Gln Asn Asn Val Leu Arg
1               5                   10

<210> SEQ ID NO 43
<211> LENGTH: 11
<212> TYPE: PRT
<213> ORGANISM: Homo sapiens

<400> SEQUENCE: 43

Asp Ser Cys Thr Leu Pro Ala Ser Ala Glu Lys
1               5                   10

<210> SEQ ID NO 44
<211> LENGTH: 843
<212> TYPE: PRT
<213> ORGANISM: Homo sapiens

<400> SEQUENCE: 44

Met Lys Val Ile Ser Leu Phe Ile Leu Val Gly Phe Ile Gly Glu Phe
1               5                   10                  15

Gln Ser Phe Ser Ser Ala Ser Ser Pro Val Asn Cys Gln Trp Asp Phe
            20                  25                  30

Tyr Ala Pro Trp Ser Glu Cys Asn Gly Cys Thr Lys Thr Gln Thr Arg
        35                  40                  45

Arg Arg Ser Val Ala Val Tyr Gly Gln Tyr Gly Gly Gln Pro Cys Val
50                  55                  60

Gly Asn Ala Phe Glu Thr Gln Ser Cys Glu Pro Thr Arg Gly Cys Pro
65                  70                  75                  80

Thr Glu Glu Gly Cys Gly Glu Arg Phe Arg Cys Phe Ser Gly Gln Cys
                85                  90                  95

Ile Ser Lys Ser Leu Val Cys Asn Gly Asp Ser Asp Cys Asp Glu Asp
            100                 105                 110

Ser Ala Asp Glu Asp Arg Cys Glu Asp Ser Glu Arg Arg Pro Ser Cys
        115                 120                 125

Asp Ile Asp Lys Pro Pro Asn Ile Glu Leu Thr Gly Asn Gly Tyr
    130                 135                 140

Asn Glu Leu Thr Gly Gln Phe Arg Asn Arg Val Ile Asn Thr Lys Ser
145                 150                 155                 160

Phe Gly Gly Gln Cys Arg Lys Val Phe Ser Gly Asp Gly Lys Asp Phe
                165                 170                 175

Tyr Arg Leu Ser Gly Asn Val Leu Ser Tyr Thr Phe Gln Val Lys Ile
            180                 185                 190

Asn Asn Asp Phe Asn Tyr Glu Phe Tyr Asn Ser Thr Trp Ser Tyr Val
        195                 200                 205

Lys His Thr Ser Thr Glu His Thr Ser Ser Ser Arg Lys Arg Ser Phe
```

```
            210                 215                 220
Phe Arg Ser Ser Ser Ser Ser Arg Ser Tyr Thr Ser His Thr Asn
225                 230                 235                 240

Glu Ile His Lys Gly Lys Ser Tyr Gln Leu Leu Val Val Glu Asn Thr
                245                 250                 255

Val Glu Val Ala Gln Phe Ile Asn Asn Asn Pro Glu Phe Leu Gln Leu
                260                 265                 270

Ala Glu Pro Phe Trp Lys Glu Leu Ser His Leu Pro Ser Leu Tyr Asp
                275                 280                 285

Tyr Ser Ala Tyr Arg Arg Leu Ile Asp Gln Tyr Gly Thr His Tyr Leu
                290                 295                 300

Gln Ser Gly Ser Leu Gly Gly Glu Tyr Arg Val Leu Phe Tyr Val Asp
305                 310                 315                 320

Ser Glu Lys Leu Lys Gln Asn Asp Phe Asn Ser Val Glu Glu Lys Lys
                325                 330                 335

Cys Lys Ser Ser Gly Trp His Phe Val Val Lys Phe Ser Ser His Gly
                340                 345                 350

Cys Lys Glu Leu Glu Asn Ala Leu Lys Ala Ala Ser Gly Thr Gln Asn
                355                 360                 365

Asn Val Leu Arg Gly Glu Pro Phe Ile Arg Gly Gly Ala Gly Phe
                370                 375                 380

Ile Ser Gly Leu Ser Tyr Leu Glu Leu Asp Asn Pro Ala Gly Asn Lys
385                 390                 395                 400

Arg Arg Tyr Ser Ala Trp Ala Glu Ser Val Thr Asn Leu Pro Gln Val
                405                 410                 415

Ile Lys Gln Lys Leu Thr Pro Leu Tyr Glu Leu Val Lys Glu Val Pro
                420                 425                 430

Cys Ala Ser Val Lys Lys Leu Tyr Leu Lys Trp Ala Leu Glu Glu Tyr
                435                 440                 445

Leu Asp Glu Phe Asp Pro Cys His Cys Arg Pro Cys Gln Asn Gly Gly
                450                 455                 460

Leu Ala Thr Val Glu Gly Thr His Cys Leu Cys His Cys Lys Pro Tyr
465                 470                 475                 480

Thr Phe Gly Ala Ala Cys Glu Gln Gly Val Leu Val Gly Asn Gln Ala
                485                 490                 495

Gly Gly Val Asp Gly Gly Trp Ser Cys Trp Ser Ser Trp Ser Pro Cys
                500                 505                 510

Val Gln Gly Lys Lys Thr Arg Ser Arg Glu Cys Asn Asn Pro Pro Pro
                515                 520                 525

Ser Gly Gly Gly Arg Ser Cys Val Gly Glu Thr Thr Glu Ser Thr Gln
                530                 535                 540

Cys Glu Asp Glu Glu Leu Glu His Leu Arg Leu Leu Glu Pro His Cys
545                 550                 555                 560

Phe Pro Leu Ser Leu Val Pro Thr Glu Phe Cys Pro Ser Pro Pro Ala
                565                 570                 575

Leu Lys Asp Gly Phe Val Gln Asp Glu Gly Thr Met Phe Pro Val Gly
                580                 585                 590

Lys Asn Val Val Tyr Thr Cys Asn Glu Gly Tyr Ser Leu Ile Gly Asn
                595                 600                 605

Pro Val Ala Arg Cys Gly Glu Asp Leu Arg Trp Leu Val Gly Glu Met
                610                 615                 620

His Cys Gln Lys Ile Ala Cys Val Leu Pro Val Leu Met Asp Gly Ile
625                 630                 635                 640
```

Gln Ser His Pro Gln Lys Pro Phe Tyr Thr Val Gly Glu Lys Val Thr
            645                 650                 655

Val Ser Cys Ser Gly Gly Met Ser Leu Glu Gly Pro Ser Ala Phe Leu
        660                 665                 670

Cys Gly Ser Ser Leu Lys Trp Ser Pro Glu Met Lys Asn Ala Arg Cys
            675                 680                 685

Val Gln Lys Glu Asn Pro Leu Thr Gln Ala Val Pro Lys Cys Gln Arg
    690                 695                 700

Trp Glu Lys Leu Gln Asn Ser Arg Cys Val Cys Lys Met Pro Tyr Glu
705                 710                 715                 720

Cys Gly Pro Ser Leu Asp Val Cys Ala Gln Asp Glu Arg Ser Lys Arg
                725                 730                 735

Ile Leu Pro Leu Thr Val Cys Lys Met His Val Leu His Cys Gln Gly
            740                 745                 750

Arg Asn Tyr Thr Leu Thr Gly Arg Asp Ser Cys Thr Leu Pro Ala Ser
    755                 760                 765

Ala Glu Lys Ala Cys Gly Ala Cys Pro Leu Trp Gly Lys Cys Asp Ala
770                 775                 780

Glu Ser Ser Lys Cys Val Cys Arg Glu Ala Ser Glu Cys Glu Glu Glu
785                 790                 795                 800

Gly Phe Ser Ile Cys Val Glu Val Asn Gly Lys Glu Gln Thr Met Ser
                805                 810                 815

Glu Cys Glu Ala Gly Ala Leu Arg Cys Arg Gly Gln Ser Ile Ser Val
                820                 825                 830

Thr Ser Ile Arg Pro Cys Ala Ala Glu Thr Gln
            835                 840

<210> SEQ ID NO 45
<211> LENGTH: 16
<212> TYPE: PRT
<213> ORGANISM: Homo sapiens

<400> SEQUENCE: 45

Ser Ser Ser Gly Thr Pro Asp Leu Pro Val Leu Leu Thr Asp Leu Lys
1               5                   10                  15

<210> SEQ ID NO 46
<211> LENGTH: 24
<212> TYPE: PRT
<213> ORGANISM: Homo sapiens

<400> SEQUENCE: 46

Tyr Ile Leu Gly Asn Pro Leu Thr Pro Gly Val Thr Gln Gly Pro Gln
1               5                   10                  15

Ile Asp Lys Glu Gln Tyr Asp Lys
            20

<210> SEQ ID NO 47
<211> LENGTH: 501
<212> TYPE: PRT
<213> ORGANISM: Homo sapiens

<400> SEQUENCE: 47

Met Ser Ser Ser Gly Thr Pro Asp Leu Pro Val Leu Leu Thr Asp Leu
1               5                   10                  15

Lys Ile Gln Tyr Thr Lys Ile Phe Ile Asn Asn Glu Trp His Asp Ser
            20                  25                  30

-continued

```
Val Ser Gly Lys Lys Phe Pro Val Phe Asn Pro Ala Thr Glu Glu
         35                  40                  45

Leu Cys Gln Val Glu Glu Gly Asp Lys Glu Asp Val Asp Lys Ala Val
 50                  55                  60

Lys Ala Ala Arg Gln Ala Phe Gln Ile Gly Ser Pro Trp Arg Thr Met
 65                  70                  75                  80

Asp Ala Ser Glu Arg Gly Arg Leu Leu Tyr Lys Leu Ala Asp Leu Ile
                 85                  90                  95

Glu Arg Asp Arg Leu Leu Leu Ala Thr Met Glu Ser Met Asn Gly Gly
                100                 105                 110

Lys Leu Tyr Ser Asn Ala Tyr Leu Asn Asp Leu Ala Gly Cys Ile Lys
            115                 120                 125

Thr Leu Arg Tyr Cys Ala Gly Trp Ala Asp Lys Ile Gln Gly Arg Thr
130                 135                 140

Ile Pro Ile Asp Gly Asn Phe Phe Thr Tyr Thr Arg His Glu Pro Ile
145                 150                 155                 160

Gly Val Cys Gly Gln Ile Ile Pro Trp Asn Phe Pro Leu Val Met Leu
                165                 170                 175

Ile Trp Lys Ile Gly Pro Ala Leu Ser Cys Gly Asn Thr Val Val Val
            180                 185                 190

Lys Pro Ala Glu Gln Thr Pro Leu Thr Ala Leu His Val Ala Ser Leu
        195                 200                 205

Ile Lys Glu Ala Gly Phe Pro Pro Gly Val Val Asn Ile Val Pro Gly
210                 215                 220

Tyr Gly Pro Thr Ala Gly Ala Ala Ile Ser Ser His Met Asp Ile Asp
225                 230                 235                 240

Lys Val Ala Phe Thr Gly Ser Thr Glu Val Gly Lys Leu Ile Lys Glu
                245                 250                 255

Ala Ala Gly Lys Ser Asn Leu Lys Arg Val Thr Leu Glu Leu Gly Gly
            260                 265                 270

Lys Ser Pro Cys Ile Val Leu Ala Asp Ala Asp Leu Asp Asn Ala Val
        275                 280                 285

Glu Phe Ala His His Gly Val Phe Tyr His Gln Gly Gln Cys Cys Ile
290                 295                 300

Ala Ala Ser Arg Ile Phe Val Glu Glu Ser Ile Tyr Asp Glu Phe Val
305                 310                 315                 320

Arg Arg Ser Val Glu Arg Ala Lys Lys Tyr Ile Leu Gly Asn Pro Leu
                325                 330                 335

Thr Pro Gly Val Thr Gln Gly Pro Gln Ile Asp Lys Glu Gln Tyr Asp
            340                 345                 350

Lys Ile Leu Asp Leu Ile Glu Ser Gly Lys Lys Glu Gly Ala Lys Leu
        355                 360                 365

Glu Cys Gly Gly Gly Pro Trp Gly Asn Lys Gly Tyr Phe Val Gln Pro
370                 375                 380

Thr Val Phe Ser Asn Val Thr Asp Glu Met Arg Ile Ala Lys Glu Glu
385                 390                 395                 400

Ile Phe Gly Pro Val Gln Gln Ile Met Lys Phe Lys Ser Leu Asp Asp
                405                 410                 415

Val Ile Lys Arg Ala Asn Asn Thr Phe Tyr Gly Leu Ser Ala Gly Val
            420                 425                 430

Phe Thr Lys Asp Ile Asp Lys Ala Ile Thr Ile Ser Ser Ala Leu Gln
        435                 440                 445

Ala Gly Thr Val Trp Val Asn Cys Tyr Gly Val Val Ser Ala Gln Cys
```

```
                450             455             460
Pro Phe Gly Gly Phe Lys Met Ser Gly Asn Gly Arg Glu Leu Gly Glu
465                 470                 475                 480

Tyr Gly Phe His Glu Tyr Thr Glu Val Lys Thr Val Thr Val Lys Ile
                485                 490                 495

Ser Gln Lys Asn Ser
            500

<210> SEQ ID NO 48
<211> LENGTH: 15
<212> TYPE: PRT
<213> ORGANISM: Homo sapiens

<400> SEQUENCE: 48

Val Thr Glu Pro Ile Ser Ala Glu Ser Gly Glu Gln Val Glu Arg
1               5                   10                  15

<210> SEQ ID NO 49
<211> LENGTH: 398
<212> TYPE: PRT
<213> ORGANISM: Homo sapiens

<400> SEQUENCE: 49

Met Glu Gly Ala Ala Leu Leu Arg Val Ser Val Leu Cys Ile Trp Met
1               5                   10                  15

Ser Ala Leu Phe Leu Gly Val Gly Val Arg Ala Glu Glu Ala Gly Ala
                20                  25                  30

Arg Val Gln Gln Asn Val Pro Ser Gly Thr Asp Thr Gly Asp Pro Gln
            35                  40                  45

Ser Lys Pro Leu Gly Asp Trp Ala Ala Gly Thr Met Asp Pro Glu Ser
        50                  55                  60

Ser Ile Phe Ile Glu Asp Ala Ile Lys Tyr Phe Lys Glu Lys Val Ser
65                  70                  75                  80

Thr Gln Asn Leu Leu Leu Leu Thr Asp Asn Glu Ala Trp Asn Gly
                85                  90                  95

Phe Val Ala Ala Ala Glu Leu Pro Arg Asn Glu Ala Asp Glu Leu Arg
                100                 105                 110

Lys Ala Leu Asp Asn Leu Ala Arg Gln Met Ile Met Lys Asp Lys Asn
            115                 120                 125

Trp His Asp Lys Gly Gln Gln Tyr Arg Asn Trp Phe Leu Lys Glu Phe
        130                 135                 140

Pro Arg Leu Lys Ser Glu Leu Glu Asp Asn Ile Arg Arg Leu Arg Ala
145                 150                 155                 160

Leu Ala Asp Gly Val Gln Lys Val His Lys Gly Thr Thr Ile Ala Asn
                165                 170                 175

Val Val Ser Gly Ser Leu Ser Ile Ser Ser Gly Ile Leu Thr Leu Val
            180                 185                 190

Gly Met Gly Leu Ala Pro Phe Thr Glu Gly Gly Ser Leu Val Leu Leu
        195                 200                 205

Glu Pro Gly Met Glu Leu Gly Ile Thr Ala Ala Leu Thr Gly Ile Thr
    210                 215                 220

Ser Ser Thr Met Asp Tyr Gly Lys Lys Trp Trp Thr Gln Ala Gln Ala
225                 230                 235                 240

His Asp Leu Val Ile Lys Ser Leu Asp Lys Leu Lys Glu Val Arg Glu
                245                 250                 255

Phe Leu Gly Glu Asn Ile Ser Asn Phe Leu Ser Leu Ala Gly Asn Thr
```

```
                260               265               270
Tyr Gln Leu Thr Arg Gly Ile Gly Lys Asp Ile Arg Ala Leu Arg Arg
        275               280               285
Ala Arg Ala Asn Leu Gln Ser Val Pro His Ala Ser Ala Ser Arg Pro
        290               295               300
Arg Val Thr Glu Pro Ile Ser Ala Glu Ser Gly Glu Gln Val Glu Arg
305               310               315               320
Val Asn Glu Pro Ser Ile Leu Glu Met Ser Arg Gly Val Lys Leu Thr
                325               330               335
Asp Val Ala Pro Val Ser Phe Phe Leu Val Leu Asp Val Val Tyr Leu
                340               345               350
Val Tyr Glu Ser Lys His Leu His Glu Gly Ala Lys Ser Glu Thr Ala
                355               360               365
Glu Glu Leu Lys Lys Val Ala Gln Glu Leu Glu Lys Leu Asn Ile
                370               375               380
Leu Asn Asn Asn Tyr Lys Ile Leu Gln Ala Asp Gln Glu Leu
385               390               395

<210> SEQ ID NO 50
<211> LENGTH: 11
<212> TYPE: PRT
<213> ORGANISM: Homo sapiens

<400> SEQUENCE: 50

Asp Ile Ser Glu Met Phe Ile Gln Leu Tyr Lys
1               5                  10

<210> SEQ ID NO 51
<211> LENGTH: 11
<212> TYPE: PRT
<213> ORGANISM: Homo sapiens

<400> SEQUENCE: 51

Gln Gly Gly Phe Leu Gly Leu Ser Asn Ile Lys
1               5                  10

<210> SEQ ID NO 52
<211> LENGTH: 1255
<212> TYPE: PRT
<213> ORGANISM: Homo sapiens

<400> SEQUENCE: 52

Met Thr Pro Gly Thr Gln Ser Pro Phe Phe Leu Leu Leu Leu Leu Thr
1               5                  10                  15
Val Leu Thr Val Val Thr Gly Ser Gly His Ala Ser Ser Thr Pro Gly
                20                  25                  30
Gly Glu Lys Glu Thr Ser Ala Thr Gln Arg Ser Ser Val Pro Ser Ser
            35                  40                  45
Thr Glu Lys Asn Ala Val Ser Met Thr Ser Ser Val Leu Ser Ser His
        50                  55                  60
Ser Pro Gly Ser Gly Ser Ser Thr Thr Gln Gly Gln Asp Val Thr Leu
65                  70                  75                  80
Ala Pro Ala Thr Glu Pro Ala Ser Gly Ser Ala Ala Thr Trp Gly Gln
                85                  90                  95
Asp Val Thr Ser Val Pro Val Thr Arg Pro Ala Leu Gly Ser Thr Thr
                100                 105                 110
Pro Pro Ala His Asp Val Thr Ser Ala Pro Asp Asn Lys Pro Ala Pro
                115                 120                 125
```

```
Gly Ser Thr Ala Pro Pro Ala His Gly Val Thr Ser Ala Pro Asp Thr
        130                 135                 140

Arg Pro Ala Pro Gly Ser Thr Ala Pro Pro Ala His Gly Val Thr Ser
145                 150                 155                 160

Ala Pro Asp Thr Arg Pro Ala Pro Gly Ser Thr Ala Pro Pro Ala His
                165                 170                 175

Gly Val Thr Ser Ala Pro Asp Thr Arg Pro Ala Pro Gly Ser Thr Ala
            180                 185                 190

Pro Pro Ala His Gly Val Thr Ser Ala Pro Asp Thr Arg Pro Ala Pro
        195                 200                 205

Gly Ser Thr Ala Pro Pro Ala His Gly Val Thr Ser Ala Pro Asp Thr
        210                 215                 220

Arg Pro Ala Pro Gly Ser Thr Ala Pro Pro Ala His Gly Val Thr Ser
225                 230                 235                 240

Ala Pro Asp Thr Arg Pro Ala Pro Gly Ser Thr Ala Pro Pro Ala His
                245                 250                 255

Gly Val Thr Ser Ala Pro Asp Thr Arg Pro Ala Pro Gly Ser Thr Ala
            260                 265                 270

Pro Pro Ala His Gly Val Thr Ser Ala Pro Asp Thr Arg Pro Ala Pro
        275                 280                 285

Gly Ser Thr Ala Pro Pro Ala His Gly Val Thr Ser Ala Pro Asp Thr
        290                 295                 300

Arg Pro Ala Pro Gly Ser Thr Ala Pro Pro Ala His Gly Val Thr Ser
305                 310                 315                 320

Ala Pro Asp Thr Arg Pro Ala Pro Gly Ser Thr Ala Pro Pro Ala His
                325                 330                 335

Gly Val Thr Ser Ala Pro Asp Thr Arg Pro Ala Pro Gly Ser Thr Ala
            340                 345                 350

Pro Pro Ala His Gly Val Thr Ser Ala Pro Asp Thr Arg Pro Ala Pro
        355                 360                 365

Gly Ser Thr Ala Pro Pro Ala His Gly Val Thr Ser Ala Pro Asp Thr
        370                 375                 380

Arg Pro Ala Pro Gly Ser Thr Ala Pro Pro Ala His Gly Val Thr Ser
385                 390                 395                 400

Ala Pro Asp Thr Arg Pro Ala Pro Gly Ser Thr Ala Pro Pro Ala His
                405                 410                 415

Gly Val Thr Ser Ala Pro Asp Thr Arg Pro Ala Pro Gly Ser Thr Ala
            420                 425                 430

Pro Pro Ala His Gly Val Thr Ser Ala Pro Asp Thr Arg Pro Ala Pro
        435                 440                 445

Gly Ser Thr Ala Pro Pro Ala His Gly Val Thr Ser Ala Pro Asp Thr
        450                 455                 460

Arg Pro Ala Pro Gly Ser Thr Ala Pro Pro Ala His Gly Val Thr Ser
465                 470                 475                 480

Ala Pro Asp Thr Arg Pro Ala Pro Gly Ser Thr Ala Pro Pro Ala His
                485                 490                 495

Gly Val Thr Ser Ala Pro Asp Thr Arg Pro Ala Pro Gly Ser Thr Ala
            500                 505                 510

Pro Pro Ala His Gly Val Thr Ser Ala Pro Asp Thr Arg Pro Ala Pro
        515                 520                 525

Gly Ser Thr Ala Pro Pro Ala His Gly Val Thr Ser Ala Pro Asp Thr
        530                 535                 540
```

```
Arg Pro Ala Pro Gly Ser Thr Ala Pro Pro His Gly Val Thr Ser
545                 550                 555                 560

Ala Pro Asp Thr Arg Pro Ala Pro Gly Ser Thr Ala Pro Pro His
        565                 570                 575

Gly Val Thr Ser Ala Pro Asp Thr Arg Pro Ala Pro Gly Ser Thr Ala
            580                 585                 590

Pro Pro Ala His Gly Val Thr Ser Ala Pro Asp Thr Arg Pro Ala Pro
        595                 600                 605

Gly Ser Thr Ala Pro Pro Ala His Gly Val Thr Ser Ala Pro Asp Thr
    610                 615                 620

Arg Pro Ala Pro Gly Ser Thr Ala Pro Pro His Gly Val Thr Ser
625                 630                 635                 640

Ala Pro Asp Thr Arg Pro Ala Pro Gly Ser Thr Ala Pro Pro Ala His
        645                 650                 655

Gly Val Thr Ser Ala Pro Asp Thr Arg Pro Ala Pro Gly Ser Thr Ala
            660                 665                 670

Pro Pro Ala His Gly Val Thr Ser Ala Pro Asp Thr Arg Pro Ala Pro
        675                 680                 685

Gly Ser Thr Ala Pro Pro Ala His Gly Val Thr Ser Ala Pro Asp Thr
    690                 695                 700

Arg Pro Ala Pro Gly Ser Thr Ala Pro Pro Ala His Gly Val Thr Ser
705                 710                 715                 720

Ala Pro Asp Thr Arg Pro Ala Pro Gly Ser Thr Ala Pro Pro Ala His
        725                 730                 735

Gly Val Thr Ser Ala Pro Asp Thr Arg Pro Ala Pro Gly Ser Thr Ala
            740                 745                 750

Pro Pro Ala His Gly Val Thr Ser Ala Pro Asp Thr Arg Pro Ala Pro
        755                 760                 765

Gly Ser Thr Ala Pro Pro Ala His Gly Val Thr Ser Ala Pro Asp Thr
    770                 775                 780

Arg Pro Ala Pro Gly Ser Thr Ala Pro Pro Ala His Gly Val Thr Ser
785                 790                 795                 800

Ala Pro Asp Thr Arg Pro Ala Pro Gly Ser Thr Ala Pro Pro Ala His
        805                 810                 815

Gly Val Thr Ser Ala Pro Asp Thr Arg Pro Ala Pro Gly Ser Thr Ala
            820                 825                 830

Pro Pro Ala His Gly Val Thr Ser Ala Pro Asp Thr Arg Pro Ala Pro
        835                 840                 845

Gly Ser Thr Ala Pro Pro Ala His Gly Val Thr Ser Ala Pro Asp Thr
    850                 855                 860

Arg Pro Ala Pro Gly Ser Thr Ala Pro Pro Ala His Gly Val Thr Ser
865                 870                 875                 880

Ala Pro Asp Thr Arg Pro Ala Pro Gly Ser Thr Ala Pro Pro Ala His
        885                 890                 895

Gly Val Thr Ser Ala Pro Asp Thr Arg Pro Ala Pro Gly Ser Thr Ala
            900                 905                 910

Pro Pro Ala His Gly Val Thr Ser Ala Pro Asp Thr Arg Pro Ala Pro
        915                 920                 925

Gly Ser Thr Ala Pro Pro Ala His Gly Val Thr Ser Ala Pro Asp Asn
    930                 935                 940

Arg Pro Ala Leu Gly Ser Thr Ala Pro Pro Val His Asn Val Thr Ser
945                 950                 955                 960

Ala Ser Gly Ser Ala Ser Gly Ser Ala Ser Thr Leu Val His Asn Gly
```

```
                965                 970                 975
Thr Ser Ala Arg Ala Thr Thr Thr Pro Ala Ser Lys Ser Thr Pro Phe
                980                 985                 990

Ser Ile Pro Ser His His Ser Asp Thr Pro Thr Thr Leu Ala Ser His
            995                1000                1005

Ser Thr Lys Thr Asp Ala Ser Ser His His Ser Ser Val Pro
       1010                1015                1020

Pro Leu Thr Ser Ser Asn His Ser Thr Ser Pro Gln Leu Ser Thr
       1025                1030                1035

Gly Val Ser Phe Phe Leu Ser Phe His Ile Ser Asn Leu Gln
       1040                1045                1050

Phe Asn Ser Ser Leu Glu Asp Pro Ser Thr Asp Tyr Tyr Gln Glu
       1055                1060                1065

Leu Gln Arg Asp Ile Ser Glu Met Phe Leu Gln Ile Tyr Lys Gln
       1070                1075                1080

Gly Gly Phe Leu Gly Leu Ser Asn Ile Lys Phe Arg Pro Gly Ser
       1085                1090                1095

Val Val Val Gln Leu Thr Leu Ala Phe Arg Glu Gly Thr Ile Asn
       1100                1105                1110

Val His Asp Val Glu Thr Gln Phe Asn Gln Tyr Lys Thr Glu Ala
       1115                1120                1125

Ala Ser Arg Tyr Asn Leu Thr Ile Ser Asp Val Ser Val Ser Asp
       1130                1135                1140

Val Pro Phe Pro Phe Ser Ala Gln Ser Gly Ala Gly Val Pro Gly
       1145                1150                1155

Trp Gly Ile Ala Leu Leu Val Leu Val Cys Val Leu Val Ala Leu
       1160                1165                1170

Ala Ile Val Tyr Leu Ile Ala Leu Ala Val Cys Gln Cys Arg Arg
       1175                1180                1185

Lys Asn Tyr Gly Gln Leu Asp Ile Phe Pro Ala Arg Asp Thr Tyr
       1190                1195                1200

His Pro Met Ser Glu Tyr Pro Thr Tyr His Thr His Gly Arg Tyr
       1205                1210                1215

Val Pro Pro Ser Ser Thr Asp Arg Ser Pro Tyr Glu Lys Val Ser
       1220                1225                1230

Ala Gly Asn Gly Gly Ser Ser Leu Ser Tyr Thr Asn Pro Ala Val
       1235                1240                1245

Ala Ala Thr Ser Ala Asn Leu
       1250                1255

<210> SEQ ID NO 53
<211> LENGTH: 20
<212> TYPE: PRT
<213> ORGANISM: Homo sapiens

<400> SEQUENCE: 53

Ala Gln His Val Phe Gln His Ala Val Pro Gln Glu Gly Lys Pro Ile
1               5                   10                  15

Thr Asn Gln Lys
            20

<210> SEQ ID NO 54
<211> LENGTH: 16
<212> TYPE: PRT
<213> ORGANISM: Homo sapiens
```

```
<400> SEQUENCE: 54

Ser Ser Ser Gly Leu Asn Ser Glu Lys Val Ala Ala Leu Ile Gln Lys
1               5                   10                  15

<210> SEQ ID NO 55
<211> LENGTH: 455
<212> TYPE: PRT
<213> ORGANISM: Homo sapiens

<400> SEQUENCE: 55

Met Ser Ser Ser Gly Leu Asn Ser Glu Lys Val Ala Ala Leu Ile Gln
1               5                   10                  15

Lys Leu Asn Ser Asp Pro Gln Phe Val Leu Ala Gln Asn Val Gly Thr
                20                  25                  30

Thr His Asp Leu Leu Asp Ile Cys Leu Lys Arg Ala Thr Val Gln Arg
        35                  40                  45

Ala Gln His Val Phe Gln His Ala Val Pro Gln Glu Gly Lys Pro Ile
    50                  55                  60

Thr Asn Gln Lys Ser Ser Gly Arg Cys Trp Ile Phe Ser Cys Leu Asn
65                  70                  75                  80

Val Met Arg Leu Pro Phe Met Lys Lys Leu Asn Ile Glu Glu Phe Glu
                85                  90                  95

Phe Ser Gln Ser Tyr Leu Phe Phe Trp Asp Lys Val Glu Arg Cys Tyr
            100                 105                 110

Phe Phe Leu Ser Ala Phe Val Asp Thr Ala Gln Arg Lys Glu Pro Glu
        115                 120                 125

Asp Gly Arg Leu Val Gln Phe Leu Leu Met Asn Pro Ala Asn Asp Gly
    130                 135                 140

Gly Gln Trp Asp Met Leu Val Asn Ile Val Glu Lys Tyr Gly Val Ile
145                 150                 155                 160

Pro Lys Lys Cys Phe Pro Glu Ser Tyr Thr Thr Glu Ala Thr Arg Arg
                165                 170                 175

Met Asn Asp Ile Leu Asn His Lys Met Arg Glu Phe Cys Ile Arg Leu
            180                 185                 190

Arg Asn Leu Val His Ser Gly Ala Thr Lys Gly Glu Ile Ser Ala Thr
        195                 200                 205

Gln Asp Val Met Met Glu Glu Ile Phe Arg Val Cys Ile Cys Leu
    210                 215                 220

Gly Asn Pro Pro Glu Thr Phe Thr Trp Glu Tyr Arg Asp Lys Asp Lys
225                 230                 235                 240

Asn Tyr Gln Lys Ile Gly Pro Ile Thr Pro Leu Glu Phe Tyr Arg Glu
                245                 250                 255

His Val Lys Pro Leu Phe Asn Met Glu Asp Lys Ile Cys Leu Val Asn
            260                 265                 270

Asp Pro Arg Pro Gln His Lys Tyr Asn Lys Leu Tyr Thr Val Glu Tyr
        275                 280                 285

Leu Ser Asn Met Val Gly Gly Arg Lys Thr Leu Tyr Asn Asn Gln Pro
    290                 295                 300

Ile Asp Phe Leu Lys Lys Met Val Ala Ala Ser Ile Lys Asp Gly Glu
305                 310                 315                 320

Ala Val Trp Phe Gly Cys Asp Val Gly Lys His Phe Asn Ser Lys Leu
                325                 330                 335

Gly Leu Ser Asp Met Asn Leu Tyr Asp His Glu Leu Val Phe Gly Val
            340                 345                 350
```

```
Ser Leu Lys Asn Met Asn Lys Ala Glu Arg Leu Thr Phe Gly Glu Ser
        355                 360                 365

Leu Met Thr His Ala Met Thr Phe Thr Ala Val Ser Glu Lys Asp Asp
    370                 375                 380

Gln Asp Gly Ala Phe Thr Lys Trp Arg Val Glu Asn Ser Trp Gly Glu
385                 390                 395                 400

Asp His Gly His Lys Gly Tyr Leu Cys Met Thr Asp Glu Trp Phe Ser
                405                 410                 415

Glu Tyr Val Tyr Glu Val Val Asp Arg Lys His Val Pro Glu Glu
            420                 425                 430

Val Leu Ala Val Leu Glu Gln Glu Pro Ile Ile Leu Pro Ala Trp Asp
        435                 440                 445

Pro Met Gly Ala Leu Ala Glu
    450                 455

<210> SEQ ID NO 56
<211> LENGTH: 15
<212> TYPE: PRT
<213> ORGANISM: Homo sapiens

<400> SEQUENCE: 56

Gln Pro Cys Thr Pro Pro Gln Leu Gln Gln Gln Gln Val Lys
1               5                   10                  15

<210> SEQ ID NO 57
<211> LENGTH: 17
<212> TYPE: PRT
<213> ORGANISM: Homo sapiens

<400> SEQUENCE: 57

Val Pro Glu Pro Cys Pro Ser Ile Val Thr Pro Ala Pro Ala Gln Gln
1               5                   10                  15

Lys

<210> SEQ ID NO 58
<211> LENGTH: 89
<212> TYPE: PRT
<213> ORGANISM: Homo sapiens

<400> SEQUENCE: 58

Met Ser Ser Gln Gln Gln Lys Gln Pro Cys Thr Pro Pro Gln Leu
1               5                   10                  15

Gln Gln Gln Gln Val Lys Gln Pro Cys Gln Pro Pro Gln Glu Pro
            20                  25                  30

Cys Ile Pro Lys Thr Lys Glu Pro Cys His Pro Lys Val Pro Glu Pro
        35                  40                  45

Cys His Pro Lys Val Pro Glu Pro Cys Gln Pro Lys Val Pro Glu Pro
    50                  55                  60

Cys His Pro Lys Val Pro Glu Pro Cys Pro Ser Ile Val Thr Pro Ala
65                  70                  75                  80

Pro Ala Gln Gln Lys Thr Lys Gln Lys
                85

<210> SEQ ID NO 59
<211> LENGTH: 17
<212> TYPE: PRT
<213> ORGANISM: Homo sapiens

<400> SEQUENCE: 59
```

Gly Lys Ile Pro Asn Leu Leu Pro Glu Gly Ser Val Asp Gly Asp Thr
1               5                   10                  15

Arg

<210> SEQ ID NO 60
<211> LENGTH: 415
<212> TYPE: PRT
<213> ORGANISM: Homo sapiens

<400> SEQUENCE: 60

Met Glu Asp Leu Cys Val Ala Asn Thr Leu Phe Ala Leu Asn Leu Phe
1               5                   10                  15

Lys His Leu Ala Lys Ala Ser Pro Thr Gln Asn Leu Phe Leu Ser Pro
                20                  25                  30

Trp Ser Ile Ser Ser Thr Met Ala Met Val Tyr Met Gly Ser Arg Gly
            35                  40                  45

Ser Thr Glu Asp Gln Met Ala Lys Val Leu Gln Phe Asn Glu Val Gly
        50                  55                  60

Ala Asn Ala Val Thr Pro Met Thr Pro Glu Asn Phe Thr Ser Cys Gly
65                  70                  75                  80

Phe Met Gln Gln Ile Gln Lys Gly Ser Tyr Pro Asp Ala Ile Leu Gln
                85                  90                  95

Ala Gln Ala Ala Asp Lys Ile His Ser Ser Phe Arg Ser Leu Ser Ser
            100                 105                 110

Ala Ile Asn Ala Ser Thr Gly Asn Tyr Leu Leu Glu Ser Val Asn Lys
        115                 120                 125

Leu Phe Gly Glu Lys Ser Ala Ser Phe Arg Glu Glu Tyr Ile Arg Leu
130                 135                 140

Cys Gln Lys Tyr Tyr Ser Ser Glu Pro Gln Ala Val Asp Phe Leu Glu
145                 150                 155                 160

Cys Ala Glu Glu Ala Arg Lys Lys Ile Asn Ser Trp Val Lys Thr Gln
                165                 170                 175

Thr Lys Gly Lys Ile Pro Asn Leu Leu Pro Glu Gly Ser Val Asp Gly
            180                 185                 190

Asp Thr Arg Met Val Leu Val Asn Ala Val Tyr Phe Lys Gly Lys Trp
        195                 200                 205

Lys Thr Pro Phe Glu Lys Lys Leu Asn Gly Leu Tyr Pro Phe Arg Val
210                 215                 220

Asn Ser Ala Gln Arg Thr Pro Val Gln Met Met Tyr Leu Arg Glu Lys
225                 230                 235                 240

Leu Asn Ile Gly Tyr Ile Glu Asp Leu Lys Ala Gln Ile Leu Glu Leu
                245                 250                 255

Pro Tyr Ala Gly Asp Val Ser Met Phe Leu Leu Leu Pro Asp Glu Ile
            260                 265                 270

Ala Asp Val Ser Thr Gly Leu Glu Leu Leu Glu Ser Glu Ile Thr Tyr
        275                 280                 285

Asp Lys Leu Asn Lys Trp Thr Ser Lys Asp Lys Met Ala Glu Asp Glu
290                 295                 300

Val Glu Val Tyr Ile Pro Gln Phe Lys Leu Glu Glu His Tyr Glu Leu
305                 310                 315                 320

Arg Ser Ile Leu Arg Ser Met Gly Met Glu Asp Ala Phe Asn Lys Gly
                325                 330                 335

Arg Ala Asn Phe Ser Gly Met Ser Glu Arg Asn Asp Leu Phe Leu Ser
            340                 345                 350

```
Glu Val Phe His Gln Ala Met Val Asp Val Asn Glu Gly Thr Glu
            355                 360                 365
Ala Ala Ala Gly Thr Gly Gly Val Met Thr Gly Arg Thr Gly His Gly
    370                 375                 380
Gly Pro Gln Phe Val Ala Asp His Pro Phe Leu Phe Leu Ile Met His
385                 390                 395                 400
Lys Ile Thr Asn Cys Ile Leu Phe Phe Gly Arg Phe Ser Ser Pro
                405                 410                 415
```

<210> SEQ ID NO 61
<211> LENGTH: 13
<212> TYPE: PRT
<213> ORGANISM: Homo sapiens

<400> SEQUENCE: 61

```
Asp Ile Asn Ala Tyr Asn Cys Glu Glu Pro Thr Glu Lys
1               5                   10
```

<210> SEQ ID NO 62
<211> LENGTH: 7
<212> TYPE: PRT
<213> ORGANISM: Homo sapiens

<400> SEQUENCE: 62

```
Asn Phe Asp Glu Ile Leu Arg
1               5
```

<210> SEQ ID NO 63
<211> LENGTH: 224
<212> TYPE: PRT
<213> ORGANISM: Homo sapiens

<400> SEQUENCE: 63

```
Met Pro Gly Gly Leu Leu Gly Asp Val Ala Pro Asn Phe Glu Ala
1               5                   10                  15
Asn Thr Thr Val Gly Arg Ile Arg Phe His Asp Phe Leu Gly Asp Ser
                20                  25                  30
Trp Gly Ile Leu Phe Ser His Pro Arg Asp Phe Thr Pro Val Cys Thr
            35                  40                  45
Thr Glu Leu Gly Arg Ala Ala Lys Leu Ala Pro Glu Phe Ala Lys Arg
    50                  55                  60
Asn Val Lys Leu Ile Ala Leu Ser Ile Asp Ser Val Glu Asp His Leu
65                  70                  75                  80
Ala Trp Ser Lys Asp Ile Asn Ala Tyr Asn Cys Glu Glu Pro Thr Glu
                85                  90                  95
Lys Leu Pro Phe Pro Ile Ile Asp Asp Arg Asn Arg Glu Leu Ala Ile
                100                 105                 110
Leu Leu Gly Met Leu Asp Pro Ala Glu Lys Asp Glu Lys Gly Met Pro
            115                 120                 125
Val Thr Ala Arg Val Val Phe Val Phe Gly Pro Asp Lys Lys Leu Lys
    130                 135                 140
Leu Ser Ile Leu Tyr Pro Ala Thr Thr Gly Arg Asn Phe Asp Glu Ile
145                 150                 155                 160
Leu Arg Val Val Ile Ser Leu Gln Leu Thr Ala Glu Lys Arg Val Ala
                165                 170                 175
Thr Pro Val Asp Trp Lys Asp Gly Asp Ser Val Met Val Leu Pro Thr
                180                 185                 190
Ile Pro Glu Glu Glu Ala Lys Lys Leu Phe Pro Lys Gly Val Phe Thr
```

```
                195                 200                 205
Lys Glu Leu Pro Ser Gly Lys Lys Tyr Leu Arg Tyr Thr Pro Gln Pro
    210                 215                 220
```

<210> SEQ ID NO 64
<211> LENGTH: 13
<212> TYPE: PRT
<213> ORGANISM: Homo sapiens

<400> SEQUENCE: 64

```
Ile Thr Cys Thr Glu Glu Gly Trp Ser Pro Thr Pro Lys
1               5                   10
```

<210> SEQ ID NO 65
<211> LENGTH: 10
<212> TYPE: PRT
<213> ORGANISM: Homo sapiens

<400> SEQUENCE: 65

```
Thr Gly Glu Ser Ala Glu Phe Val Cys Lys
1               5                   10
```

<210> SEQ ID NO 66
<211> LENGTH: 20
<212> TYPE: PRT
<213> ORGANISM: Homo sapiens

<400> SEQUENCE: 66

```
Ser Thr Asp Thr Ser Cys Val Asn Pro Pro Thr Val Gln Asn Ala His
1               5                   10                  15
Ile Leu Ser Arg
            20
```

<210> SEQ ID NO 67
<211> LENGTH: 330
<212> TYPE: PRT
<213> ORGANISM: Homo sapiens

<400> SEQUENCE: 67

```
Met Trp Leu Leu Val Ser Val Ile Leu Ile Ser Arg Ile Ser Ser Val
1               5                   10                  15

Gly Gly Glu Ala Thr Phe Cys Asp Phe Pro Lys Ile Asn His Gly Ile
            20                  25                  30

Leu Tyr Asp Glu Glu Lys Tyr Lys Pro Phe Ser Gln Val Pro Thr Gly
        35                  40                  45

Glu Val Phe Tyr Tyr Ser Cys Glu Tyr Asn Phe Val Ser Pro Ser Lys
    50                  55                  60

Ser Phe Trp Thr Arg Ile Thr Cys Thr Glu Glu Gly Trp Ser Pro Thr
65                  70                  75                  80

Pro Lys Cys Leu Arg Leu Cys Phe Phe Pro Phe Val Glu Asn Gly His
                85                  90                  95

Ser Glu Ser Ser Gly Gln Thr His Leu Glu Gly Asp Thr Val Gln Ile
            100                 105                 110

Ile Cys Asn Thr Gly Tyr Arg Leu Gln Asn Asn Glu Asn Asn Ile Ser
        115                 120                 125

Cys Val Glu Arg Gly Trp Ser Thr Pro Pro Lys Cys Arg Ser Thr Asp
    130                 135                 140

Thr Ser Cys Val Asn Pro Pro Thr Val Gln Asn Ala His Ile Leu Ser
145                 150                 155                 160
```

-continued

```
Arg Gln Met Ser Lys Tyr Pro Ser Gly Glu Arg Val Arg Tyr Glu Cys
            165                 170                 175

Arg Ser Pro Tyr Glu Met Phe Gly Asp Glu Val Met Cys Leu Asn
        180                 185                 190

Gly Asn Trp Thr Glu Pro Pro Gln Cys Lys Asp Ser Thr Gly Lys Cys
        195                 200                 205

Gly Pro Pro Pro Ile Asp Asn Gly Asp Ile Thr Ser Phe Pro Leu
    210                 215                 220

Ser Val Tyr Ala Pro Ala Ser Ser Val Glu Tyr Gln Cys Gln Asn Leu
225                 230                 235                 240

Tyr Gln Leu Glu Gly Asn Lys Arg Ile Thr Cys Arg Asn Gly Gln Trp
            245                 250                 255

Ser Glu Pro Pro Lys Cys Leu His Pro Cys Val Ile Ser Arg Glu Ile
            260                 265                 270

Met Glu Asn Tyr Asn Ile Ala Leu Arg Trp Thr Ala Lys Gln Lys Leu
            275                 280                 285

Tyr Leu Arg Thr Gly Glu Ser Ala Glu Phe Val Cys Lys Arg Gly Tyr
            290                 295                 300

Arg Leu Ser Ser Arg Ser His Thr Leu Arg Thr Thr Cys Trp Asp Gly
305                 310                 315                 320

Lys Leu Glu Tyr Pro Thr Cys Ala Lys Arg
                325                 330

<210> SEQ ID NO 68
<211> LENGTH: 11
<212> TYPE: PRT
<213> ORGANISM: Homo sapiens

<400> SEQUENCE: 68

Ala Thr Trp Ser Gly Ala Val Leu Ala Gly Arg
1               5                   10

<210> SEQ ID NO 69
<211> LENGTH: 9
<212> TYPE: PRT
<213> ORGANISM: Homo sapiens

<400> SEQUENCE: 69

Cys Leu Ala Pro Leu Glu Gly Ala Arg
1               5

<210> SEQ ID NO 70
<211> LENGTH: 7
<212> TYPE: PRT
<213> ORGANISM: Homo sapiens

<400> SEQUENCE: 70

Gly Val Thr Phe Leu Leu Arg
1               5

<210> SEQ ID NO 71
<211> LENGTH: 12
<212> TYPE: PRT
<213> ORGANISM: Homo sapiens

<400> SEQUENCE: 71

His Gln Phe Leu Leu Thr Gly Asp Thr Gln Gly Arg
1               5                   10

<210> SEQ ID NO 72
```

```
<211> LENGTH: 8
<212> TYPE: PRT
<213> ORGANISM: Homo sapiens

<400> SEQUENCE: 72

Leu Leu Glu Leu Thr Gly Pro Lys
1               5

<210> SEQ ID NO 73
<211> LENGTH: 12
<212> TYPE: PRT
<213> ORGANISM: Homo sapiens

<400> SEQUENCE: 73

Ser Gly Leu Ser Thr Gly Trp Thr Gln Leu Ser Lys
1               5                   10

<210> SEQ ID NO 74
<211> LENGTH: 495
<212> TYPE: PRT
<213> ORGANISM: Homo sapiens

<400> SEQUENCE: 74

Met Ser Met Leu Val Val Phe Leu Leu Trp Gly Val Thr Trp Gly
1               5                   10                  15

Pro Val Thr Glu Ala Ala Ile Phe Tyr Glu Thr Gln Pro Ser Leu Trp
            20                  25                  30

Ala Glu Ser Glu Ser Leu Leu Lys Pro Leu Ala Asn Val Thr Leu Thr
        35                  40                  45

Cys Gln Ala His Leu Glu Thr Pro Asp Phe Gln Leu Phe Lys Asn Gly
    50                  55                  60

Val Ala Gln Glu Pro Val His Leu Asp Ser Pro Ala Ile Lys His Gln
65                  70                  75                  80

Phe Leu Leu Thr Gly Asp Thr Gln Gly Arg Tyr Arg Cys Arg Ser Gly
                85                  90                  95

Leu Ser Thr Gly Trp Thr Gln Leu Ser Lys Leu Leu Glu Leu Thr Gly
            100                 105                 110

Pro Lys Ser Leu Pro Ala Pro Trp Leu Ser Met Ala Pro Val Ser Trp
        115                 120                 125

Ile Thr Pro Gly Leu Lys Thr Thr Ala Val Cys Arg Gly Val Leu Arg
    130                 135                 140

Gly Val Thr Phe Leu Leu Arg Arg Glu Gly Asp His Glu Phe Leu Glu
145                 150                 155                 160

Val Pro Glu Ala Gln Glu Asp Val Glu Ala Thr Phe Pro Val His Gln
                165                 170                 175

Pro Gly Asn Tyr Ser Cys Ser Tyr Arg Thr Asp Gly Glu Gly Ala Leu
            180                 185                 190

Ser Glu Pro Ser Ala Thr Val Thr Ile Glu Glu Leu Ala Ala Pro Pro
        195                 200                 205

Pro Pro Val Leu Met His His Gly Glu Ser Ser Gln Val Leu His Pro
    210                 215                 220

Gly Asn Lys Val Thr Leu Thr Cys Val Ala Pro Leu Ser Gly Val Asp
225                 230                 235                 240

Phe Gln Leu Arg Arg Gly Glu Lys Glu Leu Leu Val Pro Arg Ser Ser
                245                 250                 255

Thr Ser Pro Asp Arg Ile Phe Phe His Leu Asn Ala Val Ala Leu Gly
            260                 265                 270
```

-continued

Asp Gly Gly His Tyr Thr Cys Arg Tyr Arg Leu His Asp Asn Gln Asn
            275                 280                 285

Gly Trp Ser Gly Asp Ser Ala Pro Val Glu Leu Ile Leu Ser Asp Glu
    290                 295                 300

Thr Leu Pro Ala Pro Glu Phe Ser Pro Glu Pro Glu Ser Gly Arg Ala
305                 310                 315                 320

Leu Arg Leu Arg Cys Leu Ala Pro Leu Glu Gly Ala Arg Phe Ala Leu
                325                 330                 335

Val Arg Glu Asp Arg Gly Gly Arg Arg Val His Arg Phe Gln Ser Pro
            340                 345                 350

Ala Gly Thr Glu Ala Leu Phe Glu Leu His Asn Ile Ser Val Ala Asp
    355                 360                 365

Ser Ala Asn Tyr Ser Cys Val Tyr Val Asp Leu Lys Pro Pro Phe Gly
370                 375                 380

Gly Ser Ala Pro Ser Glu Arg Leu Glu Leu His Val Asp Gly Pro Pro
385                 390                 395                 400

Pro Arg Pro Gln Leu Arg Ala Thr Trp Ser Gly Ala Val Leu Ala Gly
                405                 410                 415

Arg Asp Ala Val Leu Arg Cys Glu Gly Pro Ile Pro Asp Val Thr Phe
            420                 425                 430

Glu Leu Leu Arg Glu Gly Glu Thr Lys Ala Val Lys Thr Val Arg Thr
    435                 440                 445

Pro Gly Ala Ala Ala Asn Leu Glu Leu Ile Phe Val Gly Pro Gln His
450                 455                 460

Ala Gly Asn Tyr Arg Cys Arg Tyr Arg Ser Trp Val Pro His Thr Phe
465                 470                 475                 480

Glu Ser Glu Leu Ser Asp Pro Val Glu Leu Leu Val Ala Glu Ser
                485                 490                 495

<210> SEQ ID NO 75
<211> LENGTH: 13
<212> TYPE: PRT
<213> ORGANISM: Homo sapiens

<400> SEQUENCE: 75

Asn Leu Asp Gly Ile Ser His Ala Pro Asn Ala Val Lys
1               5                   10

<210> SEQ ID NO 76
<211> LENGTH: 318
<212> TYPE: PRT
<213> ORGANISM: Homo sapiens

<400> SEQUENCE: 76

Met Ala Ser Pro Gly Cys Leu Leu Cys Val Leu Gly Leu Leu Leu Cys
1               5                   10                  15

Gly Ala Ala Ser Leu Glu Leu Ser Arg Pro His Gly Asp Thr Ala Lys
            20                  25                  30

Lys Pro Ile Ile Gly Ile Leu Met Gln Lys Cys Arg Asn Lys Val Met
        35                  40                  45

Lys Asn Tyr Gly Arg Tyr Tyr Ile Ala Ala Ser Tyr Val Lys Tyr Leu
    50                  55                  60

Glu Ser Ala Gly Ala Arg Val Val Pro Val Arg Leu Asp Leu Thr Glu
65                  70                  75                  80

Lys Asp Tyr Glu Ile Leu Phe Lys Ser Ile Asn Gly Ile Leu Phe Pro
                85                  90                  95

-continued

```
Gly Gly Ser Val Asp Leu Arg Arg Ser Asp Tyr Ala Lys Val Ala Lys
            100                 105                 110

Ile Phe Tyr Asn Leu Ser Ile Gln Ser Phe Asp Asp Gly Asp Tyr Phe
        115                 120                 125

Pro Val Trp Gly Thr Cys Leu Gly Phe Glu Glu Leu Ser Leu Leu Ile
    130                 135                 140

Ser Gly Glu Cys Leu Leu Thr Ala Thr Asp Thr Val Asp Val Ala Met
145                 150                 155                 160

Pro Leu Asn Phe Thr Gly Gly Gln Leu His Ser Arg Met Phe Gln Asn
                165                 170                 175

Phe Pro Thr Glu Leu Leu Leu Ser Leu Ala Val Glu Pro Leu Thr Ala
            180                 185                 190

Asn Phe His Lys Trp Ser Leu Ser Val Lys Asn Phe Thr Met Asn Glu
        195                 200                 205

Lys Leu Lys Lys Phe Phe Asn Val Leu Thr Thr Asn Thr Asp Gly Lys
    210                 215                 220

Ile Glu Phe Ile Ser Thr Met Glu Gly Tyr Lys Tyr Pro Val Tyr Gly
225                 230                 235                 240

Val Gln Trp His Pro Glu Lys Ala Pro Tyr Glu Trp Lys Asn Leu Asp
                245                 250                 255

Gly Ile Ser His Ala Pro Asn Ala Val Lys Thr Ala Phe Tyr Leu Ala
            260                 265                 270

Glu Phe Phe Val Asn Glu Ala Arg Lys Asn Asn His His Phe Lys Ser
        275                 280                 285

Glu Ser Glu Glu Glu Lys Ala Leu Ile Tyr Gln Phe Ser Pro Ile Tyr
    290                 295                 300

Thr Gly Asn Ile Ser Ser Phe Gln Gln Cys Tyr Ile Phe Asp
305                 310                 315

<210> SEQ ID NO 77
<211> LENGTH: 8
<212> TYPE: PRT
<213> ORGANISM: Homo sapiens

<400> SEQUENCE: 77

Ala Leu Gln Leu Glu Glu Glu Arg
1               5

<210> SEQ ID NO 78
<211> LENGTH: 10
<212> TYPE: PRT
<213> ORGANISM: Homo sapiens

<400> SEQUENCE: 78

Ala Pro Asp Phe Val Phe Tyr Ala Pro Arg
1               5                   10

<210> SEQ ID NO 79
<211> LENGTH: 8
<212> TYPE: PRT
<213> ORGANISM: Homo sapiens

<400> SEQUENCE: 79

Glu Leu Ser Glu Gln Ile Gln Arg
1               5

<210> SEQ ID NO 80
<211> LENGTH: 8
<212> TYPE: PRT
```

```
<213> ORGANISM: Homo sapiens

<400> SEQUENCE: 80

Ile Ala Leu Leu Glu Glu Ala Arg
1               5

<210> SEQ ID NO 81
<211> LENGTH: 9
<212> TYPE: PRT
<213> ORGANISM: Homo sapiens

<400> SEQUENCE: 81

Ile Gly Phe Pro Trp Ser Glu Ile Arg
1               5

<210> SEQ ID NO 82
<211> LENGTH: 9
<212> TYPE: PRT
<213> ORGANISM: Homo sapiens

<400> SEQUENCE: 82

Gln Arg Ile Asp Glu Phe Glu Ala Leu
1               5

<210> SEQ ID NO 83
<211> LENGTH: 8
<212> TYPE: PRT
<213> ORGANISM: Homo sapiens

<400> SEQUENCE: 83

Ser Gly Tyr Leu Ser Ser Glu Arg
1               5

<210> SEQ ID NO 84
<211> LENGTH: 15
<212> TYPE: PRT
<213> ORGANISM: Homo sapiens

<400> SEQUENCE: 84

Ser Gln Glu Gln Leu Ala Ala Glu Leu Ala Glu Tyr Thr Ala Lys
1               5                   10                  15

<210> SEQ ID NO 85
<211> LENGTH: 8
<212> TYPE: PRT
<213> ORGANISM: Homo sapiens

<400> SEQUENCE: 85

Val Ser Ala Gln Glu Val Arg Lys
1               5

<210> SEQ ID NO 86
<211> LENGTH: 586
<212> TYPE: PRT
<213> ORGANISM: Homo sapiens

<400> SEQUENCE: 86

Met Pro Lys Pro Ile Asn Val Arg Val Thr Thr Met Asp Ala Glu Leu
1               5                   10                  15

Glu Phe Ala Ile Gln Pro Asn Thr Thr Gly Lys Gln Leu Phe Asp Gln
                20                  25                  30

Val Val Lys Thr Ile Gly Leu Arg Glu Val Trp Tyr Phe Gly Leu His
            35                  40                  45
```

-continued

```
Tyr Val Asp Asn Lys Gly Phe Pro Thr Trp Leu Lys Leu Asp Lys Lys
    50                  55                  60

Val Ser Ala Gln Glu Val Arg Lys Glu Asn Pro Leu Gln Phe Lys Phe
65                  70                  75                  80

Arg Ala Lys Phe Tyr Pro Glu Asp Val Ala Glu Glu Leu Ile Gln Asp
                85                  90                  95

Ile Thr Gln Lys Leu Phe Phe Leu Gln Val Lys Glu Gly Ile Leu Ser
                100                 105                 110

Asp Glu Ile Tyr Cys Pro Pro Glu Thr Ala Val Leu Leu Gly Ser Tyr
                115                 120                 125

Ala Val Gln Ala Lys Phe Gly Asp Tyr Asn Lys Glu Val His Lys Ser
130                 135                 140

Gly Tyr Leu Ser Ser Glu Arg Leu Ile Pro Gln Arg Val Met Asp Gln
145                 150                 155                 160

His Lys Leu Thr Arg Asp Gln Trp Glu Asp Arg Ile Gln Val Trp His
                165                 170                 175

Ala Glu His Arg Gly Met Leu Lys Asp Asn Ala Met Leu Glu Tyr Leu
                180                 185                 190

Lys Ile Ala Gln Asp Leu Glu Met Tyr Gly Ile Asn Tyr Phe Glu Ile
                195                 200                 205

Lys Asn Lys Lys Gly Thr Asp Leu Trp Leu Gly Val Asp Ala Leu Gly
                210                 215                 220

Leu Asn Ile Tyr Glu Lys Asp Asp Lys Leu Thr Pro Lys Ile Gly Phe
225                 230                 235                 240

Pro Trp Ser Glu Ile Arg Asn Ile Ser Phe Asn Asp Lys Lys Phe Val
                245                 250                 255

Ile Lys Pro Ile Asp Lys Lys Ala Pro Asp Phe Val Phe Tyr Ala Pro
                260                 265                 270

Arg Leu Arg Ile Asn Lys Arg Ile Leu Gln Leu Cys Met Gly Asn His
                275                 280                 285

Glu Leu Tyr Met Arg Arg Arg Lys Pro Asp Thr Ile Glu Val Gln Gln
                290                 295                 300

Met Lys Ala Gln Ala Arg Glu Glu Lys His Gln Lys Gln Leu Glu Arg
305                 310                 315                 320

Gln Gln Leu Glu Thr Glu Lys Lys Arg Arg Glu Thr Val Glu Arg Glu
                325                 330                 335

Lys Glu Gln Met Met Arg Glu Lys Glu Leu Met Leu Arg Leu Gln
                340                 345                 350

Asp Tyr Glu Glu Lys Thr Lys Lys Ala Glu Arg Glu Leu Ser Glu Gln
                355                 360                 365

Ile Gln Arg Ala Leu Gln Leu Glu Glu Arg Lys Arg Ala Gln Glu
                370                 375                 380

Glu Ala Glu Arg Leu Glu Ala Asp Arg Met Ala Ala Leu Arg Ala Lys
385                 390                 395                 400

Glu Glu Leu Glu Arg Gln Ala Val Asp Gln Ile Lys Ser Gln Glu Gln
                405                 410                 415

Leu Ala Ala Glu Leu Ala Glu Tyr Thr Ala Lys Ile Ala Leu Leu Glu
                420                 425                 430

Glu Ala Arg Arg Arg Lys Glu Asp Glu Val Glu Glu Trp Gln His Arg
                435                 440                 445

Ala Lys Glu Ala Gln Asp Asp Leu Val Lys Thr Lys Glu Glu Leu His
450                 455                 460

Leu Val Met Thr Ala Pro Pro Pro Pro Pro Pro Val Tyr Glu Pro
```

```
                   465                 470                 475                 480
Val Ser Tyr His Val Gln Glu Ser Leu Gln Asp Glu Gly Ala Glu Pro
                485                 490                 495

Thr Gly Tyr Ser Ala Glu Leu Ser Ser Glu Gly Ile Arg Asp Asp Arg
                500                 505                 510

Asn Glu Glu Lys Arg Ile Thr Glu Ala Glu Lys Asn Glu Arg Val Gln
                515                 520                 525

Arg Gln Leu Leu Thr Leu Ser Ser Glu Leu Ser Gln Ala Arg Asp Glu
                530                 535                 540

Asn Lys Arg Thr His Asn Asp Ile Ile His Asn Glu Asn Met Arg Gln
545                 550                 555                 560

Gly Arg Asp Lys Tyr Lys Thr Leu Arg Gln Ile Arg Gln Gly Asn Thr
                565                 570                 575

Lys Gln Arg Ile Asp Glu Phe Glu Ala Leu
                580                 585

<210> SEQ ID NO 87
<211> LENGTH: 13
<212> TYPE: PRT
<213> ORGANISM: Homo sapiens

<400> SEQUENCE: 87

Leu Gly Asn Gln Glu Pro Gly Gly Gln Thr Ala Leu Lys
1               5                   10

<210> SEQ ID NO 88
<211> LENGTH: 491
<212> TYPE: PRT
<213> ORGANISM: Homo sapiens

<400> SEQUENCE: 88

Met Ala Leu Leu Trp Gly Leu Val Leu Ser Trp Ser Cys Leu Gln
1               5                   10                  15

Gly Pro Cys Ser Val Phe Ser Pro Val Ser Ala Met Glu Pro Leu Gly
                20                  25                  30

Arg Gln Leu Thr Ser Gly Pro Asn Gln Glu Gln Val Ser Pro Leu Thr
                35                  40                  45

Leu Leu Lys Leu Gly Asn Gln Glu Pro Gly Gly Gln Thr Ala Leu Lys
                50                  55                  60

Ser Pro Pro Gly Val Cys Ser Arg Asp Pro Thr Pro Glu Gln Thr His
65                  70                  75                  80

Arg Leu Ala Arg Ala Met Met Ala Phe Thr Ala Asp Leu Phe Ser Leu
                85                  90                  95

Val Ala Gln Thr Ser Thr Cys Pro Asn Leu Ile Leu Ser Pro Leu Ser
                100                 105                 110

Val Ala Leu Ala Leu Ser His Leu Ala Leu Gly Ala Gln Asn His Thr
                115                 120                 125

Leu Gln Arg Leu Gln Gln Val Leu His Ala Gly Ser Gly Pro Cys Leu
                130                 135                 140

Pro His Leu Leu Ser Arg Leu Cys Gln Asp Leu Gly Pro Gly Ala Phe
145                 150                 155                 160

Arg Leu Ala Ala Arg Met Tyr Leu Gln Lys Gly Phe Pro Ile Lys Glu
                165                 170                 175

Asp Phe Leu Glu Gln Ser Glu Gln Leu Phe Gly Ala Lys Pro Val Ser
                180                 185                 190

Leu Thr Gly Lys Gln Glu Asp Asp Leu Ala Asn Ile Asn Gln Trp Val
```

```
            195                 200                 205
Lys Glu Ala Thr Glu Gly Lys Ile Gln Glu Phe Leu Ser Gly Leu Pro
    210                 215                 220

Glu Asp Thr Val Leu Leu Leu Asn Ala Ile His Phe Gln Gly Phe
225                 230                 235                 240

Trp Arg Asn Lys Phe Asp Pro Ser Leu Thr Gln Arg Asp Ser Phe His
                245                 250                 255

Leu Asp Glu Gln Phe Thr Val Pro Val Glu Met Met Gln Ala Arg Thr
            260                 265                 270

Tyr Pro Leu Arg Trp Phe Leu Leu Glu Gln Pro Glu Ile Gln Val Ala
        275                 280                 285

His Phe Pro Phe Lys Asn Asn Met Ser Phe Val Val Leu Val Pro Thr
    290                 295                 300

His Phe Glu Trp Asn Val Ser Gln Val Leu Ala Asn Leu Ser Trp Asp
305                 310                 315                 320

Thr Leu His Pro Pro Leu Val Trp Glu Arg Pro Thr Lys Val Arg Leu
                325                 330                 335

Pro Lys Leu Tyr Leu Lys His Gln Met Asp Leu Val Ala Thr Leu Ser
            340                 345                 350

Gln Leu Gly Leu Gln Glu Leu Phe Gln Ala Pro Asp Leu Arg Gly Ile
        355                 360                 365

Ser Glu Gln Ser Leu Val Val Ser Gly Val Gln His Gln Ser Thr Leu
    370                 375                 380

Glu Leu Ser Glu Val Gly Val Glu Ala Ala Ala Thr Ser Ile Ala
385                 390                 395                 400

Met Ser Arg Met Ser Leu Ser Ser Phe Ser Val Asn Arg Pro Phe Leu
                405                 410                 415

Phe Phe Ile Phe Glu Asp Thr Thr Gly Leu Pro Leu Phe Val Gly Ser
            420                 425                 430

Val Arg Asn Pro Asn Pro Ser Ala Pro Arg Glu Leu Lys Glu Gln Gln
        435                 440                 445

Asp Ser Pro Gly Asn Lys Asp Phe Leu Gln Ser Leu Lys Gly Phe Pro
    450                 455                 460

Arg Gly Asp Lys Leu Phe Gly Pro Asp Leu Lys Leu Val Pro Pro Met
465                 470                 475                 480

Glu Glu Asp Tyr Pro Gln Phe Gly Ser Pro Lys
                485                 490

<210> SEQ ID NO 89
<211> LENGTH: 12
<212> TYPE: PRT
<213> ORGANISM: Homo sapiens

<400> SEQUENCE: 89

Asp Val Arg Asp Tyr Phe Met Pro Cys Pro Gly Arg
1               5                   10

<210> SEQ ID NO 90
<211> LENGTH: 9
<212> TYPE: PRT
<213> ORGANISM: Homo sapiens

<400> SEQUENCE: 90

Asp Tyr Phe Met Pro Cys Pro Gly Arg
1               5
```

```
<210> SEQ ID NO 91
<211> LENGTH: 24
<212> TYPE: PRT
<213> ORGANISM: Homo sapiens

<400> SEQUENCE: 91

Glu Val Gly Thr Pro His Gly Ile Ile Leu Asp Ser Val Asp Ala Ala
1               5                   10                  15

Phe Ile Cys Pro Gly Ser Ser Arg
            20

<210> SEQ ID NO 92
<211> LENGTH: 15
<212> TYPE: PRT
<213> ORGANISM: Homo sapiens

<400> SEQUENCE: 92

Gly Glu Cys Gln Ala Glu Gly Val Leu Phe Phe Gln Gly Asp Arg
1               5                   10                  15

<210> SEQ ID NO 93
<211> LENGTH: 6
<212> TYPE: PRT
<213> ORGANISM: Homo sapiens

<400> SEQUENCE: 93

Gly Glu Phe Val Trp Lys
1               5

<210> SEQ ID NO 94
<211> LENGTH: 11
<212> TYPE: PRT
<213> ORGANISM: Homo sapiens

<400> SEQUENCE: 94

Gly Gly Tyr Thr Leu Val Ser Gly Tyr Pro Lys
1               5                   10

<210> SEQ ID NO 95
<211> LENGTH: 21
<212> TYPE: PRT
<213> ORGANISM: Homo sapiens

<400> SEQUENCE: 95

Leu Leu Gln Asp Glu Phe Pro Gly Ile Pro Ser Pro Ile Asp Ala Ala
1               5                   10                  15

Val Glu Cys His Arg
            20

<210> SEQ ID NO 96
<211> LENGTH: 11
<212> TYPE: PRT
<213> ORGANISM: Homo sapiens

<400> SEQUENCE: 96

Asn Phe Pro Ser Pro Val Asp Ala Ala Phe Arg
1               5                   10

<210> SEQ ID NO 97
<211> LENGTH: 10
<212> TYPE: PRT
<213> ORGANISM: Homo sapiens

<400> SEQUENCE: 97
```

Gln Gly His Asn Ser Val Phe Leu Ile Lys
1               5                   10

<210> SEQ ID NO 98
<211> LENGTH: 16
<212> TYPE: PRT
<213> ORGANISM: Homo sapiens

<400> SEQUENCE: 98

Ser Gly Ala Gln Ala Thr Trp Thr Glu Leu Pro Trp Pro His Glu Lys
1               5                   10                  15

<210> SEQ ID NO 99
<211> LENGTH: 9
<212> TYPE: PRT
<213> ORGANISM: Homo sapiens

<400> SEQUENCE: 99

Val Asp Gly Ala Leu Cys Met Glu Lys
1               5

<210> SEQ ID NO 100
<211> LENGTH: 13
<212> TYPE: PRT
<213> ORGANISM: Homo sapiens

<400> SEQUENCE: 100

Trp Lys Asn Phe Pro Ser Pro Val Asp Ala Ala Phe Arg
1               5                   10

<210> SEQ ID NO 101
<211> LENGTH: 462
<212> TYPE: PRT
<213> ORGANISM: Homo sapiens

<400> SEQUENCE: 101

Met Ala Arg Val Leu Gly Ala Pro Val Ala Leu Gly Leu Trp Ser Leu
1               5                   10                  15

Cys Trp Ser Leu Ala Ile Ala Thr Pro Leu Pro Pro Thr Ser Ala His
                20                  25                  30

Gly Asn Val Ala Glu Gly Glu Thr Lys Pro Asp Pro Asp Val Thr Glu
                35                  40                  45

Arg Cys Ser Asp Gly Trp Ser Phe Asp Ala Thr Thr Leu Asp Asp Asn
        50                  55                  60

Gly Thr Met Leu Phe Phe Lys Gly Glu Phe Val Trp Lys Ser His Lys
65                  70                  75                  80

Trp Asp Arg Glu Leu Ile Ser Glu Arg Trp Lys Asn Phe Pro Ser Pro
                85                  90                  95

Val Asp Ala Ala Phe Arg Gln Gly His Asn Ser Val Phe Leu Ile Lys
                100                 105                 110

Gly Asp Lys Val Trp Val Tyr Pro Pro Glu Lys Lys Glu Lys Gly Tyr
                115                 120                 125

Pro Lys Leu Leu Gln Asp Glu Phe Pro Gly Ile Pro Ser Pro Leu Asp
        130                 135                 140

Ala Ala Val Glu Cys His Arg Gly Glu Cys Gln Ala Glu Gly Val Leu
145                 150                 155                 160

Phe Phe Gln Gly Asp Arg Glu Trp Phe Trp Asp Leu Ala Thr Gly Thr
                165                 170                 175

Met Lys Glu Arg Ser Trp Pro Ala Val Gly Asn Cys Ser Ser Ala Leu
                180                 185                 190

```
Arg Trp Leu Gly Arg Tyr Tyr Cys Phe Gln Gly Asn Gln Phe Leu Arg
            195                 200                 205

Phe Asp Pro Val Arg Gly Glu Val Pro Pro Arg Tyr Pro Arg Asp Val
210                 215                 220

Arg Asp Tyr Phe Met Pro Cys Pro Gly Arg Gly His Gly His Arg Asn
225                 230                 235                 240

Gly Thr Gly His Gly Asn Ser Thr His His Gly Pro Glu Tyr Met Arg
            245                 250                 255

Cys Ser Pro His Leu Val Leu Ser Ala Leu Thr Ser Asp Asn His Gly
            260                 265                 270

Ala Thr Tyr Ala Phe Ser Gly Thr His Tyr Trp Arg Leu Asp Thr Ser
            275                 280                 285

Arg Asp Gly Trp His Ser Trp Pro Ile Ala His Gln Trp Pro Gln Gly
290                 295                 300

Pro Ser Ala Val Asp Ala Ala Phe Ser Trp Glu Glu Lys Leu Tyr Leu
305                 310                 315                 320

Val Gln Gly Thr Gln Val Tyr Val Phe Leu Thr Lys Gly Gly Tyr Thr
            325                 330                 335

Leu Val Ser Gly Tyr Pro Lys Arg Leu Glu Lys Glu Val Gly Thr Pro
            340                 345                 350

His Gly Ile Ile Leu Asp Ser Val Asp Ala Ala Phe Ile Cys Pro Gly
            355                 360                 365

Ser Ser Arg Leu His Ile Met Ala Gly Arg Arg Leu Trp Trp Leu Asp
370                 375                 380

Leu Lys Ser Gly Ala Gln Ala Thr Trp Thr Glu Leu Pro Trp Pro His
385                 390                 395                 400

Glu Lys Val Asp Gly Ala Leu Cys Met Glu Lys Ser Leu Gly Pro Asn
            405                 410                 415

Ser Cys Ser Ala Asn Gly Pro Gly Leu Tyr Leu Ile His Gly Pro Asn
            420                 425                 430

Leu Tyr Cys Tyr Ser Asp Val Glu Lys Leu Asn Ala Ala Lys Ala Leu
            435                 440                 445

Pro Gln Pro Gln Asn Val Thr Ser Leu Leu Gly Cys Thr His
            450                 455                 460

<210> SEQ ID NO 102
<211> LENGTH: 8
<212> TYPE: PRT
<213> ORGANISM: Homo sapiens

<400> SEQUENCE: 102

Trp Ala Asn Gln Cys Asn Tyr Arg
1               5

<210> SEQ ID NO 103
<211> LENGTH: 240
<212> TYPE: PRT
<213> ORGANISM: Homo sapiens

<400> SEQUENCE: 103

Met Thr Leu Phe Pro Val Leu Leu Phe Leu Val Ala Gly Leu Leu Pro
1               5                   10                  15

Ser Phe Pro Ala Asn Glu Asp Lys Asp Pro Ala Phe Thr Ala Leu Leu
            20                  25                  30

Thr Thr Gln Thr Gln Val Gln Arg Glu Ile Val Asn Lys His Asn Glu
            35                  40                  45
```

```
Leu Arg Arg Ala Val Ser Pro Pro Ala Arg Asn Met Leu Lys Met Glu
        50                  55                  60
Trp Asn Lys Glu Ala Ala Asn Ala Gln Lys Trp Ala Asn Gln Cys
65                  70                  75                  80
Asn Tyr Arg His Ser Asn Pro Lys Asp Arg Met Thr Ser Leu Lys Cys
                85                  90                  95
Gly Glu Asn Leu Tyr Met Ser Ser Ala Ser Ser Ser Trp Ser Gln Ala
                100                 105                 110
Ile Gln Ser Trp Phe Asp Glu Tyr Asn Asp Phe Asp Phe Gly Val Gly
            115                 120                 125
Pro Lys Thr Pro Asn Ala Val Val Gly His Tyr Thr Gln Val Val Trp
            130                 135                 140
Tyr Ser Ser Tyr Leu Val Gly Cys Gly Asn Ala Tyr Cys Pro Asn Gln
145                 150                 155                 160
Lys Val Leu Lys Tyr Tyr Tyr Val Cys Gln Tyr Cys Pro Ala Gly Asn
                165                 170                 175
Trp Ala Asn Arg Leu Tyr Val Pro Tyr Glu Gln Gly Ala Pro Cys Ala
                180                 185                 190
Ser Cys Pro Asp Asn Cys Asp Asp Gly Leu Cys Thr Asn Gly Cys Lys
            195                 200                 205
Tyr Glu Asp Leu Tyr Ser Asn Cys Lys Ser Leu Lys Leu Thr Leu Thr
210                 215                 220
Cys Lys His Gln Leu Val Arg Asp Ser Cys Lys Ala Ser Cys Asn Cys
225                 230                 235                 240

<210> SEQ ID NO 104
<211> LENGTH: 10
<212> TYPE: PRT
<213> ORGANISM: Homo sapiens

<400> SEQUENCE: 104

Asp Pro Ala Ile Thr Ser Ile Leu Glu Lys
1               5                   10

<210> SEQ ID NO 105
<211> LENGTH: 15
<212> TYPE: PRT
<213> ORGANISM: Homo sapiens

<400> SEQUENCE: 105

Ser Arg Asn Pro Gly Ser Ser Cys Ile Gly Ala Asp Pro Asn Arg
1               5                   10                  15

<210> SEQ ID NO 106
<211> LENGTH: 23
<212> TYPE: PRT
<213> ORGANISM: Homo sapiens

<400> SEQUENCE: 106

Gly Ala Ser Asp Asn Pro Cys Ser Glu Val Tyr His Gly Pro His Ala
1               5                   10                  15

Asn Ser Glu Val Glu Val Lys
            20

<210> SEQ ID NO 107
<211> LENGTH: 8
<212> TYPE: PRT
<213> ORGANISM: Homo sapiens
```

<400> SEQUENCE: 107

Ser Val Val Asp Phe Ile Gln Lys
1               5

<210> SEQ ID NO 108
<211> LENGTH: 13
<212> TYPE: PRT
<213> ORGANISM: Homo sapiens

<400> SEQUENCE: 108

Asn Pro Gly Ser Ser Cys Ile Gly Ala Asp Pro Asn Arg
1               5                   10

<210> SEQ ID NO 109
<211> LENGTH: 420
<212> TYPE: PRT
<213> ORGANISM: Homo sapiens

<400> SEQUENCE: 109

Met Arg Trp Ile Leu Phe Ile Gly Ala Leu Ile Gly Ser Ser Ile Cys
1               5                   10                  15

Gly Gln Glu Lys Phe Phe Gly Asp Gln Val Leu Arg Ile Asn Val Arg
                20                  25                  30

Asn Gly Asp Glu Ile Ser Lys Leu Ser Gln Leu Val Asn Ser Asn Asn
            35                  40                  45

Leu Lys Leu Asn Phe Trp Lys Ser Pro Ser Ser Phe Asn Arg Pro Val
    50                  55                  60

Asp Val Leu Val Pro Ser Val Ser Leu Gln Ala Phe Lys Ser Phe Leu
65                  70                  75                  80

Arg Ser Gln Gly Leu Glu Tyr Ala Val Thr Ile Glu Asp Leu Gln Ala
                85                  90                  95

Leu Leu Asp Asn Glu Asp Glu Met Gln His Asn Glu Gly Gln Glu
                100                 105                 110

Arg Ser Ser Asn Asn Phe Asn Tyr Gly Ala Tyr His Ser Leu Glu Ala
            115                 120                 125

Ile Tyr His Glu Met Asp Asn Ile Ala Ala Asp Phe Pro Asp Leu Ala
130                 135                 140

Arg Arg Val Lys Ile Gly His Ser Phe Glu Asn Arg Pro Met Tyr Val
145                 150                 155                 160

Leu Lys Phe Ser Thr Gly Lys Gly Val Arg Arg Pro Ala Val Trp Leu
                165                 170                 175

Asn Ala Gly Ile His Ser Arg Glu Trp Ile Ser Gln Ala Thr Ala Ile
            180                 185                 190

Trp Thr Ala Arg Lys Ile Val Ser Asp Tyr Gln Arg Asp Pro Ala Ile
    195                 200                 205

Thr Ser Ile Leu Glu Lys Met Asp Ile Phe Leu Leu Pro Val Ala Asn
210                 215                 220

Pro Asp Gly Tyr Val Tyr Thr Gln Thr Gln Asn Arg Leu Trp Arg Lys
225                 230                 235                 240

Thr Arg Ser Arg Asn Pro Gly Ser Ser Cys Ile Gly Ala Asp Pro Asn
                245                 250                 255

Arg Asn Trp Asn Ala Ser Phe Ala Gly Lys Gly Ala Ser Asp Asn Pro
            260                 265                 270

Cys Ser Glu Val Tyr His Gly Pro His Ala Asn Ser Glu Val Glu Val
    275                 280                 285

Lys Ser Val Val Asp Phe Ile Gln Lys His Gly Asn Phe Lys Gly Phe

```
                    290                 295                 300

Ile Asp Leu His Ser Tyr Ser Gln Leu Leu Met Tyr Pro Tyr Gly Tyr
305                 310                 315                 320

Ser Val Lys Lys Ala Pro Asp Ala Glu Glu Leu Asp Lys Val Ala Arg
                325                 330                 335

Leu Ala Ala Lys Ala Leu Ala Ser Val Ser Gly Thr Glu Tyr Gln Val
            340                 345                 350

Gly Pro Thr Cys Thr Thr Val Tyr Pro Ala Ser Gly Ser Ser Ile Asp
        355                 360                 365

Trp Ala Tyr Asp Asn Gly Ile Lys Phe Ala Phe Thr Phe Glu Leu Arg
    370                 375                 380

Asp Thr Gly Thr Tyr Gly Phe Leu Leu Pro Ala Asn Gln Ile Ile Pro
385                 390                 395                 400

Thr Ala Glu Glu Thr Trp Leu Gly Leu Lys Thr Ile Met Glu His Val
                405                 410                 415

Arg Asp Asn Leu
            420

<210> SEQ ID NO 110
<211> LENGTH: 23
<212> TYPE: PRT
<213> ORGANISM: Homo sapiens

<400> SEQUENCE: 110

Gly Ser Gln Thr Gln Ser His Pro Asp Leu Gly Thr Glu Gly Cys Trp
1               5                   10                  15

Asp Gln Leu Ser Ala Pro Arg
            20

<210> SEQ ID NO 111
<211> LENGTH: 8
<212> TYPE: PRT
<213> ORGANISM: Homo sapiens

<400> SEQUENCE: 111

Thr Phe Thr Leu Leu Asp Pro Lys
1               5

<210> SEQ ID NO 112
<211> LENGTH: 576
<212> TYPE: PRT
<213> ORGANISM: Homo sapiens

<400> SEQUENCE: 112

Met Ala Gln Gly Val Leu Trp Ile Leu Leu Gly Leu Leu Trp Ser
1               5                   10                  15

Asp Pro Gly Thr Ala Ser Leu Pro Leu Met Asp Ser Val Ile Gln
                20                  25                  30

Ala Leu Ala Glu Leu Glu Gln Lys Val Pro Ala Ala Lys Thr Arg His
            35                  40                  45

Thr Ala Ser Ala Trp Leu Met Ser Ala Pro Asn Ser Gly Pro His Asn
50                  55                  60

Arg Leu Tyr His Phe Leu Leu Gly Ala Trp Ser Leu Asn Ala Thr Glu
65                  70                  75                  80

Leu Asp Pro Cys Pro Leu Ser Pro Glu Leu Leu Gly Leu Thr Lys Glu
                85                  90                  95

Val Ala Arg His Asp Val Arg Glu Gly Lys Glu Tyr Gly Val Val Leu
                100                 105                 110
```

```
Ala Pro Asp Gly Ser Thr Val Ala Val Glu Pro Leu Leu Ala Gly Leu
    115                 120                 125

Glu Ala Gly Leu Gln Gly Arg Arg Val Ile Asn Leu Pro Leu Asp Ser
130                 135                 140

Met Ala Ala Pro Trp Glu Thr Gly Asp Thr Phe Pro Asp Val Val Ala
145                 150                 155                 160

Ile Ala Pro Asp Val Arg Ala Thr Ser Ser Pro Gly Leu Arg Asp Gly
                165                 170                 175

Ser Pro Asp Val Thr Thr Ala Asp Ile Gly Ala Asn Thr Pro Asp Ala
                180                 185                 190

Thr Lys Gly Cys Pro Asp Val Gln Ala Ser Leu Pro Asp Ala Lys Ala
            195                 200                 205

Lys Ser Pro Pro Thr Met Val Asp Ser Leu Leu Ala Val Thr Leu Ala
210                 215                 220

Gly Asn Leu Gly Leu Thr Phe Leu Arg Gly Ser Gln Thr Gln Ser His
225                 230                 235                 240

Pro Asp Leu Gly Thr Glu Gly Cys Trp Asp Gln Leu Ser Ala Pro Arg
                245                 250                 255

Thr Phe Thr Leu Leu Asp Pro Lys Ala Ser Leu Leu Thr Met Ala Phe
                260                 265                 270

Leu Asn Gly Ala Leu Asp Gly Val Ile Leu Gly Asp Tyr Leu Ser Arg
            275                 280                 285

Thr Pro Glu Pro Arg Pro Ser Leu Ser His Leu Leu Ser Gln Tyr Tyr
    290                 295                 300

Gly Ala Gly Val Ala Arg Asp Pro Gly Phe Arg Ser Asn Phe Arg Arg
305                 310                 315                 320

Gln Asn Gly Ala Ala Leu Thr Ser Ala Ser Ile Leu Ala Gln Gln Val
                325                 330                 335

Trp Gly Thr Leu Val Leu Leu Gln Arg Leu Glu Pro Val His Leu Gln
                340                 345                 350

Leu Gln Cys Met Ser Gln Glu Gln Leu Ala Gln Val Ala Ala Asn Ala
            355                 360                 365

Thr Lys Glu Phe Thr Glu Ala Phe Leu Gly Cys Pro Ala Ile His Pro
    370                 375                 380

Arg Cys Arg Trp Gly Ala Ala Pro Tyr Arg Gly Arg Pro Lys Leu Leu
385                 390                 395                 400

Gln Leu Pro Leu Gly Phe Leu Tyr Val His His Thr Tyr Val Pro Ala
                405                 410                 415

Pro Pro Cys Thr Asp Phe Thr Arg Cys Ala Ala Asn Met Arg Ser Met
            420                 425                 430

Gln Arg Tyr His Gln Asp Thr Gln Gly Trp Gly Asp Ile Gly Tyr Ser
    435                 440                 445

Phe Val Val Gly Ser Asp Gly Tyr Val Tyr Glu Gly Arg Gly Trp His
450                 455                 460

Trp Val Gly Ala His Thr Leu Gly His Asn Ser Arg Gly Phe Gly Val
465                 470                 475                 480

Ala Ile Val Gly Asn Tyr Thr Ala Ala Leu Pro Thr Glu Ala Ala Leu
                485                 490                 495

Arg Thr Val Arg Asp Thr Leu Pro Ser Cys Ala Val Arg Ala Gly Leu
                500                 505                 510

Leu Arg Pro Asp Tyr Ala Leu Leu Gly His Arg Gln Leu Val Arg Thr
    515                 520                 525
```

Asp Cys Pro Gly Asp Ala Leu Phe Asp Leu Leu Arg Thr Trp Pro His
            530                 535                 540

Phe Thr Ala Thr Val Lys Pro Arg Pro Ala Arg Ser Val Ser Lys Arg
545                 550                 555                 560

Ser Arg Arg Glu Pro Pro Pro Arg Thr Leu Pro Ala Thr Asp Leu Gln
                565                 570                 575

<210> SEQ ID NO 113
<211> LENGTH: 17
<212> TYPE: PRT
<213> ORGANISM: Homo sapiens

<400> SEQUENCE: 113

Ala Arg Glu Gly Ser Glu Glu Asp Leu Asp Ala Leu Glu His Met Phe
1               5                   10                  15

Arg

<210> SEQ ID NO 114
<211> LENGTH: 13
<212> TYPE: PRT
<213> ORGANISM: Homo sapiens

<400> SEQUENCE: 114

Asp Pro Thr Ala Glu Gln Phe Gln Glu Glu Leu Glu Lys
1               5                   10

<210> SEQ ID NO 115
<211> LENGTH: 8
<212> TYPE: PRT
<213> ORGANISM: Homo sapiens

<400> SEQUENCE: 115

Phe Gln Gln Ala Ile Asp Ser Arg
1               5

<210> SEQ ID NO 116
<211> LENGTH: 11
<212> TYPE: PRT
<213> ORGANISM: Homo sapiens

<400> SEQUENCE: 116

Lys Thr Asn Pro Glu Ile Gln Ser Thr Leu Arg
1               5                   10

<210> SEQ ID NO 117
<211> LENGTH: 11
<212> TYPE: PRT
<213> ORGANISM: Homo sapiens

<400> SEQUENCE: 117

Met Ala Glu Ala Glu Leu Val Gln Glu Gly Lys
1               5                   10

<210> SEQ ID NO 118
<211> LENGTH: 14
<212> TYPE: PRT
<213> ORGANISM: Homo sapiens

<400> SEQUENCE: 118

Arg Asp Pro Thr Ala Glu Gln Phe Gln Glu Glu Leu Glu Lys
1               5                   10

<210> SEQ ID NO 119

```
<211> LENGTH: 12
<212> TYPE: PRT
<213> ORGANISM: Homo sapiens

<400> SEQUENCE: 119

Arg Met Ala Glu Ala Glu Leu Val Gln Glu Gly Lys
1               5                   10

<210> SEQ ID NO 120
<211> LENGTH: 13
<212> TYPE: PRT
<213> ORGANISM: Homo sapiens

<400> SEQUENCE: 120

Ser Leu Glu Glu Glu Lys Tyr Asp Met Ser Gly Ala Arg
1               5                   10

<210> SEQ ID NO 121
<211> LENGTH: 10
<212> TYPE: PRT
<213> ORGANISM: Homo sapiens

<400> SEQUENCE: 121

Thr Asn Pro Glu Ile Gln Ser Thr Leu Arg
1               5                   10

<210> SEQ ID NO 122
<211> LENGTH: 8
<212> TYPE: PRT
<213> ORGANISM: Homo sapiens

<400> SEQUENCE: 122

Val Tyr Ile Ile Gln Ala Cys Arg
1               5

<210> SEQ ID NO 123
<211> LENGTH: 242
<212> TYPE: PRT
<213> ORGANISM: Homo sapiens

<400> SEQUENCE: 123

Met Ser Asn Pro Arg Ser Leu Glu Glu Glu Lys Tyr Asp Met Ser Gly
1               5                   10                  15

Ala Arg Leu Ala Leu Ile Leu Cys Val Thr Lys Ala Arg Glu Gly Ser
                20                  25                  30

Glu Glu Asp Leu Asp Ala Leu Glu His Met Phe Arg Gln Leu Arg Phe
            35                  40                  45

Glu Ser Thr Met Lys Arg Asp Pro Thr Ala Glu Gln Phe Gln Glu Glu
        50                  55                  60

Leu Glu Lys Phe Gln Gln Ala Ile Asp Ser Arg Glu Asp Pro Val Ser
65                  70                  75                  80

Cys Ala Phe Val Val Leu Met Ala His Gly Arg Glu Gly Phe Leu Lys
                85                  90                  95

Gly Glu Asp Gly Glu Met Val Lys Leu Glu Asn Leu Phe Glu Ala Leu
                100                 105                 110

Asn Asn Lys Asn Cys Gln Ala Leu Arg Ala Lys Pro Lys Val Tyr Ile
            115                 120                 125

Ile Gln Ala Cys Arg Gly Glu Gln Arg Asp Pro Gly Glu Thr Val Gly
        130                 135                 140

Gly Asp Glu Ile Val Met Val Ile Lys Asp Ser Pro Gln Thr Ile Pro
145                 150                 155                 160
```

```
Thr Tyr Thr Asp Ala Leu His Val Tyr Ser Thr Val Glu Gly Tyr Ile
                165                 170                 175

Ala Tyr Arg His Asp Gln Lys Gly Ser Cys Phe Ile Gln Thr Leu Val
            180                 185                 190

Asp Val Phe Thr Lys Arg Lys Gly His Ile Leu Glu Leu Leu Thr Glu
        195                 200                 205

Val Thr Arg Arg Met Ala Glu Ala Glu Leu Val Gln Glu Gly Lys Ala
    210                 215                 220

Arg Lys Thr Asn Pro Glu Ile Gln Ser Thr Leu Arg Lys Arg Leu Tyr
225                 230                 235                 240

Leu Gln

<210> SEQ ID NO 124
<211> LENGTH: 9
<212> TYPE: PRT
<213> ORGANISM: Homo sapiens

<400> SEQUENCE: 124

Leu Leu Ile Tyr Gly Ala Ser Thr Arg
1               5

<210> SEQ ID NO 125
<211> LENGTH: 129
<212> TYPE: PRT
<213> ORGANISM: Homo sapiens

<400> SEQUENCE: 125

Met Glu Ala Pro Ala Gln Leu Leu Phe Leu Leu Leu Leu Trp Leu Pro
1               5                   10                  15

Asp Thr Thr Gly Glu Ile Val Met Thr Gln Ser Pro Ala Thr Leu Ser
            20                  25                  30

Val Ser Pro Gly Glu Arg Ala Thr Leu Ser Cys Arg Ala Ser Gln Ser
        35                  40                  45

Val Ser Asn Asn Leu Ala Trp Tyr Gln Gln Lys Pro Gly Gln Pro Pro
    50                  55                  60

Arg Leu Leu Ile Tyr Gly Ala Ser Thr Arg Ala Thr Gly Ile Pro Ala
65                  70                  75                  80

Arg Phe Ser Gly Ser Gly Ser Gly Thr Glu Phe Thr Leu Thr Ile Ser
                85                  90                  95

Arg Leu Gln Ser Glu Asp Phe Ala Val Tyr Tyr Cys Gln Gln Tyr Asn
            100                 105                 110

Asn Trp Pro Pro Trp Thr Phe Gly Gln Gly Thr Arg Val Glu Ile Lys
        115                 120                 125

Arg

<210> SEQ ID NO 126
<211> LENGTH: 18
<212> TYPE: PRT
<213> ORGANISM: Homo sapiens

<400> SEQUENCE: 126

Glu Ile Val Met Thr Gln Ser Pro Val Thr Leu Ser Val Ser Pro Gly
1               5                   10                  15

Glu Arg

<210> SEQ ID NO 127
<211> LENGTH: 109
```

<212> TYPE: PRT
<213> ORGANISM: Homo sapiens

<400> SEQUENCE: 127

Glu Ile Val Met Thr Gln Ser Pro Val Thr Leu Ser Val Ser Pro Gly
1               5                   10                  15

Glu Arg Ala Thr Leu Ser Cys Arg Ala Ser Gln Ser Ile Ser Asn Ser
            20                  25                  30

Tyr Leu Ala Trp Tyr Gln Gln Lys Pro Ser Gly Ser Pro Arg Leu Leu
        35                  40                  45

Ile Tyr Gly Ala Ser Thr Arg Ala Thr Gly Ile Pro Ala Arg Phe Ser
    50                  55                  60

Gly Ser Gly Ser Gly Thr Glu Phe Thr Leu Thr Ile Ser Ser Leu Gln
65                  70                  75                  80

Ser Glu Asp Phe Ala Val Tyr Tyr Cys Gln Gln Tyr Asn Asn Trp Pro
                85                  90                  95

Pro Thr Phe Gly Gln Gly Thr Arg Val Glu Ile Lys Arg
            100                 105

<210> SEQ ID NO 128
<211> LENGTH: 7
<212> TYPE: PRT
<213> ORGANISM: Homo sapiens

<400> SEQUENCE: 128

Ala Ala Cys Leu Leu Pro Lys
1               5

<210> SEQ ID NO 129
<211> LENGTH: 12
<212> TYPE: PRT
<213> ORGANISM: Homo sapiens

<400> SEQUENCE: 129

Ala Ala Phe Thr Glu Cys Cys Gln Ala Ala Asp Lys
1               5                   10

<210> SEQ ID NO 130
<211> LENGTH: 19
<212> TYPE: PRT
<213> ORGANISM: Homo sapiens

<400> SEQUENCE: 130

Ala Ala Phe Thr Glu Cys Cys Gln Ala Ala Asp Lys Ala Ala Cys Leu
1               5                   10                  15

Leu Pro Lys

<210> SEQ ID NO 131
<211> LENGTH: 13
<212> TYPE: PRT
<213> ORGANISM: Homo sapiens

<400> SEQUENCE: 131

Ala Asp Asp Lys Glu Thr Cys Phe Ala Glu Glu Gly Lys
1               5                   10

<210> SEQ ID NO 132
<211> LENGTH: 14
<212> TYPE: PRT
<213> ORGANISM: Homo sapiens

<400> SEQUENCE: 132

```
Ala Asp Asp Lys Glu Thr Cys Phe Ala Glu Glu Gly Lys Lys
1               5                   10
```

<210> SEQ ID NO 133
<211> LENGTH: 8
<212> TYPE: PRT
<213> ORGANISM: Homo sapiens

<400> SEQUENCE: 133

```
Ala Glu Phe Ala Glu Val Ser Lys
1               5
```

<210> SEQ ID NO 134
<211> LENGTH: 15
<212> TYPE: PRT
<213> ORGANISM: Homo sapiens

<400> SEQUENCE: 134

```
Ala Glu Phe Ala Glu Val Ser Lys Leu Val Thr Asp Leu Thr Lys
1               5                   10                  15
```

<210> SEQ ID NO 135
<211> LENGTH: 7
<212> TYPE: PRT
<213> ORGANISM: Homo sapiens

<400> SEQUENCE: 135

```
Ala Thr Lys Glu Gln Ile Lys
1               5
```

<210> SEQ ID NO 136
<211> LENGTH: 19
<212> TYPE: PRT
<213> ORGANISM: Homo sapiens

<400> SEQUENCE: 136

```
Ala Thr Lys Glu Gln Ile Lys Ala Val Met Asp Asp Phe Ala Ala Phe
1               5                   10                  15

Val Glu Lys
```

<210> SEQ ID NO 137
<211> LENGTH: 12
<212> TYPE: PRT
<213> ORGANISM: Homo sapiens

<400> SEQUENCE: 137

```
Ala Val Met Asp Asp Phe Ala Ala Phe Val Glu Lys
1               5                   10
```

<210> SEQ ID NO 138
<211> LENGTH: 10
<212> TYPE: PRT
<213> ORGANISM: Homo sapiens

<400> SEQUENCE: 138

```
Cys Ala Ser Ile Gln Lys Phe Gly Glu Arg
1               5                   10
```

<210> SEQ ID NO 139
<211> LENGTH: 13
<212> TYPE: PRT
<213> ORGANISM: Homo sapiens

<400> SEQUENCE: 139

```
Cys Cys Ala Ala Ala Asp Pro His Glu Cys Tyr Ala Lys
1               5                   10

<210> SEQ ID NO 140
<211> LENGTH: 16
<212> TYPE: PRT
<213> ORGANISM: Homo sapiens

<400> SEQUENCE: 140

Cys Cys Lys Ala Asp Asp Lys Glu Thr Cys Phe Ala Glu Glu Gly Lys
1               5                   10                  15

<210> SEQ ID NO 141
<211> LENGTH: 8
<212> TYPE: PRT
<213> ORGANISM: Homo sapiens

<400> SEQUENCE: 141

Cys Cys Lys His Pro Glu Ala Lys
1               5

<210> SEQ ID NO 142
<211> LENGTH: 9
<212> TYPE: PRT
<213> ORGANISM: Homo sapiens

<400> SEQUENCE: 142

Cys Cys Thr Glu Ser Leu Val Asn Arg
1               5

<210> SEQ ID NO 143
<211> LENGTH: 25
<212> TYPE: PRT
<213> ORGANISM: Homo sapiens

<400> SEQUENCE: 143

Cys Cys Thr Glu Ser Leu Val Asn Arg Arg Pro Cys Phe Ser Ala Leu
1               5                   10                  15

Glu Val Asp Glu Thr Tyr Val Pro Lys
            20                  25

<210> SEQ ID NO 144
<211> LENGTH: 8
<212> TYPE: PRT
<213> ORGANISM: Homo sapiens

<400> SEQUENCE: 144

Asp Asp Asn Pro Asn Leu Pro Arg
1               5

<210> SEQ ID NO 145
<211> LENGTH: 10
<212> TYPE: PRT
<213> ORGANISM: Homo sapiens

<400> SEQUENCE: 145

Asp Ala His Lys Ser Glu Val Ala His Arg
1               5                   10

<210> SEQ ID NO 146
<211> LENGTH: 8
<212> TYPE: PRT
<213> ORGANISM: Homo sapiens
```

<400> SEQUENCE: 146

Asp Leu Gly Glu Glu Asn Phe Lys
1               5

<210> SEQ ID NO 147
<211> LENGTH: 10
<212> TYPE: PRT
<213> ORGANISM: Homo sapiens

<400> SEQUENCE: 147

Asp Val Cys Lys Asn Tyr Ala Glu Ala Lys
1               5                   10

<210> SEQ ID NO 148
<211> LENGTH: 13
<212> TYPE: PRT
<213> ORGANISM: Homo sapiens

<400> SEQUENCE: 148

Asp Val Phe Leu Gly Met Phe Leu Tyr Glu Tyr Ala Arg
1               5                   10

<210> SEQ ID NO 149
<211> LENGTH: 10
<212> TYPE: PRT
<213> ORGANISM: Homo sapiens

<400> SEQUENCE: 149

Glu Cys Cys Glu Lys Pro Leu Leu Glu Lys
1               5                   10

<210> SEQ ID NO 150
<211> LENGTH: 19
<212> TYPE: PRT
<213> ORGANISM: Homo sapiens

<400> SEQUENCE: 150

Glu Phe Asn Ala Glu Thr Phe Thr Phe His Ala Asp Ile Cys Thr Leu
1               5                   10                  15

Ser Glu Lys

<210> SEQ ID NO 151
<211> LENGTH: 21
<212> TYPE: PRT
<213> ORGANISM: Homo sapiens

<400> SEQUENCE: 151

Glu Phe Asn Ala Glu Thr Phe Thr Phe His Ala Asp Ile Cys Thr Leu
1               5                   10                  15

Ser Glu Lys Glu Arg
            20

<210> SEQ ID NO 152
<211> LENGTH: 16
<212> TYPE: PRT
<213> ORGANISM: Homo sapiens

<400> SEQUENCE: 152

Glu Gln Leu Lys Ala Val Met Asp Asp Phe Ala Ala Phe Val Glu Lys
1               5                   10                  15

<210> SEQ ID NO 153
<211> LENGTH: 9

```
<212> TYPE: PRT
<213> ORGANISM: Homo sapiens

<400> SEQUENCE: 153

Glu Thr Cys Phe Ala Glu Glu Gly Lys
1               5

<210> SEQ ID NO 154
<211> LENGTH: 10
<212> TYPE: PRT
<213> ORGANISM: Homo sapiens

<400> SEQUENCE: 154

Glu Thr Cys Phe Ala Glu Glu Gly Lys Lys
1               5                   10

<210> SEQ ID NO 155
<211> LENGTH: 12
<212> TYPE: PRT
<213> ORGANISM: Homo sapiens

<400> SEQUENCE: 155

Glu Thr Tyr Gly Glu Met Ala Asp Cys Cys Ala Lys
1               5                   10

<210> SEQ ID NO 156
<211> LENGTH: 10
<212> TYPE: PRT
<213> ORGANISM: Homo sapiens

<400> SEQUENCE: 156

Phe Lys Asp Leu Gly Glu Glu Asn Phe Lys
1               5                   10

<210> SEQ ID NO 157
<211> LENGTH: 11
<212> TYPE: PRT
<213> ORGANISM: Homo sapiens

<400> SEQUENCE: 157

Phe Pro Lys Ala Glu Phe Ala Glu Val Ser Lys
1               5                   10

<210> SEQ ID NO 158
<211> LENGTH: 8
<212> TYPE: PRT
<213> ORGANISM: Homo sapiens

<400> SEQUENCE: 158

Phe Gln Asn Ala Leu Leu Val Arg
1               5

<210> SEQ ID NO 159
<211> LENGTH: 11
<212> TYPE: PRT
<213> ORGANISM: Homo sapiens

<400> SEQUENCE: 159

His Pro Asp Tyr Ser Val Val Leu Leu Leu Arg
1               5                   10

<210> SEQ ID NO 160
<211> LENGTH: 14
<212> TYPE: PRT
<213> ORGANISM: Homo sapiens
```

<400> SEQUENCE: 160

His Pro Tyr Phe Tyr Ala Pro Glu Leu Leu Phe Phe Ala Lys
1               5                   10

<210> SEQ ID NO 161
<211> LENGTH: 11
<212> TYPE: PRT
<213> ORGANISM: Homo sapiens

<400> SEQUENCE: 161

Leu Ala Lys Thr Tyr Glu Thr Thr Leu Glu Lys
1               5                   10

<210> SEQ ID NO 162
<211> LENGTH: 8
<212> TYPE: PRT
<213> ORGANISM: Homo sapiens

<400> SEQUENCE: 162

Leu Cys Thr Val Ala Thr Leu Arg
1               5

<210> SEQ ID NO 163
<211> LENGTH: 20
<212> TYPE: PRT
<213> ORGANISM: Homo sapiens

<400> SEQUENCE: 163

Leu Cys Thr Val Ala Thr Leu Arg Glu Thr Tyr Gly Glu Met Ala Asp
1               5                   10                  15

Cys Cys Ala Lys
            20

<210> SEQ ID NO 164
<211> LENGTH: 9
<212> TYPE: PRT
<213> ORGANISM: Homo sapiens

<400> SEQUENCE: 164

Leu Asp Glu Leu Arg Asp Glu Gly Lys
1               5

<210> SEQ ID NO 165
<211> LENGTH: 14
<212> TYPE: PRT
<213> ORGANISM: Homo sapiens

<400> SEQUENCE: 165

Leu Asp Glu Leu Arg Asp Glu Gly Lys Ala Ser Ser Ala Lys
1               5                   10

<210> SEQ ID NO 166
<211> LENGTH: 8
<212> TYPE: PRT
<213> ORGANISM: Homo sapiens

<400> SEQUENCE: 166

Leu Lys Cys Ala Ser Leu Gln Lys
1               5

<210> SEQ ID NO 167
<211> LENGTH: 12
<212> TYPE: PRT

-continued

```
<213> ORGANISM: Homo sapiens

<400> SEQUENCE: 167

Leu Lys Glu Cys Cys Glu Lys Pro Leu Leu Glu Lys
1               5                   10

<210> SEQ ID NO 168
<211> LENGTH: 7
<212> TYPE: PRT
<213> ORGANISM: Homo sapiens

<400> SEQUENCE: 168

Leu Ser Gln Arg Phe Pro Lys
1               5

<210> SEQ ID NO 169
<211> LENGTH: 16
<212> TYPE: PRT
<213> ORGANISM: Homo sapiens

<400> SEQUENCE: 169

Leu Phe Ser Gln Arg Phe Pro Lys Ala Glu Phe Ala Glu Val Ser Lys
1               5                   10                  15

<210> SEQ ID NO 170
<211> LENGTH: 11
<212> TYPE: PRT
<213> ORGANISM: Homo sapiens

<400> SEQUENCE: 170

Leu Val Ala Ala Ser Gln Ala Ala Leu Gly Leu
1               5                   10

<210> SEQ ID NO 171
<211> LENGTH: 10
<212> TYPE: PRT
<213> ORGANISM: Homo sapiens

<400> SEQUENCE: 171

Leu Val Asn Glu Val Thr Glu Phe Ala Lys
1               5                   10

<210> SEQ ID NO 172
<211> LENGTH: 23
<212> TYPE: PRT
<213> ORGANISM: Homo sapiens

<400> SEQUENCE: 172

Ile Val Asn Glu Val Thr Glu Phe Ala Lys Thr Cys Val Ala Asp Glu
1               5                   10                  15

Ser Ala Glu Asn Cys Asp Lys
            20

<210> SEQ ID NO 173
<211> LENGTH: 22
<212> TYPE: PRT
<213> ORGANISM: Homo sapiens

<400> SEQUENCE: 173

Leu Val Arg Pro Glu Val Asp Val Met Cys Thr Ala Phe His Asp Asn
1               5                   10                  15

Glu Glu Thr Phe Leu Lys
            20
```

```
<210> SEQ ID NO 174
<211> LENGTH: 23
<212> TYPE: PRT
<213> ORGANISM: Homo sapiens

<400> SEQUENCE: 174

Leu Val Arg Pro Glu Val Asp Val Met Cys Thr Ala Phe His Asp Asn
1               5                   10                  15

Glu Glu Thr Phe Leu Lys Lys
            20

<210> SEQ ID NO 175
<211> LENGTH: 7
<212> TYPE: PRT
<213> ORGANISM: Homo sapiens

<400> SEQUENCE: 175

Leu Val Thr Asp Leu Thr Lys
1               5

<210> SEQ ID NO 176
<211> LENGTH: 12
<212> TYPE: PRT
<213> ORGANISM: Homo sapiens

<400> SEQUENCE: 176

Lys Leu Val Ala Ala Ser Gln Ala Ala Leu Gly Leu
1               5                   10

<210> SEQ ID NO 177
<211> LENGTH: 10
<212> TYPE: PRT
<213> ORGANISM: Homo sapiens

<400> SEQUENCE: 177

Lys Gln Thr Ala Leu Val Glu Leu Val Lys
1               5                   10

<210> SEQ ID NO 178
<211> LENGTH: 16
<212> TYPE: PRT
<213> ORGANISM: Homo sapiens

<400> SEQUENCE: 178

Lys Val Pro Gln Val Ser Thr Pro Thr Leu Val Glu Val Ser Arg
1               5                   10                  15

<210> SEQ ID NO 179
<211> LENGTH: 8
<212> TYPE: PRT
<213> ORGANISM: Homo sapiens

<400> SEQUENCE: 179

Lys Tyr Leu Tyr Glu Ile Ala Arg
1               5

<210> SEQ ID NO 180
<211> LENGTH: 25
<212> TYPE: PRT
<213> ORGANISM: Homo sapiens

<400> SEQUENCE: 180

Met Pro Cys Ala Glu Asp Tyr Ile Leu Ser Val Val Ile Leu Asn Gln
1               5                   10                  15
```

Ile Leu Cys Val Ile Leu His Glu Lys
            20                  25

<210> SEQ ID NO 181
<211> LENGTH: 8
<212> TYPE: PRT
<213> ORGANISM: Homo sapiens

<400> SEQUENCE: 181

Asn Glu Cys Phe Ile Gln His Lys
1               5

<210> SEQ ID NO 182
<211> LENGTH: 16
<212> TYPE: PRT
<213> ORGANISM: Homo sapiens

<400> SEQUENCE: 182

Asn Glu Cys Phe Leu Gln His Lys Asp Asp Asn Pro Asn Leu Pro Arg
1               5                   10                  15

<210> SEQ ID NO 183
<211> LENGTH: 8
<212> TYPE: PRT
<213> ORGANISM: Homo sapiens

<400> SEQUENCE: 183

Asn Ile Gly Lys Val Gly Ser Lys
1               5

<210> SEQ ID NO 184
<211> LENGTH: 6
<212> TYPE: PRT
<213> ORGANISM: Homo sapiens

<400> SEQUENCE: 184

Asn Tyr Ala Glu Ala Lys
1               5

<210> SEQ ID NO 185
<211> LENGTH: 19
<212> TYPE: PRT
<213> ORGANISM: Homo sapiens

<400> SEQUENCE: 185

Asn Tyr Ala Glu Ala Lys Asp Val Phe Ile Gly Met Phe Ile Tyr Glu
1               5                   10                  15

Tyr Ala Arg

<210> SEQ ID NO 186
<211> LENGTH: 11
<212> TYPE: PRT
<213> ORGANISM: Homo sapiens

<400> SEQUENCE: 186

Pro Leu Val Glu Glu Pro Gln Asn Leu Ile Lys
1               5                   10

<210> SEQ ID NO 187
<211> LENGTH: 13
<212> TYPE: PRT
<213> ORGANISM: Homo sapiens

<400> SEQUENCE: 187

Gln Glu Pro Glu Arg Asn Glu Cys Phe Leu Gln His Lys
1               5                   10

<210> SEQ ID NO 188
<211> LENGTH: 21
<212> TYPE: PRT
<213> ORGANISM: Homo sapiens

<400> SEQUENCE: 188

Gln Glu Pro Glu Arg Asn Glu Cys Phe Leu Gln His Lys Asp Asp Asn
1               5                   10                  15

Pro Asn Leu Pro Arg
            20

<210> SEQ ID NO 189
<211> LENGTH: 13
<212> TYPE: PRT
<213> ORGANISM: Homo sapiens

<400> SEQUENCE: 189

Gln Asn Cys Glu Leu Phe Glu Gln Leu Gly Glu Tyr Lys
1               5                   10

<210> SEQ ID NO 190
<211> LENGTH: 21
<212> TYPE: PRT
<213> ORGANISM: Homo sapiens

<400> SEQUENCE: 190

Gln Asn Cys Glu Leu Phe Glu Gln Leu Gly Glu Tyr Lys Phe Gln Asn
1               5                   10                  15

Ala Ile Ile Val Arg
            20

<210> SEQ ID NO 191
<211> LENGTH: 9
<212> TYPE: PRT
<213> ORGANISM: Homo sapiens

<400> SEQUENCE: 191

Gln Thr Ala Ile Val Glu Ile Val Lys
1               5

<210> SEQ ID NO 192
<211> LENGTH: 12
<212> TYPE: PRT
<213> ORGANISM: Homo sapiens

<400> SEQUENCE: 192

Arg His Pro Asp Tyr Ser Val Val Leu Leu Leu Arg
1               5                   10

<210> SEQ ID NO 193
<211> LENGTH: 23
<212> TYPE: PRT
<213> ORGANISM: Homo sapiens

<400> SEQUENCE: 193

Arg Met Pro Cys Ala Glu Asp Tyr Leu Ser Val Val Leu Lys Asn Gln
1               5                   10                  15

Leu Cys Val Leu His Glu Lys
            20

```
<210> SEQ ID NO 194
<211> LENGTH: 16
<212> TYPE: PRT
<213> ORGANISM: Homo sapiens

<400> SEQUENCE: 194

Arg Pro Cys Phe Ser Ala Leu Glu Val Asp Glu Thr Tyr Val Pro Lys
1               5                   10                  15

<210> SEQ ID NO 195
<211> LENGTH: 37
<212> TYPE: PRT
<213> ORGANISM: Homo sapiens

<400> SEQUENCE: 195

Ser His Cys Ile Ala Glu Val Glu Asn Asp Glu Met Pro Ala Asp Leu
1               5                   10                  15

Pro Ser Leu Ala Ala Asp Phe Val Glu Ser Lys Asp Val Cys Lys Asn
            20                  25                  30

Tyr Ala Glu Ala Lys
        35

<210> SEQ ID NO 196
<211> LENGTH: 27
<212> TYPE: PRT
<213> ORGANISM: Homo sapiens

<400> SEQUENCE: 196

Ser His Cys Ile Ala Glu Val Glu Asn Asp Glu Met Pro Ala Asp Leu
1               5                   10                  15

Pro Ser Leu Ala Ala Asp Phe Val Glu Ser Lys
            20                  25

<210> SEQ ID NO 197
<211> LENGTH: 31
<212> TYPE: PRT
<213> ORGANISM: Homo sapiens

<400> SEQUENCE: 197

Ser His Cys Ile Ala Glu Val Glu Asn Asp Glu Met Pro Ala Asp Leu
1               5                   10                  15

Pro Ser Leu Ala Ala Asp Phe Val Glu Ser Lys Asp Val Cys Lys
            20                  25                  30

<210> SEQ ID NO 198
<211> LENGTH: 9
<212> TYPE: PRT
<213> ORGANISM: Homo sapiens

<400> SEQUENCE: 198

Ser Leu His Thr Leu Phe Gly Asp Lys
1               5

<210> SEQ ID NO 199
<211> LENGTH: 17
<212> TYPE: PRT
<213> ORGANISM: Homo sapiens

<400> SEQUENCE: 199

Ser Leu His Thr Leu Phe Gly Asp Lys Leu Cys Thr Val Ala Thr Leu
1               5                   10                  15

Arg
```

<210> SEQ ID NO 200
<211> LENGTH: 13
<212> TYPE: PRT
<213> ORGANISM: Homo sapiens

<400> SEQUENCE: 200

Thr Cys Val Ala Asp Glu Ser Ala Glu Asn Cys Asp Lys
1               5                   10

<210> SEQ ID NO 201
<211> LENGTH: 22
<212> TYPE: PRT
<213> ORGANISM: Homo sapiens

<400> SEQUENCE: 201

Thr Cys Val Ala Asp Glu Ser Ala Glu Asn Cys Asp Lys Ser Leu His
1               5                   10                  15

Thr Leu Phe Gly Asp Lys
            20

<210> SEQ ID NO 202
<211> LENGTH: 30
<212> TYPE: PRT
<213> ORGANISM: Homo sapiens

<400> SEQUENCE: 202

Thr Cys Val Ala Asp Glu Ser Ala Glu Asn Cys Asp Lys Ser Leu His
1               5                   10                  15

Thr Leu Phe Gly Asp Lys Leu Cys Thr Val Ala Thr Leu Arg
            20                  25                  30

<210> SEQ ID NO 203
<211> LENGTH: 9
<212> TYPE: PRT
<213> ORGANISM: Homo sapiens

<400> SEQUENCE: 203

Thr Pro Val Ser Asp Arg Val Thr Lys
1               5

<210> SEQ ID NO 204
<211> LENGTH: 8
<212> TYPE: PRT
<213> ORGANISM: Homo sapiens

<400> SEQUENCE: 204

Thr Tyr Glu Thr Thr Leu Glu Lys
1               5

<210> SEQ ID NO 205
<211> LENGTH: 21
<212> TYPE: PRT
<213> ORGANISM: Homo sapiens

<400> SEQUENCE: 205

Thr Tyr Glu Thr Thr Ile Glu Lys Cys Cys Ala Ala Ala Asp Pro His
1               5                   10                  15

Glu Cys Tyr Ala Lys
            20

<210> SEQ ID NO 206
<211> LENGTH: 17

```
<212> TYPE: PRT
<213> ORGANISM: Homo sapiens

<400> SEQUENCE: 206

Val Phe Asp Glu Phe Lys Pro Leu Val Glu Glu Pro Gln Asn Leu Ile
1               5                   10                  15

Lys

<210> SEQ ID NO 207
<211> LENGTH: 17
<212> TYPE: PRT
<213> ORGANISM: Homo sapiens

<400> SEQUENCE: 207

Val His Thr Glu Cys Cys His Gly Asp Leu Leu Glu Cys Ala Asp Asp
1               5                   10                  15

Arg

<210> SEQ ID NO 208
<211> LENGTH: 22
<212> TYPE: PRT
<213> ORGANISM: Homo sapiens

<400> SEQUENCE: 208

Val His Thr Glu Cys Cys His Gly Asp Leu Leu Glu Cys Ala Asp Asp
1               5                   10                  15

Arg Ala Asp Leu Ala Lys
            20

<210> SEQ ID NO 209
<211> LENGTH: 34
<212> TYPE: PRT
<213> ORGANISM: Homo sapiens

<400> SEQUENCE: 209

Val His Thr Glu Cys Cys His Gly Asp Leu Leu Glu Cys Ala Asp Asp
1               5                   10                  15

Arg Ala Asp Leu Ala Lys Tyr Ile Cys Glu Asn Gln Asp Ser Ile Ser
            20                  25                  30

Ser Lys

<210> SEQ ID NO 210
<211> LENGTH: 14
<212> TYPE: PRT
<213> ORGANISM: Homo sapiens

<400> SEQUENCE: 210

Val Pro Gln Val Ser Thr Pro Thr Leu Val Glu Val Ser Arg
1               5                   10

<210> SEQ ID NO 211
<211> LENGTH: 12
<212> TYPE: PRT
<213> ORGANISM: Homo sapiens

<400> SEQUENCE: 211

Tyr Ile Cys Glu Asn Gln Asp Ser Ile Ser Ser Lys
1               5                   10

<210> SEQ ID NO 212
<211> LENGTH: 14
<212> TYPE: PRT
```

-continued

<213> ORGANISM: Homo sapiens

<400> SEQUENCE: 212

Tyr Ile Cys Glu Asn Gln Asp Ser Ile Ser Ser Lys Leu Lys
1               5                   10

<210> SEQ ID NO 213
<211> LENGTH: 7
<212> TYPE: PRT
<213> ORGANISM: Homo sapiens

<400> SEQUENCE: 213

Tyr Leu Tyr Glu Ile Ala Arg
1               5

<210> SEQ ID NO 214
<211> LENGTH: 8
<212> TYPE: PRT
<213> ORGANISM: Homo sapiens

<400> SEQUENCE: 214

Tyr Leu Tyr Glu Ile Ala Arg Arg
1               5

<210> SEQ ID NO 215
<211> LENGTH: 14
<212> TYPE: PRT
<213> ORGANISM: Homo sapiens

<400> SEQUENCE: 215

Tyr Lys Ala Ala Phe Thr Glu Cys Cys Gln Ala Ala Asp Lys
1               5                   10

<210> SEQ ID NO 216
<211> LENGTH: 21
<212> TYPE: PRT
<213> ORGANISM: Homo sapiens

<400> SEQUENCE: 216

Tyr Lys Ala Ala Phe Thr Glu Cys Cys Gln Ala Ala Asp Lys Ala Ala
1               5                   10                  15

Cys Leu Leu Pro Lys
            20

<210> SEQ ID NO 217
<211> LENGTH: 609
<212> TYPE: PRT
<213> ORGANISM: Homo sapiens

<400> SEQUENCE: 217

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
                20                  25                  30

His Arg Phe Lys Asp Leu Gly Glu Glu Asn Phe Lys Ala Leu Val Leu
            35                  40                  45

Ile Ala Phe Ala Gln Tyr Leu Gln Gln Cys Pro Phe Glu Asp His Val
        50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

```
Lys Leu Cys Thr Val Ala Thr Leu Arg Glu Thr Tyr Gly Glu Met Ala
                100                 105                 110

Asp Cys Cys Ala Lys Gln Glu Pro Glu Arg Asn Glu Cys Phe Leu Gln
                115                 120                 125

His Lys Asp Asp Asn Pro Asn Leu Pro Arg Leu Val Arg Pro Glu Val
            130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                    165                 170                 175

Glu Leu Leu Phe Phe Ala Lys Arg Tyr Lys Ala Ala Phe Thr Glu Cys
                180                 185                 190

Cys Gln Ala Ala Asp Lys Ala Ala Cys Leu Leu Pro Lys Leu Asp Glu
                195                 200                 205

Leu Arg Asp Glu Gly Lys Ala Ser Ser Ala Lys Gln Arg Leu Lys Cys
            210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
                260                 265                 270

Asp Leu Leu Glu Cys Ala Asp Asp Arg Ala Asp Leu Ala Lys Tyr Ile
            275                 280                 285

Cys Glu Asn Gln Asp Ser Ile Ser Ser Lys Leu Lys Glu Cys Cys Glu
                290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
                340                 345                 350

Met Phe Leu Tyr Glu Tyr Ala Arg Arg His Pro Asp Tyr Ser Val Val
            355                 360                 365

Leu Leu Leu Arg Leu Ala Lys Thr Tyr Glu Thr Thr Leu Glu Lys Cys
370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
                420                 425                 430

Val Arg Tyr Thr Lys Lys Val Pro Gln Val Ser Thr Pro Thr Leu Val
            435                 440                 445

Glu Val Ser Arg Asn Leu Gly Lys Val Gly Ser Lys Cys Cys Lys His
                450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
                500                 505                 510
```

```
Ser Ala Leu Glu Val Asp Glu Thr Tyr Val Pro Lys Glu Phe Asn Ala
        515                 520                 525

Glu Thr Phe Thr Phe His Ala Asp Ile Cys Thr Leu Ser Glu Lys Glu
    530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
        595                 600                 605

Leu

<210> SEQ ID NO 218
<211> LENGTH: 14
<212> TYPE: PRT
<213> ORGANISM: Homo sapiens

<400> SEQUENCE: 218

Ala Gly Glu Gln Val Thr Tyr Thr Cys Ala Thr Tyr Tyr Lys
1               5                   10

<210> SEQ ID NO 219
<211> LENGTH: 9
<212> TYPE: PRT
<213> ORGANISM: Homo sapiens

<400> SEQUENCE: 219

Cys Leu His Pro Cys Val Ile Ser Arg
1               5

<210> SEQ ID NO 220
<211> LENGTH: 11
<212> TYPE: PRT
<213> ORGANISM: Homo sapiens

<400> SEQUENCE: 220

Asp Gly Trp Ser Ala Gln Pro Thr Cys Ile Lys
1               5                   10

<210> SEQ ID NO 221
<211> LENGTH: 18
<212> TYPE: PRT
<213> ORGANISM: Homo sapiens

<400> SEQUENCE: 221

Asp Thr Ser Cys Val Asn Pro Pro Thr Val Gln Asn Ala Tyr Ile Val
1               5                   10                  15

Ser Arg

<210> SEQ ID NO 222
<211> LENGTH: 9
<212> TYPE: PRT
<213> ORGANISM: Homo sapiens

<400> SEQUENCE: 222

Glu Phe Asp His Asn Ser Asn Ile Arg
1               5

<210> SEQ ID NO 223
```

```
<211> LENGTH: 11
<212> TYPE: PRT
<213> ORGANISM: Homo sapiens

<400> SEQUENCE: 223

Glu Ile Met Glu Asn Tyr Asn Ile Ala Leu Arg
1               5                   10

<210> SEQ ID NO 224
<211> LENGTH: 11
<212> TYPE: PRT
<213> ORGANISM: Homo sapiens

<400> SEQUENCE: 224

Gly Asp Ala Val Cys Thr Glu Ser Gly Trp Arg
1               5                   10

<210> SEQ ID NO 225
<211> LENGTH: 19
<212> TYPE: PRT
<213> ORGANISM: Homo sapiens

<400> SEQUENCE: 225

Gly Asp Ala Val Cys Thr Glu Ser Gly Trp Arg Pro Leu Pro Ser Cys
1               5                   10                  15

Glu Glu Lys

<210> SEQ ID NO 226
<211> LENGTH: 9
<212> TYPE: PRT
<213> ORGANISM: Homo sapiens

<400> SEQUENCE: 226

Ile Asp Val His Leu Val Pro Asp Arg
1               5

<210> SEQ ID NO 227
<211> LENGTH: 10
<212> TYPE: PRT
<213> ORGANISM: Homo sapiens

<400> SEQUENCE: 227

Leu Ser Tyr Thr Cys Glu Gly Gly Phe Arg
1               5                   10

<210> SEQ ID NO 228
<211> LENGTH: 19
<212> TYPE: PRT
<213> ORGANISM: Homo sapiens

<400> SEQUENCE: 228

Ile Val Ser Ser Ala Met Glu Pro Asp Arg Glu Tyr His Phe Gly Gln
1               5                   10                  15

Ala Val Arg

<210> SEQ ID NO 229
<211> LENGTH: 23
<212> TYPE: PRT
<213> ORGANISM: Homo sapiens

<400> SEQUENCE: 229

Asn Thr Glu Ile Leu Thr Gly Ser Trp Ser Asp Gln Thr Tyr Pro Glu
1               5                   10                  15
```

Gly Thr Gln Ala Ile Tyr Lys
            20

<210> SEQ ID NO 230
<211> LENGTH: 10
<212> TYPE: PRT
<213> ORGANISM: Homo sapiens

<400> SEQUENCE: 230

Arg Pro Tyr Phe Pro Val Ala Val Gly Lys
1               5                   10

<210> SEQ ID NO 231
<211> LENGTH: 11
<212> TYPE: PRT
<213> ORGANISM: Homo sapiens

<400> SEQUENCE: 231

Ser Cys Asp Ile Pro Val Phe Met Asn Ala Arg
1               5                   10

<210> SEQ ID NO 232
<211> LENGTH: 14
<212> TYPE: PRT
<213> ORGANISM: Homo sapiens

<400> SEQUENCE: 232

Ser Ile Asp Val Ala Cys His Pro Gly Tyr Ala Leu Pro Lys
1               5                   10

<210> SEQ ID NO 233
<211> LENGTH: 10
<212> TYPE: PRT
<213> ORGANISM: Homo sapiens

<400> SEQUENCE: 233

Ser Leu Gly Asn Val Ile Met Val Cys Arg
1               5                   10

<210> SEQ ID NO 234
<211> LENGTH: 12
<212> TYPE: PRT
<213> ORGANISM: Homo sapiens

<400> SEQUENCE: 234

Ser Ser Asn Leu Ile Ile Leu Glu Glu His Leu Lys
1               5                   10

<210> SEQ ID NO 235
<211> LENGTH: 11
<212> TYPE: PRT
<213> ORGANISM: Homo sapiens

<400> SEQUENCE: 235

Ser Ser Gln Glu Ser Tyr Ala His Gly Thr Lys
1               5                   10

<210> SEQ ID NO 236
<211> LENGTH: 10
<212> TYPE: PRT
<213> ORGANISM: Homo sapiens

<400> SEQUENCE: 236

Thr Gly Asp Glu Ile Thr Tyr Gln Cys Arg
1               5                   10

<210> SEQ ID NO 237
<211> LENGTH: 10
<212> TYPE: PRT
<213> ORGANISM: Homo sapiens

<400> SEQUENCE: 237

Thr Gly Glu Ser Val Glu Phe Val Cys Lys
1               5                   10

<210> SEQ ID NO 238
<211> LENGTH: 9
<212> TYPE: PRT
<213> ORGANISM: Homo sapiens

<400> SEQUENCE: 238

Thr Lys Asn Asp Phe Thr Trp Phe Lys
1               5

<210> SEQ ID NO 239
<211> LENGTH: 15
<212> TYPE: PRT
<213> ORGANISM: Homo sapiens

<400> SEQUENCE: 239

Thr Thr Cys Trp Asp Gly Lys Leu Glu Tyr Pro Thr Cys Ala Lys
1               5                   10                  15

<210> SEQ ID NO 240
<211> LENGTH: 23
<212> TYPE: PRT
<213> ORGANISM: Homo sapiens

<400> SEQUENCE: 240

Val Ser Val Leu Cys Gln Glu Asn Tyr Leu Ile Gln Glu Gly Glu
1               5                   10                  15

Leu Thr Cys Lys Asp Gly Arg
            20

<210> SEQ ID NO 241
<211> LENGTH: 10
<212> TYPE: PRT
<213> ORGANISM: Homo sapiens

<400> SEQUENCE: 241

Trp Gln Ser Ile Pro Leu Cys Val Glu Lys
1               5                   10

<210> SEQ ID NO 242
<211> LENGTH: 13
<212> TYPE: PRT
<213> ORGANISM: Homo sapiens

<400> SEQUENCE: 242

Trp Ser Ser Pro Pro Gln Cys Glu Gly Leu Pro Cys Lys
1               5                   10

<210> SEQ ID NO 243
<211> LENGTH: 1231
<212> TYPE: PRT
<213> ORGANISM: Homo sapiens

<400> SEQUENCE: 243

Met Arg Leu Leu Ala Lys Ile Ile Cys Leu Met Leu Trp Ala Ile Cys

-continued

```
1               5                   10                  15
Val Ala Glu Asp Cys Asn Glu Leu Pro Pro Arg Arg Asn Thr Glu Ile
                20                  25                  30

Leu Thr Gly Ser Trp Ser Asp Gln Thr Tyr Pro Glu Gly Thr Gln Ala
                35                  40                  45

Ile Tyr Lys Cys Arg Pro Gly Tyr Arg Ser Leu Gly Asn Val Ile Met
                50                  55                  60

Val Cys Arg Lys Gly Glu Trp Val Ala Leu Asn Pro Leu Arg Lys Cys
65                  70                  75                  80

Gln Lys Arg Pro Cys Gly His Pro Gly Asp Thr Pro Phe Gly Thr Phe
                85                  90                  95

Thr Leu Thr Gly Gly Asn Val Phe Glu Tyr Gly Val Lys Ala Val Tyr
                100                 105                 110

Thr Cys Asn Glu Gly Tyr Gln Leu Leu Gly Glu Ile Asn Tyr Arg Glu
                115                 120                 125

Cys Asp Thr Asp Gly Trp Thr Asn Asp Ile Pro Ile Cys Glu Val Val
                130                 135                 140

Lys Cys Leu Pro Val Thr Ala Pro Glu Asn Gly Lys Ile Val Ser Ser
145                 150                 155                 160

Ala Met Glu Pro Asp Arg Glu Tyr His Phe Gly Gln Ala Val Arg Phe
                165                 170                 175

Val Cys Asn Ser Gly Tyr Lys Ile Glu Gly Asp Glu Glu Met His Cys
                180                 185                 190

Ser Asp Asp Gly Phe Trp Ser Lys Glu Lys Pro Lys Cys Val Glu Ile
                195                 200                 205

Ser Cys Lys Ser Pro Asp Val Ile Asn Gly Ser Pro Ile Ser Gln Lys
210                 215                 220

Ile Ile Tyr Lys Glu Asn Glu Arg Phe Gln Tyr Lys Cys Asn Met Gly
225                 230                 235                 240

Tyr Glu Tyr Ser Glu Arg Gly Asp Ala Val Cys Thr Glu Ser Gly Trp
                245                 250                 255

Arg Pro Leu Pro Ser Cys Glu Glu Lys Ser Cys Asp Asn Pro Tyr Ile
                260                 265                 270

Pro Asn Gly Asp Tyr Ser Pro Leu Arg Ile Lys His Arg Thr Gly Asp
                275                 280                 285

Glu Ile Thr Tyr Gln Cys Arg Asn Gly Phe Tyr Pro Ala Thr Arg Gly
                290                 295                 300

Asn Thr Ala Lys Cys Thr Ser Thr Gly Trp Ile Pro Ala Pro Arg Cys
305                 310                 315                 320

Thr Leu Lys Pro Cys Asp Tyr Pro Asp Ile Lys His Gly Gly Leu Tyr
                325                 330                 335

His Glu Asn Met Arg Arg Pro Tyr Phe Pro Val Ala Val Gly Lys Tyr
                340                 345                 350

Tyr Ser Tyr Tyr Cys Asp Glu His Phe Glu Thr Pro Ser Gly Ser Tyr
                355                 360                 365

Trp Asp His Ile His Cys Thr Gln Asp Gly Trp Ser Pro Ala Val Pro
                370                 375                 380

Cys Leu Arg Lys Cys Tyr Phe Pro Tyr Leu Glu Asn Gly Tyr Asn Gln
385                 390                 395                 400

Asn Tyr Gly Arg Lys Phe Val Gln Gly Lys Ser Ile Asp Val Ala Cys
                405                 410                 415

His Pro Gly Tyr Ala Leu Pro Lys Ala Gln Thr Thr Val Thr Cys Met
                420                 425                 430
```

```
Glu Asn Gly Trp Ser Pro Thr Pro Arg Cys Ile Arg Val Lys Thr Cys
        435                 440                 445

Ser Lys Ser Ser Ile Asp Ile Glu Asn Gly Phe Ile Ser Glu Ser Gln
    450                 455                 460

Tyr Thr Tyr Ala Leu Lys Glu Lys Ala Lys Tyr Gln Cys Lys Leu Gly
465                 470                 475                 480

Tyr Val Thr Ala Asp Gly Glu Thr Ser Gly Ser Ile Thr Cys Gly Lys
                485                 490                 495

Asp Gly Trp Ser Ala Gln Pro Thr Cys Ile Lys Ser Cys Asp Ile Pro
            500                 505                 510

Val Phe Met Asn Ala Arg Thr Lys Asn Asp Phe Thr Trp Phe Lys Leu
        515                 520                 525

Asn Asp Thr Leu Asp Tyr Glu Cys His Asp Gly Tyr Glu Ser Asn Thr
    530                 535                 540

Gly Ser Thr Thr Gly Ser Ile Val Cys Gly Tyr Asn Gly Trp Ser Asp
545                 550                 555                 560

Leu Pro Ile Cys Tyr Glu Arg Glu Cys Glu Leu Pro Lys Ile Asp Val
                565                 570                 575

His Leu Val Pro Asp Arg Lys Lys Asp Gln Tyr Lys Val Gly Glu Val
            580                 585                 590

Leu Lys Phe Ser Cys Lys Pro Gly Phe Thr Ile Val Gly Pro Asn Ser
        595                 600                 605

Val Gln Cys Tyr His Phe Gly Leu Ser Pro Asp Leu Pro Ile Cys Lys
    610                 615                 620

Glu Gln Val Gln Ser Cys Gly Pro Pro Glu Leu Leu Asn Gly Asn
625                 630                 635                 640

Val Lys Glu Lys Thr Lys Glu Glu Tyr Gly His Ser Glu Val Val Glu
                645                 650                 655

Tyr Tyr Cys Asn Pro Arg Phe Leu Met Lys Gly Pro Asn Lys Ile Gln
            660                 665                 670

Cys Val Asp Gly Glu Trp Thr Thr Leu Pro Val Cys Ile Val Glu Glu
        675                 680                 685

Ser Thr Cys Gly Asp Ile Pro Glu Leu Glu His Gly Trp Ala Gln Leu
    690                 695                 700

Ser Ser Pro Pro Tyr Tyr Tyr Gly Asp Ser Val Glu Phe Asn Cys Ser
705                 710                 715                 720

Glu Ser Phe Thr Met Ile Gly His Arg Ser Ile Thr Cys Ile His Gly
                725                 730                 735

Val Trp Thr Gln Leu Pro Gln Cys Val Ala Ile Asp Lys Leu Lys Lys
            740                 745                 750

Cys Lys Ser Ser Asn Leu Ile Ile Leu Glu Glu His Leu Lys Asn Lys
        755                 760                 765

Lys Glu Phe Asp His Asn Ser Asn Ile Arg Tyr Arg Cys Arg Gly Lys
    770                 775                 780

Glu Gly Trp Ile His Thr Val Cys Ile Asn Gly Arg Trp Asp Pro Glu
785                 790                 795                 800

Val Asn Cys Ser Met Ala Gln Ile Gln Leu Cys Pro Pro Pro Gln
                805                 810                 815

Ile Pro Asn Ser His Asn Met Thr Thr Thr Leu Asn Tyr Arg Asp Gly
            820                 825                 830

Glu Lys Val Ser Val Leu Cys Gln Glu Asn Tyr Leu Ile Gln Glu Gly
        835                 840                 845
```

```
Glu Glu Ile Thr Cys Lys Asp Gly Arg Trp Gln Ser Ile Pro Leu Cys
850                 855                 860

Val Glu Lys Ile Pro Cys Ser Gln Pro Gln Ile Glu His Gly Thr
865                 870                 875                 880

Ile Asn Ser Ser Arg Ser Ser Gln Glu Ser Tyr Ala His Gly Thr Lys
                885                 890                 895

Leu Ser Tyr Thr Cys Glu Gly Gly Phe Arg Ile Ser Glu Glu Asn Glu
                900                 905                 910

Thr Thr Cys Tyr Met Gly Lys Trp Ser Ser Pro Pro Gln Cys Glu Gly
                915                 920                 925

Leu Pro Cys Lys Ser Pro Pro Glu Ile Ser His Gly Val Val Ala His
            930                 935                 940

Met Ser Asp Ser Tyr Gln Tyr Gly Glu Glu Val Thr Tyr Lys Cys Phe
945                 950                 955                 960

Glu Gly Phe Gly Ile Asp Gly Pro Ala Ile Ala Lys Cys Leu Gly Glu
                965                 970                 975

Lys Trp Ser His Pro Pro Ser Cys Ile Lys Thr Asp Cys Leu Ser Leu
            980                 985                 990

Pro Ser Phe Glu Asn Ala Ile Pro Met Gly Glu Lys Lys Asp Val Tyr
            995                 1000                1005

Lys Ala Gly Glu Gln Val Thr Tyr Thr Cys Ala Thr Tyr Tyr Lys
    1010            1015                1020

Met Asp Gly Ala Ser Asn Val Thr Cys Ile Asn Ser Arg Trp Thr
    1025            1030                1035

Gly Arg Pro Thr Cys Arg Asp Thr Ser Cys Val Asn Pro Pro Thr
    1040            1045                1050

Val Gln Asn Ala Tyr Ile Val Ser Arg Gln Met Ser Lys Tyr Pro
    1055            1060                1065

Ser Gly Glu Arg Val Arg Tyr Gln Cys Arg Ser Pro Tyr Glu Met
    1070            1075                1080

Phe Gly Asp Glu Glu Val Met Cys Leu Asn Gly Asn Trp Thr Glu
    1085            1090                1095

Pro Pro Gln Cys Lys Asp Ser Thr Gly Lys Cys Gly Pro Pro Pro
    1100            1105                1110

Pro Ile Asp Asn Gly Asp Ile Thr Ser Phe Pro Leu Ser Val Tyr
    1115            1120                1125

Ala Pro Ala Ser Ser Val Glu Tyr Gln Cys Gln Asn Leu Tyr Gln
    1130            1135                1140

Leu Glu Gly Asn Lys Arg Ile Thr Cys Arg Asn Gly Gln Trp Ser
    1145            1150                1155

Glu Pro Pro Lys Cys Leu His Pro Cys Val Ile Ser Arg Glu Ile
    1160            1165                1170

Met Glu Asn Tyr Asn Ile Ala Leu Arg Trp Thr Ala Lys Gln Lys
    1175            1180                1185

Leu Tyr Ser Arg Thr Gly Glu Ser Val Glu Phe Val Cys Lys Arg
    1190            1195                1200

Gly Tyr Arg Leu Ser Ser Arg Ser His Thr Leu Arg Thr Thr Cys
    1205            1210                1215

Trp Asp Gly Lys Leu Glu Tyr Pro Thr Cys Ala Lys Arg
    1220            1225                1230

<210> SEQ ID NO 244
<211> LENGTH: 18
<212> TYPE: PRT
```

<213> ORGANISM: Homo sapiens

<400> SEQUENCE: 244

Glu Ala Gln Gly Glu Val Pro Ala Ser Asp Ser Lys Thr Glu Cys Thr
1               5                   10                  15

Ala Leu

<210> SEQ ID NO 245
<211> LENGTH: 11
<212> TYPE: PRT
<213> ORGANISM: Homo sapiens

<400> SEQUENCE: 245

Val Ile Ser Gln Ile Ala Met Asn Asp Glu Lys
1               5                   10

<210> SEQ ID NO 246
<211> LENGTH: 690
<212> TYPE: PRT
<213> ORGANISM: Homo sapiens

<400> SEQUENCE: 246

Met Ala Pro Trp Pro Glu Leu Gly Asp Ala Gln Pro Asn Pro Asp Lys
1               5                   10                  15

Tyr Leu Glu Gly Ala Ala Gly Gln Gln Pro Thr Ala Pro Asp Lys Ser
                20                  25                  30

Lys Glu Thr Asn Lys Thr Asp Asn Thr Glu Ala Pro Val Thr Lys Ile
            35                  40                  45

Glu Leu Leu Pro Ser Tyr Ser Thr Ala Thr Leu Ile Asp Glu Pro Thr
50                  55                  60

Glu Val Asp Asp Pro Trp Asn Leu Pro Thr Leu Gln Asp Ser Gly Ile
65                  70                  75                  80

Lys Trp Ser Glu Arg Asp Thr Lys Gly Lys Ile Leu Cys Phe Phe Gln
                85                  90                  95

Gly Ile Gly Arg Leu Ile Leu Leu Leu Gly Phe Leu Tyr Phe Phe Val
                100                 105                 110

Cys Ser Leu Asp Ile Leu Ser Ser Ala Phe Gln Leu Val Gly Gly Lys
            115                 120                 125

Met Ala Gly Gln Phe Phe Ser Asn Ser Ser Ile Met Ser Asn Pro Leu
130                 135                 140

Leu Gly Leu Val Ile Gly Val Leu Val Thr Val Leu Val Gln Ser Ser
145                 150                 155                 160

Ser Thr Ser Thr Ser Ile Val Val Ser Met Val Ser Ser Ser Leu Leu
                165                 170                 175

Thr Val Arg Ala Ala Ile Pro Ile Ile Met Gly Ala Asn Ile Gly Thr
                180                 185                 190

Ser Ile Thr Asn Thr Ile Val Ala Leu Met Gln Val Gly Asp Arg Ser
            195                 200                 205

Glu Phe Arg Arg Ala Phe Ala Gly Ala Thr Val His Asp Phe Phe Asn
210                 215                 220

Trp Leu Ser Val Leu Val Leu Leu Pro Val Glu Val Ala Thr His Tyr
225                 230                 235                 240

Leu Glu Ile Ile Thr Gln Leu Ile Val Glu Ser Phe His Phe Lys Asn
                245                 250                 255

Gly Glu Asp Ala Pro Asp Leu Leu Lys Val Ile Thr Lys Pro Phe Thr
                260                 265                 270

-continued

```
Lys Leu Ile Val Gln Leu Asp Lys Lys Val Ile Ser Gln Ile Ala Met
            275                 280                 285
Asn Asp Glu Lys Ala Lys Asn Lys Ser Leu Val Lys Ile Trp Cys Lys
290                 295                 300
Thr Phe Thr Asn Lys Thr Gln Ile Asn Val Thr Val Pro Ser Thr Ala
305                 310                 315                 320
Asn Cys Thr Ser Pro Ser Leu Cys Trp Thr Asp Gly Ile Gln Asn Trp
                325                 330                 335
Thr Met Lys Asn Val Thr Tyr Lys Glu Asn Ile Ala Lys Cys Gln His
            340                 345                 350
Ile Phe Val Asn Phe His Leu Pro Asp Leu Ala Val Gly Thr Ile Leu
        355                 360                 365
Leu Ile Leu Ser Leu Leu Val Leu Cys Gly Cys Leu Ile Met Ile Val
    370                 375                 380
Lys Ile Leu Gly Ser Val Leu Lys Gly Gln Val Ala Thr Val Ile Lys
385                 390                 395                 400
Lys Thr Ile Asn Thr Asp Phe Pro Phe Pro Phe Ala Trp Leu Thr Gly
                405                 410                 415
Tyr Leu Ala Ile Leu Val Gly Ala Gly Met Thr Phe Ile Val Gln Ser
            420                 425                 430
Ser Ser Val Phe Thr Ser Ala Leu Thr Pro Leu Ile Gly Ile Gly Val
        435                 440                 445
Ile Thr Ile Glu Arg Ala Tyr Pro Leu Thr Leu Gly Ser Asn Ile Gly
    450                 455                 460
Thr Thr Thr Thr Ala Ile Leu Ala Ala Leu Ala Ser Pro Gly Asn Ala
465                 470                 475                 480
Leu Arg Ser Ser Leu Gln Ile Ala Leu Cys His Phe Phe Asn Ile
                485                 490                 495
Ser Gly Ile Leu Leu Trp Tyr Pro Ile Pro Phe Thr Arg Leu Pro Ile
            500                 505                 510
Arg Met Ala Lys Gly Leu Gly Asn Ile Ser Ala Lys Tyr Arg Trp Phe
        515                 520                 525
Ala Val Phe Tyr Leu Ile Ile Phe Phe Phe Leu Ile Pro Leu Thr Val
    530                 535                 540
Phe Gly Leu Ser Leu Ala Gly Trp Arg Val Leu Val Gly Val Gly Val
545                 550                 555                 560
Pro Val Val Phe Ile Ile Leu Val Leu Cys Leu Arg Leu Leu Gln
                565                 570                 575
Ser Arg Cys Pro Arg Val Leu Pro Lys Lys Leu Gln Asn Trp Asn Phe
            580                 585                 590
Leu Pro Leu Trp Met Arg Ser Leu Lys Pro Trp Asp Ala Val Val Ser
        595                 600                 605
Lys Phe Thr Gly Cys Phe Gln Met Arg Cys Cys Cys Cys Arg Val
    610                 615                 620
Cys Cys Arg Ala Cys Cys Leu Leu Cys Asp Cys Pro Lys Cys Cys Arg
625                 630                 635                 640
Cys Ser Lys Cys Cys Glu Asp Leu Glu Glu Ala Gln Glu Gly Gln Asp
                645                 650                 655
Val Pro Val Lys Ala Pro Glu Thr Phe Asp Asn Ile Thr Ile Ser Arg
            660                 665                 670
Glu Ala Gln Gly Glu Val Pro Ala Ser Asp Ser Lys Thr Glu Cys Thr
        675                 680                 685
Ala Leu
```

-continued

690

<210> SEQ ID NO 247
<211> LENGTH: 10
<212> TYPE: PRT
<213> ORGANISM: Homo sapiens

<400> SEQUENCE: 247

Phe Ser Val Leu Gly Ser Gly Leu Asn Arg
1               5                   10

<210> SEQ ID NO 248
<211> LENGTH: 123
<212> TYPE: PRT
<213> ORGANISM: Homo sapiens

<400> SEQUENCE: 248

Met Ala Trp Ala Pro Leu Leu Leu Thr Leu Leu Ser Leu Leu Thr Gly
1               5                   10                  15

Ser Leu Ser Gln Pro Val Leu Thr Gln Pro Ser Ala Ser Ala Ser
            20                  25                  30

Leu Gly Ala Ser Val Thr Leu Thr Cys Thr Leu Ser Ser Gly Tyr Ser
        35                  40                  45

Asn Tyr Lys Val Asp Trp Tyr Gln Gln Arg Pro Gly Lys Gly Pro Arg
    50                  55                  60

Phe Val Met Arg Val Gly Thr Gly Gly Ile Val Gly Ser Lys Gly Asp
65                  70                  75                  80

Gly Ile Pro Asp Arg Phe Ser Val Leu Gly Ser Gly Leu Asn Arg Tyr
                85                  90                  95

Leu Thr Ile Lys Asn Ile Gln Glu Glu Asp Glu Ser Asp Tyr His Cys
            100                 105                 110

Gly Ala Asp His Gly Ser Gly Ser Asn Phe Val
            115                 120

<210> SEQ ID NO 249
<211> LENGTH: 11
<212> TYPE: PRT
<213> ORGANISM: Homo sapiens

<400> SEQUENCE: 249

Leu Gln Ile Trp Asp Thr Ala Gly Gln Glu Arg
1               5                   10

<210> SEQ ID NO 250
<211> LENGTH: 10
<212> TYPE: PRT
<213> ORGANISM: Homo sapiens

<400> SEQUENCE: 250

Ser Met Glu Asp Tyr Asp Phe Leu Phe Lys
1               5                   10

<210> SEQ ID NO 251
<211> LENGTH: 203
<212> TYPE: PRT
<213> ORGANISM: Homo sapiens

<400> SEQUENCE: 251

Met Ser Met Glu Asp Tyr Asp Phe Leu Phe Lys Ile Val Leu Ile Gly
1               5                   10                  15

Asn Ala Gly Val Gly Lys Thr Cys Leu Val Arg Arg Phe Thr Gln Gly

```
                  20                  25                  30
Leu Phe Pro Pro Gly Gln Gly Ala Thr Ile Gly Val Asp Phe Met Ile
            35                  40                  45

Lys Thr Val Glu Ile Asn Gly Glu Lys Val Lys Leu Gln Ile Trp Asp
 50                  55                  60

Thr Ala Gly Gln Glu Arg Phe Arg Ser Ile Thr Gln Ser Tyr Tyr Arg
 65                  70                  75                  80

Ser Ala Asn Ala Leu Ile Leu Thr Tyr Asp Ile Thr Cys Glu Glu Ser
                85                  90                  95

Phe Arg Cys Leu Pro Glu Trp Leu Arg Glu Ile Glu Gln Tyr Ala Ser
            100                 105                 110

Asn Lys Val Ile Thr Val Leu Val Gly Asn Lys Ile Asp Leu Ala Glu
        115                 120                 125

Arg Arg Glu Val Ser Gln Gln Arg Ala Glu Glu Phe Ser Glu Ala Gln
    130                 135                 140

Asp Met Tyr Tyr Leu Glu Thr Ser Ala Lys Glu Ser Asp Asn Val Glu
145                 150                 155                 160

Lys Leu Phe Leu Asp Leu Ala Cys Arg Leu Ile Ser Glu Ala Arg Gln
                165                 170                 175

Asn Thr Leu Val Asn Asn Val Ser Ser Pro Leu Pro Gly Glu Gly Lys
            180                 185                 190

Ser Ile Ser Tyr Leu Thr Cys Cys Asn Phe Asn
        195                 200

<210> SEQ ID NO 252
<211> LENGTH: 19
<212> TYPE: PRT
<213> ORGANISM: Homo sapiens

<400> SEQUENCE: 252

Cys Glu Gln Val Cys Val Asn Ser Pro Gly Ser Tyr Thr Cys His Cys
1               5                   10                  15

Asp Gly Arg

<210> SEQ ID NO 253
<211> LENGTH: 13
<212> TYPE: PRT
<213> ORGANISM: Homo sapiens

<400> SEQUENCE: 253

Gly Gln Ser Glu Val Ser Ala Ala Gln Leu Gln Glu Arg
1               5                   10

<210> SEQ ID NO 254
<211> LENGTH: 12
<212> TYPE: PRT
<213> ORGANISM: Homo sapiens

<400> SEQUENCE: 254

Ile Ala Val Ala Gly Asp Leu Phe Gln Pro Glu Arg
1               5                   10

<210> SEQ ID NO 255
<211> LENGTH: 9
<212> TYPE: PRT
<213> ORGANISM: Homo sapiens

<400> SEQUENCE: 255

Met Phe Ser Gly Thr Pro Val Ile Arg
```

```
<210> SEQ ID NO 256
<211> LENGTH: 9
<212> TYPE: PRT
<213> ORGANISM: Homo sapiens

<400> SEQUENCE: 256

Met Gln Cys Phe Ser Val Thr Glu Arg
1               5

<210> SEQ ID NO 257
<211> LENGTH: 22
<212> TYPE: PRT
<213> ORGANISM: Homo sapiens

<400> SEQUENCE: 257

Asn Ser Gly Phe Ala Thr Cys Val Gln Asn Leu Pro Asp Gln Cys Thr
1               5                   10                  15

Pro Asn Pro Cys Asp Arg
            20

<210> SEQ ID NO 258
<211> LENGTH: 720
<212> TYPE: PRT
<213> ORGANISM: Homo sapiens

<400> SEQUENCE: 258

Met Ala Pro Ser Leu Ser Pro Gly Pro Ala Ala Leu Arg Arg Ala Pro
1               5                   10                  15

Gln Leu Leu Leu Leu Leu Leu Ala Ala Glu Cys Ala Leu Ala Ala Leu
            20                  25                  30

Leu Pro Ala Arg Glu Ala Thr Gln Phe Leu Arg Pro Gln Arg Arg
            35                  40                  45

Ala Phe Gln Val Phe Glu Glu Ala Lys Gln Gly His Leu Glu Arg Glu
    50                  55                  60

Cys Val Glu Glu Leu Cys Ser Arg Glu Glu Ala Arg Glu Val Phe Glu
65                  70                  75                  80

Asn Asp Pro Glu Thr Asp Tyr Phe Tyr Pro Arg Tyr Leu Asp Cys Ile
                85                  90                  95

Asn Lys Tyr Gly Ser Pro Tyr Thr Lys Asn Ser Gly Phe Ala Thr Cys
            100                 105                 110

Val Gln Asn Leu Pro Asp Gln Cys Thr Pro Asn Pro Cys Asp Arg Lys
        115                 120                 125

Gly Thr Gln Ala Cys Gln Asp Leu Met Gly Asn Phe Phe Cys Leu Cys
    130                 135                 140

Lys Ala Gly Trp Gly Gly Arg Leu Cys Asp Lys Asp Val Asn Glu Cys
145                 150                 155                 160

Ser Gln Glu Asn Gly Gly Cys Leu Gln Ile Cys His Asn Lys Pro Gly
                165                 170                 175

Ser Phe His Cys Ser Cys His Ser Gly Phe Glu Leu Ser Ser Asp Gly
            180                 185                 190

Arg Thr Cys Gln Asp Ile Asp Glu Cys Ala Asp Ser Glu Ala Cys Gly
        195                 200                 205

Glu Ala Arg Cys Lys Asn Leu Pro Gly Ser Tyr Ser Cys Leu Cys Asp
    210                 215                 220

Glu Gly Phe Ala Tyr Ser Ser Gln Glu Lys Ala Cys Arg Asp Val Asp
225                 230                 235                 240
```

```
Glu Cys Leu Gln Gly Arg Cys Glu Gln Val Cys Val Asn Ser Pro Gly
                245                 250                 255

Ser Tyr Thr Cys His Cys Asp Gly Arg Gly Leu Lys Leu Ser Gln
            260                 265                 270

Asp Met Asp Thr Cys Glu Leu Glu Ala Gly Trp Pro Cys Pro Arg His
        275                 280                 285

Arg Arg Asp Gly Ser Pro Ala Ala Arg Pro Gly Arg Gly Ala Gln Gly
    290                 295                 300

Ser Arg Ser Glu Gly His Ile Pro Asp Arg Arg Gly Pro Arg Pro Trp
305                 310                 315                 320

Gln Asp Ile Leu Pro Cys Val Pro Phe Ser Val Ala Lys Ser Val Lys
                325                 330                 335

Ser Leu Tyr Leu Gly Arg Met Phe Ser Gly Thr Pro Val Ile Arg Leu
            340                 345                 350

Arg Phe Lys Arg Leu Gln Pro Thr Arg Leu Val Ala Glu Phe Asp Phe
        355                 360                 365

Arg Thr Phe Asp Pro Glu Gly Ile Leu Leu Phe Ala Gly Gly His Gln
    370                 375                 380

Asp Ser Thr Trp Ile Val Leu Ala Leu Arg Ala Gly Arg Leu Glu Leu
385                 390                 395                 400

Gln Leu Arg Tyr Asn Gly Val Gly Arg Val Thr Ser Ser Gly Pro Val
                405                 410                 415

Ile Asn His Gly Met Trp Gln Thr Ile Ser Val Glu Glu Leu Ala Arg
            420                 425                 430

Asn Leu Val Ile Lys Val Asn Arg Asp Ala Val Met Lys Ile Ala Val
        435                 440                 445

Ala Gly Asp Leu Phe Gln Pro Glu Arg Gly Leu Tyr His Leu Asn Leu
    450                 455                 460

Thr Val Gly Gly Ile Pro Phe His Glu Lys Asp Leu Val Gln Pro Ile
465                 470                 475                 480

Asn Pro Arg Leu Asp Gly Cys Met Arg Ser Trp Asn Trp Leu Asn Gly
                485                 490                 495

Glu Asp Thr Thr Ile Gln Glu Thr Val Lys Val Asn Thr Arg Met Gln
            500                 505                 510

Cys Phe Ser Val Thr Glu Arg Gly Ser Phe Tyr Pro Gly Ser Gly Phe
        515                 520                 525

Ala Phe Tyr Ser Leu Asp Tyr Met Arg Thr Pro Leu Asp Val Gly Thr
    530                 535                 540

Glu Ser Thr Trp Glu Val Glu Val Val Ala His Ile Arg Pro Ala Ala
545                 550                 555                 560

Asp Thr Gly Val Leu Phe Ala Leu Trp Ala Pro Asp Leu Arg Ala Val
                565                 570                 575

Pro Leu Ser Val Ala Leu Val Asp Tyr His Ser Thr Lys Lys Leu Lys
            580                 585                 590

Lys Gln Leu Val Val Leu Ala Val Glu His Thr Ala Leu Ala Leu Met
        595                 600                 605

Glu Ile Lys Val Cys Asp Gly Gln His Val Thr Val Ser Leu
    610                 615                 620

Arg Asp Gly Glu Ala Thr Leu Glu Val Asp Gly Thr Arg Gly Gln Ser
625                 630                 635                 640

Glu Val Ser Ala Ala Gln Leu Gln Glu Arg Leu Ala Val Leu Glu Arg
                645                 650                 655
```

```
His Leu Arg Ser Pro Val Leu Thr Phe Ala Gly Gly Leu Pro Asp Val
            660                 665                 670

Pro Val Thr Ser Ala Pro Val Thr Ala Phe Tyr Arg Gly Cys Met Thr
        675                 680                 685

Leu Glu Val Asn Arg Arg Leu Leu Asp Leu Asp Glu Ala Ala Tyr Lys
    690                 695                 700

His Ser Asp Ile Thr Ala His Ser Cys Pro Pro Val Glu Pro Ala Ala
705                 710                 715                 720

<210> SEQ ID NO 259
<211> LENGTH: 19
<212> TYPE: PRT
<213> ORGANISM: Homo sapiens

<400> SEQUENCE: 259

His Ser Phe Thr Met Ala Met Asn Ala Phe Gly Asp Met Thr Ser Glu
1               5                   10                  15

Glu Phe Arg

<210> SEQ ID NO 260
<211> LENGTH: 10
<212> TYPE: PRT
<213> ORGANISM: Homo sapiens

<400> SEQUENCE: 260

Leu Tyr Gly Met Asn Glu Glu Gly Trp Arg
1               5                   10

<210> SEQ ID NO 261
<211> LENGTH: 13
<212> TYPE: PRT
<213> ORGANISM: Homo sapiens

<400> SEQUENCE: 261

Asn His Cys Gly Ile Ala Ser Ala Ala Ser Tyr Pro Val
1               5                   10

<210> SEQ ID NO 262
<211> LENGTH: 14
<212> TYPE: PRT
<213> ORGANISM: Homo sapiens

<400> SEQUENCE: 262

Asn Ser Trp Gly Glu Glu Trp Gly Met Gly Gly Tyr Val Lys
1               5                   10

<210> SEQ ID NO 263
<211> LENGTH: 333
<212> TYPE: PRT
<213> ORGANISM: Homo sapiens

<400> SEQUENCE: 263

Met Asn Pro Thr Leu Ile Leu Ala Ala Phe Cys Leu Gly Ile Ala Ser
1               5                   10                  15

Ala Thr Leu Thr Phe Asp His Ser Leu Glu Ala Gln Trp Thr Lys Trp
            20                  25                  30

Lys Ala Met His Asn Arg Leu Tyr Gly Met Asn Glu Glu Gly Trp Arg
        35                  40                  45

Arg Ala Val Trp Glu Lys Asn Met Lys Met Ile Glu Leu His Asn Gln
    50                  55                  60

Glu Tyr Arg Glu Gly Lys His Ser Phe Thr Met Ala Met Asn Ala Phe
```

65                  70                  75                  80
Gly Asp Met Thr Ser Glu Glu Phe Arg Gln Val Met Asn Gly Phe Gln
                    85                  90                  95
Asn Arg Lys Pro Arg Lys Gly Lys Val Phe Gln Glu Pro Leu Phe Tyr
                100                 105                 110
Glu Ala Pro Arg Ser Val Asp Trp Arg Glu Lys Gly Tyr Val Thr Pro
                115                 120                 125
Val Lys Asn Gln Gly Gln Cys Gly Ser Cys Trp Ala Phe Ser Ala Thr
130                 135                 140
Gly Ala Leu Glu Gly Gln Met Phe Arg Lys Thr Gly Arg Leu Ile Ser
145                 150                 155                 160
Leu Ser Glu Gln Asn Leu Val Asp Cys Ser Gly Pro Gln Gly Asn Glu
                165                 170                 175
Gly Cys Asn Gly Gly Leu Met Asp Tyr Ala Phe Gln Tyr Val Gln Asp
                180                 185                 190
Asn Gly Gly Leu Asp Ser Glu Glu Ser Tyr Pro Tyr Glu Ala Thr Glu
                195                 200                 205
Glu Ser Cys Lys Tyr Asn Pro Lys Tyr Ser Val Ala Asn Asp Thr Gly
                210                 215                 220
Phe Val Asp Ile Pro Lys Gln Glu Lys Ala Leu Met Lys Ala Val Ala
225                 230                 235                 240
Thr Val Gly Pro Ile Ser Val Ala Ile Asp Ala Gly His Glu Ser Phe
                245                 250                 255
Leu Phe Tyr Lys Glu Gly Ile Tyr Phe Glu Pro Asp Cys Ser Ser Glu
                260                 265                 270
Asp Met Asp His Gly Val Leu Val Gly Tyr Gly Phe Glu Ser Thr
                275                 280                 285
Glu Ser Asp Asn Asn Lys Tyr Trp Leu Val Lys Asn Ser Trp Gly Glu
                290                 295                 300
Glu Trp Gly Met Gly Gly Tyr Val Lys Met Ala Lys Asp Arg Arg Asn
305                 310                 315                 320
His Cys Gly Ile Ala Ser Ala Ala Ser Tyr Pro Thr Val
                325                 330

<210> SEQ ID NO 264
<211> LENGTH: 16
<212> TYPE: PRT
<213> ORGANISM: Homo sapiens

<400> SEQUENCE: 264

Phe Tyr Thr Lys Pro Pro Gln Cys Val Asp Ile Pro Ala Asp Leu Arg
1               5                   10                  15

<210> SEQ ID NO 265
<211> LENGTH: 8
<212> TYPE: PRT
<213> ORGANISM: Homo sapiens

<400> SEQUENCE: 265

Leu Cys His Asn Val Gly Tyr Lys
1               5

<210> SEQ ID NO 266
<211> LENGTH: 9
<212> TYPE: PRT
<213> ORGANISM: Homo sapiens

<400> SEQUENCE: 266

```
Leu Cys His Asn Val Gly Tyr Lys Lys
1               5
```

<210> SEQ ID NO 267
<211> LENGTH: 16
<212> TYPE: PRT
<213> ORGANISM: Homo sapiens

<400> SEQUENCE: 267

```
Met Val Leu Pro Asn Leu Leu Glu His Glu Thr Met Ala Glu Val Lys
1               5                   10                  15
```

<210> SEQ ID NO 268
<211> LENGTH: 15
<212> TYPE: PRT
<213> ORGANISM: Homo sapiens

<400> SEQUENCE: 268

```
Pro Gln Gly Thr Thr Val Cys Pro Pro Cys Asp Asn Glu Leu Lys
1               5                   10                  15
```

<210> SEQ ID NO 269
<211> LENGTH: 12
<212> TYPE: PRT
<213> ORGANISM: Homo sapiens

<400> SEQUENCE: 269

```
Gln Gln Ala Ser Ser Trp Val Pro Leu Leu Asn Lys
1               5                   10
```

<210> SEQ ID NO 270
<211> LENGTH: 16
<212> TYPE: PRT
<213> ORGANISM: Homo sapiens

<400> SEQUENCE: 270

```
Ser Glu Ala Ile Ile Glu His Leu Cys Ala Ser Glu Phe Ala Leu Arg
1               5                   10                  15
```

<210> SEQ ID NO 271
<211> LENGTH: 10
<212> TYPE: PRT
<213> ORGANISM: Homo sapiens

<400> SEQUENCE: 271

```
Ser Gln Tyr Leu Leu Thr Ala Ile His Lys
1               5                   10
```

<210> SEQ ID NO 272
<211> LENGTH: 314
<212> TYPE: PRT
<213> ORGANISM: Homo sapiens

<400> SEQUENCE: 272

```
Met Gly Ile Gly Arg Ser Glu Gly Gly Arg Arg Gly Ala Ala Leu Gly
1               5                   10                  15

Val Leu Leu Ala Leu Gly Ala Ala Leu Leu Ala Val Gly Ser Ala Ser
                20                  25                  30

Glu Tyr Asp Tyr Val Ser Phe Gln Ser Asp Ile Gly Pro Tyr Gln Ser
            35                  40                  45

Gly Arg Phe Tyr Thr Lys Pro Pro Gln Cys Val Asp Ile Pro Ala Asp
        50                  55                  60
```

```
Leu Arg Leu Cys His Asn Val Gly Tyr Lys Lys Met Val Leu Pro Asn
 65                  70                  75                  80

Leu Leu Glu His Glu Thr Met Ala Glu Val Lys Gln Gln Ala Ser Ser
             85                  90                  95

Trp Val Pro Leu Leu Asn Lys Asn Cys His Ala Gly Thr Gln Val Phe
        100                 105                 110

Leu Cys Ser Leu Phe Ala Pro Val Cys Leu Asp Arg Pro Ile Tyr Pro
    115                 120                 125

Cys Arg Trp Leu Cys Glu Ala Val Arg Asp Ser Cys Glu Pro Val Met
130                 135                 140

Gln Phe Phe Gly Phe Tyr Trp Pro Glu Met Leu Lys Cys Asp Lys Phe
145                 150                 155                 160

Pro Glu Gly Asp Val Cys Ile Ala Met Thr Pro Pro Asn Ala Thr Glu
                165                 170                 175

Ala Ser Lys Pro Gln Gly Thr Thr Val Cys Pro Pro Cys Asp Asn Glu
            180                 185                 190

Leu Lys Ser Glu Ala Ile Ile Glu His Leu Cys Ala Ser Glu Phe Ala
        195                 200                 205

Leu Arg Met Lys Ile Lys Glu Val Lys Glu Asn Gly Asp Lys Lys
    210                 215                 220

Ile Val Pro Lys Lys Lys Pro Leu Lys Leu Gly Pro Ile Lys Lys
225                 230                 235                 240

Lys Asp Leu Lys Lys Leu Val Leu Tyr Leu Lys Asn Gly Ala Asp Cys
                245                 250                 255

Pro Cys His Gln Leu Asp Asn Leu Ser His His Phe Leu Ile Met Gly
            260                 265                 270

Arg Lys Val Lys Ser Gln Tyr Leu Leu Thr Ala Ile His Lys Trp Asp
        275                 280                 285

Lys Lys Asn Lys Glu Phe Lys Asn Phe Met Lys Lys Met Lys Asn His
    290                 295                 300

Glu Cys Pro Thr Phe Gln Ser Val Phe Lys
305                 310
```

<210> SEQ ID NO 273
<211> LENGTH: 15
<212> TYPE: PRT
<213> ORGANISM: Homo sapiens

<400> SEQUENCE: 273

```
Gly Leu Asp Tyr Ala Ser Gln Gln Gly Thr Ala Ala Leu Gln Lys
1               5                   10                  15
```

<210> SEQ ID NO 274
<211> LENGTH: 11
<212> TYPE: PRT
<213> ORGANISM: Homo sapiens

<400> SEQUENCE: 274

```
Ile Lys Ile Pro Asp Tyr Ser Asp Ser Phe Lys
1               5                   10
```

<210> SEQ ID NO 275
<211> LENGTH: 487
<212> TYPE: PRT
<213> ORGANISM: Homo sapiens

<400> SEQUENCE: 275

```
Met Arg Glu Asn Met Ala Arg Gly Pro Cys Asn Ala Pro Arg Trp Ala
```

```
1               5                   10                  15
Ser Leu Met Val Leu Val Ala Ile Gly Thr Ala Val Thr Ala Ala Val
                20                  25                  30

Asn Pro Gly Val Val Arg Ile Ser Gln Lys Gly Leu Asp Tyr Ala
            35                  40                  45

Ser Gln Gln Gly Thr Ala Ala Leu Gln Lys Glu Leu Lys Arg Ile Lys
50                      55                  60

Ile Pro Asp Tyr Ser Asp Ser Phe Lys Ile Lys His Leu Gly Lys Gly
65                      70                  75                  80

His Tyr Ser Phe Tyr Ser Met Asp Ile Arg Glu Phe Gln Leu Pro Ser
                    85                  90                  95

Ser Gln Ile Ser Met Val Pro Asn Val Gly Leu Lys Phe Ser Ile Ser
                100                 105                 110

Asn Ala Asn Ile Lys Ile Ser Gly Lys Trp Lys Ala Gln Lys Arg Phe
                115                 120                 125

Leu Lys Met Ser Gly Asn Phe Asp Leu Ser Ile Glu Gly Met Ser Ile
            130                 135                 140

Ser Ala Asp Leu Lys Leu Gly Ser Asn Pro Thr Ser Gly Lys Pro Thr
145                 150                 155                 160

Ile Thr Cys Ser Ser Cys Ser Ser His Ile Asn Ser Val His Val His
                165                 170                 175

Ile Ser Lys Ser Lys Val Gly Trp Leu Ile Gln Leu Phe His Lys Lys
                180                 185                 190

Ile Glu Ser Ala Leu Arg Asn Lys Met Asn Ser Gln Val Cys Glu Lys
                195                 200                 205

Val Thr Asn Ser Val Ser Ser Glu Leu Gln Pro Tyr Phe Gln Thr Leu
210                 215                 220

Pro Val Met Thr Lys Ile Asp Ser Val Ala Gly Ile Asn Tyr Gly Leu
225                 230                 235                 240

Val Ala Pro Pro Ala Thr Thr Ala Glu Thr Leu Asp Val Gln Met Lys
                245                 250                 255

Gly Glu Phe Tyr Ser Glu Asn His His Asn Pro Pro Phe Ala Pro
                260                 265                 270

Pro Val Met Glu Phe Pro Ala Ala His Asp Arg Met Val Tyr Leu Gly
            275                 280                 285

Leu Ser Asp Tyr Phe Phe Asn Thr Ala Gly Leu Val Tyr Gln Glu Ala
            290                 295                 300

Gly Val Leu Lys Met Thr Leu Arg Asp Asp Met Ile Pro Lys Glu Ser
305                 310                 315                 320

Lys Phe Arg Leu Thr Thr Lys Phe Phe Gly Thr Phe Leu Pro Glu Val
                325                 330                 335

Ala Lys Lys Phe Pro Asn Met Lys Ile Gln Ile His Val Ser Ala Ser
                340                 345                 350

Thr Pro Pro His Leu Ser Val Gln Pro Thr Gly Leu Thr Phe Tyr Pro
            355                 360                 365

Ala Val Asp Val Gln Ala Phe Ala Val Leu Pro Asn Ser Ser Leu Ala
            370                 375                 380

Ser Leu Phe Leu Ile Gly Met His Thr Thr Gly Ser Met Glu Val Ser
385                 390                 395                 400

Ala Glu Ser Asn Arg Leu Val Gly Glu Leu Lys Leu Asp Arg Leu Leu
                405                 410                 415

Leu Glu Leu Lys His Ser Asn Ile Gly Pro Phe Pro Val Glu Leu Leu
            420                 425                 430
```

```
Gln Asp Ile Met Asn Tyr Ile Val Pro Ile Val Leu Pro Arg Val
        435                 440                 445

Asn Glu Lys Leu Gln Lys Gly Phe Pro Leu Pro Thr Pro Ala Arg Val
    450                 455                 460

Gln Leu Tyr Asn Val Val Leu Gln Pro His Gln Asn Phe Leu Leu Phe
465                 470                 475                 480

Gly Ala Asp Val Val Tyr Lys
                485

<210> SEQ ID NO 276
<211> LENGTH: 7
<212> TYPE: PRT
<213> ORGANISM: Homo sapiens

<400> SEQUENCE: 276

Gly Leu His Ile Val Pro Arg
1               5

<210> SEQ ID NO 277
<211> LENGTH: 8
<212> TYPE: PRT
<213> ORGANISM: Homo sapiens

<400> SEQUENCE: 277

Gly Leu Val Val Thr Asp Leu Lys
1               5

<210> SEQ ID NO 278
<211> LENGTH: 14
<212> TYPE: PRT
<213> ORGANISM: Homo sapiens

<400> SEQUENCE: 278

Asn Val Leu Asp Ser Glu Asp Glu Ile Glu Glu Leu Ser Lys
1               5                   10

<210> SEQ ID NO 279
<211> LENGTH: 11
<212> TYPE: PRT
<213> ORGANISM: Homo sapiens

<400> SEQUENCE: 279

Ser Gln Phe Ser Asp Lys Pro Val Gln Asp Arg
1               5                   10

<210> SEQ ID NO 280
<211> LENGTH: 6
<212> TYPE: PRT
<213> ORGANISM: Homo sapiens

<400> SEQUENCE: 280

Tyr Ile Gln Thr Leu Lys
1               5

<210> SEQ ID NO 281
<211> LENGTH: 393
<212> TYPE: PRT
<213> ORGANISM: Homo sapiens

<400> SEQUENCE: 281

Met Arg Thr Leu Phe Asn Leu Leu Trp Leu Ala Leu Ala Cys Ser Pro
1               5                   10                  15
```

-continued

Val His Thr Thr Leu Ser Lys Ser Asp Ala Lys Ala Ala Ser Lys
            20                  25                  30

Thr Leu Leu Glu Lys Ser Gln Phe Ser Asp Lys Pro Val Gln Asp Arg
            35                  40                  45

Gly Leu Val Val Thr Asp Leu Lys Ala Glu Ser Val Val Leu Glu His
 50                  55                  60

Arg Ser Tyr Cys Ser Ala Lys Ala Arg Asp Arg His Phe Ala Gly Asp
 65                  70                  75                  80

Val Leu Gly Tyr Val Thr Pro Trp Asn Ser His Gly Tyr Asp Val Thr
                85                  90                  95

Lys Val Phe Gly Ser Lys Phe Thr Gln Ile Ser Pro Val Trp Leu Gln
                100                 105                 110

Leu Lys Arg Arg Gly Arg Glu Met Phe Glu Val Thr Gly Leu His Asp
                115                 120                 125

Val Asp Gln Gly Trp Met Arg Ala Val Arg Lys His Ala Lys Gly Leu
 130                 135                 140

His Ile Val Pro Arg Leu Leu Phe Glu Asp Trp Thr Tyr Asp Asp Phe
145                 150                 155                 160

Arg Asn Val Leu Asp Ser Glu Asp Glu Ile Glu Glu Leu Ser Lys Thr
                165                 170                 175

Val Val Gln Val Ala Lys Asn Gln His Phe Asp Gly Phe Val Val Glu
                180                 185                 190

Val Trp Asn Gln Leu Leu Ser Gln Lys Arg Val Gly Leu Ile His Met
                195                 200                 205

Leu Thr His Leu Ala Glu Ala Leu His Gln Ala Arg Leu Leu Ala Leu
 210                 215                 220

Leu Val Ile Pro Pro Ala Ile Thr Pro Gly Thr Asp Gln Leu Gly Met
225                 230                 235                 240

Phe Thr His Lys Glu Phe Glu Gln Leu Ala Pro Val Leu Asp Gly Phe
                245                 250                 255

Ser Leu Met Thr Tyr Asp Tyr Ser Thr Ala His Gln Pro Gly Pro Asn
                260                 265                 270

Ala Pro Leu Ser Trp Val Arg Ala Cys Val Gln Val Leu Asp Pro Lys
                275                 280                 285

Ser Lys Trp Arg Ser Lys Ile Leu Leu Gly Leu Asn Phe Tyr Gly Met
 290                 295                 300

Asp Tyr Ala Thr Ser Lys Asp Ala Arg Glu Pro Val Val Gly Ala Arg
305                 310                 315                 320

Tyr Ile Gln Thr Leu Lys Asp His Arg Pro Arg Met Val Trp Asp Ser
                325                 330                 335

Gln Ala Ser Glu His Phe Phe Glu Tyr Lys Lys Ser Arg Ser Gly Arg
                340                 345                 350

His Val Val Phe Tyr Pro Thr Leu Lys Ser Leu Gln Val Arg Leu Glu
                355                 360                 365

Leu Ala Arg Glu Leu Gly Val Gly Val Ser Ile Trp Glu Leu Gly Gln
 370                 375                 380

Gly Leu Asp Tyr Phe Tyr Asp Leu Leu
385                 390

<210> SEQ ID NO 282
<211> LENGTH: 8
<212> TYPE: PRT
<213> ORGANISM: Homo sapiens

<400> SEQUENCE: 282

```
Ala Leu Glu Leu Glu Gln Glu Arg
1               5

<210> SEQ ID NO 283
<211> LENGTH: 10
<212> TYPE: PRT
<213> ORGANISM: Homo sapiens

<400> SEQUENCE: 283

Ala Leu Thr Ser Glu Leu Ala Asn Ala Arg
1               5                   10

<210> SEQ ID NO 284
<211> LENGTH: 10
<212> TYPE: PRT
<213> ORGANISM: Homo sapiens

<400> SEQUENCE: 284

Ala Gln Met Val Gln Glu Asp Leu Glu Lys
1               5                   10

<210> SEQ ID NO 285
<211> LENGTH: 10
<212> TYPE: PRT
<213> ORGANISM: Homo sapiens

<400> SEQUENCE: 285

Glu Ser Glu Ala Val Glu Trp Gln Gln Lys
1               5                   10

<210> SEQ ID NO 286
<211> LENGTH: 8
<212> TYPE: PRT
<213> ORGANISM: Homo sapiens

<400> SEQUENCE: 286

Ile Ser Gln Leu Glu Met Ala Arg
1               5

<210> SEQ ID NO 287
<211> LENGTH: 9
<212> TYPE: PRT
<213> ORGANISM: Homo sapiens

<400> SEQUENCE: 287

Ile Gly Phe Pro Trp Ser Glu Ile Arg
1               5

<210> SEQ ID NO 288
<211> LENGTH: 577
<212> TYPE: PRT
<213> ORGANISM: Homo sapiens

<400> SEQUENCE: 288

Met Pro Lys Thr Ile Ser Val Arg Val Thr Thr Met Asp Ala Glu Leu
1               5                   10                  15

Glu Phe Ala Ile Gln Pro Asn Thr Thr Gly Lys Gln Leu Phe Asp Gln
            20                  25                  30

Val Val Lys Thr Ile Gly Leu Arg Glu Val Trp Phe Phe Gly Leu Gln
        35                  40                  45

Tyr Gln Asp Thr Lys Gly Phe Ser Thr Trp Leu Lys Leu Asn Lys Lys
    50                  55                  60
```

```
Val Thr Ala Gln Asp Val Arg Lys Glu Ser Pro Leu Leu Phe Lys Phe
 65                  70                  75                  80

Arg Ala Lys Phe Tyr Pro Glu Asp Val Ser Glu Glu Leu Ile Gln Asp
                 85                  90                  95

Ile Thr Gln Arg Leu Phe Phe Leu Gln Val Lys Glu Gly Ile Leu Asn
            100                 105                 110

Asp Asp Ile Tyr Cys Pro Pro Glu Thr Ala Val Leu Leu Ala Ser Tyr
        115                 120                 125

Ala Val Gln Ser Lys Tyr Gly Asp Phe Asn Lys Glu Val His Lys Ser
    130                 135                 140

Gly Tyr Leu Ala Gly Asp Lys Leu Leu Pro Gln Arg Val Leu Glu Gln
145                 150                 155                 160

His Lys Leu Asn Lys Asp Gln Trp Glu Glu Arg Ile Gln Val Trp His
                165                 170                 175

Glu Glu His Arg Gly Met Leu Arg Glu Asp Ala Val Leu Glu Tyr Leu
            180                 185                 190

Lys Ile Ala Gln Asp Leu Glu Met Tyr Gly Val Asn Tyr Phe Ser Ile
        195                 200                 205

Lys Asn Lys Lys Gly Ser Glu Leu Trp Leu Gly Val Asp Ala Leu Gly
    210                 215                 220

Leu Asn Ile Tyr Glu Gln Asn Asp Arg Leu Thr Pro Lys Ile Gly Phe
225                 230                 235                 240

Pro Trp Ser Glu Ile Arg Asn Ile Ser Phe Asn Asp Lys Lys Phe Val
                245                 250                 255

Ile Lys Pro Ile Asp Lys Lys Ala Pro Asp Phe Val Phe Tyr Ala Pro
            260                 265                 270

Arg Leu Arg Ile Asn Lys Arg Ile Leu Ala Leu Cys Met Gly Asn His
        275                 280                 285

Glu Leu Tyr Met Arg Arg Arg Lys Pro Asp Thr Ile Glu Val Gln Gln
    290                 295                 300

Met Lys Ala Gln Ala Arg Glu Glu Lys His Gln Lys Gln Met Glu Arg
305                 310                 315                 320

Ala Met Leu Glu Asn Glu Lys Lys Lys Arg Glu Met Ala Glu Lys Glu
                325                 330                 335

Lys Glu Lys Ile Glu Arg Glu Lys Glu Glu Leu Met Glu Arg Leu Lys
            340                 345                 350

Gln Ile Glu Glu Gln Thr Lys Lys Ala Gln Gln Glu Leu Glu Glu Gln
        355                 360                 365

Thr Arg Arg Ala Leu Glu Leu Glu Gln Glu Arg Lys Arg Ala Gln Ser
370                 375                 380

Glu Ala Glu Lys Leu Ala Lys Glu Arg Gln Glu Ala Glu Glu Ala Lys
385                 390                 395                 400

Glu Ala Leu Leu Gln Ala Ser Arg Asp Gln Lys Lys Thr Gln Glu Gln
                405                 410                 415

Leu Ala Leu Glu Met Ala Glu Leu Thr Ala Arg Ile Ser Gln Leu Glu
            420                 425                 430

Met Ala Arg Gln Lys Lys Glu Ser Glu Ala Val Glu Trp Gln Gln Lys
        435                 440                 445

Ala Gln Met Val Gln Glu Asp Leu Glu Lys Thr Arg Ala Glu Leu Lys
    450                 455                 460

Thr Ala Met Ser Thr Pro His Val Ala Glu Pro Ala Glu Asn Glu Gln
465                 470                 475                 480

Asp Glu Gln Asp Glu Asn Gly Ala Glu Ala Ser Ala Asp Leu Arg Ala
```

485                 490                 495
Asp Ala Met Ala Lys Asp Arg Ser Glu Glu Arg Thr Thr Glu Ala
                500                 505                 510

Glu Lys Asn Glu Arg Val Gln Lys His Leu Lys Ala Leu Thr Ser Glu
            515                 520                 525

Leu Ala Asn Ala Arg Asp Glu Ser Lys Lys Thr Ala Asn Asp Met Ile
        530                 535                 540

His Ala Glu Asn Met Arg Leu Gly Arg Asp Lys Tyr Lys Thr Leu Arg
545                 550                 555                 560

Gln Ile Arg Gln Gly Asn Thr Lys Gln Arg Ile Asp Glu Phe Glu Ser
                565                 570                 575

Met

<210> SEQ ID NO 289
<211> LENGTH: 9
<212> TYPE: PRT
<213> ORGANISM: Homo sapiens

<400> SEQUENCE: 289

Gly Ala Cys Ile Leu Asn Met Leu Arg
1               5

<210> SEQ ID NO 290
<211> LENGTH: 13
<212> TYPE: PRT
<213> ORGANISM: Homo sapiens

<400> SEQUENCE: 290

Ile Leu Ala Ser Thr Gln Phe Glu Pro Thr Ala Ala Arg
1               5                   10

<210> SEQ ID NO 291
<211> LENGTH: 9
<212> TYPE: PRT
<213> ORGANISM: Homo sapiens

<400> SEQUENCE: 291

Ser Gln Ile Glu Phe Ala Leu Cys Arg
1               5

<210> SEQ ID NO 292
<211> LENGTH: 941
<212> TYPE: PRT
<213> ORGANISM: Homo sapiens

<400> SEQUENCE: 292

Met Val Phe Leu Pro Leu Lys Trp Ser Leu Ala Thr Met Ser Phe Leu
1               5                   10                  15

Leu Ser Ser Leu Leu Ala Leu Leu Thr Val Ser Thr Pro Ser Trp Cys
            20                  25                  30

Gln Ser Thr Glu Ala Ser Pro Lys Arg Ser Asp Gly Thr Pro Phe Pro
        35                  40                  45

Trp Asn Lys Ile Arg Leu Pro Glu Tyr Val Ile Pro Val His Tyr Asp
    50                  55                  60

Leu Leu Ile His Ala Asn Leu Thr Thr Leu Thr Phe Trp Gly Thr Thr
65                  70                  75                  80

Lys Val Glu Ile Thr Ala Ser Gln Pro Thr Ser Thr Ile Ile Leu His
                85                  90                  95

Ser His Leu Gln Ile Ser Arg Ala Thr Leu Arg Lys Gly Ala Gly

-continued

```
                100                 105                 110
Glu Arg Leu Ser Glu Glu Pro Leu Gln Val Leu Glu His Pro Arg Gln
            115                 120                 125
Glu Gln Ile Ala Leu Leu Ala Pro Glu Pro Leu Leu Val Gly Leu Pro
130                 135                 140
Tyr Thr Val Val Ile His Tyr Ala Gly Asn Leu Ser Glu Thr Phe His
145                 150                 155                 160
Gly Phe Tyr Lys Ser Thr Tyr Arg Thr Lys Glu Gly Glu Leu Arg Ile
                165                 170                 175
Leu Ala Ser Thr Gln Phe Glu Pro Thr Ala Ala Arg Met Ala Phe Pro
            180                 185                 190
Cys Phe Asp Glu Pro Ala Phe Lys Ala Ser Phe Ser Ile Lys Ile Arg
            195                 200                 205
Arg Glu Pro Arg His Leu Ala Ile Ser Asn Met Pro Leu Val Lys Ser
        210                 215                 220
Val Thr Val Ala Glu Gly Leu Ile Glu Asp His Phe Asp Val Thr Val
225                 230                 235                 240
Lys Met Ser Thr Tyr Leu Val Ala Phe Ile Ile Ser Asp Phe Glu Ser
                245                 250                 255
Val Ser Lys Ile Thr Lys Ser Gly Val Lys Val Ser Val Tyr Ala Val
                260                 265                 270
Pro Asp Lys Ile Asn Gln Ala Asp Tyr Ala Leu Asp Ala Ala Val Thr
            275                 280                 285
Leu Leu Glu Phe Tyr Glu Asp Tyr Phe Ser Ile Pro Tyr Pro Leu Pro
        290                 295                 300
Lys Gln Asp Leu Ala Ala Ile Pro Asp Phe Gln Ser Gly Ala Met Glu
305                 310                 315                 320
Asn Trp Gly Leu Thr Thr Tyr Arg Glu Ser Ala Leu Leu Phe Asp Ala
                325                 330                 335
Glu Lys Ser Ser Ala Ser Ser Lys Leu Gly Ile Thr Met Thr Val Ala
            340                 345                 350
His Glu Leu Ala His Gln Trp Phe Gly Asn Leu Val Thr Met Glu Trp
        355                 360                 365
Trp Asn Asp Leu Trp Leu Asn Glu Gly Phe Ala Lys Phe Met Glu Phe
        370                 375                 380
Val Ser Val Ser Val Thr His Pro Glu Leu Lys Val Gly Asp Tyr Phe
385                 390                 395                 400
Phe Gly Lys Cys Phe Asp Ala Met Glu Val Asp Ala Leu Asn Ser Ser
                405                 410                 415
His Pro Val Ser Thr Pro Val Glu Asn Pro Ala Gln Ile Arg Glu Met
                420                 425                 430
Phe Asp Asp Val Ser Tyr Asp Lys Gly Ala Cys Ile Leu Asn Met Leu
            435                 440                 445
Arg Glu Tyr Leu Ser Ala Asp Ala Phe Lys Ser Gly Ile Val Gln Tyr
        450                 455                 460
Leu Gln Lys His Ser Tyr Lys Asn Thr Lys Asn Glu Asp Leu Trp Asp
465                 470                 475                 480
Ser Met Ala Ser Ile Cys Pro Thr Asp Gly Val Lys Gly Met Asp Gly
                485                 490                 495
Phe Cys Ser Arg Ser Gln His Ser Ser Ser Ser His Trp His Gln
            500                 505                 510
Glu Gly Val Asp Val Lys Thr Met Met Asn Thr Trp Thr Leu Gln Lys
        515                 520                 525
```

```
Gly Phe Pro Leu Ile Thr Ile Thr Val Arg Gly Arg Asn Val His Met
            530                 535                 540

Lys Gln Glu His Tyr Met Lys Gly Ser Asp Gly Ala Pro Asp Thr Gly
545                 550                 555                 560

Tyr Leu Trp His Val Pro Leu Thr Phe Ile Thr Ser Lys Ser Asp Met
                565                 570                 575

Val His Arg Phe Leu Leu Lys Thr Lys Thr Asp Val Leu Ile Leu Pro
            580                 585                 590

Glu Glu Val Glu Trp Ile Lys Phe Asn Val Gly Met Asn Gly Tyr Tyr
        595                 600                 605

Ile Val His Tyr Glu Asp Asp Gly Trp Asp Ser Leu Thr Gly Leu Leu
    610                 615                 620

Lys Gly Thr His Thr Ala Val Ser Ser Asn Asp Arg Ala Ser Leu Ile
625                 630                 635                 640

Asn Asn Ala Phe Gln Leu Val Ser Ile Gly Lys Leu Ser Ile Glu Lys
                645                 650                 655

Ala Leu Asp Leu Ser Leu Tyr Leu Lys His Glu Thr Glu Ile Met Pro
            660                 665                 670

Val Phe Gln Gly Leu Asn Glu Leu Ile Pro Met Tyr Lys Leu Met Glu
        675                 680                 685

Lys Arg Asp Met Asn Glu Val Glu Thr Gln Phe Lys Ala Phe Leu Ile
690                 695                 700

Arg Leu Leu Arg Asp Leu Ile Asp Lys Gln Thr Trp Thr Asp Glu Gly
705                 710                 715                 720

Ser Val Ser Glu Arg Met Leu Arg Ser Gln Leu Leu Leu Ala Cys
                725                 730                 735

Val His Asn Tyr Gln Pro Cys Val Gln Arg Ala Glu Gly Tyr Phe Arg
            740                 745                 750

Lys Trp Lys Glu Ser Asn Gly Asn Leu Ser Leu Pro Val Asp Val Thr
        755                 760                 765

Leu Ala Val Phe Ala Val Gly Ala Gln Ser Thr Glu Gly Trp Asp Phe
770                 775                 780

Leu Tyr Ser Lys Tyr Gln Phe Ser Leu Ser Ser Thr Glu Lys Ser Gln
785                 790                 795                 800

Ile Glu Phe Ala Leu Cys Arg Thr Gln Asn Lys Glu Lys Leu Gln Trp
                805                 810                 815

Leu Leu Asp Glu Ser Phe Lys Gly Asp Lys Ile Lys Thr Gln Glu Phe
            820                 825                 830

Pro Gln Ile Leu Thr Leu Ile Gly Arg Asn Pro Val Gly Tyr Pro Leu
        835                 840                 845

Ala Trp Gln Phe Leu Arg Lys Asn Trp Asn Lys Leu Val Gln Lys Phe
850                 855                 860

Glu Leu Gly Ser Ser Ser Ile Ala His Met Val Met Gly Thr Thr Asn
865                 870                 875                 880

Gln Phe Ser Thr Arg Thr Arg Leu Glu Glu Val Lys Gly Phe Phe Ser
                885                 890                 895

Ser Leu Lys Glu Asn Gly Ser Gln Leu Arg Cys Val Gln Gln Thr Ile
            900                 905                 910

Glu Thr Ile Glu Glu Asn Ile Gly Trp Met Asp Lys Asn Phe Asp Lys
        915                 920                 925

Ile Arg Val Trp Leu Gln Ser Glu Lys Leu Glu Arg Met
930                 935                 940
```

<210> SEQ ID NO 293
<211> LENGTH: 11
<212> TYPE: PRT
<213> ORGANISM: Homo sapiens

<400> SEQUENCE: 293

Met Ala Ser Thr Pro His Pro Gly Ala Arg
1               5                   10

<210> SEQ ID NO 294
<211> LENGTH: 11
<212> TYPE: PRT
<213> ORGANISM: Homo sapiens

<400> SEQUENCE: 294

Tyr Pro Gly Ser Pro Gly Ser Tyr Ala Ala Arg
1               5                   10

<210> SEQ ID NO 295
<211> LENGTH: 361
<212> TYPE: PRT
<213> ORGANISM: Homo sapiens

<400> SEQUENCE: 295

Met Ala Gly Gly Arg His Arg Val Val Gly Thr Leu His Leu Leu
1               5                   10                  15

Leu Leu Val Ala Ala Leu Pro Trp Ala Ser Arg Gly Val Ser Pro Ser
                20                  25                  30

Ala Ser Ala Trp Pro Glu Glu Lys Asn Tyr His Gln Pro Ala Ile Leu
            35                  40                  45

Asn Ser Ser Ala Leu Arg Gln Ile Ala Glu Gly Thr Ser Ile Ser Glu
        50                  55                  60

Met Trp Gln Asn Asp Leu Gln Pro Leu Leu Ile Glu Arg Tyr Pro Gly
65                  70                  75                  80

Ser Pro Gly Ser Tyr Ala Ala Arg Gln His Ile Met Gln Arg Ile Gln
                85                  90                  95

Arg Leu Gln Ala Asp Trp Val Leu Glu Ile Asp Thr Phe Leu Ser Gln
            100                 105                 110

Thr Pro Tyr Gly Tyr Arg Ser Phe Ser Asn Ile Ile Ser Thr Leu Asn
        115                 120                 125

Pro Thr Ala Lys Arg His Leu Val Leu Ala Cys His Tyr Asp Ser Lys
    130                 135                 140

Tyr Phe Ser His Trp Asn Asn Arg Val Phe Val Gly Ala Thr Asp Ser
145                 150                 155                 160

Ala Val Pro Cys Ala Met Met Leu Glu Leu Ala Arg Ala Leu Asp Lys
                165                 170                 175

Lys Leu Leu Ser Leu Lys Thr Val Ser Asp Ser Lys Pro Asp Leu Ser
            180                 185                 190

Leu Gln Leu Ile Phe Phe Asp Gly Glu Glu Ala Phe Leu His Trp Ser
        195                 200                 205

Pro Gln Asp Ser Leu Tyr Gly Ser Arg His Leu Ala Ala Lys Met Ala
    210                 215                 220

Ser Thr Pro His Pro Gly Ala Arg Gly Thr Ser Gln Leu His Gly Met
225                 230                 235                 240

Met Asp Leu Leu Val Leu Leu Asp Leu Ile Gly Ala Pro Asn Pro Thr
                245                 250                 255

Phe Pro Asn Phe Phe Pro Asn Ser Ala Arg Trp Phe Glu Arg Leu Gln

```
                    260                 265                 270
Ala Ile Glu His Glu Leu His Glu Leu Gly Leu Leu Lys Asp His Ser
                275                 280                 285
Leu Glu Gly Arg Tyr Phe Gln Asn Tyr Ser Tyr Gly Gly Val Ile Gln
                290                 295                 300
Asp Asp His Ile Pro Phe Leu Arg Arg Gly Val Pro Val Leu His Leu
305                 310                 315                 320
Ile Pro Ser Pro Phe Pro Glu Val Trp His Thr Met Asp Asp Asn Glu
                325                 330                 335
Glu Asn Leu Asp Glu Ser Thr Ile Asp Asn Leu Asn Lys Ile Leu Gln
                340                 345                 350
Val Phe Val Leu Glu Tyr Leu His Leu
                355                 360

<210> SEQ ID NO 296
<211> LENGTH: 11
<212> TYPE: PRT
<213> ORGANISM: Homo sapiens

<400> SEQUENCE: 296

Cys Thr Trp Leu Ile Glu Gly Gln Pro Asn Arg
1               5                   10

<210> SEQ ID NO 297
<211> LENGTH: 12
<212> TYPE: PRT
<213> ORGANISM: Homo sapiens

<400> SEQUENCE: 297

Gly Asp Glu Cys Gln Leu Cys Glu Val Glu Asn Arg
1               5                   10

<210> SEQ ID NO 298
<211> LENGTH: 15
<212> TYPE: PRT
<213> ORGANISM: Homo sapiens

<400> SEQUENCE: 298

Gly Val Lys Gly Asp Glu Cys Gln Leu Cys Glu Val Glu Asn Arg
1               5                   10                  15

<210> SEQ ID NO 299
<211> LENGTH: 7
<212> TYPE: PRT
<213> ORGANISM: Homo sapiens

<400> SEQUENCE: 299

Leu Ala Asp Asp Leu Tyr Arg
1               5

<210> SEQ ID NO 300
<211> LENGTH: 10
<212> TYPE: PRT
<213> ORGANISM: Homo sapiens

<400> SEQUENCE: 300

Ile Met Gln Ser Ser Gln Ser Met Ser Lys
1               5                   10

<210> SEQ ID NO 301
<211> LENGTH: 16
<212> TYPE: PRT
```

```
<213> ORGANISM: Homo sapiens

<400> SEQUENCE: 301

Leu Thr Gly Ser Ser Gly Phe Val Thr Asp Gly Pro Gly Asn Tyr Lys
1               5                   10                  15

<210> SEQ ID NO 302
<211> LENGTH: 13
<212> TYPE: PRT
<213> ORGANISM: Homo sapiens

<400> SEQUENCE: 302

Ser Cys Ala Leu Asp Gln Asn Cys Gln Trp Glu Pro Arg
1               5                   10

<210> SEQ ID NO 303
<211> LENGTH: 1428
<212> TYPE: PRT
<213> ORGANISM: Homo sapiens

<400> SEQUENCE: 303

Met Val Ala Ala Ala Ala Thr Glu Ala Arg Leu Arg Arg Thr
1               5                   10                  15

Ala Ala Thr Ala Ala Leu Ala Gly Arg Ser Gly Gly Pro His Trp Asp
                20                  25                  30

Trp Asp Val Thr Arg Ala Gly Arg Pro Gly Leu Gly Ala Gly Leu Arg
            35                  40                  45

Leu Pro Arg Leu Leu Ser Pro Pro Leu Arg Pro Arg Leu Leu Leu Leu
        50                  55                  60

Leu Leu Leu Leu Ser Pro Pro Leu Leu Leu Leu Leu Pro Cys Glu
65                  70                  75                  80

Ala Glu Ala Ala Ala Ala Ala Ala Val Ser Gly Ser Ala Ala Ala
                85                  90                  95

Glu Ala Lys Glu Cys Asp Arg Pro Cys Val Asn Gly Gly Arg Cys Asn
            100                 105                 110

Pro Gly Thr Gly Gln Cys Val Cys Pro Ala Gly Trp Val Gly Glu Gln
        115                 120                 125

Cys Gln His Cys Gly Gly Arg Phe Arg Leu Thr Gly Ser Ser Gly Phe
    130                 135                 140

Val Thr Asp Gly Pro Gly Asn Tyr Lys Tyr Lys Thr Lys Cys Thr Trp
145                 150                 155                 160

Leu Ile Glu Gly Gln Pro Asn Arg Ile Met Arg Leu Arg Phe Asn His
                165                 170                 175

Phe Ala Thr Glu Cys Ser Trp Asp His Leu Tyr Val Tyr Asp Gly Asp
            180                 185                 190

Ser Ile Tyr Ala Pro Leu Val Ala Phe Ser Gly Leu Ile Val Pro
        195                 200                 205

Glu Arg Asp Gly Asn Glu Thr Val Pro Glu Val Val Ala Thr Ser Gly
    210                 215                 220

Tyr Ala Leu Leu His Phe Phe Ser Asp Ala Ala Tyr Asn Leu Thr Gly
225                 230                 235                 240

Phe Asn Ile Thr Tyr Ser Phe Asp Met Cys Pro Asn Asn Cys Ser Gly
                245                 250                 255

Arg Gly Glu Cys Lys Ile Ser Asn Ser Ser Asp Thr Val Glu Cys Glu
            260                 265                 270

Cys Ser Glu Asn Trp Lys Gly Glu Ala Cys Asp Ile Pro His Cys Thr
        275                 280                 285
```

```
Asp Asn Cys Gly Phe Pro His Arg Gly Ile Cys Asn Ser Ser Asp Val
290                 295                 300

Arg Gly Cys Ser Cys Phe Ser Asp Trp Gln Gly Pro Gly Cys Ser Val
305                 310                 315                 320

Pro Val Pro Ala Asn Gln Ser Phe Trp Thr Arg Glu Glu Tyr Ser Asn
                325                 330                 335

Leu Lys Leu Pro Arg Ala Ser His Lys Ala Val Val Asn Gly Asn Ile
                340                 345                 350

Met Trp Val Val Gly Gly Tyr Met Phe Asn His Ser Asp Tyr Asn Met
            355                 360                 365

Val Leu Ala Tyr Asp Leu Ala Ser Arg Glu Trp Leu Pro Leu Asn Arg
        370                 375                 380

Ser Val Asn Asn Val Val Val Arg Tyr Gly His Ser Leu Ala Leu Tyr
385                 390                 395                 400

Lys Asp Lys Ile Tyr Met Tyr Gly Gly Lys Ile Asp Ser Thr Gly Asn
                405                 410                 415

Val Thr Asn Glu Leu Arg Val Phe His Ile His Asn Glu Ser Trp Val
                420                 425                 430

Leu Leu Thr Pro Lys Ala Lys Glu Gln Tyr Ala Val Val Gly His Ser
            435                 440                 445

Ala His Ile Val Thr Leu Lys Asn Gly Arg Val Val Met Leu Val Ile
        450                 455                 460

Phe Gly His Cys Pro Leu Tyr Gly Tyr Ile Ser Asn Val Gln Glu Tyr
465                 470                 475                 480

Asp Leu Asp Lys Asn Thr Trp Ser Ile Leu His Thr Gln Gly Ala Leu
                485                 490                 495

Val Gln Gly Gly Tyr Gly His Ser Ser Val Tyr Asp His Arg Thr Arg
            500                 505                 510

Ala Leu Tyr Val His Gly Gly Tyr Lys Ala Phe Ser Ala Asn Lys Tyr
        515                 520                 525

Arg Leu Ala Asp Asp Leu Tyr Arg Tyr Asp Val Asp Thr Gln Met Trp
    530                 535                 540

Thr Ile Leu Lys Asp Ser Arg Phe Phe Arg Tyr Leu His Thr Ala Val
545                 550                 555                 560

Ile Val Ser Gly Thr Met Leu Val Phe Gly Gly Asn Thr His Asn Asp
                565                 570                 575

Thr Ser Met Ser His Gly Ala Lys Cys Phe Ser Ser Asp Phe Met Ala
            580                 585                 590

Tyr Asp Ile Ala Cys Asp Arg Trp Ser Val Leu Pro Arg Pro Asp Leu
        595                 600                 605

His His Asp Val Asn Arg Phe Gly His Ser Ala Val Leu His Asn Ser
610                 615                 620

Thr Met Tyr Val Phe Gly Gly Phe Asn Ser Leu Leu Leu Ser Asp Ile
                625                 630                 635                 640

Leu Val Phe Thr Ser Glu Gln Cys Asp Ala His Arg Ser Glu Ala Ala
                645                 650                 655

Cys Leu Ala Ala Gly Pro Gly Ile Arg Cys Val Trp Asn Thr Gly Ser
                660                 665                 670

Ser Gln Cys Ile Ser Trp Ala Leu Ala Thr Asp Glu Gln Glu Glu Lys
        675                 680                 685

Leu Lys Ser Glu Cys Phe Ser Lys Arg Thr Leu Asp His Asp Arg Cys
    690                 695                 700
```

```
Asp Gln His Thr Asp Cys Tyr Ser Cys Thr Ala Asn Thr Asn Asp Cys
705                 710                 715                 720

His Trp Cys Asn Asp His Cys Val Pro Arg Asn His Ser Cys Ser Glu
            725                 730                 735

Gly Gln Ile Ser Ile Phe Arg Tyr Glu Asn Cys Pro Lys Asp Asn Pro
            740                 745                 750

Met Tyr Tyr Cys Asn Lys Lys Thr Ser Cys Arg Ser Cys Ala Leu Asp
            755                 760                 765

Gln Asn Cys Gln Trp Glu Pro Arg Asn Gln Cys Ile Ala Leu Pro
            770                 775                 780

Glu Asn Ile Cys Gly Ile Gly Trp His Leu Val Gly Asn Ser Cys Leu
785                 790                 795                 800

Lys Ile Thr Thr Ala Lys Glu Asn Tyr Asp Asn Ala Lys Leu Phe Cys
            805                 810                 815

Arg Asn His Asn Ala Leu Leu Ala Ser Leu Thr Thr Gln Lys Lys Val
            820                 825                 830

Glu Phe Val Leu Lys Gln Leu Arg Ile Met Gln Ser Ser Gln Ser Met
            835                 840                 845

Ser Lys Leu Thr Leu Thr Pro Trp Val Gly Leu Arg Lys Ile Asn Val
850                 855                 860

Ser Tyr Trp Cys Trp Glu Asp Met Ser Pro Phe Thr Asn Ser Leu Leu
865                 870                 875                 880

Gln Trp Met Pro Ser Glu Pro Ser Asp Ala Gly Phe Cys Gly Ile Leu
            885                 890                 895

Ser Glu Pro Ser Thr Arg Gly Leu Lys Ala Ala Thr Cys Ile Asn Pro
            900                 905                 910

Leu Asn Gly Ser Val Cys Glu Arg Pro Ala Asn His Ser Ala Lys Gln
            915                 920                 925

Cys Arg Thr Pro Cys Ala Leu Arg Thr Ala Cys Gly Asp Cys Thr Ser
            930                 935                 940

Gly Ser Ser Glu Cys Met Trp Cys Ser Asn Met Lys Gln Cys Val Asp
945                 950                 955                 960

Ser Asn Ala Tyr Val Ala Ser Phe Pro Phe Gly Gln Cys Met Glu Trp
            965                 970                 975

Tyr Thr Met Ser Thr Cys Pro Pro Glu Asn Cys Ser Gly Tyr Cys Thr
            980                 985                 990

Cys Ser His Cys Leu Glu Gln Pro Gly Cys Gly Trp Cys Thr Asp Pro
            995                 1000                1005

Ser Asn Thr Gly Lys Gly Lys Cys Ile Glu Gly Ser Tyr Lys Gly
    1010                1015                1020

Pro Val Lys Met Pro Ser Gln Ala Pro Thr Gly Asn Phe Tyr Pro
    1025                1030                1035

Gln Pro Leu Leu Asn Ser Ser Met Cys Leu Glu Asp Ser Arg Tyr
    1040                1045                1050

Asn Trp Ser Phe Ile His Cys Pro Ala Cys Gln Cys Asn Gly His
    1055                1060                1065

Ser Lys Cys Ile Asn Gln Ser Ile Cys Glu Lys Cys Glu Asn Leu
    1070                1075                1080

Thr Thr Gly Lys His Cys Glu Thr Cys Ile Ser Gly Phe Tyr Gly
    1085                1090                1095

Asp Pro Thr Asn Gly Gly Lys Cys Gln Pro Cys Lys Cys Asn Gly
    1100                1105                1110

His Ala Ser Leu Cys Asn Thr Asn Thr Gly Lys Cys Phe Cys Thr
```

```
                        1115                1120                1125

Thr Lys Gly Val Lys Gly Asp Glu Cys Gln Leu Cys Glu Val Glu
    1130                1135                1140

Asn Arg Tyr Gln Gly Asn Pro Leu Arg Gly Thr Cys Tyr Tyr Thr
    1145                1150                1155

Leu Leu Ile Asp Tyr Gln Phe Thr Phe Ser Leu Ser Gln Glu Asp
    1160                1165                1170

Asp Arg Tyr Tyr Thr Ala Ile Asn Phe Val Ala Thr Pro Asp Glu
    1175                1180                1185

Gln Asn Arg Asp Leu Asp Met Phe Ile Asn Ala Ser Lys Asn Phe
    1190                1195                1200

Asn Leu Asn Ile Thr Trp Ala Ala Ser Phe Ser Ala Gly Thr Gln
    1205                1210                1215

Ala Gly Glu Glu Met Pro Val Val Ser Lys Thr Asn Ile Lys Glu
    1220                1225                1230

Tyr Lys Asp Ser Phe Ser Asn Glu Lys Phe Asp Phe Arg Asn His
    1235                1240                1245

Pro Asn Ile Thr Phe Phe Val Tyr Val Ser Asn Phe Thr Trp Pro
    1250                1255                1260

Ile Lys Ile Gln Ile Ala Phe Ser Gln His Ser Asn Phe Met Asp
    1265                1270                1275

Leu Val Gln Phe Phe Val Thr Phe Phe Ser Cys Phe Leu Ser Leu
    1280                1285                1290

Leu Leu Val Ala Ala Val Val Trp Lys Ile Lys Gln Ser Cys Trp
    1295                1300                1305

Ala Ser Arg Arg Arg Glu Gln Leu Leu Arg Glu Met Gln Gln Met
    1310                1315                1320

Ala Ser Arg Pro Phe Ala Ser Val Asn Val Ala Leu Glu Thr Asp
    1325                1330                1335

Glu Glu Pro Pro Asp Leu Ile Gly Gly Ser Ile Lys Thr Val Pro
    1340                1345                1350

Lys Pro Ile Ala Leu Glu Pro Cys Phe Gly Asn Lys Ala Ala Val
    1355                1360                1365

Leu Ser Val Phe Val Arg Leu Pro Arg Gly Leu Gly Gly Ile Pro
    1370                1375                1380

Pro Pro Gly Gln Ser Gly Leu Ala Val Ala Ser Ala Leu Val Asp
    1385                1390                1395

Ile Ser Gln Gln Met Pro Ile Val Tyr Lys Glu Lys Ser Gly Ala
    1400                1405                1410

Val Arg Asn Arg Lys Gln Gln Pro Pro Ala Gln Pro Gly Thr Cys
    1415                1420                1425

<210> SEQ ID NO 304
<211> LENGTH: 20
<212> TYPE: PRT
<213> ORGANISM: Homo sapiens

<400> SEQUENCE: 304

Ala Asp Ala Val Thr Leu Asp Gly Gly Phe Ile Tyr Glu Ala Gly Leu
1               5                   10                  15

Ala Pro Tyr Lys
            20

<210> SEQ ID NO 305
<211> LENGTH: 14
```

```
<212> TYPE: PRT
<213> ORGANISM: Homo sapiens

<400> SEQUENCE: 305

Ala Arg Val Val Trp Cys Ala Val Gly Glu Gln Glu Leu Arg
1               5                   10

<210> SEQ ID NO 306
<211> LENGTH: 15
<212> TYPE: PRT
<213> ORGANISM: Homo sapiens

<400> SEQUENCE: 306

Ala Arg Val Val Trp Cys Ala Val Gly Glu Gln Glu Leu Arg Lys
1               5                   10                  15

<210> SEQ ID NO 307
<211> LENGTH: 17
<212> TYPE: PRT
<213> ORGANISM: Homo sapiens

<400> SEQUENCE: 307

Cys Ala Phe Ser Ser Gln Glu Pro Tyr Phe Ser Tyr Ser Gly Ala Phe
1               5                   10                  15

Lys

<210> SEQ ID NO 308
<211> LENGTH: 6
<212> TYPE: PRT
<213> ORGANISM: Homo sapiens

<400> SEQUENCE: 308

Cys Phe Gln Trp Gln Arg
1               5

<210> SEQ ID NO 309
<211> LENGTH: 12
<212> TYPE: PRT
<213> ORGANISM: Homo sapiens

<400> SEQUENCE: 309

Cys Gly Leu Val Pro Val Leu Ala Glu Asn Tyr Lys
1               5                   10

<210> SEQ ID NO 310
<211> LENGTH: 13
<212> TYPE: PRT
<213> ORGANISM: Homo sapiens

<400> SEQUENCE: 310

Cys Leu Ala Glu Asn Ala Gly Asp Val Ala Phe Val Lys
1               5                   10

<210> SEQ ID NO 311
<211> LENGTH: 13
<212> TYPE: PRT
<213> ORGANISM: Homo sapiens

<400> SEQUENCE: 311

Cys Leu Arg Asp Gly Ala Gly Asp Val Ala Phe Ile Arg
1               5                   10

<210> SEQ ID NO 312
<211> LENGTH: 15
```

```
<212> TYPE: PRT
<213> ORGANISM: Homo sapiens

<400> SEQUENCE: 312

Cys Ser Thr Ser Pro Leu Leu Glu Ala Cys Glu Phe Leu Arg Lys
1               5                   10                  15

<210> SEQ ID NO 313
<211> LENGTH: 14
<212> TYPE: PRT
<213> ORGANISM: Homo sapiens

<400> SEQUENCE: 313

Cys Ser Thr Ser Pro Leu Leu Glu Ala Cys Glu Phe Leu Arg
1               5                   10

<210> SEQ ID NO 314
<211> LENGTH: 8
<212> TYPE: PRT
<213> ORGANISM: Homo sapiens

<400> SEQUENCE: 314

Cys Val Pro Asn Ser Asn Glu Arg
1               5

<210> SEQ ID NO 315
<211> LENGTH: 17
<212> TYPE: PRT
<213> ORGANISM: Homo sapiens

<400> SEQUENCE: 315

Cys Val Pro Asn Ser Asn Glu Arg Tyr Tyr Gly Tyr Thr Gly Ala Phe
1               5                   10                  15

Arg

<210> SEQ ID NO 316
<211> LENGTH: 6
<212> TYPE: PRT
<213> ORGANISM: Homo sapiens

<400> SEQUENCE: 316

Asp Cys His Leu Ala Arg
1               5

<210> SEQ ID NO 317
<211> LENGTH: 12
<212> TYPE: PRT
<213> ORGANISM: Homo sapiens

<400> SEQUENCE: 317

Asp Glu Tyr Glu Leu Leu Cys Pro Asp Asn Thr Arg
1               5                   10

<210> SEQ ID NO 318
<211> LENGTH: 10
<212> TYPE: PRT
<213> ORGANISM: Homo sapiens

<400> SEQUENCE: 318

Asp Gly Ala Gly Asp Val Ala Phe Ile Arg
1               5                   10

<210> SEQ ID NO 319
<211> LENGTH: 36
```

```
<212> TYPE: PRT
<213> ORGANISM: Homo sapiens

<400> SEQUENCE: 319

Asp Gly Ala Gly Asp Val Ala Phe Ile Arg Glu Ser Thr Val Phe Glu
1               5                   10                  15

Asp Leu Ser Asp Glu Ala Glu Arg Asp Glu Tyr Glu Leu Leu Cys Pro
            20                  25                  30

Asp Asn Thr Arg
        35

<210> SEQ ID NO 320
<211> LENGTH: 13
<212> TYPE: PRT
<213> ORGANISM: Homo sapiens

<400> SEQUENCE: 320

Asp Leu Leu Phe Lys Asp Ser Ala Ile Gly Phe Ser Arg
1               5                   10

<210> SEQ ID NO 321
<211> LENGTH: 15
<212> TYPE: PRT
<213> ORGANISM: Homo sapiens

<400> SEQUENCE: 321

Asp Leu Lys Leu Ala Asp Phe Ala Leu Leu Cys Leu Asp Gly Lys
1               5                   10                  15

<210> SEQ ID NO 322
<211> LENGTH: 16
<212> TYPE: PRT
<213> ORGANISM: Homo sapiens

<400> SEQUENCE: 322

Asp Leu Lys Leu Ala Asp Phe Ala Leu Leu Cys Leu Asp Gly Lys Arg
1               5                   10                  15

<210> SEQ ID NO 323
<211> LENGTH: 16
<212> TYPE: PRT
<213> ORGANISM: Homo sapiens

<400> SEQUENCE: 323

Asp Lys Ser Pro Lys Phe Gln Leu Phe Gly Ser Pro Ser Gly Gln Lys
1               5                   10                  15

<210> SEQ ID NO 324
<211> LENGTH: 8
<212> TYPE: PRT
<213> ORGANISM: Homo sapiens

<400> SEQUENCE: 324

Asp Ser Ala Ile Gly Phe Ser Arg
1               5

<210> SEQ ID NO 325
<211> LENGTH: 12
<212> TYPE: PRT
<213> ORGANISM: Homo sapiens

<400> SEQUENCE: 325

Asp Ser Ala Ile Gly Phe Ser Arg Val Pro Pro Arg
1               5                   10
```

<210> SEQ ID NO 326
<211> LENGTH: 14
<212> TYPE: PRT
<213> ORGANISM: Homo sapiens

<400> SEQUENCE: 326

Asp Ser Pro Ile Gln Cys Ile Gln Ala Ile Ala Glu Asn Arg
1               5                   10

<210> SEQ ID NO 327
<211> LENGTH: 34
<212> TYPE: PRT
<213> ORGANISM: Homo sapiens

<400> SEQUENCE: 327

Asp Ser Pro Ile Gln Cys Ile Gln Ala Ile Ala Glu Asn Arg Ala Asp
1               5                   10                  15

Ala Val Thr Leu Asp Gly Gly Phe Ile Tyr Glu Ala Gly Leu Ala Pro
            20                  25                  30

Tyr Lys

<210> SEQ ID NO 328
<211> LENGTH: 18
<212> TYPE: PRT
<213> ORGANISM: Homo sapiens

<400> SEQUENCE: 328

Asp Val Thr Val Leu Gln Asn Thr Asp Gly Asn Asn Asn Glu Ala Trp
1               5                   10                  15

Ala Lys

<210> SEQ ID NO 329
<211> LENGTH: 21
<212> TYPE: PRT
<213> ORGANISM: Homo sapiens

<400> SEQUENCE: 329

Asp Val Thr Val Leu Gln Asn Thr Asp Gly Asn Asn Asn Glu Ala Trp
1               5                   10                  15

Ala Lys Asp Ile Lys
            20

<210> SEQ ID NO 330
<211> LENGTH: 18
<212> TYPE: PRT
<213> ORGANISM: Homo sapiens

<400> SEQUENCE: 330

Gly Glu Ala Asp Ala Met Ser Leu Asp Gly Gly Tyr Val Tyr Thr Ala
1               5                   10                  15

Gly Lys

<210> SEQ ID NO 331
<211> LENGTH: 13
<212> TYPE: PRT
<213> ORGANISM: Homo sapiens

<400> SEQUENCE: 331

Gly Gly Ser Phe Gln Leu Asn Glu Leu Gln Gly Leu Lys
1               5                   10

```
<210> SEQ ID NO 332
<211> LENGTH: 8
<212> TYPE: PRT
<213> ORGANISM: Homo sapiens

<400> SEQUENCE: 332

Gly Pro Pro Val Ser Cys Ile Lys
1               5

<210> SEQ ID NO 333
<211> LENGTH: 9
<212> TYPE: PRT
<213> ORGANISM: Homo sapiens

<400> SEQUENCE: 333

Gly Pro Pro Val Ser Cys Ile Lys Arg
1               5

<210> SEQ ID NO 334
<211> LENGTH: 8
<212> TYPE: PRT
<213> ORGANISM: Homo sapiens

<400> SEQUENCE: 334

Gly Gln Phe Pro Asn Leu Cys Arg
1               5

<210> SEQ ID NO 335
<211> LENGTH: 708
<212> TYPE: PRT
<213> ORGANISM: Homo sapiens

<400> SEQUENCE: 335

Met Lys Leu Val Phe Leu Val Leu Leu Phe Leu Gly Ala Leu Gly Leu
1               5                   10                  15

Cys Leu Ala Gly Arg Arg Arg Ser Val Gln Trp Cys Ala Val Ser Gln
                20                  25                  30

Pro Glu Ala Thr Lys Cys Phe Gln Trp Gln Arg Asn Met Arg Lys Val
            35                  40                  45

Arg Gly Pro Pro Val Ser Cys Ile Lys Arg Asp Ser Pro Ile Gln Cys
        50                  55                  60

Ile Gln Ala Ile Ala Glu Asn Arg Ala Asp Ala Val Thr Leu Asp Gly
65                  70                  75                  80

Gly Phe Ile Tyr Glu Ala Gly Leu Ala Pro Tyr Lys Leu Arg Pro Val
                85                  90                  95

Ala Ala Glu Val Tyr Gly Thr Glu Arg Gln Pro Arg Thr His Tyr Tyr
            100                 105                 110

Ala Val Ala Val Val Lys Lys Gly Gly Ser Phe Gln Leu Asn Glu Leu
        115                 120                 125

Gln Gly Leu Lys Ser Cys His Thr Gly Leu Arg Arg Thr Ala Gly Trp
    130                 135                 140

Asn Val Pro Ile Gly Thr Leu Arg Pro Phe Leu Asn Trp Thr Gly Pro
145                 150                 155                 160

Pro Glu Pro Ile Glu Ala Ala Val Ala Arg Phe Phe Ser Ala Ser Cys
                165                 170                 175

Val Pro Gly Ala Asp Lys Gly Gln Phe Pro Asn Leu Cys Arg Leu Cys
            180                 185                 190

Ala Gly Thr Gly Glu Asn Lys Cys Ala Phe Ser Ser Gln Glu Pro Tyr
        195                 200                 205
```

```
Phe Ser Tyr Ser Gly Ala Phe Lys Cys Leu Arg Asp Gly Ala Gly Asp
    210                 215                 220
Val Ala Phe Ile Arg Glu Ser Thr Val Phe Glu Asp Leu Ser Asp Glu
225                 230                 235                 240
Ala Glu Arg Asp Glu Tyr Glu Leu Leu Cys Pro Asp Asn Thr Arg Lys
                245                 250                 255
Pro Val Asp Lys Phe Lys Asp Cys His Leu Ala Arg Val Pro Ser His
            260                 265                 270
Ala Val Ala Arg Ser Val Asn Gly Lys Glu Asp Ala Ile Trp Asn
        275                 280                 285
Leu Leu Arg Gln Ala Gln Glu Lys Phe Gly Lys Asp Lys Ser Pro Lys
290                 295                 300
Phe Gln Leu Phe Gly Ser Pro Ser Gly Gln Lys Asp Leu Leu Phe Lys
305                 310                 315                 320
Asp Ser Ala Ile Gly Phe Ser Arg Val Pro Pro Arg Ile Asp Ser Gly
                325                 330                 335
Leu Tyr Leu Gly Ser Gly Tyr Phe Thr Ala Ile Gln Asn Leu Arg Lys
            340                 345                 350
Ser Glu Glu Val Ala Ala Arg Arg Ala Arg Val Val Trp Cys Ala
        355                 360                 365
Val Gly Glu Gln Glu Leu Arg Lys Cys Asn Gln Trp Ser Gly Leu Ser
370                 375                 380
Glu Gly Ser Val Thr Cys Ser Ser Ala Ser Thr Thr Glu Asp Cys Ile
385                 390                 395                 400
Ala Leu Lys Gly Glu Ala Asp Ala Met Ser Leu Asp Gly Gly Tyr Val
                405                 410                 415
Tyr Thr Ala Gly Lys Cys Gly Leu Val Pro Val Leu Ala Glu Asn Tyr
            420                 425                 430
Lys Ser Gln Gln Ser Ser Asp Pro Asp Pro Asn Cys Val Asp Arg Pro
        435                 440                 445
Val Glu Gly Tyr Leu Ala Val Ala Val Val Arg Arg Ser Asp Thr Ser
450                 455                 460
Leu Thr Trp Asn Ser Val Lys Gly Lys Lys Ser Cys His Thr Ala Val
465                 470                 475                 480
Asp Arg Thr Ala Gly Trp Asn Ile Pro Met Gly Leu Leu Phe Asn Gln
                485                 490                 495
Thr Gly Ser Cys Lys Phe Asp Glu Tyr Phe Ser Gln Ser Cys Ala Pro
            500                 505                 510
Gly Ser Asp Pro Arg Ser Asn Leu Cys Ala Leu Cys Ile Gly Asp Glu
        515                 520                 525
Gln Gly Glu Asn Lys Cys Val Pro Asn Ser Asn Glu Arg Tyr Tyr Gly
530                 535                 540
Tyr Thr Gly Ala Phe Arg Cys Leu Ala Glu Asn Ala Gly Asp Val Ala
545                 550                 555                 560
Phe Val Lys Asp Val Thr Val Leu Gln Asn Thr Asp Gly Asn Asn Asn
                565                 570                 575
Glu Ala Trp Ala Lys Asp Leu Lys Leu Ala Asp Phe Ala Leu Leu Cys
            580                 585                 590
Leu Asp Gly Lys Arg Lys Pro Val Thr Glu Ala Arg Ser Cys His Leu
        595                 600                 605
Ala Met Ala Pro Asn His Ala Val Val Ser Arg Met Asp Lys Val Glu
610                 615                 620
```

-continued

```
Arg Leu Lys Gln Val Leu Leu His Gln Gln Ala Lys Phe Gly Arg Asn
625             630             635             640

Gly Ser Asp Cys Pro Asp Lys Phe Cys Leu Phe Gln Ser Glu Thr Lys
            645             650             655

Asn Leu Leu Phe Asn Asp Asn Thr Glu Cys Leu Ala Arg Leu His Gly
            660             665             670

Lys Thr Thr Tyr Glu Lys Tyr Leu Gly Pro Gln Tyr Val Ala Gly Ile
        675             680             685

Thr Asn Leu Lys Lys Cys Ser Thr Ser Pro Leu Leu Glu Ala Cys Glu
    690             695             700

Phe Leu Arg Lys
705
```

METHODS OF DETECTING CANCER

CROSS REFERENCE TO RELATED APPLICATIONS

This application claims the benefit of provisional patent application No. 61/991,061 filed on 9 May 2014, which is hereby incorporated by reference in its entirety.

BACKGROUND

Field of Invention

This present application encompasses proteins and peptide fragments of those proteins produced by proteolytic digestion that are useful for diagnosing or monitoring for the presence of cancer in an individual.

Description of the Related Art

Screening mammograms typically have a sensitivity of 75% and specificity of around 98% resulting in a false positive rate of roughly 5% per mammogram (Brown, Houn, Sickles, & Kessler, 1995; Kolb, Lichy, & Newhouse, 2002; Luftner & Possinger, 2002). Follow up imaging to evaluate false positives costs the US over 4 B with an additional 1.6 B for biopsies alone. In 2010 of the 1.6 M biopsies performed as little as 16% (only 261,000) were found to have cancer (Grady, 2012). The answer to increasing the diagnostic parameters of imaging can be found in the pre and post image diagnostics which focuses on genetic and proteomic information, more specifically, biomarkers (Armstrong, Handorf, Chen, & Bristol Demeter, 2013; Li, Zhang, Rosenzweig, Wang, & Chan, 2002).

Tissue and serum are commonly the most logical place for beginning biomarker research, however the large dynamic range of both mediums makes discovery quite difficult (Schiess, Wollscheid, & Aebersold, 2009). The answers may lie in less complex biological fluids, such as saliva and tears. The use of tears as diagnostic medium is not a novel application as the tear proteome has been extensively investigated previously (Böhm et al., 2012; 2011; Lebrecht, Boehm, Schmidt, Koelbl, & Grus, 2009a; Lebrecht et al., 2009b; Wu & Zhang, 2007). In this application a quantitative assay for the detection of a panel of tear-based biomarkers in response to cancer by triple quadrupole LC mass spectrometry is proposed. From this quantitative information, the framework for a Certified Laboratory Improvement Amendments (CLIA) protocol will be defined.

SUMMARY

Methods of determining whether a subject has cancer are provided herein. The methods include obtaining a sample from the subject and performing steps for or detecting the level of at least one of the markers provided in Table 2A or Table 2B in the sample. The subject is likely to have cancer if the levels of the markers of Table 2A are increased or if the markers in Table 2B are decreased as compared to the levels in a control sample lacking cancer. The sample is optionally lacrimal secretions, such as an ocular wash, saliva or other bodily fluid.

Kits for performing the methods described herein are also provided. The kits may comprise an eye wash solution and collection materials such as tubes. The tube for collection may comprise a protease inhibitor or other protein stabilizing agent.

DETAILED DESCRIPTION

Figure 1:
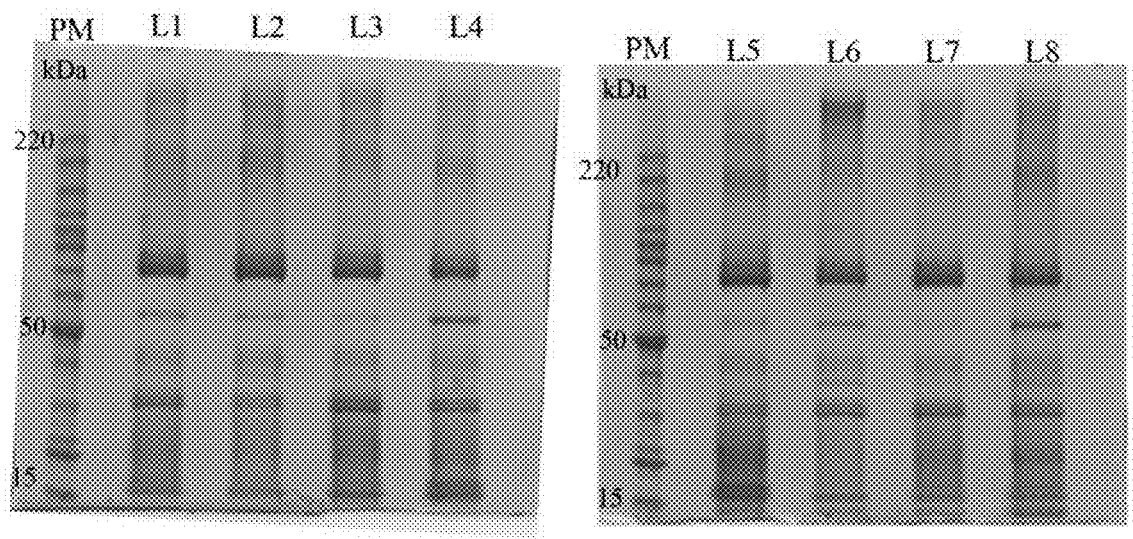
FIG. 1 is a set of photographs of a NuPAGE showing the proteins collected from each of the pooled ocular wash samples. The lane numbers correspond to pool numbers with the even numbers being breast cancer pools and the odd numbers being control pools.

Provided herein are proteins and trypsin produced polypeptides (as defined in Table 2A and 2B in the Examples and the actual trypsin sequences and full length amino acid sequences of the proteins identified as being up regulated and down regulated in cancer samples are provided in Appendix I and Appendix II, respectively) which are shown in the Examples to increase or decrease in biological samples in response to the presence of breast cancer as compared to controls. These proteins and peptides are biomarkers and will be used to determine the disease state of a patient or other subject.

Subjects include humans, domesticated animals such as cats, dogs, cows, pigs or other animals susceptible to cancer. A "patient" indicates a subject who is diagnosed with a disease or with cancer or being tested for having cancer. Thus subject and cancer may be used interchangeably herein. The subjects may be suspected of having cancer, in particular breast cancer. The subjects may have an increased risk of developing breast cancer. For example, the subject may be at increased risk of cancer or suspected of having cancer because of a positive mammography result, by detection of a lump in the breast, testing positive for a gene known to increase the risk of cancer such as BRCA, or already have had a resection, biopsy or other procedure to remove the cancer. The subject may be undergoing or have previously undergone treatment for cancer and the methods and kits herein are used to monitor progression of treatment or alternatively to monitor for recurrence or spread of the cancer. The cancer may be detected as early as stage I or II cancer, but later stages will also be detected.

Also provided herein are methods and kits to collect ocular wash samples for use to determine the expression levels of the identified proteins or polypeptides in lacrimal secretions. In addition, the use of tubes for collection containing protease inhibitor or protein stabilizing agents is covered. The kits further contain buffers or reagents for the elution of breast cancer biomarkers from the eye. The design of devices to collect the applied saline solution from the corner of the exposed ocular surface as well as the packaging of this device together with saline and a pre-prepared sample collection tube are also disclosed.

The methods disclosed herein encompass the use of these breast cancer biomarkers, singly or in multiples, in a CLIA based protocol utilizing a triple quadrupole LC-MS platform, which will be carried out at a centralized laboratory testing facility. The ocular wash samples collected from individuals may be shipped to the testing facility in this embodiment. The identified proteins and their subsequent proteolytic fragments are used for quantitative analysis of diagnostic peptides produced in the triple quad. A threshold value or a relative or actual value in terms of polypeptide concentration directly relating to the polypeptides listed in Tables 2A and 2B can be defined or samples can be compared directly to non-cancerous controls. The quantitative information in report form could be provided to physicians to help in making decisions regarding the pathway of patient care. Physicians may base treatment decisions on these results and the final step may include administration of an appropriate anti-cancer therapeutic to the subject.

In an alternative embodiment, the polypeptides of Tables 2A and 2B may be detected by implementing binding agents (i.e. antibodies, peptoids, coated surfaces) and reagents that accommodate a binding interaction specific to these proteins to produce a reaction which can be quantitated based on production of a detectable signal such as florescence, color change, or UV absorbance. Implementing these components in a cartridge with a partnering reading instrument that could be used at point of care is also provided. Binding agents for these proteins and polypeptides may also be used for detection in a lateral flow device. Thus methods of detecting the level of protein expression in the samples using a binding partner such as an antibody may be used to detect the markers provided herein in an immunoassay.

The immunoassay typically includes contacting a test sample with an antibody that specifically binds to or otherwise recognizes a biomarker, and detecting the presence of a complex of the antibody bound to the biomarker in the sample. The immunoassay procedure may be selected from a wide variety of immunoassay procedures known to the art involving recognition of antibody/antigen complexes, including enzyme-linked immunosorbent assays (ELISA), radioimmunoassay (RIA), and Western blots, and use of multiplex assays, including use of antibody arrays, wherein several desired antibodies are placed on a support, such as a glass bead or plate, and reacted or otherwise contacted with the test sample. Such assays are well-known to the skilled artisan.

The detection of the biomarkers described herein in a sample may be performed in a variety of ways. In one embodiment, the method provides the reverse-transcription of complementary DNAs from mRNAs obtained from the sample. Fluorescent dye-labeled complementary RNAs may be transcribed from complementary DNAs which are then hybridized to the arrays of oligonucleotide probes. The fluorescent color generated by hybridization is read by machine, such as an Agilent Scanner and data are obtained and processed using software, such as Agilent Feature Extraction Software (9.1). Such array based methods include microarray analysis to develop a gene expression profile. As used herein, the term "gene expression profile" refers to the expression levels of mRNAs or proteins of a panel of genes in the subject. As used herein, the term "panel of diagnostic genes" refers to a panel of genes whose expression level can be relied on to diagnose or predict the status of the disease. Included in this panel of genes are those listed in Tables 2A and 2B, as well as any combination thereof, as provided herein. In other embodiments, complementary DNAs are reverse-transcribed from mRNAs obtained from the sample, amplified and simultaneously quantified by real-time PCR, thereby enabling both detection and quantification (as absolute number of copies or relative amount when normalized to DNA input or additional normalizing genes) of a specific gene product in the complementary DNA sample as well as the original mRNA sample.

The methods of this invention include detecting at least one biomarker. However, any number of biomarkers may be detected. It is preferred that at least two biomarkers are detected in the analysis. However, it is realized that three, four, or more, including all, of the biomarkers described herein may be utilized in the analysis. Thus, not only can one or more markers be detected, one to 40, preferably two to 40, two to 30, two to 20 biomarkers, two to 10 biomarkers, or some other combination, may be detected and analyzed as described herein. In addition, other biomarkers not herein described may be combined with any of the presently disclosed biomarkers to aid in the diagnosis of cancer. Moreover, any combination of the above biomarkers may be detected in accordance with the present invention.

The markers of Table 2A may be increased at least 2 fold, 4 fold, 5 fold, 8 fold, 10 fold or more relative to the level of the marker in the control sample. The markers of Table 2B are decreased at least 1.5 fold, 2 fold, 3 fold, 4 fold or more relative to the level of the marker in the control sample. The control sample may be a sample from a subject that does not have cancer, a pooled sample from subjects that do not have cancer or may be a control or baseline expression level known to be the average expression level of subjects without cancer.

Several terms are used throughout this disclosure and should be defined as commonly used in the art, or as specifically provided herein. As provided herein, mass spectrometry or MS refers to an analytical technique generating electrical or magnetic fields to determine mass-to-charge ratio of peptides and chemical compounds in order to identify or determine peptide sequence and chemical structures. LC-MS/MS spectrometry refers to an analytical technique combining the separation capabilities of high performance liquid chromatography (HPLC) with the mass analysis of mass spectrometry. Triple quadrupole mass spectrometry refers to a tandem mass spectrometer with three ionizing chambers (Q1, Q2, &Q3). This technique allows for target detection of molecules of interest. Ion pairs refers to a parent peptide detected in Q1 in it's doubly or triply charged form and a resulting y or b ion as generated by Q2 and detected in Q3 of a triple quadrupole mass spectrometry instrument. SIS internal peptide refers to a synthesized isotopically-labeled peptide with the same sequence as the peptide to be monitored in Q1 and used as an internal standard for reference to quantify the peptide of interest. The –y ion refers to an ion generated from the c-terminal of a peptide fragment. The –b ion refers to an ion generated from the n-terminal of a peptide fragment. Quantitative Ion refers to the selected highest intensity y or b ion used to determine the quantity of it's parent protein in a biological sample. Qualitative Ion refers to ion/ions chosen to ensure the integrity of the Qualitative ion to selected protein of interest and labeled peptide to selected standards.

CLIA refers to Clinical Laboratory Improvements Amendments which are federal regulatory standards that apply to all clinical laboratory testing preformed on humans in the united states, except clinical trials and basic research. (*CLIA related Federal Register and Code of Federal Regulation Announcements*). CLIA approved laboratory refers to a clinical lab which preforms laboratory testing on human specimens for diagnosis, prevention, or treatment of disease or impairment and is approved and monitored by an FDA approved regulatory organization. CLIA waived test refers to a clinical laboratory test meeting specific criteria for risk, error and complexity as defined by the Food and Drug Association (FDA).

Point-of-care device refers to an instrument or cartridge available at the location of patient and physician care containing binding agents to a biomarker, or series of biomarkers of interest, and can generate information on the presence, absence, and in some cases concentrations of detected biomarkers. Analyte refers to any measurable biomarker which can be protein, peptide, macromolecule, metabolite, small molecule, or autoantibody. Biological fluid as used herein refers to tears, whole blood, serum, urine, and saliva. Biomarker refers to any substance (e.g. protein, peptide, metabolite, polynucleotide sequence) whose concentration level changes in the body (e.g. increased or decreased) as a result of a disease or condition. Marker and biomarker may be used interchangeably herein.

Lateral flow test refers to a device used to measure the presence of an analyte in a biological fluid using porous paper of sintered polymer. ELISA refers to Enzyme-linked immunosorbent assay which utilizes antibodies to detect the presence and concentration of an analyte of interest. Diagnostic Panel refers to a group of molecules (e.g. proteins or peptides) whose combined concentrations are used to diagnose a disease state. (e.g. cancer). A breast cancer marker refers to a molecule (e.g. protein, peptide, metabolite, polynucleotide sequence) whose concentration level in the body changes (e.g. is increased or decreased) as a result of breast cancer.

In addition to being useful to diagnose cancer and in particular breast cancer in a subject, the kits and methods provided herein may be used to monitor treatment or recurrence of cancer in an individual previously diagnosed with cancer. Thus if the levels of the markers in Table 2A begin to rise or the levels of the markers in Table 2B begin to decrease over time in the same subject after treatment, further chemotherapeutics targeting the cancer may be administered. The methods and kits may also be used to monitor the effectiveness of a chemotherapeutic treatment. In this alternative, the levels of the biomarkers in Table 2A would decrease over time if the treatment regime is effective and either would not change or may increase over time if the treatment regime is not effective in a single subject. The levels of the biomarkers in Table 2B would increase over time during treatment with a therapeutic that is effective and would either not change or decrease over time if the treatment regime is not effective in a single subject.

Treating cancer includes, but is not limited to, reducing the number of cancer cells or the size of a tumor or mass in the subject, reducing progression of a cancer to a more aggressive form, reducing proliferation of cancer cells or reducing the speed of tumor growth, killing of cancer cells, reducing metastasis of cancer cells or reducing the likelihood of recurrence of a cancer in a subject. Treating a subject as used herein refers to any type of treatment that imparts a benefit to a subject afflicted with a disease or at risk of developing the disease, including improvement in the condition of the subject (e.g., in one or more symptoms), delay in the progression of the disease, delay the onset of symptoms or slow the progression of symptoms, etc.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including." "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

The following examples are meant only to be illustrative and are not meant as limitations on the scope of the invention or of the appended claims.

EXAMPLES

Example 1: Methods for Collecting Ocular Wash Samples

This study was carried out under institutional review board approval and participants were recruited at two clinics based in Arkansas, The Breast Center and Highlands Oncology Group, as well as two clinics based in Washington, PeaceHealth Southwest and PeaceHealth Longview Surgery Center. Inclusion/exclusion criteria used by the clinic for patient selection is given in Table 1.

TABLE 1

Inclusion/Exclusion Criteria for participant selection

Individuals who are:

Between the ages of 18-100 years of age
Presenting for a routine check up
Presenting for the evaluation of an abnormal exam or test (mammogram, ultrasound, MRI, PET, ect.)
Presenting for the evaluation of a palpable lump or mass
Presenting with a mass, pre or post biopsy as long as a portion of mass is remaining
Currently have or are in treatment for breast cancer.
Individuals who are:

<18 years of age or >100 years of age.
experiencing a concurrent eye infection or trauma.
Currently experiencing acute conjunctivitis
Known to have abnormal production of tears (too much or too little)

Ocular wash samples were obtained by rinsing the exposed surface of the eye with Optics Laboratory single use Eye-Cept Rewetting drops. The single use dropper, selected to eliminate contamination, was used to apply approximately five drops of rewetting saline to the outside corner of the eye. After application the solution naturally flowed across the surface of the eye and pooled in the inner corner/duct next to the nose. The solution was then collected by suction using a one mL tuberculine syringe, with no needle attached, and transferred to a pre-labeled 0.5 mL tube with an o-ring screw top cap. The optimal total volume from each collection is approximately 100 µL, however actual volumes can vary. Samples were stored between −20° C. and −80° C. (depending on freezer unit available) within two hours of collection.

Samples collected at participating clinics were retrieved by Ascendant personnel on a weekly basis and transferred on dry ice to Ascendant's laboratory facility. In the case of the Washington based clinics, samples were shipped to Ascendant on dry ice on a monthly basis.

Data collected from the participants included: sex, race, age, previous cancer history, family history of breast cancer, stage of current cancer (I, II, III, IV) tumor size, breast cancer subtype (Ductal Carcinoma In Situ, Invasive Ductal Carcinoma, Invasive Lobular Carcinoma, Lobular Carcinoma In Situ, and Unknown) and tumor grade. A spreadsheet was created to track data and stratify samples based on selected criteria.

Control samples were collected, using the procedure detailed above, from volunteers between the ages of 18-100 who reported they were cancer and mass free as per the inclusion criteria outlined in the IRB approved collection protocol. Exclusion criteria are the same as for the breast cancer patients. All control participants were recruited from the general population; consent and sample collected was performed by Ascendant Diagnostics personnel. Data collected from control participants included: sex, age, race, previous history of breast cancer, family history of breast cancer, and current medications.

All samples in the tear bank were stored at −80° C. and freeze thaw cycles were limited to three times, as protein degradation was observed after three freeze thaw cycles. In some cases samples were aliquoted to minimize freeze thaw cycles further.

Example 2: Methods for Preparation of Sample Pools for LC MS/MS

Eight pooled samples (four breast cancer pools and four control pools) each with a total volume of 300 µL were assembled from banked tear samples for the purpose of label free quantitation using in-gel digestion. All breast cancer ocular wash samples used were taken from individuals with stage I &II breast cancer and were collected prior to treatment. Controls were age matched for accuracy of comparison.

To ensure sample integrity, MALDI-TOF data was collected on aliquots from each of the individual samples, which were included in the pooled samples. Prior to MALDI testing, tear samples were purified using ZipTip$_{c18}$. This procedure serves to remove any contaminates which may be present in the sample and to concentrate the proteins in order to increase ease of detection. A 15 µL aliquot was removed from the freezer and thawed at room temperature for 10 minutes (~22° C.). The protocol for ZipTip$_{c18}$ was adapted from the user manual supplied by Millipore and a variable pipette with a total volume capacity of 10 µL was used for all sample preparations. The ZipTip$_{c18}$ was equilibrated in a wetting solution of acetonitrile (ACN) 0.1% TFA for 10 cycles (1 cycle involves aspirating 10 µL of solution into the tip and dispensing). Following equilibration, the tip was washed with ddH$_2$O (0.1% TFA) for 10 cycles. The sample was then loaded for 10 cycles, followed by a wash with ddH$_2$O (0.1% TFA) for 10 cycles. The load procedure, followed by the wash procedure was carried out a total of five times to ensure maximum protein binding. Bound proteins were eluted in 5 µL of ACN (0.1% TFA) for 20 cycles into a clean tube. The ACN (0.1% TFA) was removed using an eppendorf vacufuge plus for 10 minutes at 45° C. Samples were then reconstituted in 5 µL ddH$_2$O (0.1% TFA) and spotted onto a ground steel MALDI target. Each sample was spotted a total of three times at 1 µL each time, allowing complete drying of the spot before more material was added. After the final spotting was completely dry, 1 µL of a saturated solution of 40 mgs of Sinapinic Acid matrix prepared in 1 mL of 50:50 solution of ACN/ddH$_2$O (0.1% TFA) was spotted onto each sample and all samples were allowed to dry completely on the bench top prior to data collection. One microliter of protein standard was added to several locations on the MALDI target as well. The protein standard was spotted only once and followed by addition of the sinapinic acid matrix used for the OW samples.

Data was collected on a Bruker Reflex III MALDI-IOF mass spectrometer in its linear positive mode, as linear mode increases the sensitivity. Acquisition of all spectra was performed both manually and automatically (user unbiased acquisition) using Bruker Daltonics flex Control software. For each spot, MALDI-TOF mass spectra were acquired at least three times, with a total of 200 laser shots accumulated for each run. Shot accumulation was programmed using a fuzzy logic operator to only consider spectra with S/N better than 20 in between m/z 2000-45,000. Sample integrity was evaluated by visual inspection of the generated MALDI-TOF spectrum. High mass peak splitting together with increased quantity of low mass peaks suggest protein degradation has occurred and the sample was not used further.

Total protein content of each pool was determined using a bicinchoninic acid protein assay kit with a 1:20 (v/v) ratio of standard and unknown to working reagent and an incubation time of 30 min at 37° C. To ensure reliable total protein content calculation, a series of dilutions were made for each sample (i.e. 1:2, 1:4, 1:6) and all dilutions were plated in triplicate. A standard curve using diluted albumin (2 mg/ml, 1.5 mg/ml, 1 m/ml, 0.75 mg/ml, 0.5 mg/ml, 0.25 mg/ml 0.125 mg/ml 0.025 mg/ml and 0 mg/ml) was generated and blank subtraction was applied to all standards and unknowns. The protein concentration for each unknown was calculated using a four-parameter fit of the standard curve. Concentrations were multiplied by the dilution factor and averaged to give an accurate total protein content calculation. Assays were only considered valid if the coefficient of variation (% CV) was 15% or below.

Using the total protein content determined by BCA, 25 µg of protein from each pool was loaded onto a NuPAGE Bis-Tris 4-12% gradient separation gel and run using methods standard for an individual skilled in the art as shown in FIG. 1. Following separation of the ocular proteome, between 20-22 slices were cut for each lane and subjected to disulfide reduction using Dithiothreitol, followed by sulfhydryl aklyation using iodoacetemide, and finally trypsin digestion. Specific slice counts for each sample were as follows: Lane 1=20 slices, Lane 2=21 slices, Lane 3=22 slices, Lane 4=21 slices, Lane 5=20 slices, Lane 6=20 slices, Lane 7=21 slices, Lane 8=21 slices.

Example 3: Methods and Results for Label Free Quantitation by LC MS/MS

Twenty µL from each trypsin digestion reaction was loaded onto a nanoAcquity UPLC (Waters) and eluted using a gradient from 3-99% 0.1% formic acid, 75% acetonitrile over 30 minutes. A LTQ Orbitrap Velos (Thermo Scientific) was used for detection of the peptides produced by proteolytic cleavage. Raw data files from the LC-MS/MS analysis were uploaded into the MASCOT database for protein identification using the UniProtKB database, 2 ppm peptide mass tolerance, and 0.5 Da fragment mass tolerance. The output from MASCOT was then uploaded into the software packages Scaffold and MaxQuant for analysis.

Figure 2:
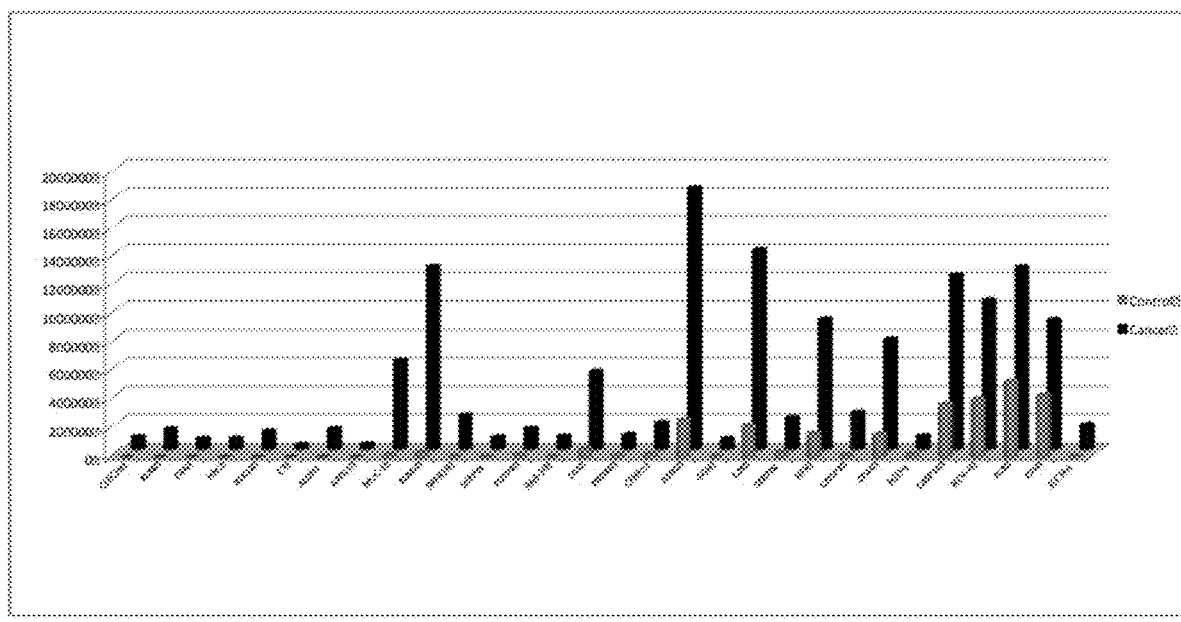
FIG. 2 is a graph comparing the protein expression in cancer and control samples showing increased expression of several proteins in breast cancer samples as compared to controls based on peak intensity as determined by LC-MS/MS.
Figure 3:
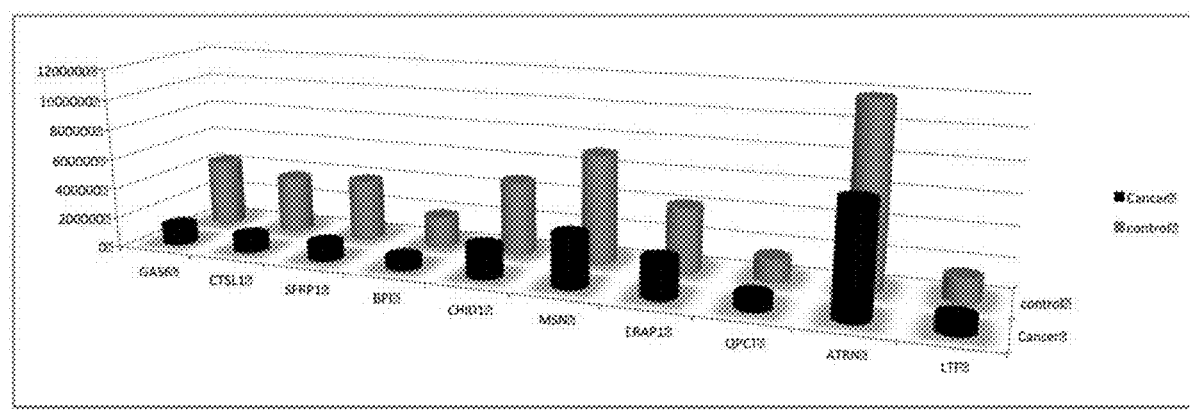
FIG. 3 is a graph comparing the protein expression in cancer and control samples showing decreased expression of several proteins in breast cancer samples as compared to controls based on peak intensity as determined by LC-MS/MS.

Greater than 700 protein hits were identified using this method. In order to isolate potential biomarker candidates, peak intensities for each group (cancer and control) were averaged for each protein and fold change was determined with respect to cancer. In addition a student's T-test was applied to each protein providing a p-value. All proteins with a fold change of greater than 1.5 and a p-value <0.05 were, considered as possible biomarker candidates. P-values and fold changes were assessed on a case by case basis and some proteins with higher p-values were included in the candidate biomarkers list. The list was then narrowed based on biological relevance to breast cancer, other cancer subtypes, and cancer processes. The complete list of candidate biomarkers is given in Tables 2A and 2B and shown in graphic form in FIGS. 2 and 3.

TABLE 2A

Biomarkers with an increase expression in cancer as compared to control samples.

| Protein ID | P-Value | Fold Change |
| --- | --- | --- |
| CLEC3B | 0.067 | No expression in control |
| KLK8 | 0.07 | No expression in control |
| C8A | 0.149 | No expression in control |
| HRC | 0.17 | No expression in control |
| KLK13 | 0.178 | No expression in control |
| C7 | 0.207 | No expression in control |
| ALDH1A1 | 0.24 | No expression in control |
| APOL1 | 0.32 | No expression in control |
| MUC-1 | 0.27 | 40.6 |

TABLE 2A-continued

Biomarkers with an increase expression in cancer as compared to control samples.

| Protein ID | P-Value | Fold Change |
| --- | --- | --- |
| BLMH | 0.212 | 38.1 |
| SPRR1B | 0.117 | 35.1 |
| SERPINB2 | 0.11 | 16.1 |
| Putative uncharacterized protein | 0.165 | 11.7 |
| RAB-30 | 0.153 | 11.3 |
| C4A | 0.099 | 9.6 |
| PRDX6 | 0.14 | 7.6 |
| CFHR1 | 0.169 | 7.4 |
| A1BG | 0.11 | 7.2 |
| GGH | 0.14 | 7.1 |
| EZR | 0.066 | 6.3 |
| SERPINF2 | 0.16 | 5.9 |
| HPX | 0.1 | 5.5 |
| CRISP3 | 0.0238 | 5.2 |
| CPA4 | 0.14 | 4.8 |
| PGLYRP2 | 0.06 | 3.9 |
| CASP14 | 0.068 | 3.3 |
| Ig Kappa Chain V-III region POM | 0.001 | 2.6 |
| ALB | 0.014 | 2.4 |
| CFH | 0.042 | 2.1 |
| SLC34A2 | 0.105 | 29.3 |

TABLE 2B

Biomarkers with a decrease in expression in cancer samples as compared to controls

| Protein ID | P-value | Fold Change |
| --- | --- | --- |
| GAS6 | 0.045 | 3.5 |
| CTSL1 | 0.051 | 3.4 |
| SFRP1 | 0.059 | 3.4 |
| BPI | 0.045 | 2.5 |
| CHID1 | 0.0546 | 2.2 |
| MSN | 0.0545 | 2.06 |
| ERAP1 | 0.014 | 1.6 |
| QPCT | 0.045 | 1.6 |
| ATRN | 0.062 | 1.6 |
| LTF | 0.051 | 1.5 |

To further confirm protein identity, the peptide sequences produced by trypsin digestion were mapped back to the original protein sequence. Trypsin products unique to particular proteins were noted, as these sequences have the potential to be used as diagnostic peptides as well as isotopically labeled standards in the final CLIA triple quadrupole mass spectrometry assay. The sequences of the trypsin products and the full-length proteins markers identified in Tables 2A and 2B are provided in Appendix I and Appendix II, respectively.

Example 4: Methods for Schirmer Strip Collections and Processing

Institutional review board approval was obtained for the collection of tears using Schirmer strips. For collection, the rounded tip of the Schirmer strip was folded over at the 0 mm line forming a lip. The folded portion was placed in the lower eyelid of the participant and they were asked to close their eye and keep it in the closed position for a period of 5 minutes. After five minutes the strip was removed and placed in a sterile 1.5 mL pre-labeled snap top tube and placed at −20° C. or −80° C. depending on availability. Collection criteria stated that if the 35 mm mark was reached prior to the five minute time, the strip could be removed.

Data collected from participants included the following, age, sex, race, currently taking birth control or on hormone replacement therapy, ophthamological infections, current or recent chemotherapy treatments, family history of cancer, genetic testing (BRAC1/2) if available, cancer stage, cancer type, hormone receptor status, size of mass, tumor grad, previous history of cancer. A spreadsheet was constructed to house this information and allow for sample stratification based on desired characteristics. Sample total protein content was also entered into the database.

To elute the proteins bound to the Schirmer strip, the strips were first diced and placed in a clean sterile 1.5 mL snap top tube. 200 µL of 1×PBS was added to the diced strip and the sample was incubated at 4° C. with mild shaking overnight. Following elution, the samples were spun briefly to collect the strip fragments at the bottom of the tube, and the supernatant was transferred to a new clean 1.5 mL snap top tube. Total protein content was determined using BCA assay, as described above, and the samples were stored at −80° C. until further use.

REFERENCES

Armstrong, K., Handorf, E. A., Chen, J., & Bristol Demeter, M. N. (2013). Breast cancer risk prediction and mammography biopsy decisions: a model-based study. *American Journal of Preventive Medicine*, 44(1), 15-22. doi: 10.1016/j.amepre.2012.10.002

Böhm, D., Keller, K., Pieter, J., Boehm, N., Wolters, D., Siggelkow, W., et al. (2012). Comparison of tear protein levels in breast cancer patients and healthy controls using a de novo proteomic approach. *Oncology Reports*, 28(2), 429-438. doi: 10.3892/or.2012.1849

Böhm, D., Keller, K., Wehrwein, N., Lebrecht, A., Schmidt, M., Kölbl, H., & Grus, F.-H. (2011). Serum proteome profiling of primary breast cancer indicates a specific biomarker profile. *Oncology Reports*, 26(5), 1051-1056. doi:10.3892/or.2011.1420

Brown, M. L., Houn, F., Sickles, E. A., & Kessler, L. G. (1995). Screening Mammography in Community Practice: Positive Predictive. *American Journal of Radiology*, 165, 1373-1377.

Grady, D. (2012). Study of Breast Biopsies Finds Surgery Used Too Extensively. *New York Times*, 1-4.

Kolb, T., Lichy, J., & Newhouse, J. (2002). Comparison of the performance of screening mammography, physical examination, and breast US and evaluation of factors that influence them: an analysis of 27,825 patient evaluations. *Radiology*, 225(1), 165-175.

Lebrecht, A., Boehm, D., Schmidt, M., Koelbl, H., & Grus, F. H. (2009a). Surface-enhanced Laser Desorption/Ionisation Time-of-flight Mass Spectrometry to Detect Breast Cancer Markers in Tears and Serum. *Cancer Genomics & Proteomics*, 6(2), 75-83.

Lebrecht, A., Boehm, D., Schmidt, M., Koelbl, H., Schwirz, R. L., & Grus, F. H. (2009b). Diagnosis of breast cancer by tear proteomic pattern. *Cancer Genomics & Proteomics*, 6(3), 177-182.

Li, J., Zhang, Z., Rosenzweig, J., Wang, Y., & Chan, D. (2002). Proteomics and bioinformatics approaches for identification of serum biomarkers to detect breast cancer. *Clin Chem*, 48(8), 1296-1304.

Luftner, D., & Possinger, K. (2002). Nuclear matrix proteins as biomarkers for breast cancer. *Expert Rev Mol Diagn*, 2(1), 23-31. doi:ERM020106 [pii]10.1586/14737159.2.1.23

Schiess, R., Wollscheid, B., & Aebersold, R. (2009). Targeted proteomic strategy for clinical biomarker discovery. *Molecular Oncology*, 3(1), 33-44. doi:10.1016/j.molonc.2008.12.001

Wu, K., & Zhang, Y. (2007). Clinical application of tear proteomics: Present and future prospects. *Proteomics. Clinical Applications*, 1(9), 972-982. doi: 10.1002/prca.200700125

| Protein Name | Uniprot | IPI | Gene Name: |
|---|---|---|---|
| Complement C4A | P0COL4 | IPI00032258 | C4A_Human |

Trypsin Fragments

1. AEFQDALEK (SEQ ID NO: 1)
2. DHAVDLIQK (SEQ ID NO: 2)
3. DKGQAGLQR (SEQ ID NO: 3)
4. EMSGSPASGIPVK (SEQ ID NO: 4)
5. FACYYPR (SEQ ID NO: 5)
6. FGLLDEDGKK (SEQ ID NO: 6)
7. GHLFLQTDQPIYNPGQR (SEQ ID NO: 7)
8. GLCVATPVQLR (SEQ ID NO: 8)
9. GIQDEDGYR (SEQ ID NO: 9)
10. GPEVQUVAHSPWLK (SEQ ID NO: 10)
11. GSFEFPVGDAVSK (SEQ ID NO: 11)
12. HLVPGAPFLLQALVR (SEQ ID NO: 12)
13. LLATLCSAEVCQCAEGK (SEQ ID NO: 13)
14. LNMGITDLQGLR (SEQ ID NO: 14)
15. ITQVLHFTK (SEQ ID NO: 15)
16. NVNFQK (SEQ ID NO: 16)
17. QGSFQGGFR (SEQ ID NO: 17)
18. SCGLHQLLR (SEQ ID NO: 18)
19. VDFTLSSER (SEQ ID NO: 19)
20. VDVQAGACEGK (SEQ ID NO: 20)
21. VFALDQK (SEQ ID NO: 21)

| | | |
|---|---|---|
| 22. VGDTININI R (SEQ ID NO: 22) | 23. VLSLAQEQV GGSPEK (SEQ ID NO: 23) | 24. VTASDPLDT LGSEGALSP GGVASLLR (SEQ ID NO: 24) |
| 25. YLDKTEQWS TLPPETK (SEQ ID NO: 25) | | |

(SEQ ID NO: 26)

```
        10         20         30         40
MRLLWGLIWA SSFFTLSLQK PRLLLFSPSV VHLGVPLSVG 50         60         70         80
VQLQDVPRGQ VVKGSVFLRN PSRNNVPCSP K(15)VDFTLSSER 90        100        110        120
DFALLSLQVP LKDAK(18)SCGLH QLLR(10)GPEVQL VAHSPWLKDS 130        140        150        160
LSRTTNIQGI NLLFSSRR(7)GH LFLQTDQPIY NPGQRVRYR(21)V 170        180        190        200
FALDQKMRPS TDTITVMVEN SHGLRVRKKE VYMPSSIFQD 210        220        230        240
DFVIPDISEP GTWKISARFS DGLESNSSTQ FEVKKYVLPN 250        260        270        280
FEVKITPGKP YILTVPGHLD EMQLDIQARY IYGKPVQGVA 290        300        310        320
YVR(6)FGLLDED GKKTFFRGLE SQTKLVNGQS HISLSK(2)AEFQ 330        340        350        360
DALEK(14)LNMGI TDLQGLRLYV AAAIIESPGG EMEEAELTSW 370        380        390        400
YFVSSPFSLD LSKTKR(12)HLVP GAPFLLQALV R(4)EMSGSPASG 410        420        430        440
IPVK VSATVS SPGSVPEVQD IQQNTDGSGQ VSIPIIIPQT 450        460        470        480
ISELQLSVSA GSPHPAIARL TVAAPPSGGP GFLSIERPDS 490        500        510        520
RPPR(22)VGDTLN LNLRAVGSGA TFSHYYMIL SRGQIVFMNR 530        540        550        560
EPKRTLTSVS VFVDHHLAPS FYFVAFYYHG DHPVANSLR(20)V 570        580        590        600
DVQAGACEGK LELSVDGAKQ YRNGESVKLH LETDSLALVA 610        620        630        640
LGALDTALYA AGSKSHKPLN MGKVFEAMNS YDLGCGPGGG 650        660        670        680
DSALQVFQAA GLAFSDGDQW TLSRKRLSCP KEKTTRKKR(16)N 690        700        710        720
VNFQKAINEK LGQYASPTAK RCCQDGVTRL PMMRSCEQRA 730        740        750        760
ARVQQPDCRE PFLSCCQFAE SLRKKSR(3)DKG QAGLQRALEI 770        780        790        800
LQEEDLIDED DIPVRSFFFE NWLWRVETVD RFQILTLWLP 810        820        830        840
DSLTTWEIHG LSLSKTK(8)GLC VATPVQLRVF REFHLHLRLP 850        860        870        880
MSVRRFEQLE LRPVLYNYLD KNLTVSVHVS PVEGLCLAGG
```

```
                890        900        910        920
          GGLAQQVLVP AGSARPVAFS VVPTAAAAVS LKVVAR(11)GSFE
                930        940        950        960
          FPVGDAVSKV LQIEKEGAIH REELVYELNP LDHRGRTLEI
                970        980        990       1000
          PGNSDPNMIP DGDFNSYVR(24)V TASDPLDTLG SEGALSPGGV
               1010       1020       1030       1040
          ASLLRLPRGC GEQTMIYLAP TLAASR(25)YLDK TEQWSTLPPE
               1050       1060       1070       1080
          TK(2)DHAVDLIQ KGYMRIQQFR KADGSYAAWL SRDSSTWLTA
               1090       1100       1110       1120
          FVLK(23)VLSLAQ EQVGGSPEKL QETSNWLLSQ QQADGSFQDP
               1130       1140       1150       1160
          CPVLDRSMQG GLVGNDETVA LTAFVTIALH HGLAVFQDEG
               1170       1180       1190       1200
          AEPLKQRVEA SISKANSFLG EKASAGLLGA HAAAITAYAL
               1210       1220       1230       1240
          TLTKAPVDLL GVAHNNLMAM AQETGDNLYW GSVTGSQSNA
               1250       1260       1270       1280
          VSPTPAPRNP SDPMPQAPAL WIETTAYALL HLLLHEGKAE
               1290       1300       1310       1320
          MADQASAWLT R(17)QGSFQGGFR STQDTVIALD ALSAYWIASH
               1330       1340       1350       1360
          TTEERGLNVT LSSTGRNGPK SHALQLNNRQ IRGLEEELQF
               1370       1380       1390       1400
          SLGSKINVKV GGNSKGTLKV LRTYNVLDMK NTTCQDLQIE
               1410       1420       1430       1440
          VTVKGHVEYT MEANEDYEDY EYDELPAKDD PDAPLQPVTP
               1450       1460       1470       1480
          LQLFEGRRNR RRREAPKVVE EQESRVHYTV CIWRNGKVGL
               1490       1500       1510       1520
          SGMAIADVTL LSGFHALRAD LEKLTSLSDR YVSHFETEGP
               1530       1540       1550       1560
          HVLLYFDSVP TSRECVGFEA VQEVPVGLVQ PASATLYDYY
               1570       1580       1590       1600
          NPERRCSVFY GAPSKSR(13)LLA TLCSAEVCQC AEGKCPRQRR
               1610       1620       1630       1640
          ALER(9)GLQDED GYRMK(5)FACYY PRVEYGFQVK VLREDSRAAF
               1650       1660       1670       1680
          RLFETK(18)ITQV LHFTKDVKAA ANQMRNFLVR ASCRLRLEPG
               1690       1700       1710       1720
          KEYLIMGLDG ATYDLEGHPQ YLLDSNSWIE EMPSERLCRS
               1730       1740
          TRQRAACAQL NDFLQEYGTQ GCQV
```

| Protein Name | Uniprot | IPI | Gene Name |
|---|---|---|---|
| Histidine Rich Protein | P04196 | IPI00022371 | HRG_Human |

| Trypsin fragments | |
|---|---|
| 1. YKEENDDFASFR (SEQ ID NO: 27) | 2. ADLFYDVEALDLESPK (SEQ ID NO: 28) |

```
          MKALIAALLL ITLQYSCAVS PTDCSAVEPE AEKALDLINK          (SEQ ID NO: 29)
                                 70         80
          RRRDGYLFQL LRIADAHLDR VENTTVYYLV LDVQESDCSV
```

```
 90         100        110        120
LSRKYWNDCE  PPDSRRPSEI VIGQCKVIAT RHSHESQDLR 130         140        150        160
VIDFNCTTSS  VSSALANTKD SPVLIDFFED TERYRKQANK 170         180        190        200
ALEK⁽¹⁾YKEEND DFASFRVDRI ERVARVRGGE GTGYFVDFSV 210         220        230        240
RNCPRHHFPR  HPNVFGFCR⁽²⁾A DLFYDVEALD LESPKNLVIN 250         260        270        280
CEVFDPQEHE  NINGVPPHLG HPFHWGGHER SSTTKPPFKP 290         300        310        320
HGSRDHHHPH  KPHEHGPPPP PDERDHSHGP PLPQGPPPLL 330         340        350        360
PMSCSSCQHA  TFGTNGAQRH SHNNNSSDLH PHKHHSHEQH 370         380        390        400
PHGHHPHAHH  PHEHDTHRQH PHGHHPHGHH PHGHHPHGHH 410         420        430        440
PHGHHPHCHD  FQDYGPCDPP PHNQGHCCHG HGPPPGHLRR 450         460        470        480
RGPGKGPRPF  HCRQIGSVYR LPPLRKGEVL PLPEANPPSF 490         500        510        520
PLPHHKHPLK  PDNQPFPQSV SESCPGKFKS GFPQVSMFFT HTFPK
```

| Protein Name | Uniprot | IPI | Gene Name |
|---|---|---|---|
| C-type lectin domain family 3, member B (Tetranectin) | P05452 | IPI00009028.2 | CLEC3B_Human |

| Trypsin fragments | |
|---|---|
| 1. EQQALQTVCLK (SEQ ID NO: 30) | 2. TFHEASEDCISR (SEQ ID NO: 31) |

```
 10         20         30         40              (SEQ ID NO: 32)
MELWGAYLLL  CLFSLLTQVT TEPPTQKPKK IVNAKKDVVN 50         60         70         80
TKMFEELKSR  LDTLAQEVAL L¹KEQQALQTV CLKGTKVHMK 90         100        110        120
CFLALTQTK²T FHEASEDCIS RGGTLGTPQT GSENDALYEY 130         140        150        160
LRQSVGNEAE  IWLGLNDMAA EGTWVDMTGA RIAYKNWETE 170         180        190        200
ITAQPDGGKT  ENCAVLSGAA NGKWFDKRCR DQLPYICQFG

IV
```

| Protein Name | Uniprot | IPI | Gene Name |
|---|---|---|---|
| Kallikrein-8 isoform 2 | O60259-2 | IPI00219892 | KLK8_Human |

Trypsin fragments

1. ENFPDTLNCAEVK
   (SEQ ID NO: 33)

```
10         20         30         40                    (SEQ ID NO: 34)
MGRPRPRAAK TWMFLLLLGG AWAGHSRAQE DKVLGGHECQ 50         60         70         80
PHSQPWQAAL FQGQQLLCGG VLVGGNWVLT AAHCKKPKYT 90         100        110        120
VRLGDHSLQN KDGPEQEIPV VQSIPHPCYN SSDVEDHNHD 130        140        150        160
LMLLQLRDQA SLGSKVKPIS LADHCTQPGQ KCTVSGWGTV 170        180        190        200
TSPR[3]ENFPDT LNCAEVKIFP QKKCEDAYPG QITDGMVCAG 210        220        230        240
SSKGADTCQG DSGGPLVCDG ALQGITSWGS DPCGRSDKPG 250        260
VYTNICRYLD WIKKIIGSKG
```

| Protein Name | Uniprot | IPI | Gene Name |
|---|---|---|---|
| Complement Component 8 alpha | P07357 | IPI00011252 | C8A_Human |

Trypsin fragments

1. AIDEDCSQY        2. LGSLGAACE        3. QAQCGQDFQ
   EPIPGSQK           QTQTEGAK            CK
   (SEQ ID NO: 35)    (SEQ ID NO: 36)     (SEQ ID NO: 37)

```
10         20         30         40                    (SEQ ID NO: 38)
MFAVVFFILS LMTCQPGVTA QEKVNQRVRR AATPAAVTCQ 50         60         70         80
LSNWSEWTDC FPCQDKKYRH RSLLQPNKFG GTICSGDIWD 90         100        110        120
QASCSSSTTC VR[3]QAQCGQDF QCKETGRCLK RHLVCNGDQD 130        140        150        160
CLDGSDEDDC EDVR[1]AIDEDC SQYEPIPGSQ KAALGYNILT 170        180        190        200
QEDAQSVYDA SYYGGQCETV YNGEWRELRY DSTCERLYYG 210        220        230        240
DDEKYFRKPY NFLKYHFEAL ADTGISSEFY DNANDLLSKV 250        260        270        280
KKDKSDSFGV TIGIGPAGSP LLVGVGVSHS QDTSFLNELN 290        300        310        320
WYNEKKFIFT RIFTKVQTAH FKMRKDDIML DEGMLQSLME 330        340        350        360
LPDQYNYGMY AKFINDYGTH YITSGSMGGI YEYILVIDKA 370        380        390        400
KMESLGITSR DITTCFGGSL GIQYEDKINV GGGLSGDHCK 410        420        430        440
KFGGGKTERA RKAMAVEDII SRVRGGSSGW SGGLAQNRST 450        460        470        480
ITYRSWGRSL KYNPVVIDFE MQPIHEVLRH TSLGPLEAKR 490        500        510        520
```

-continued

QNLRRALDQY LMEFNACRCG PCFNNGVPIL EGTSCRCQCR 530        540        550        560
(2)LGSLGAACEQ TQTEGAKADG SWSCWSSWSV CRAGIQERRR 570        580
ECDNPAPQNG GASCPGRKVQ TQAC

| Protein Name | Uniprot | IPI | Gene Name |
|---|---|---|---|
| Kallikrein-13 | Q9UKR3 | IPI00007726 | KLK13_Human |

Trypsin fragments

1. TLQCANIQLR          2. ITDNMLCAGTK
   (SEQ ID NO: 39)

10         20         30         40              (SEQ ID NO: 41)
MWPLALVIAS LTLALSGGVS QESSKVLNTN GTSGFLPGGY 50         60         70         80
TCFPHSQPWQ AALLVQGRLL CGGVLVHPKW VLTAAHCLKE 90         100        110        120
GLKVYLGKHA LGRVEAGEQV REVVHSIPHP EYRRSPTHLM 130        140        150        160
HDHDIMLLEL QSPVQLTGYI QTLPLSHNNR LTPGTTCRVS 170        180        190        200
GWGTTTSPQV NYPR(1)TLQCAN IQLRSDEECR QVYPGK(2)ITDN

210        220        230        240
MLCAGTKEGG KDSCEGDSGG PLVCNRTLYG IVSWGDFPCG 250        260        270
QPDRPGVYTR VSRYVLWIRE TIRKYETQQQ KWLKGPQ

| Protein Name | Uniprot | IPI | Gene Name |
|---|---|---|---|
| Complement Component 7 | P10643 | IPI00296608 | C7_Human |

Trypsin fragments

1. AASGTQNNVLR         2. DSCTLPASAEK
   (SEQ ID NO: 42)        (SEQ ID NO: 43)

10         20         30         40              (SEQ ID NO: 44)
MKVISLFILV GFIGEFQSFS SASSPVNCQW DFYAPWSECN 50         60         70         80
GCTKTQTRRR SVAVYGQYGG QPCVGNAFET QSCEPTRGCP 90         100        110        120
TEEGCGERFR CFSGQCISKS LVCNGDSDCD EDSADEDRCE 130        140        150        160
DSERRPSCDI DKPPPNIELT GNGYNELTGQ FRNRVINTKS 170        180        190        200
FGGQCRKVFS GDGKDFYRLS GNVLSYTFQV KINNDFNYEF 210        220        230        240
YNSTWSYVKH TSTEHTSSSR KRSFFRSSSS SSRSYTSHTN 250        260        270        280
EIHKGKSYQL LVVENTVEVA QFINNNPEFL QLAEPFWKEL 290        300        310        320
SHLPSLYDYS AYRRLIDQYG THYLQSGSLG GEYRVLFYVD 330        340        350        360
SEKLKENDFN SVEEKKCKSS GWHFVVKFSS HGCKELENAL 370        380        390        400
K(1)AASGTQNNV LRGEPFIRGG GAGFISGLSY LELDNPAGNK 410        420        430        440

-continued

```
            RRYSAWAESV  TNLPQVIKQK  LTPLYELVKE  VPCASVKKLY 450         460         470         480
LKWALEEYLD  EFDPCHCRPC  QNGGLATVEG  THCLCHCKPY 490         500         510         520
TFGAACEQGV  LVGNQAGGVD  GGWSCWSSWS  PCVQGKKTRS 530         540         550         560
RECNNPPPSG  GGRSCVGETT  ESTQCEDEEL  EHLRLLEPHC 570         580         590         600
FPLSLVPTEF  CPSPPALKDG  FVQDEGTMFP  VGKNVVYTCN 610         620         630         640
EGYSLIGNPV  ARCGEDLRWL  VGEMHCQKIA  CVLPVLMDGI 650         660         670         680
QSHPQKPFYT  VGEKVTVSCS  GGMSLEGPSA  FLCGSSLKWS 690         700         710         720
PEMKNARCVQ  KENPLTQAVP  KCQRWEKLQN  SRCVCKMPYE 730         740         750         760
CGPSLDVCAQ  DERSKRILPL  TVCKMHVLHC  QGRNYTLTGR 770         780         790         800
(2)DSCTLPASAE KACGACPLWG  KCDAESSKCV  CREASECEEE 810         820         830         840
GFSICVEVNG  KEQTMSECEA  GALRCRGQSI  SVTSIRPCAA

ETQ
```

| Protein Name | Uniprot | IPI | Gene Name |
|---|---|---|---|
| Retinal Dehydrogenase | P00352 | IPI00218914 | ALDH1A1_Human |

Trypsin fragments

1. SSSGTPDLP
   VLLTDLK
   (SEQ ID NO: 45)

2. YILGNPLTPGVTQG
   PQIDKEQYDK
   (SEQ ID NO: 46)

```
10          20          30          40                  (SEQ ID NO: 47)
M(1)SSSGTPDLP VLLTDLKIQY  TKIFINNEWH  DSVSGKKFPV 50          60          70          80
FNPATEEELC  QVEEGDKEDV  DKAVKAARQA  FQIGSPWRTM 90          100         110         120
DASERGRLLY  KLADLIERDR  LLLATMESMN  GGKLYSNAYL 130         140         150         160
NDLAGCIKTL  RYCAGWADKI  QGRTIPIDGN  FFTYTRHEPI 170         180         190         200
GVCGQIIPWN  FPLVMLIWKI  GPALSCGNTV  VVKPAEQTPL 210         220         230         240
TALHVASLIK  EAGFPPGVVN  IVPGYGPTAG  AAISSHMDID 250         260         270         280
KVAFTGSTEV  GKLIKEAAGK  SNLKRVTLEL  GGKSPCIVLA 290         300         310         320
DADLDNAVEF  AHHGVFYHQG  QCCIAASRIF  VEESIYDEFV 330         340         350         360
RRSVERAKK(2)Y ILGNPLTPGV TQGPQIDKEQ YDKILDLIES 370         380         390         400
GKKEGAKLEC  GGGPWGNKGY  FVQPTVFSNV  TDEMRIAKEE 410         420         430         440
IFGPVQQIMK  FKSLDDVIKR  ANNTFYGLSA  GVFTKDIDKA
```

```
450        460        470        480
ITISSALQAG TVWVNCYGVV SAQCPFGGFK MSGNGRELGE 490        500
YGFHEYTEVK TVTVKISQKN S
```

| Protein Name | Uniprot | IPI | Gene Name |
|---|---|---|---|
| ApoLipoprotein L1 isoform 2 | Q9UKR3 | IPI00186903 | APOL1_Human |

*Trypsin fragments*

1. VTEPISAESGEQVER
   (SEQ ID NO: 48)

```
10         20         30         40                    (SEQ ID NO: 49)
MEGAALLRVS VLCIWMSALF LGVGVRAEEA GARVQQNVPS 50         60         70         80
GTDTGDPQSK PLGDWAAGTM DPESSIFIED AIKYFKEKVS 90         100        110        120
TQNLLLLLTD NEAWNGFVAA AELPRNEADE LRKALDNLAR 130        140        150        160
QMIMKDKNWH DKGQQYRNWF LKEFPRLKSE LEDNIRRLRA 170        180        190        200
LADGVQKVHK GTTIANVVSG SLSISSGILT LVGMGLAPFT 210        220        230        240
EGGSLVLLEP GMELGITAAL TGITSSTMDY GKKWWTQAQA 250        260        270        280
HDLVIKSLDK LKEVREFLGE NISNFLSLAG NTYQLTRGIG 290        300        310        320
KDIRALRRAR ANLQSVPHAS ASRPRVTEPI SAESGEQVER 330        340        350        360
VNEPSILEMS RGVKLTDVAP VSFFLVLDVV YLVYESKHLH 370        380        390
EGAKSETAEE LKKVAQELEE KLNILNNNYK ILQADQEL
```

| Protein Name | Uniprot | IPI | Gene Name |
|---|---|---|---|
| Mucin 1 isoform 2 | P15941-2 | IPI00218163 | Muc1_Human |

*Trypsin fragments*

1. DISEMFIQLYK        2. QGGFLGLSNIK
   (SEQ ID NO: 50)       (SEQ ID NO: 51)

```
10         20         30         40                    (SEQ ID NO: 52)
MTPGTQSPFF LLLLLTVLTV VTGSGHASST PGGEKETSAT 50         60         70         80
QRSSVPSSTE KNAVSMTSSV LSSHSPGSGS STTQGQDVTL 90         100        110        120
APATEPASGS AATWGQDVTS VPVTRPALGS TTPPAHDVTS 130        140        150        160
APDNKPAPGS TAPPAHGVTS APDTRPAPGS TAPPAHGVTS 170        180        190        200
APDTRPAPGS TAPPAHGVTS APDTRPAPGS TAPPAHGVTS 210        220        230        240
APDTRPAPGS TAPPAHGVTS APDTRPAPGS TAPPAHGVTS 250        260        270        280
APDTRPAPGS TAPPAHGVTS APDTRPAPGS TAPPAHGVTS 290        300        310        320
APDTRPAPGS TAPPAHGVTS APDTRPAPGS TAPPAHGVTS
```

```
330        340        350        360
APDTRPAPGS TAPPAHGVTS APDTRPAPGS TAPPAHGVTS 370        380        390        400
APDTRPAPGS TAPPAHGVTS APDTRPAPGS TAPPAHGVTS 410        420        430        440
APDTRPAPGS TAPPAHGVTS APDTRPAPGS TAPPAHGVTS 450        460        470        480
APDTRPAPGS TAPPAHGVTS APDTRPAPGS TAPPAHGVTS 490        500        510        520
APDTRPAPGS TAPPAHGVTS APDTRPAPGS TAPPAHGVTS 530        540        550        560
APDTRPAPGS TAPPAHGVTS APDTRPAPGS TAPPAHGVTS 570        580        590        600
APDTRPAPGS TAPPAHGVTS APDTRPAPGS TAPPAHGVTS 610        620        630        640
APDTRPAPGS TAPPAHGVTS APDTRPAPGS TAPPAHGVTS 650        660        670        680
APDTRPAPGS TAPPAHGVTS APDTRPAPGS TAPPAHGVTS 690        700        710        720
APDTRPAPGS TAPPAHGVTS APDTRPAPGS TAPPAHGVTS 730        740        750        760
APDTRPAPGS TAPPAHGVTS APDTRPAPGS TAPPAHGVTS 770        780        790        800
APDTRPAPGS TAPPAHGVTS APDTRPAPGS TAPPAHGVTS 810        820        830        840
APDTRPAPGS TAPPAHGVTS APDTRPAPGS TAPPAHGVTS 850        860        870        880
APDTRPAPGS TAPPAHGVTS APDTRPAPGS TAPPAHGVTS 890        900        910        920
APDTRPAPGS TAPPAHGVTS APDTRPAPGS TAPPAHGVTS 930        940        950        960
APDTRPAPGS TAPPAHGVTS APDTRPAPGS TAPPAHGVTS 970        980        990        1000
ASGSASGSAS TLVHNGTSAR ATTTPASKST PFSIPSHHSD 1010       1020       1030       1040
TPTTLASHST KTDASSTHHS SVPPLTSSNH STSPQLSTGV 1050       1060       1070       1080
SFFFLSFHIS NLQFNSSLED PSTDYYQELQ R[1]DISEMFLQI

1090       1100       1110       1120
YK[2]QGGFLGLS NIKFRPGSVV VQLTLAFREG TINVHDVETQ 1130       1140       1150       1160
FNQYKTEAAS RYNLTISDVS VSDVPFPFSA QSGAGVPGWG 1170       1180       1190       1200
IALLVLVCVL VALAIVYLIA LAVCQCRRKN YGQLDIFPAR
```

-continued

```
1210       1220       1230       1240
DTYHPMSEYP TYHTHGRYVP PSSTDRSPYE KVSAGNGGSS

1250
LSYTNPAVAA TSANL
```

| Protein Name | Uniprot | IPI | Gene Name |
|---|---|---|---|
| Bleomycin Hydrolase | Q13867 | IPI00219575 | BLMH_Human |

Trypsin fragments

1. AQHVFQHAV
   PQEGKPITNQK
   (SEQ ID NO: 53)

2. SSSGLNSEK
   VAALIQK
   (SEQ ID NO: 54)

```
       10         20         30         40                   (SEQ ID NO: 55)
M(2)SSSGLNSEK VAALIQKLNS DPQFVLAQNV GTTHDLLDIC 50         60         70         80
LKRATVQR(1)AQ HVFQHAVPQE GKPITNQKSS GRCWIFSCLN 90        100        110        120
VMRLPFMKKL NIEEFEFSQS YLFFWDKVER CYFFLSAFVD 130        140        150        160
TAQRKEPEDG RLVQFLLMNP ANDGGQWDML VNIVEKYGVI 170        180        190        200
PKKCFPESYT TEATRRMNDI LNHKMRERCI RLRNLVHSGA 210        220        230        240
TKGEISATQD VMMEEIFRVV CICLGNPPET FTWEYRDKDK 250        260        270        280
NYQKIGPITP LEFYREHVKP LFNMEDKICL VNDPRPQHKY 290        300        310        320
NKLYTVEYLS NMVGGRKTLY NNQPIDFLKK MVAASIKDGE 330        340        350        360
AVWFGCDVGK HFNSKLGLSD MNLYDHELVF GVSLKNMNKA 370        380        390        400
ERLTFGESLM THAMTFTAVS EKDDQDGAFT KWRVENSWGE 410        420        430        440
DHGHKGYLCM TDEWFSEYVY EVVVDRKHVP EEVLAVLEQE

450
PIILPAWDPM GALAE
```

| Protein Name | Uniprot | IPI | Gene Name |
|---|---|---|---|
| Cornifin-B | P22528 | IPI00304903 | SPRRIB_Human |

Trypsin fragments

1. QPCTPPPQLQQQQVK
   (SEQ ID NO: 56)

2. VPEPCPSIVTPAPAQQK
   (SEQ ID NO: 57)

```
       10         20         30         40               (SEQ ID NO: 58)
MSSQQQK(1)QPC TPPPQLQQQQ VKQPCQPPPQ EPCIPKTKEP
```

| | | | |
|---|---|---|---|
| 50 | 60 | 70 | 80 |
| CHPKVPEPCH | PKVPEPCQPK | VPEPCHPK<sup>(2)</sup>VP | EPCPSIVTPA |

PAQQKTKQK

| Protein Name | Uniprot | IPI | Gene Name |
|---|---|---|---|
| Plasminogen activator inhibitor-2 | P05120 | IPI00007117 | SERPINB2_Human |

Trypsin fragments

1. GKIPNLLPEGSVDGDTR
   (SEQ ID NO: 59)

| | | | | |
|---|---|---|---|---|
| 10 | 20 | 30 | 40 | (SEQ ID NO: 60) |
| MEDLCVANTL | FALNLFKHLA | KASPTQNLFL | SPWSISSTMA | |
| 50 | 60 | 70 | 80 | |
| MVYMGSRGST | EDQMAKVLQF | NEVGANAVTP | MTPENFTSCG | |
| 90 | 100 | 110 | 120 | |
| FMQQIQKGSY | PDAILQAQAA | DKIHSSFRSL | SSAINASTGN | |
| 130 | 140 | 150 | 160 | |
| YLLESVNKLF | GEKSASFREE | YIRLCQKYYS | SEPQAVDFLE | |
| 170 | 180 | 190 | 200 | |
| CAEEARKKIN | SWVKTQTKGK | IPNLLPEGSV | DGDTRMVLVN | |
| 210 | 220 | 230 | 240 | |
| AVYFKGKWKT | PFEKKLNGLY | PFRVNSAQRT | PVQMMYLREK | |
| 250 | 260 | 270 | 280 | |
| LNIGYIEDLK | AQILELPYAG | DVSMFLLLPD | EIADVSTGLE | |
| 290 | 300 | 310 | 320 | |
| LLESEITYDK | LNKWTSKDKM | AEDEVEVYIP | QFKLEEHYEL | |
| 330 | 340 | 350 | 360 | |
| RSILRSMGME | DAFNKGRANF | SGMSERNDLF | LSEVFHQAMV | |
| 370 | 380 | 390 | 400 | |
| DVNEEGTEAA | AGTGGVMTGR | TGHGGPQFVA | DHPFLFLIMA | |
| 410 | | | | |
| KITNCILFFG | RFSSP | | | |

| Protein Name | Uniprot | IPI | Gene Name |
|---|---|---|---|
| Peroxiredoxin-6 | P30041 | IPI00220301 | PRDX6_Human |

Trypsin fragments

1. DINAYNCEEPTEK  
   (SEQ ID NO: 61)
2. NFDEILR  
   (SEQ ID NO: 62)

| | | | | |
|---|---|---|---|---|
| 10 | 20 | 30 | 40 | (SEQ ID NO: 63) |
| MPGGLLLGDV | APNFEANTTV | GRIRFHDFLG | DSWGILFSHP | |
| 50 | 60 | 70 | 80 | |
| RDFTPVCTTE | LGRAAKLAPE | FAKRNVKLIA | LSIDSVEDHL | |
| 90 | 100 | 110 | 120 | |
| AWSK<sup>(1)</sup>DINAYN | CEEPTEKLPF | PIIDDRNREL | AILLGMLDPA | |
| 130 | 140 | 150 | 160 | |
| EKDEKGMPVT | ARVVFVFGPD | KKLKLSILYP | ATTGR<sup>(2)</sup>NFDEI | |

```
                170        180        190        200
             LRVVISLQLT AEKRVATPVD WKDGDSVMVL PTIPEEEAKK 210        220
             LFPKGVFTKE LPSGKKYLRY TPQP
```

| Protein Name | Uniprot | IPI | Gene Name |
|---|---|---|---|
| Complement factor-H | Q03591 | IPI00011264 | CFHR1_Human |

Trypsin Fragments

| 1. ITCTEEGWSPTPK (SEQ ID NO: 64) | 2. STDTSCVNPPTVQ NAHILSR (SEQ ID NO: 65) | 3. TGESAEFVCK (SEQ ID NO: 66) |
|---|---|---|

```
                 10         20         30         40                      (SEQ ID NO: 67)
             MWLLVSVILI SRISSVGGEA TFCDFPKINH GILYDEEKYK 50         60         70         80
             PFSQVPTGEV FYYSCEYNFV SPSKSFWTR(1)I TCTEEGWSPT 90        100        110        120
             PKCLRLCFFP FVENGRSESS GQTHLEGDTV QIICNTGYRL 130        140        150        160
             QNNENNISCV ERGWSTPPKC R(2)STDTSCVNP PTVQNAHILS 170        180        190        200
             RQMSKYPSGE RVRYECRSPY EMFGDEEVMC LNGNWTEPPQ 210        220        230        240
             CKDSTGKCGP PPPIDNGDIT SFPLSVYAPA SSVEYQCQNL 250        260        270        280
             YQLEGNKRIT CRNGQWSEPP KCLHPCVISR EIMENYNIAL 290        300        310        320
             RWTAKQKLYL R(3)TGESAEFVC KRGYRLSSRS HTLRTTCWDG

330
             KLEYPTCAKR
```

| Protein Name | Uniprot | IPI | Gene Name |
|---|---|---|---|
| Isoform 1 of Alpha-1B-glycoprotein | P04217 | IPI00022895 | A1BG_Human |

Trypsin Fragments

| 1. ATWSGAVLAGR (SEQ ID NO: 68) | 2. CLAPLEGAR (SEQ ID NO: 69) | 3. GVTFLLR (SEQ ID NO: 70) |
|---|---|---|
| 4. HQFLLTGDTQGR (SEQ ID NO: 71) | 5. LLELTGPK (SEQ ID NO: 72) | 6. SGLSTGWTQLSK (SEQ ID NO: 73) |

```
                 10         20         30         40                      (SEQ ID NO: 74)
             MSMLVVFLLL WGVTWGPVTE AAIFYETQPS LWAESESLLK 50         60         70         80
             PLANVTLTCQ AHLETPDFQL FKNGVAQEPV HLDSPAIK(4)HQ 90        100        110        120
             FLLTGDTQGR YRCR(8)SGLSTG WTQLSK(5)LLEL TGPKSLPAPW 130        140        150        160
             LSMAPVSWIT PGLKTTAVCR GVLR(4)GVTFLL RREGDHEFLE 170        180        190        200
             VPEAQEDVEA TFPVHQPGNY SCSYRTDGEG ALSEPSATVT 210        220        230        240
             IEELAAPPPP VLMHHGESSQ VLHPGNKVTL TCVAPLSGVD 250        260        270        280
             FQLRRGEKEL LVPRSSTSPD RIFFHLNAVA LGDGGHYTCR
```

-continued

```
290        300        310        320
YRLHDNQNGW SGDSAPVELI LSDETLPAPE FSPEPESGRA 330        340        350        360
LRLR(2)CLAPLE GARFALVRED RGGRRVHRFQ SPAGTEALFE 370        380        390        400
LHNISVADSA NYSCVYVDLK PPFGGSAPSE RLELHVDGPP 410        420        430        440
PRPQLR(1)ATWS GAVLAGRDAV LRCEGPIPDV TFELLREGET 450        460        470        480
KAVKTVRTPG AAANLELIFV GPQHAGNYRC RYRSWVPHTF

490
ESELSDPVEL LVAES
```

| Protein Name | Uniprot | IPI | Gene Name |
|---|---|---|---|
| Gamma-glutamyl hydrolase | Q92820 | IPI00023728 | GGH_Human |

Trypsin Fragments

1. NLDGISHAPNAVK
   (SEQ ID NO: 75)

```
10         20         30         40              (SEQ ID NO: 76)
MASPGCLLCV LGLLLCGAAS LELSRPHGDT AKKPIIGILM 50         60         70         80
QKCRNKVMKN YGRYYIAASY VKYLESAGAR VVPVRLDLTE 90         100        110        120
KDYEILFKSI NGILFPGGSV DLRRSDYAKV AKIFYNLSIQ 130        140        150        160
SFDDGDYDPV WGTCLGFEEL SLLISGECLL TATDTVDVAM 170        180        190        200
PLNFTGGQLH SRMFQNFPTE LLLSLAVEPL TANFHKWSLS 210        220        230        240
VKNFTMNEKL KKFFNVLTTN TDGKIEFIST MEGYKYPVYG 250        260        270        280
VQWHPEKAPY EWKNLDGISH APNAVKTAFY LAEFFVNEAR 290        300        310
KNNHHFKSES EEERALIYQF SPIYTGHISS FQQCYIFD
```

| Protein Name | Uniprot | IPI | Gene Name |
|---|---|---|---|
| Ezrin | P15311 | IPI00843975 | EZR_Human |

Trypsin Fragments

| 1. ALQLEEER<br>(SEQ ID NO: 77) | 2. APDFVFYAPR<br>(SEQ ID NO: 78) | 3. ELSEQIQR<br>(SEQ ID NO: 89) |
|---|---|---|
| 4. IALLEEAR<br>(SEQ ID NO: 80) | 5. IGFPWSEIR<br>(SEQ ID NO: 81) | 6. QRIDEFEAL<br>(SEQ ID NO: 82) |
| 7. SGYLSSER<br>(SEQ ID NO: 83) | 8. SQEQLAAELAEYTAK<br>(SEQ ID NO: 84) | 9. VSAQEVRK<br>(SEQ ID NO: 85) |

```
10         20         30         40              (SEQ ID NO: 86)
MPKPINVRVT TMDAELEFAI QPNTTGKQLF DQVVKTIGLR 50         60         70         80
EVWYFGLHYV DNKGFPTWLK LDKK(3)VSAQEV RKENPLQFKF 90         100        110        120
RAKFYPEDVA EELIQDITQK LFFLQVKEGI LSDEIYCPPE 130        140        150        160
TAVLLGSYAV QAKFGDYNKE VHK(7)SGYLSSE RLIPQRVMDQ
```

```
                                                    -continued
─────────────────────────────────────────────────────────────────────────────
     170        180        190        200
HKLTRDQWED RIQVWHAEHR GMLKDNAMLE YLKIAQDLEM 210        220        230        240
YGINYFEIKN KKGTDLWLGV DALGLNIYEK DDKLTPK(5)IGF 250        260        270        280
PWSEIRNISF NDKKFVIKPI DKK(2)APDFVFY APRLRINKRI 290        300        310        320
LQLCMGNHEL YMRRRKPDTI EVQQMKAQAR EEKHQKQLER 330        340        350        360
QQLETEKKRR ETVEREKEQM MREKEELMLR LQDYEEKTKK 370        380        390        400
AER(3)ELSEQIQ R(1)ALQLEEERK RAQEEAERLE ADRMAALRAK 410        420        430        440
EELERQAVDQ IK(11)SQEQLAAE LAEYTAK(4)IAL LEEARRRKED 450        460        470        480
EVEEWQHRAK EAQDDLVKTK EELHLVMTAP PPPPPPVYEP 490        500        510        520
VSYHVQESLQ DEGAEPTGYS AELSSEGIRD DRNEEKRITE 530        540        550        560
AEKNERVQRQ LLTLSSELSQ ARDENKRTHN DIIHNENMRQ 570        580
GRDKYKTLRQ IRQGNTK(6)QRI DEFEAL
```

| Protein Name | Uniprot | IPI | Gene Name |
|---|---|---|---|
| Alpha-2-antiplasmin | P08697 | IPI00879231 | SERPINF2_Human |

Trypsin Fragments

1. LGNQEPGGQTALK
   (SEQ ID NO: 87)

```
     10         20         30         40              (SEQ ID NO: 88)
MALLWGLLVL SWSCLQGPCS VFSPVSAMEP LGRQLTSGPN 50         60         70         80
QEQVSPLTLL KLGNQEPGGQ TALKSPPGVC SRDPTPEQTH 90        100        110        120
RLARAMMAFT ADLFSLVAQT STCPNLILSP LSVALALSHL 130        140        150        160
ALGAQNHTLQ RLQQVLHAGS GPCLPHLLSR LCQDLGPGAF 170        180        190        200
RLAARMYLQK GFPIKEDFLE QSEQLFGAKP VSLTGKQEDD 210        220        230        240
LANINQWVKE ATEGKIQEFL SGLPEDTVLL LLNAIHFQGF 250        260        270        280
WRNKFDPSLT QRDSFHLDEQ FTVPVEMMQA RTYPLRWFLL 290        300        310        320
EQPEIQVAHF PFKNNMSFVV LVPTHFEWNV SQVLANLSWD 330        340        350        360
TLHPPLVWER PTKVRLPKLY LKHQMDLVAT LSQLGLQELF 370        380        390        400
QAPDLRGISE QSLVVSGVQH QSTLELSEVG VEAAAATSIA 410        420        430        440
MSRMSLSSFS VNRPFLFFIF EDTTGLPLFV GSVRNPNPSA 450        460        470        480
PRELKEQQDS PGNKDFLQSL KGFPRGDKLF GPDLKLVPPM
```

| | | | |
|---|---|---|---|
| 490 | | | |
| EEDYPQFGSP K | | | |

| Protein Name | Uniprot | IPI | Gene Name |
|---|---|---|---|
| Hemopexin | P02790 | IPI00022488 | HPX_Human |

Trypsin Fragments

| | | |
|---|---|---|
| 1. DVRDYFMPCPGR (SEQ ID NO: 89) | 2. DYFMPCPGR (SEQ ID NO: 90) | 3. EVGTPHGIILDSVD AAFICPGSSR (SEQ ID NO: 91) |
| 4. GECQAEGVLFFQGDR (SEQ ID NO: 92) | 5. GEFVWK (SEQ ID NO: 93) | 6. GGYTLVSGYPK (SEQ ID NO: 94) |
| 7. LLQDEFPGI PSPIDAAVECHR (SEQ ID NO: 95) | 8. NFPSPVDAAFR (SEQ ID NO: 96) | 9. QGHNSVFLIK (SEQ ID NO: 97) |
| 10. SGAQATWTELPWPHEK (SEQ ID NO: 98) | 11. VDGALCMEK (SEQ ID NO: 99) | 12. WKNFPSPVDAAFR (SEQ ID NO: 100) |

```
        10         20         30         40                    (SEQ ID NO: 101)
MARVLGAPVA LGLWSLCWSL AIATPLPPTS AHGNVAEGET 50         60         70         80
KPDPDVTERC SDGWSFDATT LDDNGTMLFF K(5)GEFVWKSHK 90        100        110        120
WDRELISERW K(8)NFPSPVDAA FR(9)QGHNSVFL IKGDKVWVYP 130        140        150        160
PEKKEKGYPK (7)LLQDEFPGIP SPLDAAVECH R(4)GECQAEGVL 170        180        190        200
FFQGDREWFW DLATGTMKER SWPAVGNCSS ALRWLGRYYC 210        220        230        240
FQGNQFLRFD PVRGEVPPRY PR(1)DVR(2)DYFMP CPGRGHGHRN 250        260        270        280
GTGHGNSTHH GPEYMRCSPH LVLSALTSDN HGATYAFSGT 290        300        310        320
HYWRLDTSRD GWHSWPIAHQ WPQGPSAVDA AFSWEEKLYL 330        340        350        360
VQGTQVYVFL TK(6)GGYTLVSG YPKRLEK(3)EVG TPHGIILDSV 370        380        390        400
DAAFICPGSS RLHIMAGRRL WWLDLK(10)SGAQ ATWTELPWPH 410        420        430        440
EK(11)VDGALCME KSLGPNSCSA NGPGLYLIHG PNLYCYSDVE 450        460
KLNAAKALPQ PQNVTSLLGC TH
```

| Protein Name | Uniprot | IPI | Gene Name |
|---|---|---|---|
| Cysteine Rich Secretory Protein 3 | P54108 | IPI00974055 | Crisp3_Human |

Trypsin Fragments

1. WANQCNYR
   (SEQ ID NO: 102)

```
        10         20         30         40                    (SEQ ID NO: 103)
MTLFPVLLFL VAGLLPSFPA NEDKDPAFTA LLTTQTQVQR 50         60         70         80
EIVNKHNELR RAVSPPARNM LKMEWNKEAA ANAQKWANQC 90        100        110        120
NYRHSNPKDR MTSLKCGENL YMSSASSSWS QAIQSWFDEY
```

|  |  |  |  |
|---|---|---|---|
| 130 | 140 | 150 | 160 |
| NDFDFGVGPK | TPNAVVGHYT | QVVWYSSYLV | GCGNAYCPNQ |
| 170 | 180 | 190 | 200 |
| KVLKYYYVCQ | YCPAGNWANR | LYVPYEQGAP | CASCPDNCDD |
| 210 | 220 | 230 | 240 |
| GLCTNGCKYE | DLYSNCKSLK | LTLTCKHQLV | RDSCKASCNC |

| Protein Name | Uniprot | IPI | Gene Name |
|---|---|---|---|
| Carboxypeptidase A4 | Q9UI42 | IPI00008894 | CP4A_Human |

Trypsin Fragments

1. DPAITSILEK (SEQ ID NO: 104)
2. SRNPGSSCIGADPNR (SEQ ID NO: 105)
3. GASDNPCSEVYHGPH ANSEVEVK (SEQ ID NO: 106)
4. SVVDFIQK (SEQ ID NO: 107)
5. NPGSSCIGADPNR (SEQ ID NO: 108)

(SEQ ID NO: 109)

|  |  |  |  |
|---|---|---|---|
| 10 | 20 | 30 | 40 |
| MRWILFIGAL | IGSSICGQEK | FFGDQVLRIN | VRNGDEISKL |
| 50 | 60 | 70 | 80 |
| SQLVNSNNLK | LNFWKSPSSF | NRPVDVLVPS | VSLQAFKSFL |
| 90 | 100 | 110 | 120 |
| RSQGLEYAVT | IEDLQALLDN | EDDEMQHNEG | QERSSNNFNY |
| 130 | 140 | 150 | 160 |
| GAYHSLEAIY | HEMDNIAADF | PDLARRVKIG | HSFENRPMYV |
| 170 | 180 | 190 | 200 |
| LKFSTGKGVR | RPAVWLNAGI | HSREWISQAT | AIWTARKIVS |
| 210 | 220 | 230 | 240 |
| DYQR[1]DPAITS ILEKMDIFLL | PVANPDGYVY | TQTQNRLWRK | |
| 250 | 260 | 270 | 280 |
| TR[2]SR[5]NPGSSC IGADPNRNWN | ASFAGK[3]GASD NPCSEVYHGP | | |
| 290 | 300 | 310 | 320 |
| HANSEVEVK[4]SVVDFIQKHGN | FKGFIDLHSY | SQLLMYPYGY | |
| 330 | 340 | 350 | 360 |
| SVKKAPDAEE | LDKVARLAAK | ALASVSGTEY | QVGPTCTTVY |
| 370 | 380 | 390 | 400 |
| PASGSSIDWA | YDNGIKFAFT | FELRDTGTYG | FLLPANQIIP |
| 410 | 420 | | |
| TAEETWLGLK | TIMEHVRDNL | | |

| Protein Name | Uniprot | IPI | Gene Name |
|---|---|---|---|
| N-acetylmuramyl-L-alanine amidase | Q96PD5-2 | IPI00394992 | PGLYRP2_Human |

Trypsin Fragments

1. GSQTQSHPDLGTEG CWDQLSAPR (SEQ ID NO: 110)
2. TFTLLDPK (SEQ ID NO: 111)

(SEQ ID NO: 112)

|  |  |  |  |
|---|---|---|---|
| 10 | 20 | 30 | 40 |
| MAQGVLWILL | GLLLWSDPGT | ASLPLLMDSV | IQALAELEQK |
| 50 | 60 | 70 | 80 |
| VPAAKTRHTA | SAWLMSAPNS | GPHNRLYHFL | LGAWSLNATE |
| 90 | 100 | 110 | 120 |
| LDPCPLSPEL | LGLTKEVARH | DVREGKEYGV | VLAPDGSTVA |

```
         130        140        150        160
VEPLLAGLEA GLQGRRVINL PLDSMAAPWE TGDTFPDVVA 170        180        190        200
IAPDVRATSS PGLRDGSPDV TTADIGANTP DATKGCPDVQ 210        220        230        240
ASLPDAKAKS PPTMVDSLLA VTLAGNLGLT FLR(1)GSQTQSH 250        260        270        280
PDLGTEGCWD QLSAPR(2)TFTL LDPKASLLTM AFLNGALDGV 290        300        310        320
ILGDYLSRTP EPRPSLSHLL SQYYGAGVAR DPGFRSNFRR 330        340        350        360
QNGAALTSAS ILAQQVWGTL VLLQRLEPVH LQLQCMSQEQ 370        380        390        400
LAQVAANATK EFTEAFLGCP ATHPRCRWGA APYRGRPKLL 410        420        430        440
QLPLGFLYVH HTYVPAPPCT DFTRCAANMR SMQRYHQDTQ 450        460        470        480
GWGDIGYSFV VGSDGYVYEG RGWHWVGAHT LGHNSRGFGV 490        500        510        520
AIVGNYTAAL PTEAALRTVR DTLPSCAVRA GLLRPDYALL 530        540        550        560
GHRQLVRTDC PGDALFDLLR TWPHFTATVK PRPARSVSKR

570
SRREPPPRTL PATDLQ
```

| Protein Name | Uniprot | Gene Name |
| --- | --- | --- |
| Caspase-14 | P31944 | CASP14_Human |

Trypsin Fragments

1. AREGSEEDLDALEHMFR
   (SEQ ID NO: 113)

2. DPTAEQFQEELEK
   (SEQ ID NO: 114)

3. FQQAIDSR
   (SEQ ID NO: 115)

4. KTNPEIQSTLR
   (SEQ ID NO: 116)

5. MAEAELVQEGK
   (SEQ ID NO: 117)

6. RDPTAEQFQEELEK
   (SEQ ID NO: 118)

7. RMAEAELVQEGK
   (SEQ ID NO: 119)

8. SLEEEKYDMSGAR
   (SEQ ID NO: 120)

9. TNPEIQSTLR
   (SEQ ID NO: 121)

10. VYIIQACR
    (SEQ ID NO: 122)

```
         10         20         30         40          (SEQ ID NO: 123)
MSNPR(8)SLEEE KYDMSGARLA LILCVTK(1)ARE GSEEDLDALE 50         60         70         80
HMFR(6)QLRFES TMK(6)R(2)DPTAEQ FQEELEK(3)FQQ AIDSREDPVS 90        100        110        120
CAFVVLMAHG REGFLKGEDG EMVKLENLFE ALNNKNCQAL 130        140        150        160
RAKPKV(10)YIIQ ACRGEQRDPG ETVGGDEIVM VIKDSPQTIP 170        180        190        200
TYTDALHVYS TVEGYIAYRH DQKGSCFIQT LVDVFTKRKG
```

-continued

```
       210        220        230        240
HILELLTEVT R(7)R(5)MAEAELVQ EGKAR(4)K(9)TNPE IQSTLRKRLY
LQ
```

| Protein Name | Uniprot | IPI | Gene Name |
|---|---|---|---|
| Ig Kappa chain V-III region POM | P04207 | IPI00385253 | KV308_Human |

Trypsin Fragments

1. LLIYGASTR
   (SEQ ID NO: 124)

```
       10         20         30         40              (SEQ ID NO: 125)
MEAPAQLLFL LLLWLPDTTG SIVMTQSPAT LSVSPGERAT 50         60         70         80
LSCRASQSVS NNLAWYQQKP GQPPRLLIYG ASTRATGIPA 90        100        110        120
RFSGSGSGTE FTLTISRLQS EDFAVYYCQQ YNNWPPWTFG

QGTRVEIKR
```

| Protein Name | Uniprot | IPI | Gene Name |
|---|---|---|---|
| Ig Kappa chain V-III region POM | P01624 | IPI00387119 | KV306_Human |

Trypsin Fragments

1. EIVMTQSPVTLSVSPGER
   (SEQ ID NO: 126)

```
       10         20         30         40              (SEQ ID NO: 127)
EIVMTQSPVT LSVSPGERAT LSCRASQSIS NSYLAWYQQK 50         60         70         80
PSGSPRLLIY GASTRATGIP ARFSGSGSGT EFTLTISSLQ 90        100
SEDFAVYYCQ QYNNWPPTFG QGTRVEIKR
```

| Protein Name | Uniprot | IPI | Gene Name |
|---|---|---|---|
| Isoform 1 Serum Albumin | P02768-1 | IPI00387119 | ALB_Human |

Trypsin Fragments

1. AACLLPK
   (SEQ ID NO: 128)

2. AAFTECCQAADK
   (SEQ ID NO: 129)

3. AAFTECCQAADKAACLLPK
   (SEQ ID NO: 130)

4. ADDKETCFAEEGK
   (SEQ ID NO: 131)

5. ADDKETCFAEEGKK
   (SEQ ID NO: 132)

6. AEFAEVSK
   (SEQ ID NO: 133)

7. AEFAEVSKLVTDLTK
   (SEQ ID NO: 134)

8. ATKEQIK
   (SEQ ID NO: 135)

9. ATKEQIKAVMDDFAAFVEK
   (SEQ ID NO: 136)

11. AVMDDFAAFVEK
    (SEQ ID NO: 137)

12. CASIQKFGER
    (SEQ ID NO: 138)

13. CCAAADPHECYAK
    (SEQ ID NO: 139)

14. CCKADDKETCFAEEGK
    (SEQ ID NO: 140)

15. CCKHPEAK
    (SEQ ID NO: 141)

16. CCTESLVNR
    (SEQ ID NO: 142)

17. CCTESLVNRRPCFSALEV
    DETYVPK
    (SEQ ID NO: 143)

18. DDNPNLPR
    (SEQ ID NO: 144)

19. DAHKSEVAHR
    (SEQ ID NO: 145)

20. DLGEENFK
    (SEQ ID NO: 146)

21. DVCKNYAEAK
    (SEQ ID NO: 147)

22. DVFLGMFLYEYAR
    (SEQ ID NO: 148)

23. ECCEKPLLEK
    (SEQ ID NO: 149)

24. EFNAETFTFHADICTLSEK
    (SEQ ID NO: 150)

25. EFNAETFTFHADICTLSE
    KER
    (SEQ ID NO: 151)

-continued

26. EQLKAVMDDFAAFVEK (SEQ ID NO: 152)
27. ETCFAEGK (SEQ ID NO: 153)
28. ETCFAEEGKK (SEQ ID NO: 154)
29. ETYGEMADCCAK (SEQ ID NO: 155)
30. FKDLGEENFK (SEQ ID NO: 156)
31. FPKAEFAEVSK (SEQ ID NO: 157)
32. FQNALLVR (SEQ ID NO: 158)
33. HPDYSVVLLLR (SEQ ID NO: 159)
34. HPYFYAPELLFFAK (SEQ ID NO: 160)
35. LAKTYETTLEK (SEQ ID NO: 161)
36. LCTVATLR (SEQ ID NO: 162)
37. LCTVATLRETYGEMADCCAK (SEQ ID NO: 163)
38. LDELRDEGK (SEQ ID NO: 164)
39. LDELRDEGKASSAK (SEQ ID NO: 165)
40. LKCASLQK (SEQ ID NO: 166)
41. LKECCEKPLLEK (SEQ ID NO: 167)
42. LSQRFPK (SEQ ID NO: 168)
43. LFSQRFPKAEFAEVSK (SEQ ID NO: 169)
44. LVAASQAALGL (SEQ ID NO: 170)
45. LVNEVTEFAK (SEQ ID NO: 171)
46. IVNEVTEFAKTCVADESAENCDK (SEQ ID NO: 172)
47. LVRPEVDVMCTAFHDNEETFLK (SEQ ID NO: 173)
48. LVRPEVDVMCTAFHDNEETFLKK (SEQ ID NO: 174)
49. LVTDLTK (SEQ ID NO: 175)
50. KLVAASQAALGL (SEQ ID NO: 176)
51. KQTALVELVK (SEQ ID NO: 177)
52. KVPQVSTPTLLVEVSR (SEQ ID NO: 178)
53. KYLYEIAR (SEQ ID NO: 179)
54. MPCAEDYILSVVILNQILCVILHEK (SEQ ID NO: 180)
55. NECFIQHK (SEQ ID NO: 181)
56. NECFLQHKDDNPNLPR (SEQ ID NO: 182)
57. NIGKVGSK (SEQ ID NO: 183)
58. NYAEAK (SEQ ID NO: 184)
59. NYAEAKDVFIGMFIYEYAR (SEQ ID NO: 185)
60. PLVEEPQNLIK (SEQ ID NO: 186)
61. QEPERNECFLQHK (SEQ ID NO: 187)
62. QEPERNECFLQHKDDNPNLPR (SEQ ID NO: 188)
63. QNCELFEQLGEYK (SEQ ID NO: 189)
64. QNCELFEQLGEYKFQNAIIVR (SEQ ID NO: 190)
65. QTAIVEIVK (SEQ ID NO: 191)
66. RHPDYSVVLLLR (SEQ ID NO: 192)
67. RMPCAEDYILSVVLKNQLCVLHEK (SEQ ID NO: 193)
68. RPCFSALEVDETYVPK (SEQ ID NO: 194)
69. SHCIAEVENDEMPADLPSLAADFVESKDVCKNYAEAK (SEQ ID NO: 195)
70. SHCIAEVENDEMPADLPSLAADFVESK (SEQ ID NO: 196)
71. SHCIAEVENDEMPADLPSLAADFVESKDVCK (SEQ ID NO: 197)
72. SLHTLFGDK (SEQ ID NO: 198)
73. SLHTLFGDKLCTVATLR (SEQ ID NO: 199)
74. TCVADESAENCDK (SEQ ID NO: 200)
75. TCVADESAENCDKSLHTLFGDK (SEQ ID NO: 201)
76. TCVADESAENCDKSLHTLFGDKLCTVATLR (SEQ ID NO: 202)
77. TPVSDRVTK (SEQ ID NO: 203)
78. TYETTLEK (SEQ ID NO: 204)
79. TYETTIEKCCAAADPHECYAK (SEQ ID NO: 205)
80. VFDEFKPLVEEPQNLIK (SEQ ID NO: 206)
81. VHTECCHGDLLECADDR (SEQ ID NO: 207)
82. VHTECCHGDLLECADDRADLAK (SEQ ID NO: 208)
83. VHTECCHGDLLECADDRADLAKYICENQDSISSK (SEQ ID NO: 209)
84. VPQVSTPTLVEVSR (SEQ ID NO: 210)
85. YICENQDSISSK (SEQ ID NO: 211)

| | | |
|---|---|---|
| 86. YICENQDSISSKLK (SEQ ID NO: 212) | 87. YLYEIAR (SEQ ID NO: 213) | 88. YLYEIARR (SEQ ID NO: 214) |
| 89. YKAAFTECC QAADK (SEQ ID NO: 215) | 90. YKAAFTECC QAADKAACLLPK (SEQ ID NO: 216) | |

MKWVTFISLL FLFSSAYSRG VFRR[10]DAHKSE VAHR[30]FK[20]DLGE ENFK (SEQ ID NO: 217)

ALVLIA FAQYLQQCPFEDHVK[45] LVNEV TEFAK[74,75,76] TCVAD ESAENCDK[72,73]SL HTLFGD

K[37,36]LCTVATLR[23]ETYGE MADCCAK[61] [62]QEP ER[55] [56]NECFLQHK[18] DDNPNLPR[47] [48]LV

RPEVDVMCTA FHDNEETFLK [53]K[87,88]YLYEIARR[24]H PYFYAPELLF FAKR[89,90]YK[2] [3]AAFT

ECCQAADK[1]AA CLLPK[39] [38]LDELR DEGKASSAKQ R[49]LK[12]CASLQKFGERAFKAWAV

AR[43] [48]LSQR[31]FPK[4]A EFAEV[7]SK[49]LVT DLTK[81,82,83]VHTECC HGDLLECADD

RADLAK[85,86]YICE NQDSISSK[41]LK [23]ECCEKPLLEK [69,70,71]SHCIAEVEND EMPADLPSLA

ADFVESK[21]DVC K[58] [59]NYAEAK[22]DVFLGMFLYEYAR [68]R[33]HPDYSVVLL

LR[35]LAK[78,79]TYETT LEK[12]CCAAADP HECYAK[80]VFDE FK[40]PLVEEPQN

LIK[63] [64]QNCELFE QLGEYK[32]FQNA LLVRYTK[52]K[54]VP QVSTPTLVEV SR[57]NLGKVGSK

[15]CCKHPEAK[67]R[64]M PCAEDYLSVV LNQLCVLHEK [77]TPVSDRVTK[17] [16]C CTESLVNR[68]RP

CFSALEVDET YVPK[25] [24]EFNAETFTF HADICTL

SEKERQIK[51]K[65]Q TALVELVKHK PK[10] [9]ATK[26]EQLK[11]A

VMDDFAAFVEK[14]CCK[4]ADDK[28] [27]ET CFAEEGK[5] [56]K[44]LV

AASQAALGL

| Protein Name | Uniprot | IPI | Gene Name |
|---|---|---|---|
| Isoform 1 of Complement factor H | P08603 | IPI00029739 | CFH_Human |

| Trypsin Fragments | | |
|---|---|---|
| 1. *AGEQVTYTCATYYK (SEQ ID NO: 218) | 2. CLHPCVISR (SEQ ID NO: 219) | 3. *DGWSAQPTCIK (SEQ ID NO: 220) |
| 4. *DTSCVNPP TVQNAYIVSR (SEQ ID NO: 221) | 5. *EFDHNSNIR (SEQ ID NO: 222) | 6. EIMENYNIALR (SEQ ID NO: 223) |
| 7. GDAVCTESGWR (SEQ ID NO: 224) | 8. GDAVCTESG WRPLPSCEEK (SEQ ID NO: 225) | 9. *IDVHLVPDR (SEQ ID NO: 226) |
| 10. *LSYTCEGGFR (SEQ ID NO: 227) | 11. IVSSAMEPD REYHFGQAVR (SEQ ID NO: 228) | 12. NTEILTGSW SDQTYPEGTQAIYK (SEQ ID NO: 229) |
| 13. RPYFPVAVGK (SEQ ID NO: 230) | 14. *SCDIPVFMNAR (SEQ ID NO: 231) | 15. SIDVACHPGYALPK (SEQ ID NO: 232) |
| 16. SLGNVIMVCR (SEQ ID NO: 233) | 17. *SSNLIILEEHLK (SEQ ID NO: 234) | 18. *SSQESYAHGTK (SEQ ID NO: 235) |
| 19. TGDEITYQCR (SEQ ID NO: 236) | 20. TGESVEFVCK (SEQ ID NO: 237) | 21. *TKNDFTWFK (SEQ ID NO: 238) |

-continued

| 22. TTCWDGKLE<br>YPTCAK<br>(SEQ ID NO: 239) | 23. *VSVLCQEN<br>YLIQEGEELTCKDGR<br>(SEQ ID NO: 240) | 24. *WQSIPLCVEK<br>(SEQ ID NO: 241) |
|---|---|---|
| 25. *WSSPPQCEGLPCK<br>(SEQ ID NO: 242) | | |

(SEQ ID NO: 243)

```
         10         20         30         40
 MRLLAKIICL MLWAICVAED CNELPPRR(12)NT EILTGSWSDQ 50         60         70         80
 TYPEGTQAIY KCRPGYR(16)SLG NVIMVCRKGE WVALNPLRKC 90        100        110        120
 QKRPCGHPGD TPEGTFTLTG GNVFEYGVKA VYTCNEGYQL 130        140        150        160
 LGEINYRECD TDGWTNDIPI CEVVKCLPVT APENGK(11)IVSS 170        180        190        200
 AMEPDREYHF GQAVRFVCNS GYKIEGDEEM HCSDDGFWSK 210        220        230        240
 EKPKCVEISC KSPDVINGSP ISQKIIYKEN ERFQYKCNMG 250        260        270        280
 YEYSER(7)GDAV CTESGWR(8)PLP SCEEKSCDNP YIPNGDYSPL 290        300        310        320
 RIKHR(19)TGDEI TYQCRNGFYP ATRGNTAKCT STGWIPAPRC 330        340        350        360
 TLKPCDYPDI KHGGLYHENM R(13)RPYFPVAVG KYYSYYCDEH 370        380        390        400
 FETPSGSYWD HIHCTQDGWS PAVPCLRKCY FPYLENGYNQ 410        420        430        440
 NYGRKFVQGK (15)SIDVACHPGY ALPKAQTTVT CMENGWSPTP 450        460        470        480
 RCIRVKTCSK SSIDIENGFI SESQYTYALK EKAKYQCKLG 490        500        510        520
 YVTADGETSG SITCGK(3)DGWS AQPTCIK(14)SCD IPVFMNAR(21)TK 530        540        550        560
 NDFTWFKLND TLDYECHDGY ESNTGSTTGS IVCGYNGWSD 570        580        590        600
 LPICYERECE LPK(9)IDVHLVP DRKKDQYKVG EVLKFSCKPG 610        620        630        640
 FTIVGPNSVQ CYHFGLSPDL PICKEQVQSC GPPPELLNGN 650        660        670        680
 VKEKTKEEYG HSEVVEYYCN PRFLMKGPNK IQCVDGEWTT 690        700        710        720
 LPVCIVEEST CGDIPELEHG WAQLSSPPYY YGDSVEFNCS 730        740        750        760
 ESFTMIGHRS ITCIHGVWTQ LPQCVAIDKL KKCK(17)SSNLII 770        780        790        800
 LEEHLKNKK(5)E FDHNSNIRYR CRGKEGWIHT VCINGRWDPE 810        820        830        840
 VNCSMAQIQL CPPPPQIPNS HNMTTTLNYR DGEK(23)VSVLCQ 850        860        870        880
 ENYLIQEGEE ITCKDGR(24)WQS IPLCVEKIPC SQPPQIEHGT 890        900        910        920
 INSSR(18)SSQES YAHGTK(10)LSYT CEGGFRISEE NETTCYMGK(25)W 930        940        950        960
 SSPPQCEGLP CKSPPEISHG VVAHMSDSYQ YGEEVTYKCF
```

```
                       970        980        990        1000
                       EGFGIDGPAI AKCLGEKWSH PPSCIKTDCL SLPSFENAIP 1010       1020       1030       1040
                       MGEKKDVYK⁽¹⁾A GEQVTYTCAT YYKMDGASNV TCINSRWTGR 1050    1060       1070       1080
                       PTCR⁽⁴⁾DTSCVN PPTVQNAYIV SRQMSKYPSG ERVRYQCRSP 1090       1100       1110       1120
                       YEMFGDEEVM CLNGNWTEPP QCKDSTGKCG PPPPIDNGDI 1130       1140       1150       1160
                       TSFPLSVYAP ASSVEYQCQN LYQLEGNKRI TCRNGQWSEP 1170     1180        1190        1200
                       PK⁽²⁾CLHPCVIS R⁽⁶⁾EIMENYNIA LRNTAKQKLY SR⁽²⁰⁾TGESVEFV 1210       1220       1230
                       CKRGYRLSSR SHTLR⁽²²⁾TTCWD GKLEYPTCAK R
```

| Protein Name | Uniprot | IPI | Gene Name |
|---|---|---|---|
| Isoform 1 of Sodium-dependent phosphate transport protein | O95436-1 | IPI00007910 | SLC34A2_Human |

| Trypsin Fragments | |
|---|---|
| 1. EAQGEVPASDSKTECTAL (SEQ ID NO: 244) | 2. VISQIAMNDEK (SEQ ID NO: 245) |

```
10         20         30         40                    (SEQ ID NO: 246)
MAPWPELGDA QPNPDKYLEG AAGQQPTAPD KGKETNKTDN 50         60         70         80
TEAPVTKIEL LPSYSTATLI DEPTEVDDPW NLPTLQDSGI 90         100        110        120
KWSERDTKGK ILCFFQGIGR LILLLGFLYF FVCSLDILSS 130        140        150        160
AFQLVGGKMA GQFFSNSSIM SNPLLGLVIG VLVTVLVQSS 170        180        190        200
STSTSIVVSM VSSSLLTVRA AIPIIMGANI GTSITNTIVA 210        220        230        240
LMQVGDRSEF RRAFAGATVH DEFNWLSVLC LLPVEVATHY 250        260        270        280
LEIITQLIVE SFHFKNGEDA PDLLKVITKP FTKLIVQLDK 290        300        310        320
K⁽²⁾VISQIAMND EKAKNKSLVK IWCKTFTNKT QINVTVPSTA 330        340        350        360
NCTSPSLCWT DGIQNWTMKN VTYKENIAKC QHIFVNFHLP 370        380        390        400
DLAVGTILLI LSLLVLCGCL IMIVKILGSV LKGQVALVIK 410        420        430        440
KTINTDFPFP FAWLTGYLAI LVGAGMTFIV QSSSVFTSAL 450        460        470        480
TPLIGIGVIT IERAYPLTLG SNIGTTTTAI LAALASPGNA 490        500        510        520
LRSSLQIALC HFFFNISGIL LWYPIPFTRL PIRMAKGLGN 530        540        550        560
ISAKYRWFAV FYLIIFFFLI PLTVFGLSLA GWRLVGVGV 570        580        590        600
PVVFIIILVL CLRLLQSRCP RVLPKKLQNW NFLPLWMRSL 610        620        630        640
KPWDAVVSKF TGCFQMRCCC CCRVCCRACC LLCDCPKCCR
```

|  |  |  |  |
|---|---|---|---|
| 650 | 660 | 670 | 680 |
| CSKCCEDLEE | AQEGQDVPVK | APETFDNITI | SR[(1)]EAQGEVPA |
| 690 |  |  |  |
| SDSKTECTAL |  |  |  |

| Protein Name | Uniprot | IPI | Gene Name |
|---|---|---|---|
| Putative Uncharacterized protein |  | IPI00152189 |  |

Trypsin Fragments

1. FSVLGSGLNR

MAWAPLLLTLLSLLTGSLSQPVLTQPPSASASLGASVTLTCTLSSGYSNYKVD    (SEQ ID NO: 248)

WYQQRPGKGPRFVMRVGTGGIVGSKGDGIPDRFSVLGSGLNRYLTIKNIQEEDESDYHCGADHGSGS

NFV

| Protein Name | Uniprot | IPI | Gene Name |
|---|---|---|---|
| Ras Related Protein Rab-30 | Q15771 | IPI00302030 | RAB_30_Human |

Trypsin Fragments

1. LQIWDTAGQER
   (SEQ ID NO: 249)
2. SMEDYDFLFK
   (SEQ ID NO: 250)

|  |  |  |  |  |
|---|---|---|---|---|
| 10 | 20 | 30 | 40 | (SEQ ID NO: 251) |
| M[(2)]SMEDYDFLF | KIVLIGNAGV | GKTCLVRRFT | QGLFPPGQGA |  |
| 50 | 60 | 70 | 80 |  |
| TIGVDFMIKT | VEINGEKVK[(2)]L | QIWDTAGQER | FRSITQSYYR |  |
| 90 | 100 | 110 | 120 |  |
| SANALILTYD | ITCEESFRCL | PEWLREIEQY | ASNKVITVLV |  |
| 130 | 140 | 150 | 160 |  |
| GNKIDLAERR | EVSQQRAEEF | SEAQDMYYLE | TSAKESDNVE |  |
| 170 | 180 | 190 | 200 |  |
| KLFLDLACRL | ISEAPQNTLV | NHVSSPLPGE | GKSISYLTCC |  |

NFN

| Protein Name | Uniprot | IPI | Gene Name |
|---|---|---|---|
| Isoform 1 of growth arrest-specific protein 6 | Q14393 | IPI00412410 | GAS6_Human |

Trypsin Fragments

1. CEQVCVNSP GSYTCHCDGR
   (SEQ ID NO: 252)
2. GQSEVSAAQ LQER
   (SEQ ID NO: 253)
3. IAVAGDLFQ PER
   (SEQ ID NO: 254)
4. MFSGTPVIR
   (SEQ ID NO: 255)
5. MQCFSVTER
   (SEQ ID NO: 256)
6. NSGFATCVQ NLPDQCTPNPCDR
   (SEQ ID NO: 257)

|  |  |  |  |  |
|---|---|---|---|---|
| 10 | 20 | 30 | 40 | (SEQ ID NO: 258) |
| MAPSLSPGPA | ALRRAPQLLL | LLLAAECALA | ALLPAREATQ |  |
| 50 | 60 | 70 | 80 |  |
| FLRPRQRRAF | QVFEEAKQGH | LERECVEELC | SREEAREVFE |  |
| 90 | 100 | 110 | 120 |  |
| NDPETDYFYP | RYLDCINKYG | SPYTK[(8)]NSGFA | TCVQNLPDQC |  |

```
         130        140        150        160
TPNPCDRKGT QACQDLMGNF FCLCKAGWGG RLCDKDVNEC 170        180        190        200
SQENGGCLQI CHNKPGSFHC SCHSGFELSS DGRTCQDIDE 210        220        230        240
CADSEACGEA RCKNLPGSYS CLCDEGFAYS SQEKACRDVD 250        260        270        280
ECLQGR⁽¹⁾CEQV CVNSPGSYTC HCDGRGGLKL SQDMDTCELE 290        300        310        320
AGWPCPRHRR DGSPAARPGR GAQGSRSEGH IPDRRGPRPW 330        340        350        360
QDILPCVPFS VAKSVKSLYL GR⁽⁴⁾MFSGTPVI RLRFKRLQPT 370        380        390        400
RLVAEFDFRT FDPEGILLFA GGHQDSTWIV LALRAGRLEL 410        420        430        440
QLRYNGVGRV TSSGPVINHG MWQTISVEEL ARNLVIKVNR 450        460        470        480
DAVMK⁽³⁾IAVAG DLFQPERGLY HLNLTVGGIP FHEKDLVQPI 490        500        510        520
NPRLDGCMRS WNWLNGEDTT IQETVKVNTR⁽⁵⁾MQCFSVTERG 530        540        550        560
SFYPGSGFAF YSLDYMRTPL DVGTESTWEV EVVAHIRPAA 570        580        590        600
DTGVLFALWA PDLRAVPLSV ALVDYHSTKK LKKQLVVLAV 610        620        630        640
EHTALALMEI KVCDGQEHVV TVSLRDGEAT LEVDGTR⁽²⁾GQS 650        660        670        680
EVSAAQLQER LAVLERHLRS PVLTFAGGLP DVPVTSAPVT 690        700        710        720
AFYRGCMTLE VNRRLLDLDE AAYKHSDITA KSCPPVEPAA
```

| Protein Name | Uniprot | IPI | Gene Name |
|---|---|---|---|
| Cathepsin L1 | P07711 | IPI00012887 | CTSL1_Human |

| Trypsin Fragments |||
|---|---|---|
| 1. HSFTMAMNA FGDMTSEEFR (SEQ ID NO: 259) | 2. LYGMNEEGWR (SEQ ID NO: 260) | 3. NHCGIASAASYPV (SEQ ID NO: 261) |
| 4. NSWGEEWGMGGYVK (SEQ ID NO: 262) | | |

```
10         20         30         40                    (SEQ ID NO: 263)
MNPTLILAAF CLGIASATLT FDHSLEAQWT KWKAMGNR⁽²⁾LY 50         60         70         80
GMNEEGWRRA VWEKNMKMIE LHNQEYREGK⁽¹⁾HSFTMAMNAF 90         100        110        120
GDMTSEEFRQ VMNGFQNRKP RKGKVFQEPL FYEAPRSVDW 130        140        150        160
REKGYVTPVK NQGQCGSCWA FSATGALEGQ MFRKTGRLIS 170        180        190        200
LSEQNLVDCS GPQGNEGCNG GLMDYAFQYV QDNGGLDSEE 210        220        230        240
SYPYEATEES CKYNPKYSVA NDTGFVDIPK QEKALMKAVA 250        260        270        280
TVGPISVAID AGHESFLFYK EGIYFEPDCS SEDMDHGVLV
```

```
             290        300        310        320
VGYGFESTES DNNKYWLVK⁽⁴⁾N SWGEEWGMGG YVKMAKDRR⁽³⁾N

330
HCGIASAASY PTV
```

| Protein Name | Uniprot | IPI | Gene Name |
|---|---|---|---|
| Secreted frizzled-related protein 1 | Q8N474 | IPI00749245 | SFRP1_Human |

| Trypsin Fragments | | |
|---|---|---|
| 1. FYTKPPQCVDIPADLR (SEQ ID NO: 264) | 2. LCHNVGYK (SEQ ID NO: 265) | 3. LCHNVGYKK (SEQ ID NO: 266) |
| 4. MVLPNLLEHETMAEVK (SEQ ID NO: 267) | 5. PQGTTVCPPCDNELK (SEQ ID NO: 268) | 6. QQASSWVPLLNK (SEQ ID NO: 269) |
| 7. SEAIIEHLCASEFALR (SEQ ID NO: 270) | 8. SQYLLTAIHK (SEQ ID NO: 271) | |

```
         10         20         30         40             (SEQ ID NO: 272)
MGIGRSEGGR RGAALGVLLA LGAALLAVGS ASEYDYVSFQ 50         60         70         80
SDIGPYQSGR ⁽¹⁾FYTKPPQCVD IPADLR⁽²,³⁾LCHN VGYKK⁽⁴⁾MVLPN 90        100        110        120
LLEHETMAEV K⁽⁶⁾QQASSWVPL LNKNCHAGTQ VFLCSLFAPV 130        140        150        160
CLDRPIYPCR WLCEAVRDSC EPVMQFFGFY WPEMLKCDKF 170        180        190        200
PEGDVCIAMT PPNATEASK⁽⁵⁾P QGTTVCPPCD NELK⁽⁷⁾SEAIIE 210        220        230        240
HLCASEFALR MKIKEVKKEN GDKKIVPKKK KPLKLGPIKK 250        260        270        280
KDLKKLVLYL KNGADCPCHQ LDNLSHHFLI MGRKVK⁽⁸⁾SQYL 290        300        310
LTAIHKWDKK NKEFKNFMKK MKNHECPTFQ SVFK
```

| Protein Name | Uniprot | IPI | Gene Name |
|---|---|---|---|
| Bactericidal permeability-increasing protein | P17213 | IPI00827847 | BPI_Human |

| Trypsin Fragments | |
|---|---|
| 1. GLDYASQQGTAALQK (SEQ ID NO: 273) | 2. IKIPDYSDSFK (SEQ ID NO: 274) |

```
         10         20         30         40             (SEQ ID NO: 275)
MRENMARGFC NAPRWASLMV LVAIGTAVTA AVNPGVVVRI 50         60         70         80
SQK⁽²⁾GLDYASQ QGTAALQKEL KR⁽²⁾IKIPDYSD SFKIKHLGKG 90        100        110        120
HYSFYSMDIR EFQLPSSQIS MVPNVGLKFS ISNANIKISG 130        140        150        160
KWKAQKRFLK MSGNFDLSIE GMSISADLKL GSNPTSGKPT 170        180        190        200
ITCSSCSSHI NSVHVHISKS KVGWLIQLFH KKIESALRNK 210        220        230        240
MNSQVCEKVT NSVSSELQPY FQTLPVMTKI DSVAGINYGL
```

```
250        260        270        280
VAPPATTAET LDVQMKGEFY SENHHNPPPF APPVMEFPAA 290        300        310        320
HDRMVYLGLS DYFFNTAGLV YQEAGVLKMT LRDDMIPKES 330        340        350        360
KFRLTTKFFG TFLPEVAKKF PNMKIQIHVS ASTPPHLSVQ 370        380        390        400
PTGLTFYPAV DVQAFAVLPN SSLASLFLIG MHTTGSMEVS 410        420        430        440
AESNRLVGEL KLDRLLLELK HSNIGPFPVE LLQDIMNYIV 450        460        470        480
PILVLPRVNE KLQKGFPLPT PARVQLYNVV LQPHQNFLLF

GADVVYK
```

| Protein Name | Uniprot | IPI | Gene Name |
|---|---|---|---|
| Chitinase domain containing protein 1 | Q9BWS9-2 | IPI00306719 | CHID1_Human |

Trypsin Fragments

1. GLHIVPR  
   (SEQ ID NO: 276)
2. GLVVTDLK  
   (SEQ ID NO: 277)
3. NVLDSEDEIEELSK  
   (SEQ ID NO: 278)
4. SQFSDKPVQDR  
   (SEQ ID NO: 279)
5. YIQTLK  
   (SEQ ID NO: 280)

(SEQ ID NO: 281)
```
10         20         30         40
MRTLFNLLWL ALACSPVHTT LSKSDAKKAA SKTLLEK(4)SQF 50         60         70         80
SDKPVQDR(2)GL VVTDLKAESV VLEHRSYCSA KARDRHFAGD 90         100        110        120
VLGYVTPWNS HGYDVTKVFG SKFTQISPVW LQLKRRGREM 130        140        150        160
FEVTGLHDVD QGWMRAVRKH AK(1)GLHIVPRL LFEDWTYDDF 170        180        190        200
R(3)NVLDSEDEI EELSKTVVQV AKNQHFDGFV VEVWNQLLSQ 210        220        230        240
KRVGLIHMLT HLAEALHQAR LLALLVIPPA ITPGTDQLGM 250        260        270        280
FTHKEFEQLA PVLDGFSLMT YDYSTAHQPG PNAPLSWVRA 290        300        310        320
CVQVLDPKSK WRSKILLGLN FYGMDYATSK DAREPVVGAR 330        340        350        360
(5)YIQTLKDHRP RMVWDSQASE HFFEYKKSRS GRHVVFYPTL 370        380        390
KSLQVRLELA RELGVGVSIW ELGQGLDYFY DLL
```

| Protein Name | Uniprot | IPI | Gene Name |
|---|---|---|---|
| Moesin | P26038 | IPI00219365 | MSN_Human |

Trypsin Fragments

1. ALELEQER  
   (SEQ ID NO: 282)
2. ALTSELANAR  
   (SEQ ID NO: 283)
3. AQMVQEDLEK  
   (SEQ ID NO: 284)

| 4. ESEAVEWQQK (SEQ ID NO: 285) | 5. ISQLEMAR (SEQ ID NO: 286) | 6. IGFPWSEIR (SEQ ID NO: 287) |
|---|---|---|

```
         10         20         30         40                (SEQ ID NO: 288)
  MPKTISVRVT TMDAELEFAI QPNTTGKQLF DQVVKTIGLR 50         60         70         80
  EVWFFGLQYQ DTKGFSTWLK LNKKVTAQDV RKESPLLFKF 90        100        110        120
  RAKFYPEDVS EELIQDITQR LFFLQVKEGI LNDDIYCPPE 130        140        150        160
  TAVLLASYAV QSKYGDFNKE VHKSGYLAGD KLLPQRVLEQ 170        180        190        200
  HKLNKDQWEE RIQVWHEEHR GMLREDAVLE YLKIAQDLEM 210        220        230        240
  YGVNYFSIKN KKGSELWLGV DALGLNIYEQ NDRLTPK(5)IGF 250        260        270        280
  PWSEIRNISF NDKKFVIKPI DKKAPDFVFY APRLRINKRI 290        300        310        320
  LALCMGNHEL YMRRRKPDTI EVQQMKAQAR EEKHQKQMER 330        340        350        360
  AMLENEKKKR EMAEKEKEKI EREKEELMER LKQIEEQTKK 370        380        390        400
  AQQELEEQTR R(1)ALLEQERK RAQSEAEKLA KERQEAEEEAK 410        420        430        440
  EALLQASRDQ KKTQEQLALE MAELTAR(5)ISQ LEMARQKK(4)ES 450        460        470        480
  EAVEWQQK(3)AQ MVQEDLEKTR AELKTAMSTP HVAEPAENEQ 490        500        510        520
  DEQDENGAEA SADLRADAMA KDRSEEERTT EAEKNERVQK 530        540        550        560
  HLK(2)ALTSELA NARDESKKTA NDMIHAENMR LGRDKYKTLR

570
  QIRQGNTKQR IDEFESM
```

| Protein Name | Uniprot | IPI | Gene Name |
|---|---|---|---|
| Isoform 2 of Endoplasmic reticulum aminopeptidase 1 | Q9NZ08-2 | IPI00165949 | ERAP1_Human |

| Trypsin Fragments | | |
|---|---|---|
| 1. GACILNMLR (SEQ ID NO: 289) | 2. ILASTQFEPTAAR (SEQ ID NO: 290) | 3. SQIEFALCR (SEQ ID NO: 291) |

```
         10         20         30         40                (SEQ ID NO: 292)
  MVFLPLKWSL ATMSFLLSSL LALLTVSTPS WCQSTEASPK 50         60         70         80
  RSDGTPFPWN KIRLPEYVIP VHYDLLIHAN LTTLTFWGTT 90        100        110        120
  KVEITASQPT STIILHSHHL QISRATLRKG AGERLSEEPL 130        140        150        160
  QVLEHPRQEQ IALLAPEPLL VGLPYTVVIH YAGNLSETFH 170        180        190        200
  GFYKSTYRTK EGELR(2)ILAST QFEPTAARMA FPCFDEPAFK 210        220        230        240
  ASFSIKIRRE PRHLAISNMP LVKSVTAEG LIEDHFDVTV 250        260        270        280
  KMSTYLVAFI ISDFESVSKI TKSGVKVSVY AVPDKINQAD
```

```
              290        300        310        320
              YALDAAVTLL EFYEDYFSIP YPLPKQDLAA IPDFQSGAME 330        340        350        360
              NWGLTTYRES ALLFDAEKSS ASSKLGITMT VAHELAHQWF 370        380        390        400
              GNLVTMEWWN DLWLNEGFAK FMEFVSVSVT HPELKVGDYP 410        420        430        440
              FGKCFDAMEV DALNSSHPVS TPVENPAQIR EMFDDVSYDK 450        460        470        480
              (1)GACILNMLRE YLSADAFKSG IVQYLQKHSY KNTKNEDLWD 490        500        510        520
              SMASICPTDG VKGMDGFCSR SQHSSSSSHW HQEGVDVKTM 530        540        550        560
              MNTWTLQKGF PLITITVRGR NVHMKQEHYM KGSDGAPDTG 570        580        590        600
              YLWHVPLTFI TSKSDMVHRF LLKTKTDVLI LPEEVEWIKF 610        620        630        640
              NVGMNGYYIV HYEDDGWDSL TGLLKGTHTA VSSNDRASLI 650        660        670        680
              NNAFQLVSIG KLSIEKALDL SLYLKHETEI MPVFQGLNEL 690        700        710        720
              IPMYKLMEKR DMNEVETQFK AFLIRLLRDL IDKQTWTDEG 730        740        750        760
              SVSERMLRSQ LLLLACVHNY QPCVQRAEGY FRKWKESNGN 770        780        790        800
              LSLPVDVTLA VFAVGAQSTE GWDFLYSKYQ FSLSSTEK(3)SQ 810        820        830        840
              IEFALCRTQN KEKLQWLLDE SFKGDKIKTQ EFPQILTLIG 850        860        870        880
              RNPVGYPLAW QFLRKNWNKL VQKFELGSSS IAHMNMGTTN 890        900        910        920
              QFSTRTRLEE VKGFFSSLKE NGSQLRCVQQ TIETIEENIG 930        940
              WMDKNFDKIR VWLQSEKLER M
```

| Protein Name | Uniprot | IPI | Gene Name |
|---|---|---|---|
| Isoform 1 of glutaminyl-peptide | QPCT | IPI00003919 | Q16769-1 |

| Trypsin Fragments | |
|---|---|
| 1. MASTPHPPGAR (SEQ ID NO: 293) | 2. YPGSPGSYAAR (SEQ ID NO: 294) |

```
              10         20         30         40           (SEQ ID NO: 295)
              MAGGRHRRVV GTLHLLLLVA ALPWASRGVS PSASAWPEEK 50         60         70         80
              NYHQPAILNS SALRQIAEGT SISEMWQNDL QPLLIER(2)YPG 90         100        110        120
              SPGSYAARQH IMQRIQRLQA DWVLEIDTFL SQTPYGYRSF 130        140        150        160
              SNIISTLNPT AKRHLVLACH YDSKYFSHWN NRVFVGATDS 170        180        190        200
              AVPCAMMLEL ARALDKKLLS LKTVSDSKPD LSLQLIFFDG 210        220        230        240
              EEAFLHWSPQ DSLYGSRHLA AK(1)MASTPHPP GARGTSQLHG
```

```
250        260        270        280
MDLLVLLDLI GAPNPTFPNF FPNSARWFER LQAIEHELHE 290        300        310        320
LGLLKDHSLE GRYFQNYSYG GVIQDDHIPF LRRGVPVLHL 330        340        350        360
IPSPFPEVWH TMDDNEENLD ESTIDNLKNI LQVFVLEYLH

L
```

| Protein Name | Uniprot | IPI | Gene Name |
|---|---|---|---|
| Isoform 1 of Attraction | O75882 | IPI00027235 | ATRN_Human |

| Trypsin Fragments ||||||
|---|---|---|---|---|---|
| 1. CTWLIEGQPNR (SEQ ID NO: 296) | | 2. GDECQLCEVENR (SEQ ID NO: 297) | | 3. GVKGDECQLCEVENR (SEQ ID NO: 298) | |
| 4. LADDLYR (SEQ ID NO: 299) | | 5. IMQSSQSMSK (SEQ ID NO: 300) | | 6. LTGSSGFVTDGPGNYK (SEQ ID NO: 301) | |
| 7. SCALDQNCQWEPR (SEQ ID NO: 302) | | | | | |

```
10         20         30         40                  (SEQ ID NO: 303)
MVAAAAATEA RLRRRTAATA ALAGRSGGPH WDWDVTRAGR 50         60         70         80
PGLGAGLRLP RLLSPPLRPR LLLLLLLLSP PLLLLLLPCE 90         100        110        120
AEAAAAAAAV SGSAAAEAKE CDRPCVNGGR CNPGTGQCVC 130        140        150        160
PAGWVGEQCQ HCGGRFR⁽⁶⁾LTG SSGFVTDGPG NYKYKTK⁽¹⁾CTW 170        180        190        200
LIEGQPNRIM RLRFNHFATE CSWDHLYVYD GDSIYAPLVA 210        220        230        240
AFSGLIVPER DGNETVPEVV ATSGYALLHF FSDAAYNLTG 250        260        270        280
FNITYSFDMC PNNCSGRGEC KISNSSDTVE CECSENWKGE 290        300        310        320
ACDIPHCTDN CGFPHRGICN SSDVRGCSCF SDWQGPGCSV 330        340        350        360
PVPANQSFWT REEYSNLKLP RASHKAVVNG NIMWVVGGYM 370        380        390        400
FNHSDYNMVL AYDLASREWL PLNRSVNNVV VRYGHSLALY 410        420        430        440
KDKIYMYGGK IDSTGNVTNE LRVFHIHNES WVLLTPKAKE 450        460        470        480
QYAVVGHSAH IVTLKNGRVV MLVIFGHCPL YGYISNVQEY 490        500        510        520
DLDKNTWSIL HTQGALVQGG YGHSSVYDHR TRALYVHGGY 530        540        550        560
KAFSANKYR⁽⁶⁾L ADDLYRYDVD TQMWTILKDS RFFRYLHTAV 570        580        590        600
IVSGTMLVFG GNTHNDTSMS HGAKCFSSDF MAYDIACDRW 610        620        630        640
SVLPRPDLHH DVNRFGHSAV LHNSTMYVFG GFNSLLLSDI 650        660        670        680
LVFTSEQCDA HRSEAACLAA GPGIRCVWNT GSSQCISWAL
```

```
690        700        710        720
ATDEQEEKLK SECFSKRTLD HDRCDQHTDC YSCTANTNDC 730        740        750        760
HWCNDHCVPR NHSCSEGQIS IFRYENCPKD NPMYYCNKKT 770        780        790        800
SCR⁽⁷⁾SCALDQN CQWEPRNQEC IALPENICGI GWHLVGNSCL 810        820        830        840
KITTAKENYD NAKLFCRNHN ALLASLTTQK KVEFVLKQLR 850        860        870        880
⁽⁵⁾IMQSSQSMSK LTLTPWVGLR KINVSYWCWE DMSPFTNSLL 890        900        910        920
QWMPSEPSDA GFCGILSEPS TRGLKAATCI NPLNGSVCER 930        940        950        960
PANHSAKQCR TPCALRTACG SCTSGSSECM WCSNMKQCVD 970        980        990        1000
SNAYVASFPF GQCMEWYTMS TCPPENCSGY CTCSHCLEQP 1010       1020       1030       1040
GCGWCTDPSN TGKGKCIEGS YKGPVKMPSQ APTGNFYPQP 1050       1060       1070       1080
LLNSSMCLED SRYNWSFIHC PACQCNGHSK CINQSICEKC 1090       1100       1110       1120
ENLTTGKHCE TCISGFYGDP TNGGKCQPCK CNGHASLCNT 1130       1140       1150       1160
NTGKCFCTTK ⁽⁹⁾GVK⁽²⁾GDECQLC EVENRYQGNP LRGTCYYTLL 1170       1180       1190       1200
IDYQFTFSLS QEDDRYYTAI NFVATPDEQN RDLDMFINAS 1210       1220       1230       1240
KNFNLNITWA ASFSAGTQAG EEMPVVSKTN IKEYKDSFSN 1250       1260       1270       1280
EKFDFRNHPN ITFFVYVSNF TWPIKIQIAF SQHSNFMDLV 1290       1300       1310       1320
QFFVTFFSCF LSLLLVAAVV WKIKQSCWAS RRREQLLREM 1330       1340       1350       1360
QQMASRPFAS VNVALETDEE PPDLIGGSIK TVPKPIALEP 1370       1380       1390       1400
CFGNKAAVLS VFVRLPRGLG GIPPPGQSGL AVASALVDIS 1410       1420
QQMPIVYKEK SGAVRNRKQQ PPAQPGTC
```

| Protein Name | Uniprot | IPI | Gene Name |
|---|---|---|---|
| Uncharacterized protein | | IPI00925547 | LTF_Human |

| Trypsin Fragments | | |
|---|---|---|
| 1. ADAVTLDGG FIYEAGLAPYK (SEQ ID NO: 304) | 2. ARVVWCAVG EQELR (SEQ ID NO: 305) | 3. ARVVWCAVG EQELRK (SEQ ID NO: 306) |
| 4. CAFSSQEPYFSYSGAFK (SEQ ID NO: 307) | 5. CFQWQR (SEQ ID NO: 308) | 6. CGLVPVLAENYK (SEQ ID NO: 309) |
| 7. CLAENAGDVAFVK (SEQ ID NO: 310) | 8. CLRDGAGDVAFIR (SEQ ID NO: 311) | 9. CSTSPLLEACEFLRK (SEQ ID NO: 312) |
| 10. CSTSPLLEACEFLR (SEQ ID NO: 313) | 11. CVPNSNER (SEQ ID NO: 314) | 12. CVPNSNERYYGYTGAFR (SEQ ID NO: 315) |
| 13. DCHLAR (SEQ ID NO: 316) | 14. DEYELLCPDNTR (SEQ ID NO: 317) | 15. DGAGDVAFIR (SEQ ID NO: 318) |

| | | |
|---|---|---|
| 16. DGAGDVAFIRESTV<br>FEDLSDEAERDEY<br>ELLCPDNTR<br>(SEQ ID NO: 319) | 17. DLLFKDSAI<br>GFSR<br>(SEQ ID NO: 320) | 18. DLKLADFAL<br>LCLDGK<br>(SEQ ID NO: 321) |
| 19. DLKLADFALLCLDGKR<br>(SEQ ID NO: 322) | 20. DKSPKFQLFGSPSGQK<br>(SEQ ID NO: 323) | 21. DSAIGFSR<br>(SEQ ID NO: 324) |
| 22. DSAIGFSRV<br>PPR<br>(SEQ ID NO: 325) | 23. DSPIQCIQA<br>IAENR<br>(SEQ ID NO: 326) | 24. DSPIQCIQAIAENRA<br>DAVTLDGGFIYE<br>AGLAPYK<br>(SEQ ID NO: 327) |
| 25. DVTVLQNTD<br>GNNNEAWAK<br>(SEQ ID NO: 328) | 26. DVTVLQNTD<br>GNNNEAWAKDIK<br>(SEQ ID NO: 329) | 27. GEADAMSLD<br>GGYVYTAGK<br>(SEQ ID NO: 330) |
| 28. GGSFQLNELQGLK<br>(SEQ ID NO: 331) | 29. GPPVSCIK<br>(SEQ ID NO: 332) | 30. GPPVSCIKR<br>(SEQ ID NO: 333) |
| 31. GQFPNLCR<br>(SEQ ID NO: 334) | | |

(SEQ ID NO: 335)
MKLVFLVLLF LGALGLCLAG RRRSVQWCA VSQPEATK[5]CF QWQRNMRK VR[29,30]GPPV SCIKR[23,24]DS PIQCIQAIAE NR[1]ADAVTLDG GFIYEAGLAP YKLRPVAAE VYGTERQPR THYYAV AVVKK[28]G GSFQLNELQG LKSCHTGLRR TAGWNVPIGT LRPFLNWTG PPEPIEAAV ARFFSA SCVPGA DK[31]GQFPNLCR LCAGTGENK[8]C AFSSQEPYFS YSGAFK[8]CLR [15,16]DGAGDVAFI RESTVFE DLSDE AER[14]DEYELL CPDNTRKPVDK FK[13]DCHLARVP SHAVVARSV NGKEDAIWN LLRQAQE KFGK[20]D KSPKFQLFG SPSGQK[17]DLLFK [21,22]DSAIGFSRVP PRIDSGLYL GSGYFTAIQ NLRKSEE EVAAR R[2,3]ARVVWCAV GEQELRKCNQW SGLSEGSVTC SSASTTEDC IALK[23]GEADA MSLDGGY VYTAG K[6]CGLVPVLA ENYKSQQSSDP DPNCVDRPVE GYLAVAVVR RSDTSLTWN SVKGKKS CHTAV DRTAGWNIP MGLLFNQTGSC KFDEYFSQSC APGSDPRSN LCALCIGDE QGENK[11,12]CV PNSNE RYYGYTGAF R[7]CLAENAGDVA FVK[25,26]DVTVLQN TDGNNNEAW AK[18,19]DLKLADF ALLCLDG KRKPV TEARSCHLA MAPNHAVVSRM DKVERLKQVL LHQQAKFGR NGSDCPDKF CLFQSET KNLLF NDNTECLAR LHGKTTYEKYL GPQYVAGITN LKK[9,10]CSTSPL LEACEFLRK

---

We claim:

1. A method of detecting markers in lacrimal secretions from a human subject, comprising:

obtaining a lacrimal secretion sample from the human subject, wherein the human subject has breast cancer, or has a palpable lump in the breast suspected of being cancerous;

contacting the lacrimal secretion sample in an immunoassay with antibodies that specifically bind to at least two protein markers, wherein the at least two protein markers comprise A1BG and at least one protein marker provided in Table 2A or Table 2B; and detecting the levels of the at least two protein markers in the immunoassay by detecting the antibodies bound to the markers.

2. The method of claim 1, wherein the lacrimal secretion sample from the human subject is an ocular wash sample.

3. The method of claim 1, wherein the human subject has Stage I cancer or Stage II cancer, or a later stage.

4. The method of claim 1, comprising detecting the levels of A1BG protein and at least two protein markers from Table 2A or Table 2B.

5. The method of claim 1, further comprising administering an anti-cancer therapeutic to the subject.

* * * * *